US007435541B2

(12) United States Patent
Olson et al.

(10) Patent No.: US 7,435,541 B2
(45) Date of Patent: *Oct. 14, 2008

(54) RESTRICTION ENZYME GENOTYPING

(75) Inventors: Jeffrey Olson, Chelmsford, MA (US); Martin Zillmann, Shrewsbury, MA (US); Vincent P. Stanton, Jr., Belmont, MA (US)

(73) Assignee: Sequenom, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/116,420

(22) Filed: Apr. 4, 2002

(65) Prior Publication Data

US 2003/0073101 A1 Apr. 17, 2003

Related U.S. Application Data

(63) Continuation-in-part of application No. 09/863,733, filed on May 23, 2001, now abandoned, which is a continuation-in-part of application No. 09/697,028, filed on Oct. 25, 2000, which is a continuation-in-part of application No. 09/696,998, filed on Oct. 25, 2000, now Pat. No. 6,475,736, which is a continuation-in-part of application No. 09/697,013, filed on Oct. 25, 2000.

(60) Provisional application No. 60/206,613, filed on May 23, 2000.

(51) Int. Cl.
*C12Q 1/68* (2006.01)
*C12P 19/34* (2006.01)
*C07H 21/04* (2006.01)

(52) U.S. Cl. .......................... 435/6; 435/91.2; 536/24.33

(58) Field of Classification Search .................. 435/6, 435/91.2; 536/22.1, 23.1, 24.33, 24.37
See application file for complete search history.

(56) References Cited

U.S. PATENT DOCUMENTS

| | | | |
|---|---|---|---|
| 5,595,890 A | | 1/1997 | Newton et al. |
| 5,612,179 A | | 3/1997 | Simons |
| 5,639,611 A | | 6/1997 | Wallace et al. |
| 5,695,937 A | * | 12/1997 | Kinzler et al. ............ 435/6 |
| 5,710,000 A | * | 1/1998 | Sapolsky et al. ........... 435/6 |
| 5,789,568 A | | 8/1998 | Simons |
| 5,804,383 A | | 9/1998 | Gruenert et al. |
| 5,851,762 A | | 12/1998 | Simons |
| 5,853,989 A | | 12/1998 | Jeffreys et al. |
| 5,871,908 A | * | 2/1999 | Henco et al. ............. 435/6 |
| 5,972,614 A | | 10/1999 | Ruano et al. |
| 6,124,120 A | * | 9/2000 | Lizardi ................ 435/91.2 |
| 6,277,578 B1 | * | 8/2001 | Shultz et al. ............. 435/6 |
| 6,440,705 B1 | * | 8/2002 | Stanton et al. ........... 435/91.2 |
| 6,458,544 B1 | * | 10/2002 | Miller ................... 435/6 |
| 6,475,736 B1 | * | 11/2002 | Stanton, Jr. ............. 435/6 |

FOREIGN PATENT DOCUMENTS

| | | |
|---|---|---|
| EP | 1176212 A1 | 1/2002 |
| WO | WO 95/16791 | 6/1995 |
| WO | WO 96/06187 | 2/1996 |
| WO | WO 99/09211 * | 2/1999 |
| WO | WO 99/40226 | 8/1999 |
| WO | WO 99/53102 | 10/1999 |
| WO | WO 00/56925 | 9/2000 |
| WO | WO/01/79234 A2 | 10/2001 |
| WO | WO 02/009931 A2 | 1/2002 |

OTHER PUBLICATIONS

Deguchi et al. Rapid detection of point mutations of the neisseria gonorrhoeae gyrA gene associated with decreased susceptibilities to quinolones. J Clin Microbiol., vol. 34, No. 9, pp. 2255-2258, 1996.*
Laken et al. Genotyping by mass spectrometric analysis of short DNA fragments. Nature Biotechnology., vol. 16, pp. 1352-1356, 1998.*
Laken et al. Genotyping by mass spectrometric analysis of short DNA fragments. Nature Biotechnology., vol. 16, pp. 1352-1356, 1998.*
Clark, A.G., et al. "Haplotype Structure and Population Genetic Inferences from . . . ", *American Journal of Human Genetics* 63: 595-612, 1998.
Griffin et al., "Direct Genetic Analysis by Matrix-Assisted Laser Desorption/Ionization Mass Spectrometry" *Proc. Nat'l. Acad. Sci. USA* 96:6301-6306, 1999.
Hubert et al., "Sperm Typing Allows Accurate Measurement Of The Recombination Fraction Between D3S2 And D3S3 On The Short Arm Of Human Chromosome 3", *Genomics.* Apr. 1992;12(4):683-687).
Lo, Y.M. et al., "Direct haplotype determination by double ARMS: specificity, sensitivity and genetic applications", *Nucleic Acids Research* Jul. 11:19 (13):3561-7, 1991).
Newton et al., "Amplification Refractory Mutation System For Prenatal Diagnosis And Carrier Assessment In Cystic Fibrosis", *Lancet.* Dec. 23-30; 2 (8678-8679):1481-3, 1989.
Newton et al., "Analysis Of Any Point Mutation In DNA. The Amplification Refractory Mutation System (ARMS)", *Nucleic Acids Res.* vol. 17, 2503-2516, 1989).
Nickerson, D. A., et al., "DNA sequence diversity in a 9.7-kb . . . ", *Nature Genetics* 19: 233-240, 1998.
Ruano et al., "Haplotype Of Multiple Polymorphisms Resolved By Enzymatic Amplification Of Single DNA Molecules", *Proc Natl Acad Sci U S A* 1990 87(16):6296-6300.
Terwilliger et al., "Linkage disequilibrium mapping of complex disease: fantasy or reality?", *Current Opinion in Biotechnology* 9: 578-594, 1998.

* cited by examiner

*Primary Examiner*—Suryaprabha Chunduru
(74) *Attorney, Agent, or Firm*—Fish & Richardson P.C.

(57) ABSTRACT

Methods for determining genotypes and haplotypes of genes are described. Also described are single nucleotide polymorphisms and haplotypes in the ApoE gene and methods of using that information.

12 Claims, 45 Drawing Sheets

Figure 4:
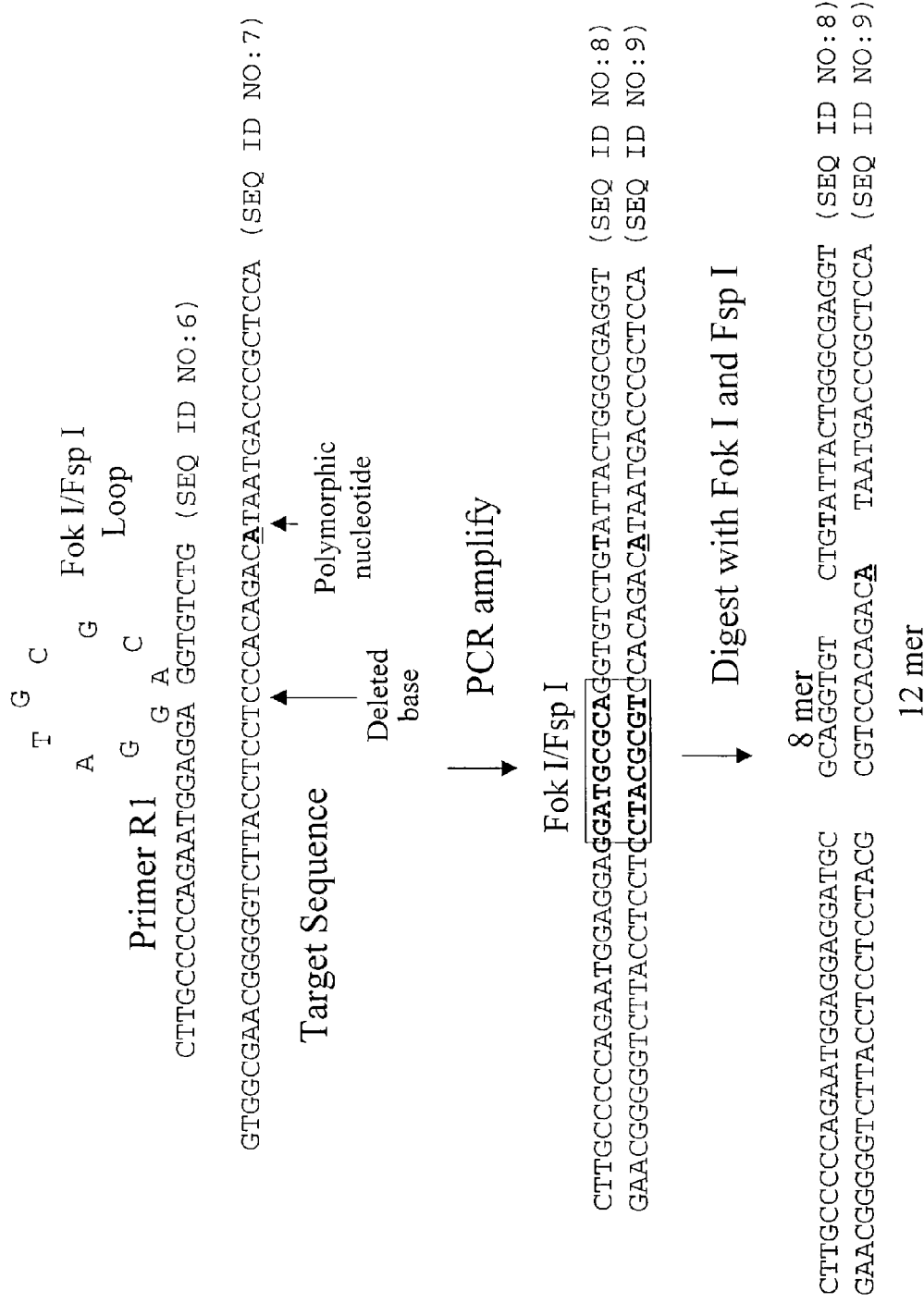

Figure 4. Restriction Enzyme Genotyping

Figure 5:
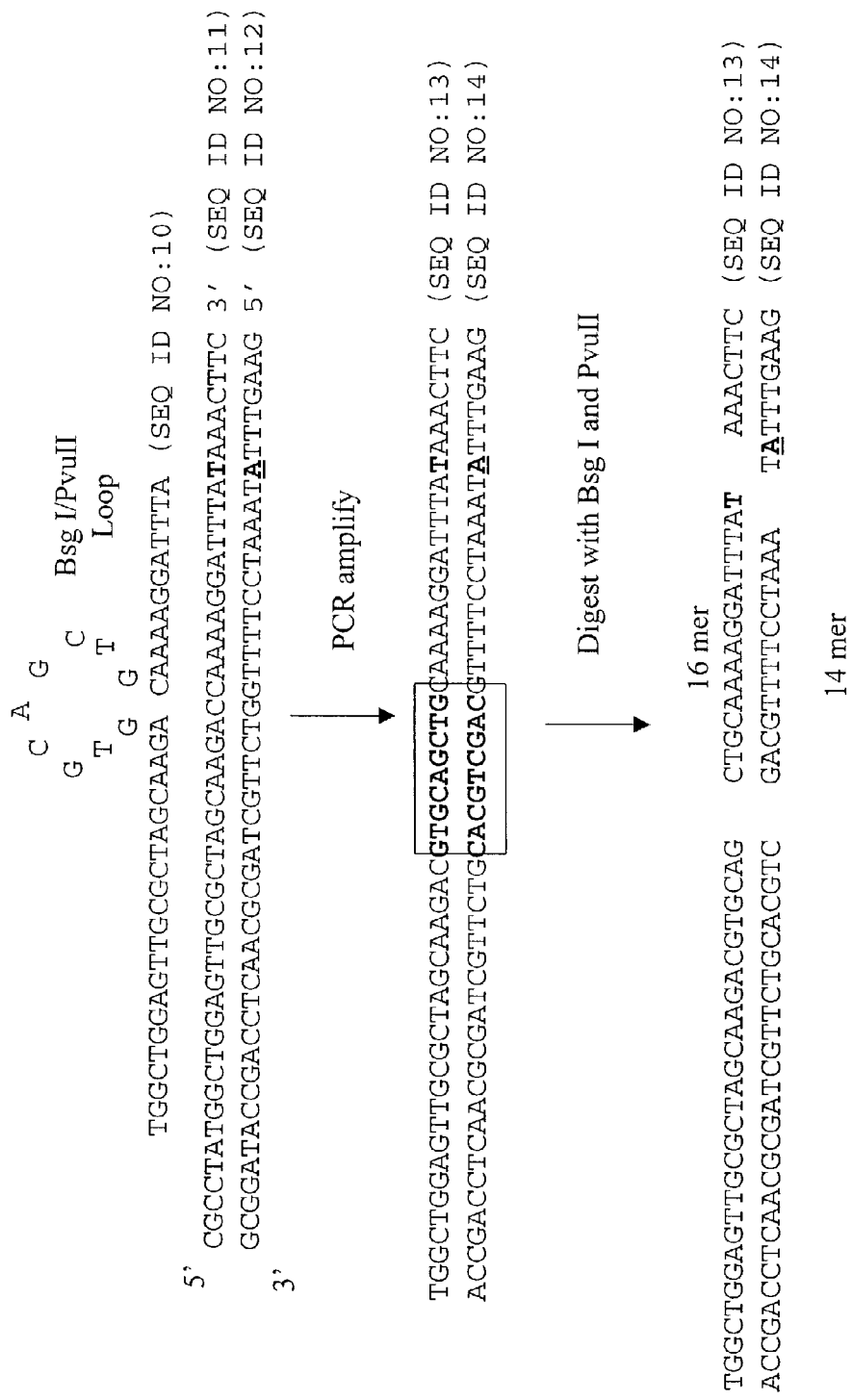

Figure 5. Introduction of Bsg I and Pvu II sites during PCR by loop followed by endonuclease digestion.

Figure 6:
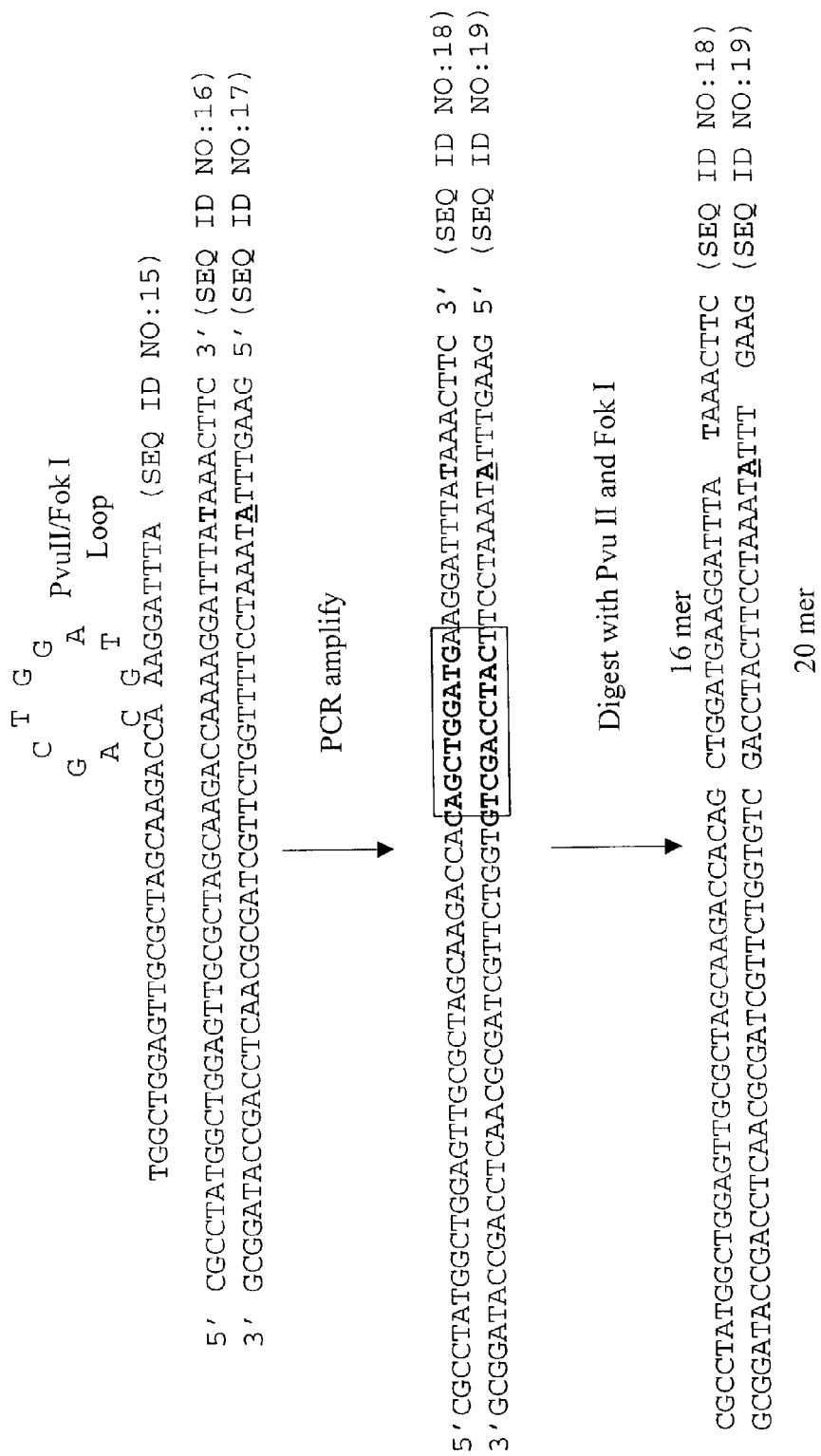

Figure 6. Introduction of Fok I and Pvu II sites during PCR by loop followed by endonuclease digestion

Figure 11:
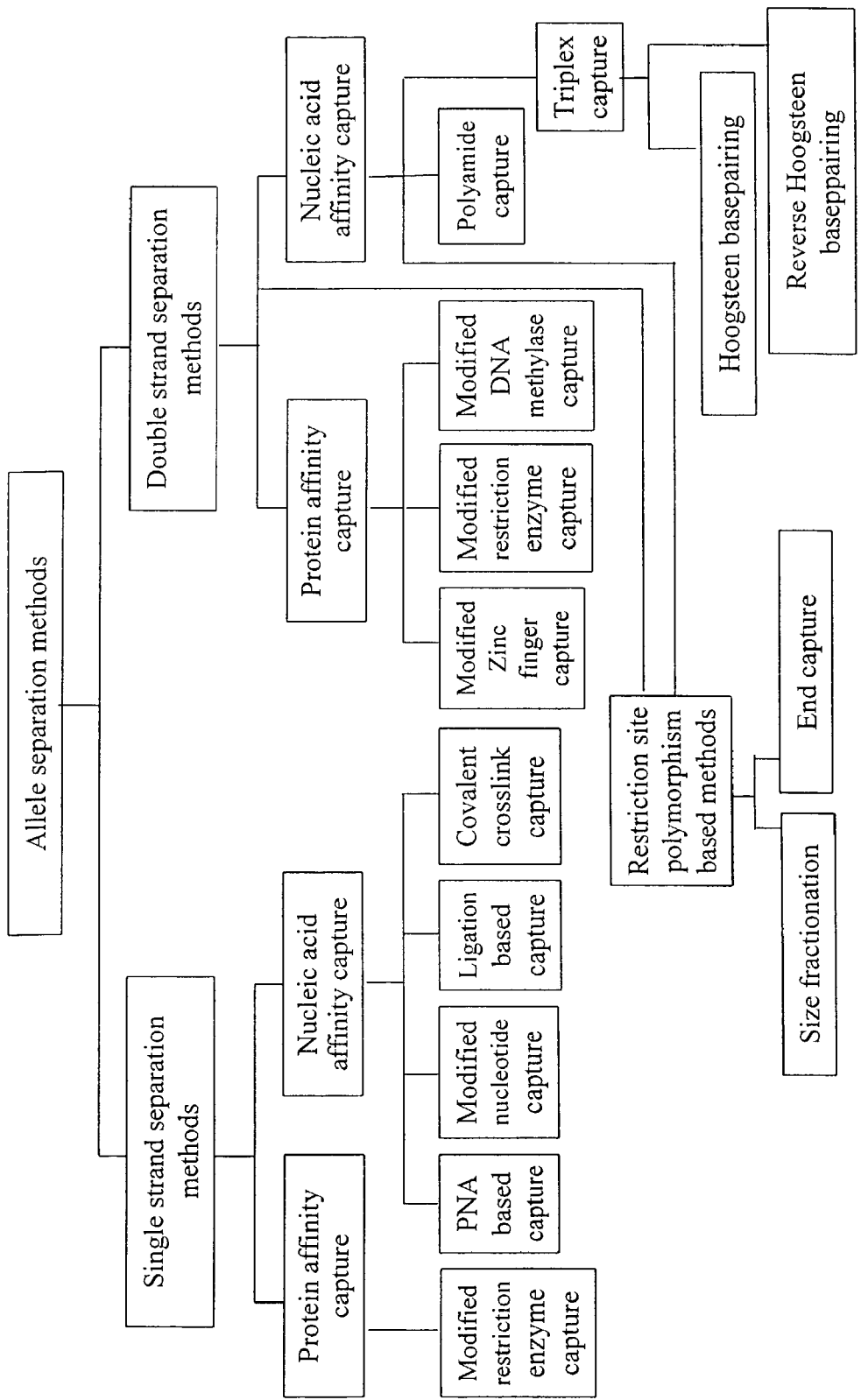

Figure 11. Methods for haplotyping based on physical allele separation

Figure 12:
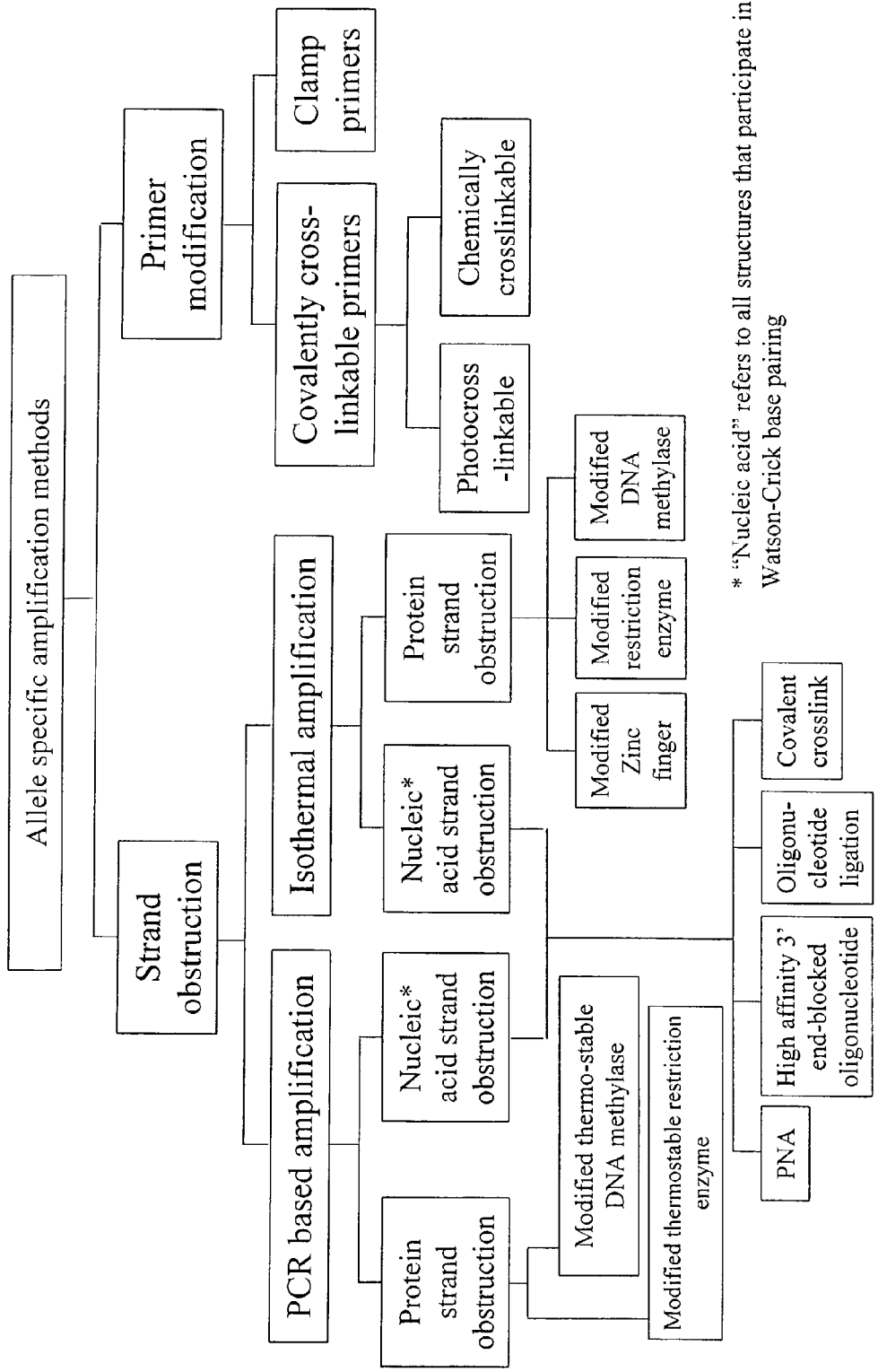

Figure 12. Methods for haplotyping based on allele specific amplification

Figure 13:
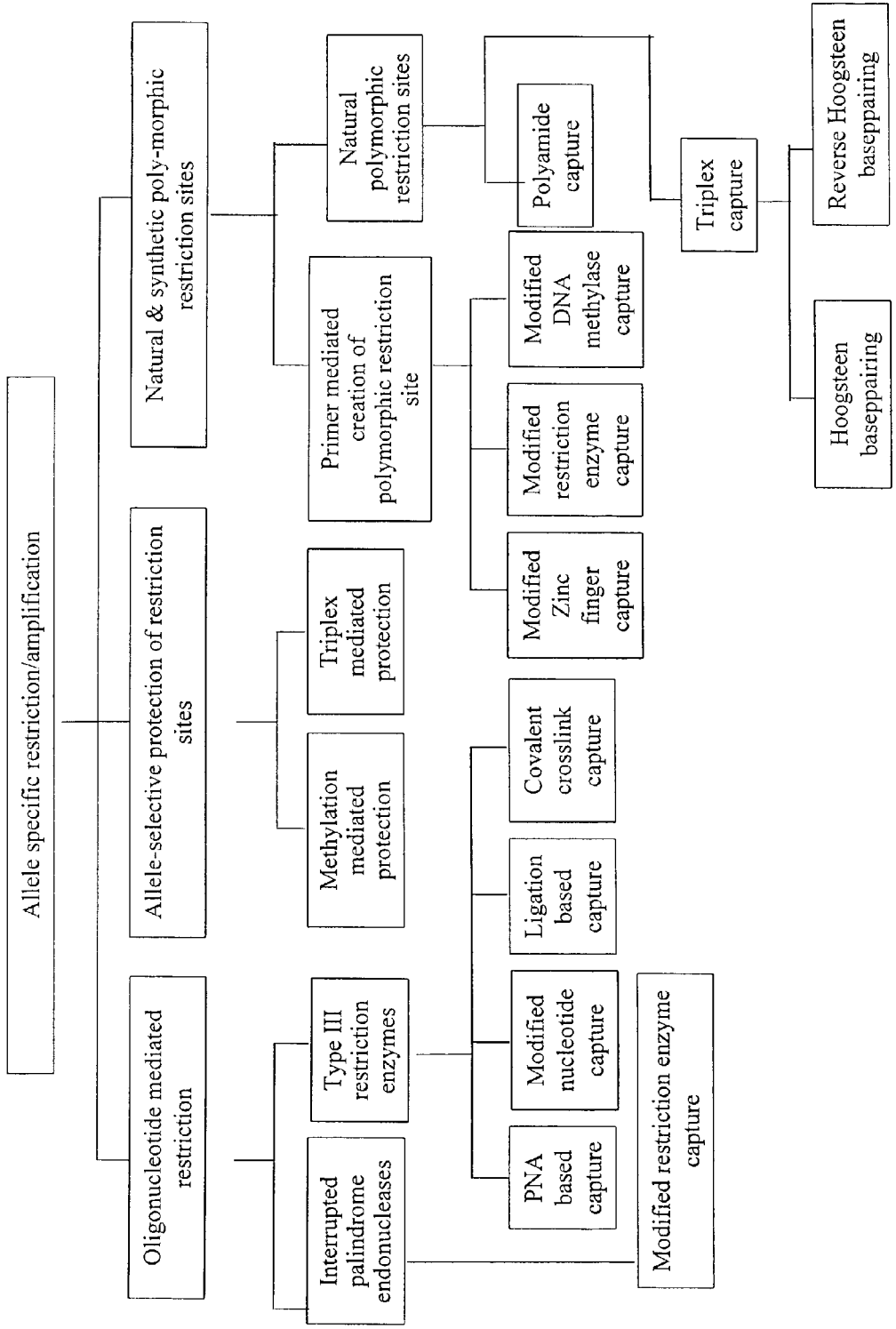

Figure 13. Methods for haplotyping based on allele specific restriction

Figure 16: Hairpin PCR Primers
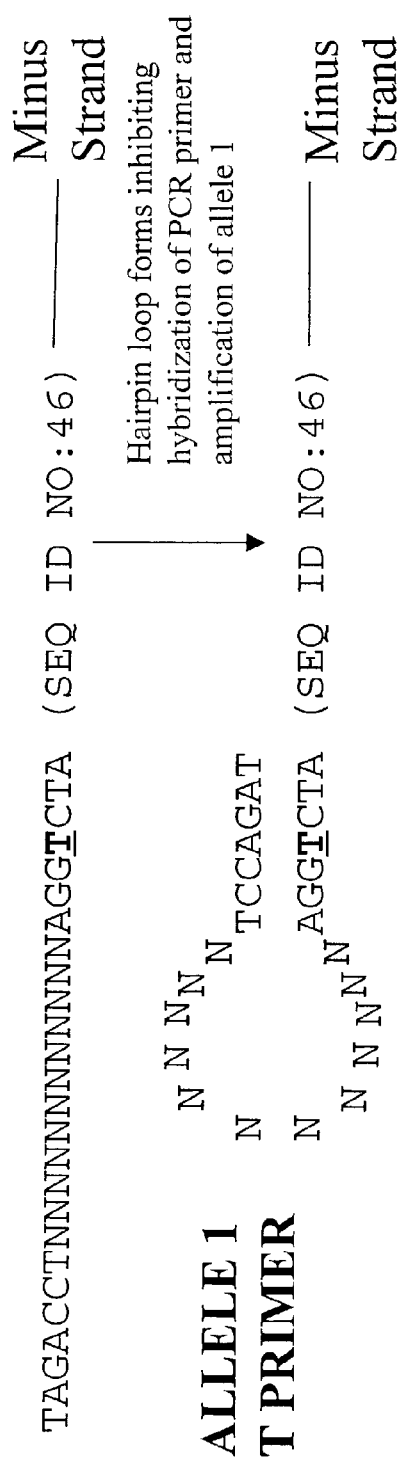
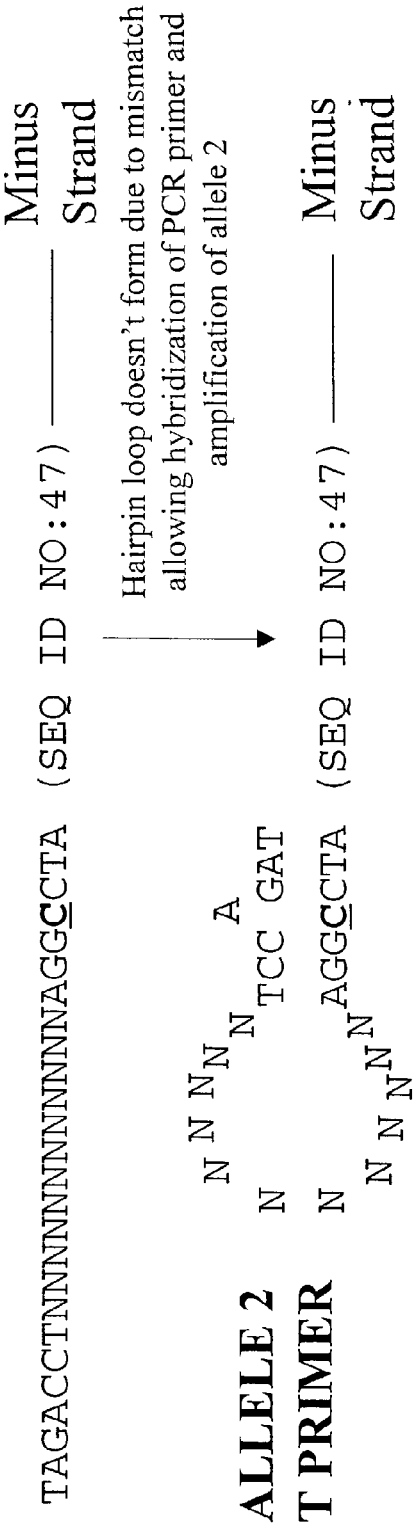

Figure 17

Hairpin PCR Primers

Minus strand resulting from PCR of allele 1

TAGGCCTNNNNNNNNNNNNNNAGG<u>T</u>CTA (SEQ ID NO:48) —— Minus Strand

→ Hairpin loop doesn't form due to mismatch allowing hybridization of PCR primer and amplification of allele 1

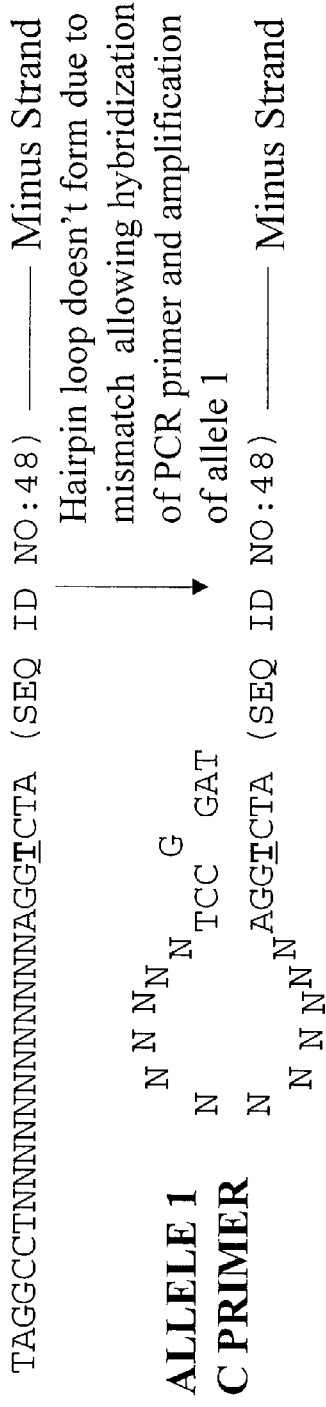

AGG<u>T</u>CTA (SEQ ID NO:48) —— Minus Strand

ALLELE 1 C PRIMER

Minus strand resulting from PCR of allele 2

TAGACCTNNNNNNNNNNNNNNAGG<u>C</u>CTA (SEQ ID NO:47) —— Minus Strand

→ Hairpin loop forms inhibiting hybridization of PCR primer and amplification of allele 2

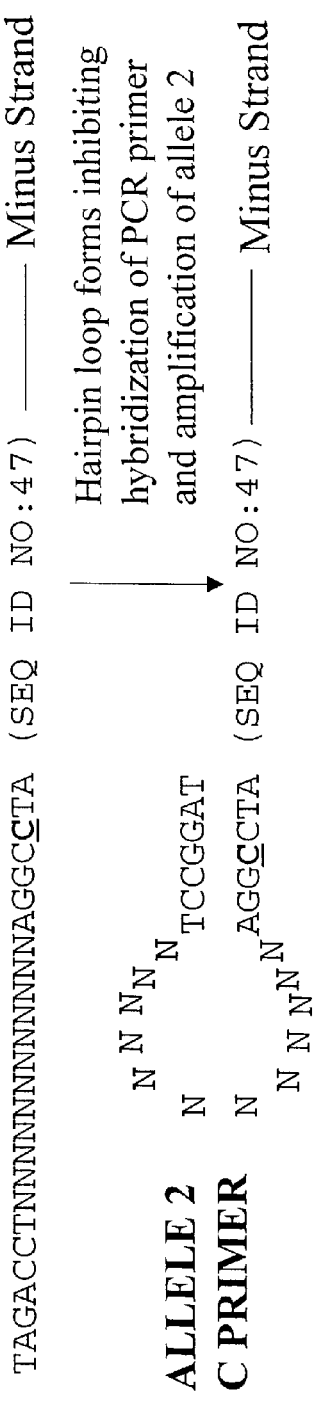

AGG<u>C</u>CTA (SEQ ID NO:47) —— Minus Strand

ALLELE 2 C PRIMER

Figure 21. Dihydropyrimidine dehydrogenase (DPD) polymorphisms used in haplotyping assay.
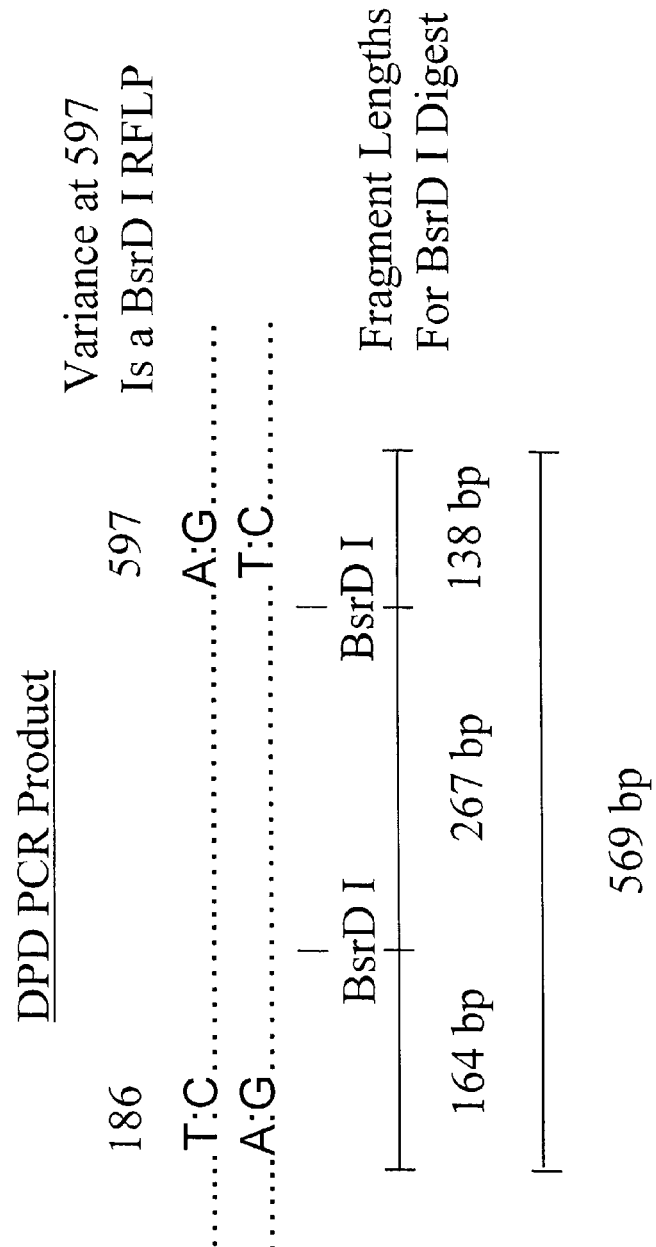

Figure 22. Allele Specific Primers for DPD

A.

DPD Primers
- DPDASCF 5' Acacagactcatgcaactctg 3' (SEQ ID NO:49)
- DPDASTF 5' acgcagactcatgcaactctg 3' (SEQ ID NO:50)
- DPDNSF 5' actcatgcaactctg 3' (SEQ ID NO:51)

B.

DPD Sequence
5' actcatgcaactctg[T or C]gttccacttcggccaagaa 3' (SEQ ID NO:52)
3' tgagtacgttgagac[A or G]caaggtgaagccggttctt 5' (SEQ ID NO:53)

Figure 23. PCR Amplification Using DPDNSF Primer

```
DPDNSF primer        5'  actcatgcaactctg  3'  (SEQ ID NO:51)
                         |||||||||||||||
Template: T allele   3'  tgagtacgttgagacacaaggtg  5'  (SEQ ID NO:54)

DPDNSF primer        5'  Actcatgcaactctg  3'  (SEQ ID NO:51)
                         |||||||||||||||
Template: C allele   3'  tgagtacgttgagacgcaaggtg  5'  (SEQ ID NO:55)

T allele             5'  actcatgcaactctgtgttccac...3'  (SEQ ID NO:56)
PCR Product              ||||||||||||||||||||||||
                     3'  tgagtacgttgagacacaaggtg...5'  (SEQ ID NO:54)

C allele             5'  actcatgcaactctggcgttccac...3'  (SEQ ID NO:57)
PCR Product              ||||||||||||||||||||||||
                     3'  tgagtacgttgagacgcaaggtg...5'  (SEQ ID NO:55)
```

Figure 24. PCR Amplification Using DPDASCF Primer

```
DPDASCF primer    5' Acacagactcatgcaactctg 3' (SEQ ID NO:49)
                     ||||||||||||||||||||||
Template T allele 3' ........tgagtacgttgagaca caaggtg 5' (SEQ ID NO:54)

DPDASCF primer    5' Acacagactcatgcaactctg 3' (SEQ ID NO:49)
                     ||||||||||||||||||||
Template C allele 3' ........tgagtacgttgagacgcaaggtg 5' (SEQ ID NO:55)

T allele       5' Acacagactcatgcaactctgtgttccac 3' (SEQ ID NO:58)
PCR Product       ||||||||||||||||||||||||||||
               3' Tgtgtctgagtacgttgagacacaaggtg 5' (SEQ ID NO:59)

C allele       5' Acacagactcatgcaactctggttccac 3' (SEQ ID NO:60)
PCR Product       ||||||||||||||||||||||||||||
               3' Tgtgtctgagtacgttgagacgcaaggtg 5' (SEQ ID NO:61)
```

Figure 25. PCR Amplification Using DPDASTF Primer.

```
DPDASTF primer   5' Acgcagactcatgcaactctg 3'  (SEQ ID NO:50)
                    |||||||||||||||||||||
Template T allele 3' ........tgagtacgttgagacacaaggtg 5' (SEQ ID NO:54)

DPDASTF primer   5' Acgcagactcatgcaactctg 3'  (SEQ ID NO:50)
                    |||||||||||||||||||||
Template C allele 3' ........tgagtacgttgagacgcaaggtg 5' (SEQ ID NO:55)

T allele      5' Acgcagactcatgcaactctgtgttccac 3' (SEQ ID NO:62)
                 ||||||||||||||||||||||||||||
PCR Product   3' Tgcgtctgagtacgttgagacacaaggtg 5' (SEQ ID NO:63)

C allele      5' Acgcagactcatgcaactctgcgttccac 3' (SEQ ID NO:64)
                 ||||||||||||||||||||||||||||
PCR Product   3' Tgcgtctgagtacgttgagacgcaaggtg 5' (SEQ ID NO:65)
```

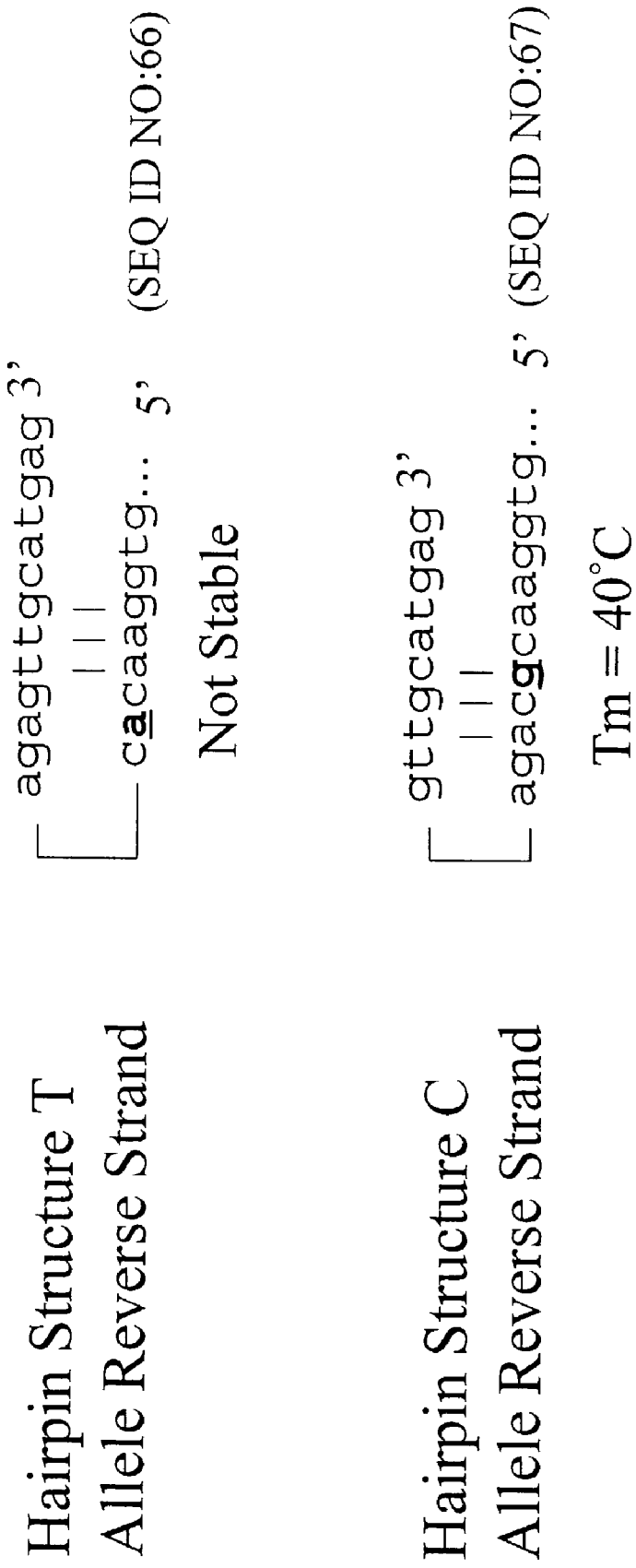
Figure 26. Hairpin Structures for PCR Products Generated Using DPDNSF Primer

Figure 27. Hairpin Structures for PCR Products Generated Using DPDASCF Primer
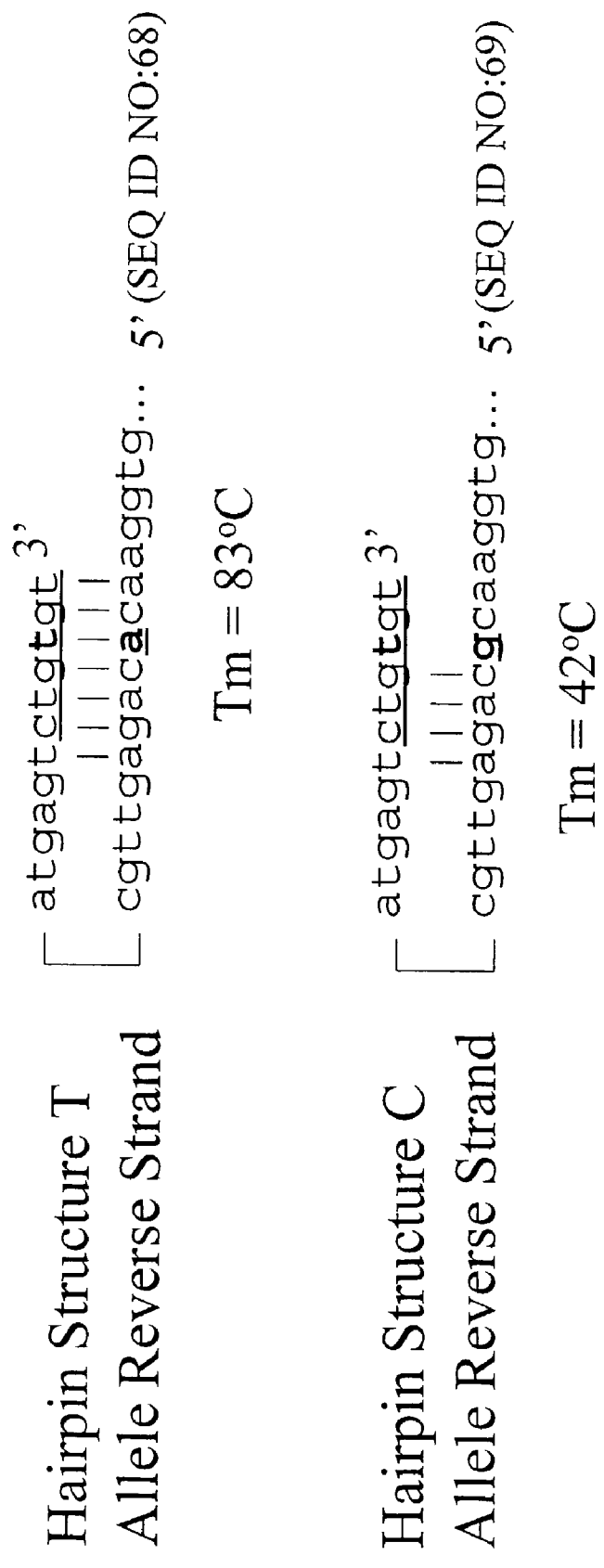
Hairpin Structure T
Allele Reverse Strand
```
     ┌ atgagtctgtgt 3'
     │ ||||||
     └ cgttgagacacaaggtg... 5' (SEQ ID NO:68)
```
Tm = 83°C
Hairpin Structure C
Allele Reverse Strand
```
     ┌ atgagtctgtgt 3'
     │ ||||
     └ cgttgagacgcaaggtg... 5' (SEQ ID NO:69)
```
Tm = 42°C

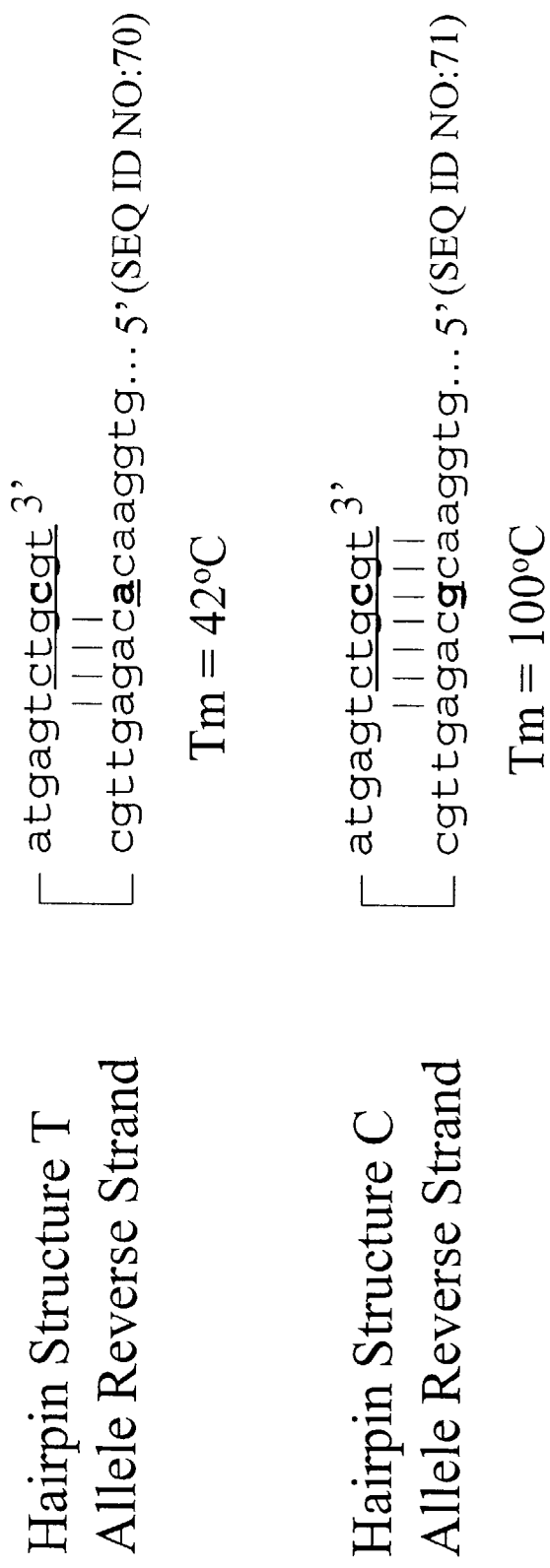
Figure 28. Hairpin Structures for PCR Products Generated Using DPDASTF Primer
Hairpin Structure T
Allele Reverse Strand
```
 ┌ atgagtctgcgt 3'
 │   ||||  ||||
 └ cgttgagacacaaggtg...5' (SEQ ID NO:70)
```
Tm = 42°C
Hairpin Structure C
Allele Reverse Strand
```
 ┌ atgagtctgcgt 3'
 │   ||||||||||
 └ cgttgagacgcaaggtg...5' (SEQ ID NO:71)
```
Tm = 100°C

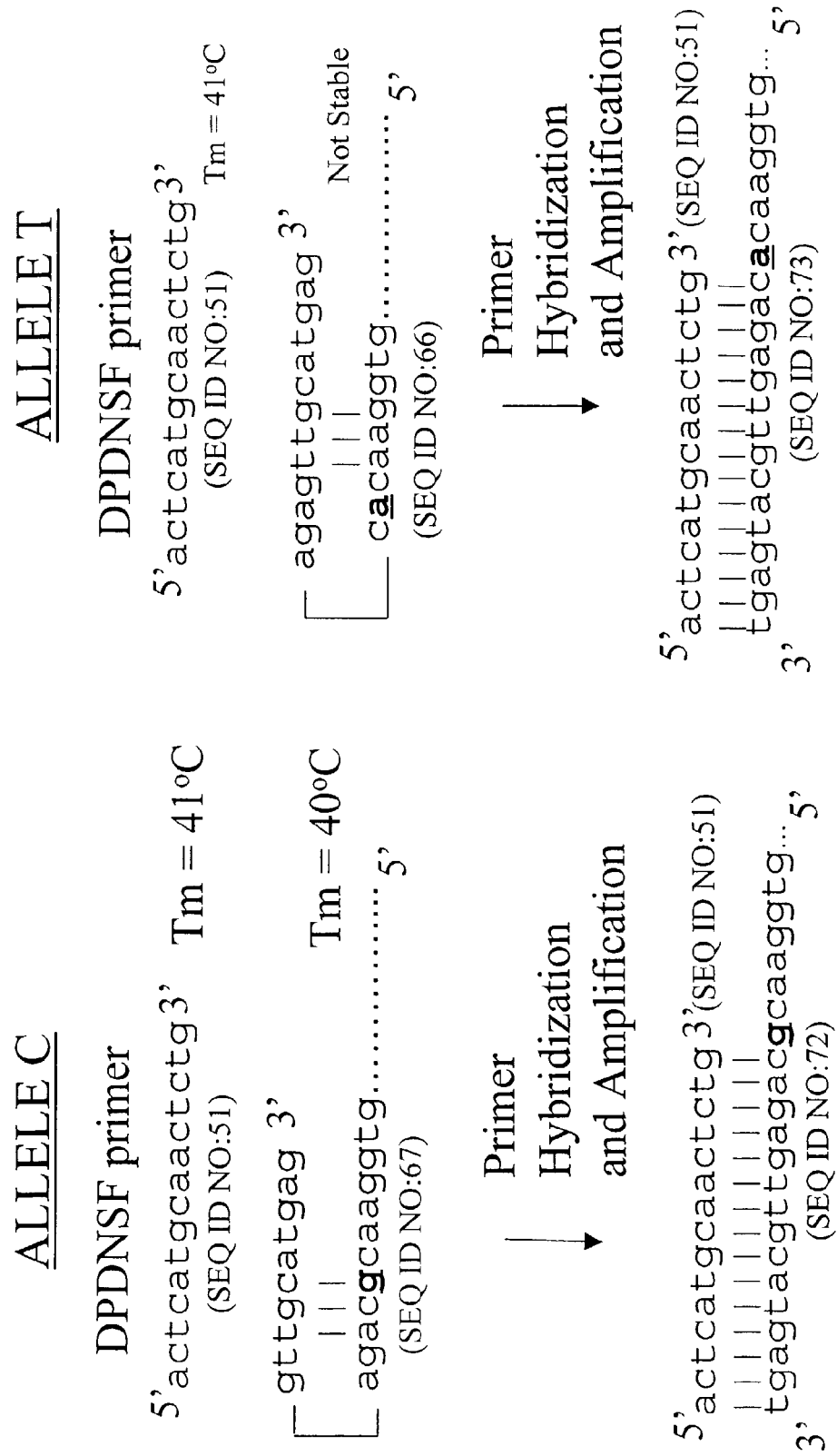
Figure 29. Non-Allele Specific Amplification Using DPDNSF Primer.

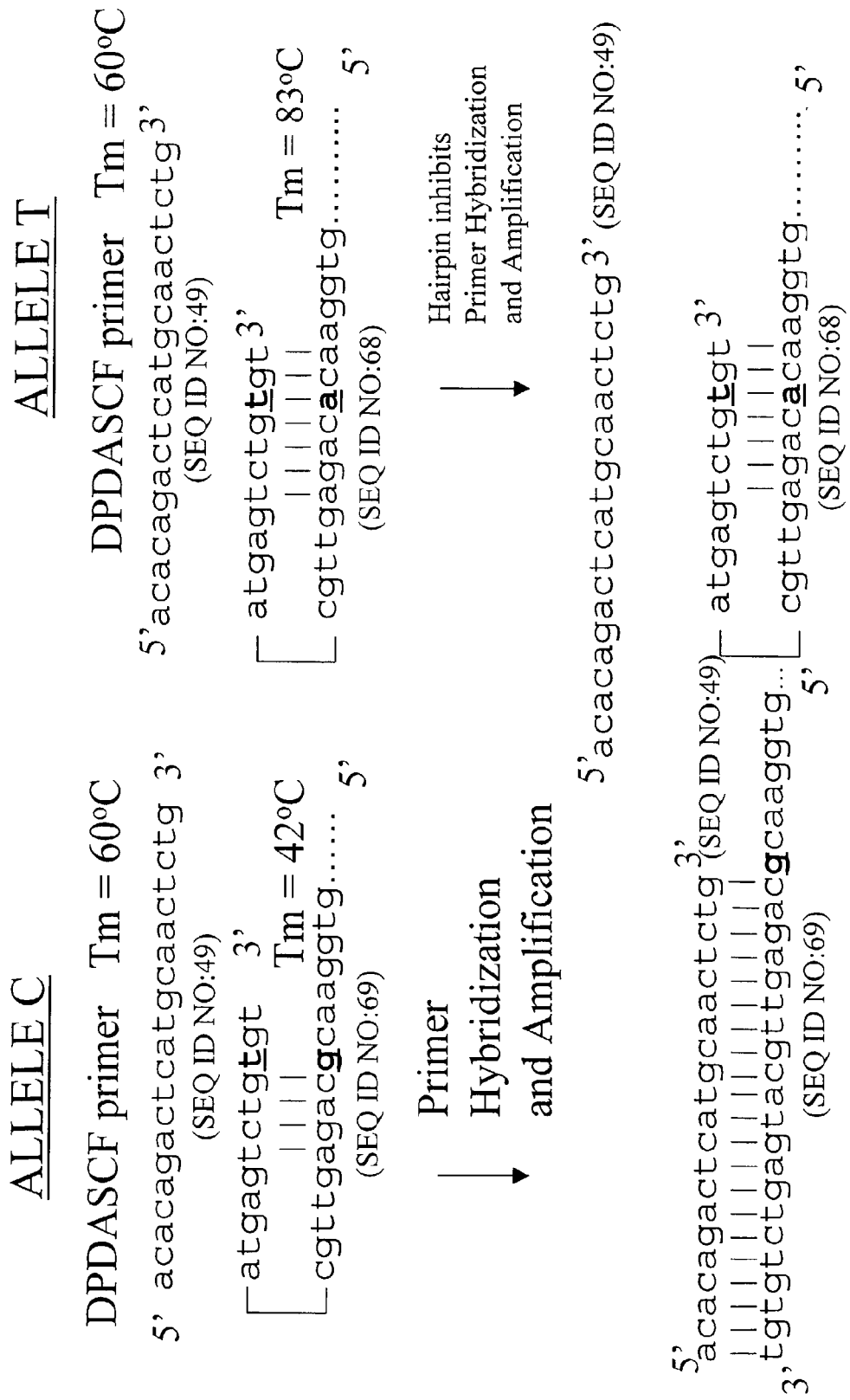
Figure 30. Allele Specific Amplification Using DPDASCF Primer

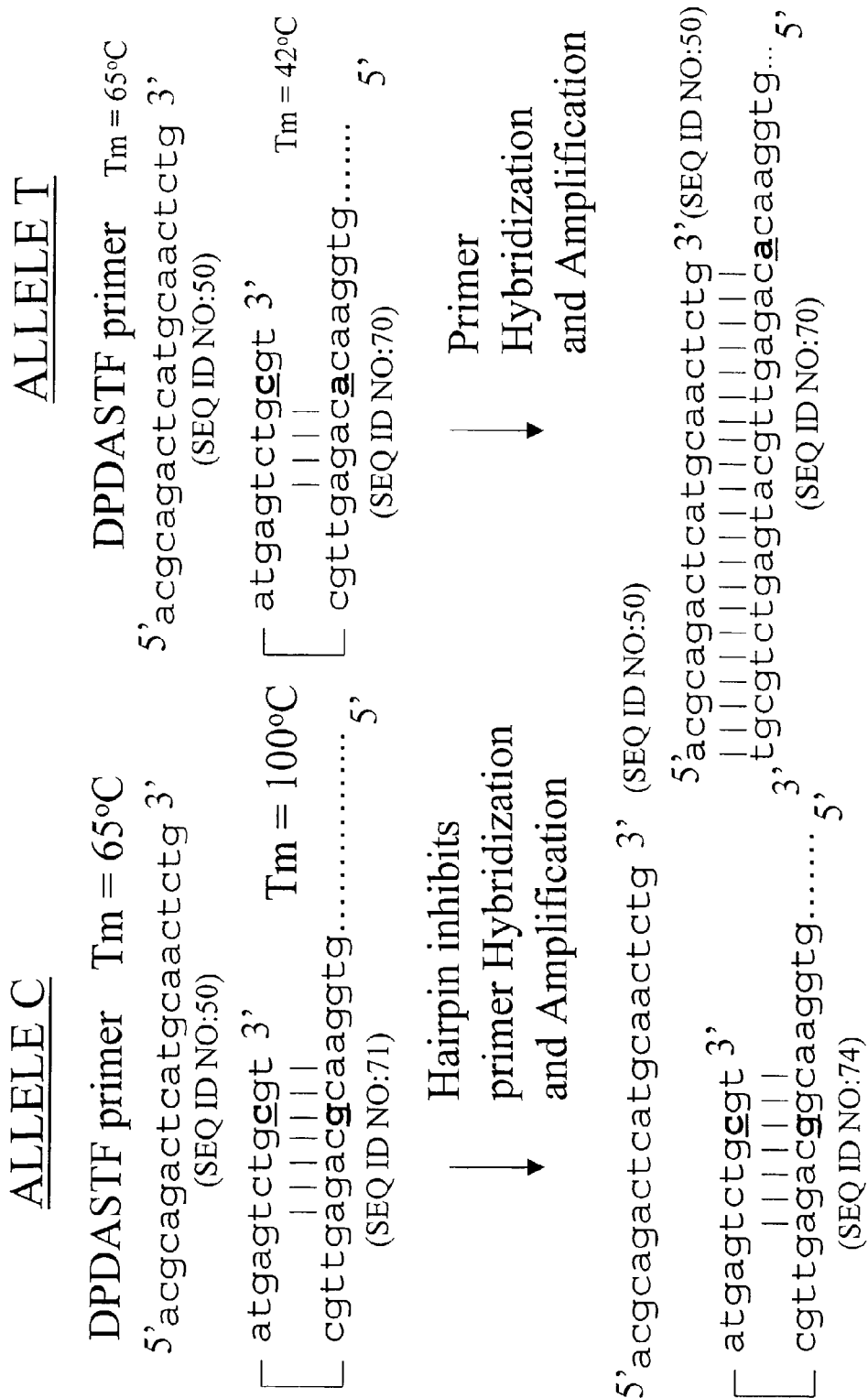
Figure 31. Allele Specific Amplification Using DPDASTF Primer

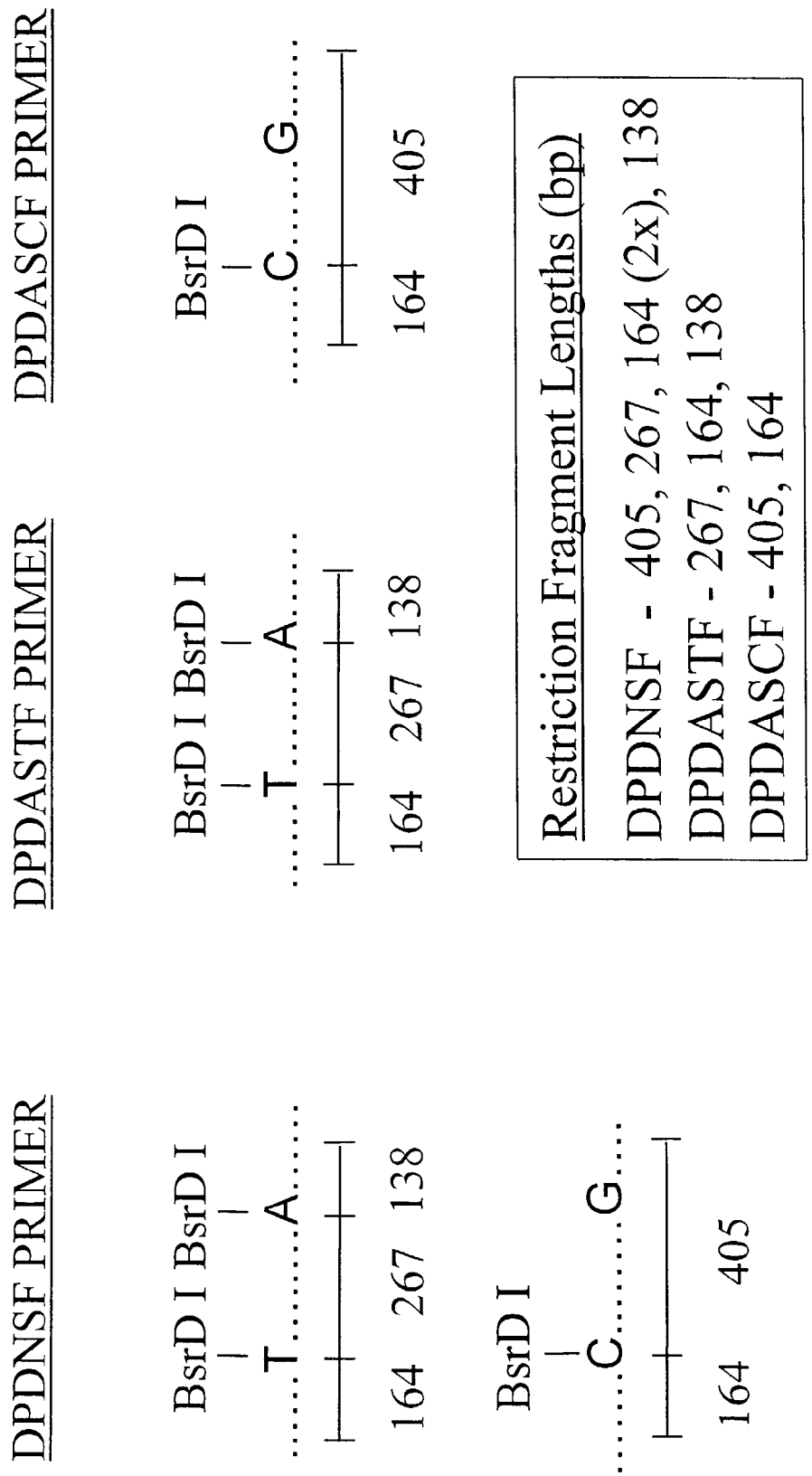
Figure 32. Allele Specific Amplification of a Heterozygous Sample with Haplotype $T^{186}, A^{597}$ and $C^{186}, G^{597}$

Figure 33. BsrD I Digest of Allele Specific PCR Products.
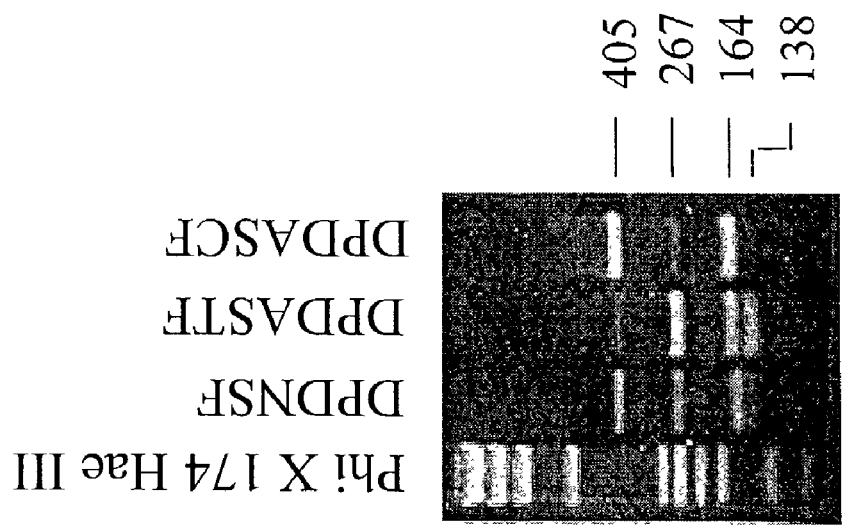

Figure 35

T Allele Amplicon

CCCGGCTGGGCGGGACATGGGATGCGCAAGGAGTGTGCGGCCGCCTGGTGCAGTAC (SEQ ID NO:83)
GGGCCGACCCGCCCTGTACCCTACGCGTTCCTGCACACGCCGGCGGACCACGTCATG (SEQ ID NO:84)

CGCGGGCGAGGTGCAGGCCATGCTCTCGGCCAGAGCACCGAGGAGCTGCGCGGGTGCGCCCTCG (SEQ ID NO:85)
GCGCCGCTCCACGTCCGGTACGAGCGCCGGTCTCGTGGCTCCTCGACGCGCCACGGCGGAGC (SEQ ID NO:86)

CCTCCACCTGCGCAAGCTGCGTAAGCGGCTCCTCCGCGATGCCGATGACCTGCAGAAGC (SEQ ID NO:87)
GGAGGTGGACGCGTTCGACGCATTCGCCGAGGAGGCGCTACGGCTACTGGACGTCTTCG (SEQ ID NO:88)

C Allele Amplicon

CCCGGCTGGGCGGGACATGGGATGCGCAAGGACGTGCGGGCCGCCTGGTGCAGTAC (SEQ ID NO:89)
GGGCCGACCCGCCCTGTACCCTACGCGTTCCTGCACGCGCCGGCGGACCACGTCATG (SEQ ID NO:90)

CGCGGGCGAGGTGCAGGCCATGCTCTCGGCCAGAGCACCGAGGAGCTGCGGGTGCGCCCTCG (SEQ ID NO:91)
GCGCCGCTCCAGTTCCGGTACGAGCGCCGGTCTCGTGGCTCCTCGACGCCCACGCGGAGC (SEQ ID NO:92)

CCTCCACCTGCGCAAGCTGCGTAAGCGGCTCCTCCGCGATGACCTGCAGAAGC (SEQ ID NO:93)
GGAGGTGGACGCGTTCGACGCATTCGCCGAGGAGGCGCTACGGCTACTGACGTCTTCG (SEQ ID NO:94)

(-ENZYME AT SITE 16747)

(+ENZYME AT SITE 16747)

(-ENZYME AT SITE 17030)

(+ENZYME AT SITE 17030)

Binuclear platinum (II) Complexes (n = 4, 5 or 6)

Figure 40
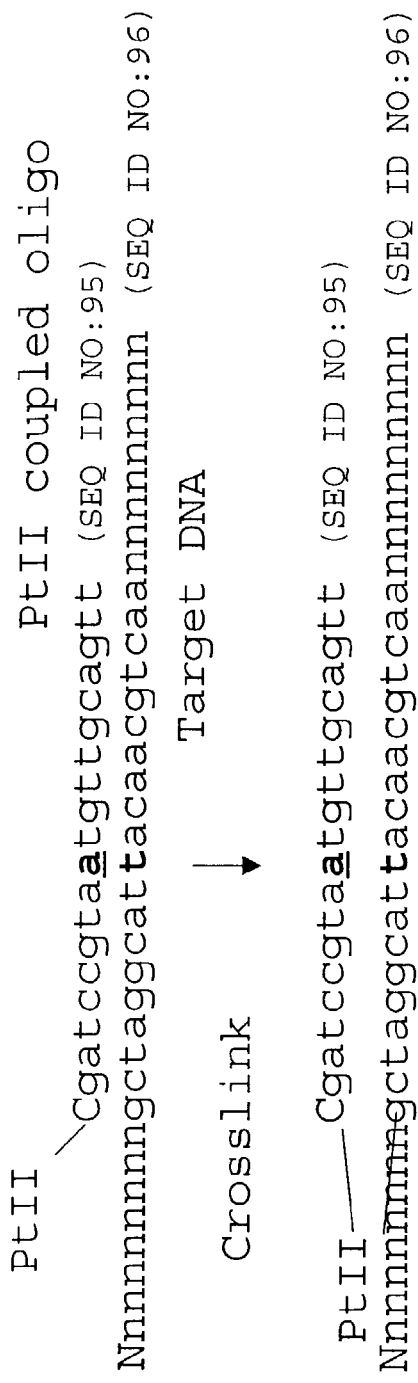
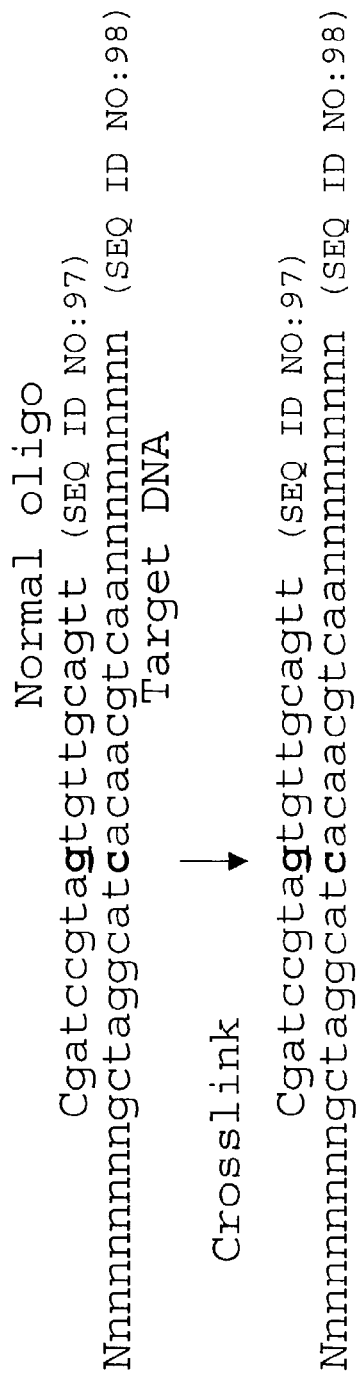

Figure 41

Allele 1

```
PtII──Cgatccgtaatgttgcagtt  (SEQ ID NO:95)
Nnnnnnnngctaggcattacaacgtcaannnnnnnnn  (SEQ ID NO:96)
```

Digest with exonuclease →

```
PtII──Cgatccgtaatgttgcagtt  (SEQ ID NO:95)
       gctaggcattacaacgtcaannnnnnnnn  (SEQ ID NO:99)
```

Released mononucleotides

```
        n
  n   n
n   n   n
```

Allele 2

```
PtII──Cgatccgtagtgttgcagtt  (SEQ ID NO:97)
Nnnnnnnngctaggcatcacaacgtcaannnnnnnnn  (SEQ ID NO:98)
```

Digest with exonuclease →

Released mononucleotides

```
              n       n     n   t
            g   a   g   n c       t
          t   g   c   t   n   c
        n   c   c   g   g
      c   a   a
    n   t
  a
n
```

RESTRICTION ENZYME GENOTYPING

RELATED APPLICATIONS

This application is a continuation-in-part of U.S. application Ser. No. 09/863,733, filed May 23, 2001 now abandoned, which is a continuation-in-part of U.S. application Ser. No. 09/697,028, filed Oct. 25, 2000; U.S. application Ser. No. 09/696,998 now U.S. Pat. No. 6,475,736, filed Oct. 25, 2000; and U.S. application Ser. No. 09/697,013, filed Oct. 25, 2000; and claims the benefit of Stanton et al., U.S. Provisional Application No. 60/206,613, filed May 23, 2000, all of which are hereby incorporated by reference in their entirety, including drawings.

BACKGROUND OF THE INVENTION

Genetic analysis refers to the determination of the nucleotide sequence of a gene or genes of interest in a subject organism, including methods for analysis of one site of sequence variation (i.e., genotyping methods) and methods for analysis of a collection of sequence variations (haplotyping methods). Genetic analysis further includes methods for correlating sequence variation with disease risk, diagnosis, prognosis or therapeutic management.

At present, DNA diagnostic testing is largely concerned with identification of rare polymorphisms related to Mendelian traits. These tests have been in use for well over a decade. In the future genetic testing will come into much wider clinical and research use, as a means of making predictive, diagnostic, prognostic and pharmacogenetic assessments. These new genetic tests will in many cases involve multigenic conditions, where the correlation of genotype and phenotype is significantly more complex than for Mendelian phenotypes. To produce genetic tests with the requisite accuracy will require new methods that can simultaneously track multiple DNA sequence variations at low cost and high speed, without compromising accuracy. The ideal tests will be relatively inexpensive to set up and run, while providing extremely high accuracy, and, most important, enabling sophisticated genetic analysis.

Genotypes

The association of specific genotypes with disease risk, prognosis, and diagnosis as well as selection of optimal therapy for disease are some of the benefits expected to flow from the human genome project. At present, the most common type of genetic study design for testing the association of genotypes with medically important phenotypes is a case control study where the frequencies of variant forms of a gene are measured in one or more phenotypically defined groups of cases and compared to the frequencies in controls. (Alternatively, phenotype frequencies in two or more genotypically defined groups are compared.) The majority of such published genetic association studies have focused on measuring the contribution of a single polymorphic site (usually a single nucleotide polymorphism, abbreviated SNP) to variation in a medically important phenotype or phenotypes. In these studies one polymorphism serves as a proxy for all variation in a gene (or even a cluster of adjacent genes).

Recent articles (e.g., Terwilliger and Weiss. Linkage disequilibrium mapping of complex disease: fantasy or reality? *Current Opinion in Biotechnology* 9: 578-594, 1998) have drawn attention to the low degree of reproducibility of most association studies using single polymorphic sites. Some of the reasons for the lack of reproducibility of many association studies are apparent. In particular, the extent of human DNA polymorphism—most genes contain 10 or more polymorphic sites, and many genes contain over 100 polymorphic sites—is such that a single polymorphic site can only rarely serve as a reliable proxy for all variation in a gene (which typically covers at least several thousand nucleotides and can extend over 1,000,000 nucleotides). Even in cases where one polymorphic site is responsible for significant biological variation, there is no reliable method for identifying such a site. Several recent studies have begun to outline the extent of human molecular genetic variation. For example, a comprehensive survey of genetic variation in the human lipoprotein lipase (LPL) gene (Nickerson, D. A., et al. *Nature Genetics* 19: 233-240, 1998; Clark, A. G., et al. *American Journal of Human Genetics* 63: 595-612, 1998) compared 71 human subjects and found 88 varying sites in a 9.7 kb region. On average any two versions of the gene differed at 17 sites. This and other studies show that sequence variation may be present at approximately 1 in 100 nucleotides when 50 to 100 unrelated subjects are compared. The implications of the this data are that, in order to create genetic diagnostic tests of sufficient specificity and selectivity to justify widespread medical use, more sophisticated methods are needed for measuring human genetic variation.

Beyond tests that measure the status of a single polymorphic site, the next level of sophistication in genetic testing is to genotype two or more polymorphic sites and keep track of the genotypes at each of the polymorphic sites when calculating the association between genotypes and phenotypes (e.g., using multiple regression methods). However, this approach, while an improvement on the single polymorphism method in terms of considering possible interactions between polymorphisms, is limited in power as the number of polymorphic sites increases. The reason is that the number of genetic subgroups that must be compared increases exponentially as the number of polymorphic sites increases. In a medical study of fixed size this has the effect of dramatically increasing the number of groups that must be compared, while reducing the size of each subgroup to a small number. The consequence of these effects is an unacceptable loss of statistical power. Consider, for example, a clinical study of a gene that contains 10 variable sites. If each site is biallelic then there are $2^{10}$ or 1024 possible combinations of polymorphic sites. If the study population is 500 subjects then it is likely that many genetically defined subgroups will contain only a small number of subjects. Thus, consideration of multiple polymorphisms (as can be determined from DNA sequence data, for example) does not get at the problem that the DNA sequence from a diploid subject does not sufficiently constrain the sequence of the subject's two chromosomes to be very useful for statistical analysis. Only direct determination of the DNA sequence on each chromosome (a haplotype) can constrain the number of genetic variables in each subject to two (allele 1 and allele 2), while accounting for all, or preferably at least a substantial subset of, the polymorphisms.

Haplotypes

A much more powerful measure of variation in a DNA segment than a genotype is a haplotype—that is, the set of polymorphisms that are found on a single chromosome.

In mammals, as in many other organisms, there are two copies (alleles) of each gene in every cell (except some genes which map to the sex chromosomes —X and Y in man). One allele is inherited from each parent. In general the two alleles in any organism are substantially similar in sequence, with polymorphic sites occurring less than every 100 nucleotides, and in some cases in less than every 1,000 nucleotides. Determination of the sequence of the non-variant nucleotide positions is not relevant to haplotyping. Thus, haplotyping comes down to determining the identity (e.g., the nucleotide sequence) of the polymorphisms on each of the two alleles at the polymorphic sites. For a subject that is heterozygous at two sites, where polymorphic site #1 is A or C, and polymorphic site #2 is G or T, we wish to know if the alleles are A-G and C-T, or if they are A-T and C-G. When DNA is extracted from a diploid organism the two alleles are mixed together in the same test tube at a 1:1 ratio. Thus, DNA analysis procedures performed on total genomic DNA, such as DNA sequencing or standard genotyping procedures which query the status of polymorphic sites one at a time, do not provide information required to determine haplotypes from DNA samples that are heterozygous at two or more sites.

Because of the evolutionary history of human populations, only a small fraction of all possible haplotypes (given a set of polymorphic sites at a locus) actually occur at appreciable frequency. For example, in a gene with 10 polymorphic sites only a small fraction—perhaps in the range of 1%—of the 1,024 possible genotypes is likely to exist at a frequency greater than 5% in a human population. Further, as described below, haplotypes can be clustered in groups of related sequences to facilitate genetic analysis. Thus determination of haplotypes is a simplifying step in performing a genetic association study (compared to the analysis of multiple polymorphisms), particularly when applied to DNA segments characterized by many polymorphic sites. There is also a potent biological rationale for sorting genes by haplotype, rather than by genotype at one polymorphic site: polymorphic sites on the same chromosome may interact in a specific way to determine gene function. For example, consider two sites of polymorphism in a gene, both of which encode amino acid changes. The two polymorphic residues may lie in close proximity in three dimensional space (i.e., in the folded structure of the encoded protein). If one of the polymorphic amino acids encoded at each of the two sites has a bulky side chain and the other has a small side chain then one can imagine a situation in which proteins that have either [bulky-small], [small-bulky] or [small-small] pairs of polymorphic residues are fully functional, but proteins with [bulky-bulky] residues at the two sites are impaired, due to a disruptive shape change caused by the interaction of the two bulky side groups. Now consider a subject whose genotype is heterozygous bulky/small at both polymorphic sites. The possible haplotype pairs in such a subject are [bulky-small]/[small-bulky], or [small-small]/[bulky-bulky]. The functional implications of these two haplotype pairs are quite different: active/active or active/inactive, respectively. A genotype test would simply reveal that the subject is doubly heterozygous. Only a haplotype test would reveal the biologically consequential structure of the variation. The interaction of polymorphic sites need not involve amino acid changes, of course, but could also involve virtually any combination of polymorphic sites.

The genetic analysis of complex traits can be made still more powerful by the use of schemes to cluster haplotypes into related groups based on parsimony, for example. Templeton and coworkers have demonstrated the power of cladograms for analysis of haplotype data. (Templeton et al. A Cladistic Analysis of Phenotypic Associations With Haplotypes Inferred From Restriction Endonuclease Mapping. I. Basic Theory and an Analysis of Alcohol Dehydrogenase Activity in Drosophila *Genetics* 117: 343-351, 1987. Templeton et al. A Cladistic Analysis of Phenotypic Associations With Haplotypes Inferred From Restriction Endonuclease Mapping and DNA Sequence Data. III. Cladogram Estimation *Genetics* 132: 619-633, 1992. Templeton and Sing. A Cladistic Analysis of Phenotypic Associations With Haplotypes Inferred From Restriction Endonuclease Mapping. IV. Nested Analyses with Cladogram Uncertainty and Recombination. *Genetics* 134: 659-669, 1993. Templeton et al. Recombinational And Mutational Hotspots Within The Human Lipoprotein Lipase Gene. *Am J Hum Genet*. 66: 69-83, 2000). These analyses describe a set of rules for clustering haplotypes into hierarchical groups based on their presumed evolutionary relatedness. This phylogenetic trees can be constructed using standard software packages for phylogenetic analysis such as PHYLIP or PAUP (Felsenstein, J. Phylogenies from molecular sequences: inference and reliability. *Annu Rev Genet*. 22:521-65, 1988; Retief, J. D. Phylogenetic analysis using PHYLIP. *Methods Mol. Biol*. 132: 243-58, 2000), and hierarchical haplotype clustering can be accomplished using the rules described by Templeton and co-workers. The methods described by Templeton and colleagues further provide for a nested analysis of variance between different haplotype groups at each level of clustering. The results of this analysis can lead to identification of polymorphic sites responsible for phenotypic variation, or at a minimum narrow the possible phenotypically important sites. Thus, methods for determination of haplotypes have great utility in studies designed to test association between genetic variation and variation in phenotypes of medical interest, such as disease risk and prognosis and response to therapy.

Currently available methods for the experimental determination of haplotypes, particularly methods for the determination of haplotypes over long distances (e.g., more than 5 kb), are based primarily on PCR amplification techniques. One haplotyping method currently in use is based on allele specific amplification using oligonucleotide primers that terminate at polymorphic sites (Newton et al. Amplification Refractory Mutation System For Prenatal Diagnosis And Carrier Assessment In Cystic Fibrosis. *Lancet*. December 23-30; 2 (8678-8679):1481-3, 1989; Newton et al., Analysis Of Any Point Mutation In DNA. The Amplification Refractory Mutation System (ARMS). *Nucleic Acids Res*. Vol. 17, 2503-2516, 1989). The ARMS system was subsequently further developed (Lo, Y. M. et al., Direct haplotype determination by double ARMS: specificity, sensitivity and genetic applications. *Nucleic Acids Research* July 11:19 (13):3561-7, 1991) and has since been used in a number of other studies. ARMS is the subject of U.S. Pat. Nos. 5,595,890 and 5,853,989. This method requires the amplification of long DNA segments. In addition, different primers and assay conditions for allele specific amplification must be established for each polymorphic site that is to be haplotyped. For example, consider a locus with five polymorphic sites. Subject A is heterozygous at sites 1, 2 and 4; subject B at sites 2 and 3, and subject C at sites 3 and 5. To haplotype A requires allele specific amplification conditions from sites 1 or 4; to haplotype B requires allele specific amplification conditions from sites 2 or 3, and to haplotype C requires allele specific amplification conditions from sites 3 or 5 (with the allele specific primer from site 3 on the opposite strand from that used to haplotype B).

A similar method for achieving allele specific amplification takes advantage of some thermostable polymerases' ability to proofread and remove a mismatch at the 3' end of a primer. Primers are designed with the 3' terminal base positioned opposite to the variant base in the template. In this case the 3' base of the primer is modified in a way that prevents it from being extended by the 5'-3' polymerase activity of a DNA polymerase. Upon hybridization of the end-blocked primer to the complementary template sequence, the 3' base is either matched or mismatched, depending on which alleles are present in the sample. If the 3' base of the primer is properly base paired the polymerase does not remove it from the primer and thus the blocked 3' end remains intact and the primer can not be extended. However, if there is a mismatch between the 3' end of the primer and the template, then the 3'-5' proofreading activity of the polymerase removes the blocked base and then the primer can be extended and amplification occurs.

Other allele specific PCR amplification methods include further methods in which the 3' terminal primer forms a match with one allele and a mismatch with the other allele (U.S. Pat. No. 5,639,611), PCR amplification and analysis of intron sequences (U.S. Pat. No. 5,612,179 and U.S. 5,789,568), or amplification and identification of polymorphic markers in a chromosomal region of DNA (U.S. Pat. No. 5,851,762). Further, methods for allele-specific reverse transcription and PCR amplification to detect mutations (U.S. Pat. No. 5,804,383), and a primer-specific and mispair extension assay to detect mutations or polymorphisms (PCT/CA99/00733) have been described. Several of these methods are directed to genotyping, not to haplotyping.

Other haplotyping methods that have been described are based on analysis of single sperm cells (Hubert et al. Sperm Typing Allows Accurate Measurement Of The Recombination Fraction Between D3S2 And D3S3 On The Short Arm Of Human Chromosome 3. *Genomics*. 1992 April;12(4):683-687); on limiting dilution of a DNA sample until only one template molecule is present in each test tube, on average (Ruano et al. Haplotype Of Multiple Polymorphisms Resolved By Enzymatic Amplification Of Single DNA Molecules. *Proc Natl Acad Sci USA* 1990 87(16):6296-6300); or on cloning DNA into various vectors and host microorganisms (U.S. Pat. No. 5,972,614).

The pattern of genetic variation in most species, including humans, is not random; as a result of human evolutionary history some sets of polymorphisms occur together on chromosomes, so that knowing the sequence of one polymorphic site may allow one to predict with some probability the sequence of certain other sites on the same chromosome. Once the relationships between a set of polymorphic sites have been worked out, a subset of all the polymorphic sites may be used in the development of a haplotyping test. The polymorphisms that comprise a haplotype may be of any type. Most polymorphisms (about 90% of all DNA polymorphisms) involve the substitution of one nucleotide for another, and are referred to as single nucleotide polymorphisms (SNPs). Another type of polymorphism involves a change in the length of a DNA segment as a result of an insertion or deletion of anywhere from one nucleotide to thousands of nucleotides. Insertion/deletion polymorphisms (also referred to as indels) account for most non-SNP polymorphisms. Common kinds of indels include variation in the length of homopolymeric sequences (e.g., AAAAAA vs. AAAAA), variation in the number of short tandem repeat sequences such as CA (e.g., 13 repeats of CA vs. 15 repeats), and variation in the number of more complex repeated sequences (sometimes referred to as VNTR polymorphisms, for variable number of tandem repeats), as well as any other type of inter-individual variation in the length of a given DNA segment. The repeat units may also vary in sequence.

ApoE

Apolipoproteins are found on the surface of various classes of lipoproteins—membrane bound particles which transport lipids (mainly cholesterol and triglycerides) throughout the body, including the brain. The function of apolipoproteins is to direct lipoproteins to specific cells that require lipids, for example cells that store fat. The apolipoproteins bind to specific receptors on the surface of lipid requiring cells, thereby directing the transport of lipids to the target cell. Apolipoprotein E (ApoE) is one of about a dozen apolipoproteins on blood lipoproteins, but it is the major apolipoprotein in the brain. One important function of ApoE in the brain is to transport lipids to cells that are performing membrane synthesis, which often occurs as a response to acute or chronic brain injury. After injury there is usually extensive synaptic remodeling as the surviving neurons receive new inputs from cells that were formerly wired to injured cells. This neuronal remodeling, or plasticity, is an important part of the physiologic response to the disease process and modulates the course of disease. Patients with low ApoE levels or impaired ApoE function have impaired neuronal plasticity.

Variation at the ApoE gene has been associated with risk of Alzheimer's disease (AD) and other neurodegenerative diseases, recovery or protection from organic or traumatic brain injury, and response to pharmacotherapy of AD. In Alzheimer's disease one injured brain region is the cholinergic pathways of the basal forebrain and elsewhere. The degree of neuronal remodeling in such areas may affect the response to cholinomimetic therapy. Thus impaired brain lipid transport alters patterns of neuronal remodeling in cholinergic (and other) pathways and thereby potentially affects response to acetylcholinesterase inhibitors and possibly other cholinergic agonists.

Variation at the ApoE gene has also been associated with coronary heart disease, dyslipidemia, and immunomodulatory functions. Specific apolipoprotein E genotypes have been associated with high cholesterol and LDL-cholesterol levels, and may serve as an independent predictors of coronary events. ApoE genotypes and haplotypes may identify individuals that are at risk of developing coronary artery disease (CAD) at an earlier age of onset, are more susceptible to developing lipidemia following environmental exposure (to infection, drug treatment or diet), of developing lesions at an accelerated rate, or of developing more severe signs of disease pathology or symptoms. In clinical studies in the cardiovascular area, apoE haplotyping may be used to identify patients at risk for CAD and thus differentiate candidates for dietary, pharmacologic or surgical intervention. ApoE haplotyping may identify individuals at risk for earlier coronary artery bypass graft (CABG) intervention. ApoE may interact synergistically with additional genes that contribute significantly to developing pathology in CAD, including other lipoproteins containing apoB, apoC, apoj, and other genes involved in lipid metabolism, such as OATP2, CETP, LPL, FABP2, ABC1, CYP7 and PON. Since CAD can develop from underlying and chronic conditions such as hypertension, apoE may serve as a gene that contributes to diagnosis or treatment guidelines along in combination with other genetic markers, for example, apoE and PAI-1, AGT and AT1-receptor.

ApoE also modulates the accumulation of cholesterol in macrophages and their transition to foamy cells as well as formation of the fatty streak pathology of atherosclerosis. The role of apoE in modulating the immune response and inflammatory cytokine network may be a therapeutic strategy to slow progression or reverse pathological lesions caused by foamy cell activation. ApoE genotypes may differentiate interactions on specific cells, for example, endothelial cell or glial cell subtypes. The overlapping role of apoE in macrophage biology and nerve repair suggests that apoE may be a marker for increased risk of developing peripheral neuropathies, such as diabetic peripheral neuropathy or retinopathy. Furthermore, apoE may be an independent risk factor for CAD, independent of cholesterol levels. Apo E genotype may also be associated with peripheral arterial disease (PAD). This association may be expanded by the presence of co-morbid conditions, for example diabetes, which is also associated with dyslipidemia and a predisposition to macrovascular disease. In addition, apoE genotypes may further refine diagnosis of cerebral pathology and cerebrovascular lesions in cerebral amyloid angiopathy, neurodegenerative diseases such as multiple sclerosis, and epilepsy and reparative potential following brain injury in trauma or ischemic stroke events.

The existence of three major variant forms of ApoE (referred to as ε2, ε3 and ε4) has been known for over two decades. The well established three variant classification of ApoE is based on two polymorphisms in the coding sequence of the ApoE gene, both of which result in cysteine vs. arginine amino acid polymorphisms in APOE protein at positions 112 and 158 of the mature protein. DNA based diagnostic tests for ApoE have been available since the 1980s.

The ApoE ε4 allele has been consistently correlated with elevated total cholesterol, elevated LDL cholesterol, low levels of ApoE protein and increased risk of coronary heart disease (CHD). The CHD risk attributable to ε4 is apparent even after correcting for cholesterol levels and other CHD risk factors (smoking, age, obesity, diabetes, blood pressure). Thus, consideration of a subject's ApoE genotype is reasonable for any disease category in which there is hyperlipidemia, hypercholesterolemia, hypertriglyceridemia or any disorder leading to inordinate lipid metabolism. Furthermore, studies in normolipidemic populations have shown an association with apoE variants and increased risk for coronary artery disease. The ε4 allele is also a risk factor for late onset Alzheimer's disease and Multiple Sclerosis (MS), apparently due to effects on the rate of disease progression. Presence of the ApoE ε4 allele also portends a poor prognosis for patients with a variety of other neurological diseases (stroke, brain trauma, amyotrophic lateral sclerosis and other diseases) and psychiatric diseases (e.g., schizophrenia), compared to patients without an ε4 allele.

In addition to effects on disease risk and disease prognosis there are reports that ApoE genotype predicts response of AD patients to medications. In particular, the response of AD patients to acetylcholinesterase inhibitors has been studied by several groups. ApoE genotype may also be useful for predicting patient response to other medical treatments, particularly treatments for neurological and cardiovascular diseases. The ApoE ε4 variant is a major risk for Alzheimer's disease, perhaps because it is expressed in brain at lower levels than the ε2 or ε3 variants, and thus impairs neuronal remodeling. The ε2 allele is mildly protective for AD. Several clinical trials for Alzheimer's disease drugs, including both acetylcholinesterase inhibitors and vasopressinergic agonists, have shown significant interactions with ApoE genotype and sex. The ε4 allele has been associated with lack of response to acetylcholinesterases.

The relative risk of AD conferred by the ε4 allele varies almost ten fold between different populations. The highest relative risk has consistently been reported in the Japanese, who have a 30-fold relative risk in ε4/ε4 homozygotes relative to ε3/ε3 homozygotes. African and Hispanic ε4/ε4 homozygotes have relative risks of only ~3-4 fold. On the other hand, in the presence of an ε4 allele the cumulative risk of AD to age 90 is similar in all three groups (Japanese, Hispanics and Africans). This suggests that other factors contribute significantly to the causation of AD in the non-Japanese populations. It may be that these non-ε4 AD patients are the best responders to acetylcholinesterases. If true, this may account for a lack of response in Japanese, where the fraction of patients with ApoE ε4 mediated AD appears to be the highest in the world.

It is well established that the three common variants at the ApoE locus are correlated with risk of AD in various populations. Recent studies have also shown that ApoE genotype correlates with response of AD patients to two classes of drugs. Specifically, Poirier et al. demonstrated an interaction of apoE genotype, sex and response of AD patients to the cholinomimetic drug tacrine, while Richard et al. showed an interaction between apoE genotype and response to an investigational noradrenergic/vasopressinergic agent, S 12024. In both studies the analysis was restricted to analysis of the two amino acid variances that determine the three common ApoE variants. Other variances have been described at the ApoE locus, including promoter variances, that may plausibly affect ApoE function. Also, studies have been published (but often not confirmed) associating polymorphisms in other genes with risk of late onset AD; there have been no investigations of the effect of variation at these loci on response to cholinomimetic drugs.

There are two FDA approved drugs for therapy of Alzheimer's Disease (tacrine, donezepil), and at least a dozen additional agents in late stage clinical trials or under FDA review. The FDA approved drugs work by inhibiting acetylcholinesterase, thereby boosting brain acetylcholine levels. This symptomatic therapy provides modest benefit to less than half of treated patients but does not affect disease progression. Available evidence suggests the products in the pipeline, which likewise partially reverse symptoms without affecting the underlying disease process, will also be of modest benefit to some patients. Despite their limited efficacy, these drugs will likely be expensive. They may also be associated with serious adverse effects in some patients. As a result, the cost of providing a modest benefit to a limited number of AD patients will be high.

As more AD therapeutics becomes available, physicians will face the difficult task of differentiating between multiple products. These products may produce similar response rates in a population, however, the crucial decision clinicians face is selecting the appropriate therapeutic for each individual AD patient at the time of diagnosis. This is particularly the case if there are several therapeutic choices, only one of which may be optimal for a particular patient. This selection is critical because failure to provide optimal treatment at the time of diagnosis may result in a diminished level of function during a period when the greatest benefit could be achieved. Inadequate treatment may continue for some time because measures of clinical response in AD are notoriously imprecise; six months or longer may pass before it is clear whether a drug is working to a significant degree. During this time, the disease continues to progress which may limit the efficacy of a second drug or therapeutic regimen. A test that could predict likely responders to one or more AD drugs would thus be of great value in optimizing patient care and reducing the cost of ineffective treatment.

Data has been published suggesting that ApoE genotype may be such a test. Specifically, Farlow, Poirier and colleagues have shown that female patients with the ApoE ε4 allele do not respond to tacrine, while female patients with the ε2 and ε3 alleles have significant response; males do not respond significantly regardless of genotype. Conversely, Richard et al. have demonstrated that patients with the ε4 allele, but not the ε2 and ε3 alleles, have a statistically significant response to S12024, an enhancer of vasopressinergic/noradrenergic signaling. Thus the two drugs—one an acetylcholinesterase inhibitor and the other a vasopressinergic/noradrenergic agonist—are useful in different groups of patients, delimited by ApoE genotype.

ApoE gene activity or allele variants are known to alter the course of several other neurological diseases. In multiple sclerosis, the relative concentration of ApoE is reduced in cerebrospinal fluid as well as intrathecal synthesis. Other neurological disorders such as temporal lobe epilepsy and cerebral trauma, the presence of the ApoE ε4 variant is associated with increased vulnerability to disease progression, whereas presence of ApoE ε3 appears to provide moderate neuroprotection. Wilson's disease, a disorder of the biliary copper excretion that may result in severe neurological symptoms and advanced liver, was the subject of a study that examined the ApoE genotype as well as the H1069Q mutation (the most common mutation identified in Wilson's disease). The presence of ApoE ε3/ε3 attenuates the clinical manifestations in Wilson's disease by a proposed mechanism of antioxidant and membrane stabilizing properties of ApoE ε3 protein.

In patients undergoing routine ambulatory peritoneal dialysis (CAPD), it has been shown that these patients develop various abnormalities of lipid metabolism and are prone to develop accelerated atherosclerosis. It has been shown that the ApoE ε3/ε3 genotype appears to the most common genotype in CAPD and that the ApoE ε2/ε3 genotype appears to be associated with high cholesterol and triglyceride levels.

Recent data has suggested that there is an association between the ApoE epsilon variant and reduced risk of age related macular degeneration.

Glycogen storage disease type Ia patients have elevated serum triglyceride concentrations and VLDL as well as LDL fractions but only moderately elevated phospholipid and cholesterol levels. In a recent study, the ε3 and ε4 variants were predominant in patients with glycogen storage disease type Ia and had a high triglyceride binding capacity and thus are thought to increase the triglyceride clearance.

Further, there has been an association of ApoE ε4/ε3 phenotype in persons with non-insulin dependent diabetes mellitus and associated metabolic syndrome X.

However, despite the many genetic associations described above, diagnostic tests for determining ApoE genotype are not widely used, nor is ApoE genotyping widely used for prognostic or pharmacogenetic testing. To the contrary, a large number of studies address the limitations of ApoE as a diagnostic marker, particularly in the setting of AD diagnosis. The conclusion of most of these studies is that testing for the ε2, ε3 and ε4 variants does not provide a sufficiently sensitive or selective test to justify use outside of clinical research. Concern has also been expressed that, because in many settings ApoE testing results do not affect medical decision making, there is little reason to obtain information on ApoE genotype.

Recent studies of the ApoE gene in a number of laboratories have led to identification of several new DNA polymorphisms. The biological effects and medical import of these new polymorphisms has not been established, although some studies suggest that polymorphisms in the promoter affect ApoE transcription rates. Most published work has been limited to the analysis of individual polymorphisms or sets of only a few polymorphisms and their effect on one or two biological or clinical endpoints.

The ability to predict response to therapy for progressive debilitating diseases like AD and others discussed above would be of enormous clinical importance as there is generally only one opportunity to treat patients with these diseases at their maximal level of functioning; any delay in selecting optimal therapy represents a lost opportunity to preserve the maximal possible level of function. With multiple drugs in development for AD as well the other disease indications, it will become increasingly important to predict the best drug for each patient.

SUMMARY OF THE INVENTION

The inventors have developed methods for determining haplotypes (i.e., the organization of DNA sequence polymorphisms on individual chromosomes) and genotypes. Genotype or haplotype information, or a combination of the two, can be used, e.g., to make diagnostic tests useful for disease risk assessment, for prognostic prediction of the course or outcome of a disease, to diagnose a disease or condition, or to select an optimal therapy for a disease or condition.

In a first aspect, the invention features haplotyping methods based on allele-specific enrichment. Such methods involve three basic steps: (i) optionally genotyping a sample of genomic DNA (or RNA or cDNA) of a subject to identify two or more polymorphisms in a selected gene; (ii) enriching for one of two alleles of the selected gene by a method not requiring amplification of DNA, e.g., enriching for one allele to a ratio of at least 1.5:1 based on a starting ratio of 1:1; and (iii) determining the genotype of the two or more polymorphisms in the enriched allele.

The first step (i) of the procedure described above is mostly dispensable; it is possible to proceed directly to DNA strand enrichment knowing the location of only one polymorphic site (which will provide the basis for designing an enrichment procedure for one allele). The second step (ii) entails obtaining, from a sample of genomic DNA (or RNA or cDNA) containing two alleles of a gene or other DNA segment of interest, a population of DNA molecules enriched for only one allele. This can be accomplished using any of a variety of novel methods described herein below. The third step (iii) is a genotyping procedure performed on the enriched DNA. Virtually any genotyping procedure will work in this step. However, because allele enrichment may not be complete, quantitative or semi-quantitative genotyping methods are preferred. Good quantitative genotyping methods will permit accurate haplotypes to be determined even when the degree of allele enrichment from step (ii) is only 2:1, or even less. On the other hand, if substantial allele enrichment is achieved in step two then the genotyping procedure of step three may consist of performing DNA sequencing reactions on the enriched material. For example, chain terminating DNA sequencing reactions could be used to determine the haplotype of the enriched DNA.

In a preferred embodiment, the nucleotides present on the non-enriched allele can be deduced by "subtracting" the haplotype of the enriched allele from the genotype of the starting DNA, determined in step (i). For example, for a DNA segment that is heterozygous at three sites, where site 1 has A or T, site 2 has C or T and site 3 has A or G, if a first haplotype is: 1=A, 2=T, 3=A, then the other haplotype must be: 1=T, 2=C, 3=G.

In another preferred embodiment, haplotype analysis entails the independent determination of both haplotypes present in a sample—by enriching and subsequently genotyping each of the two alleles present in a sample in separate experiments; they should collectively account for the genotype determined from the DNA sample in step one. This practice increases the accuracy of the haplotyping methods described herein.

In a preferred embodiment, two or more polymorphic sites are genotyped in step (iii), and most preferably all polymorphic sites in the DNA segment of interest are genotyped.

In a preferred embodiment, information from the first genotyping step (i) can be used to select an optimal heterozygous site or sites for allele enrichment.

Several methods for enriching for one of two alleles (step ii) are provided herein below, e.g., methods for allele enrichment by allele "capture" or physical separation of one allele from the other (see section II.A.1 of detailed description); allele enrichment by allele specific cross-linking combined with exonuclease digestion (see section II.A.2 of detailed description); allele enrichment by endonuclease restriction followed by either allele specific size separation or exonuclease digestion (see section II.A.3 of detailed description); allele enrichment by endonuclease restriction followed by allele specific amplification (see section II.A.4 of detailed description); or allele enrichment by allele specific amplification using hairpin loop primers (see section II.A.5 of detailed description).

In a preferred embodiment, the DNA to be haplotyped is genomic DNA. In some cases total cellular RNA (or cDNA) may be the starting material. RNA or cDNA-based methods are predicated on the assumption that both alleles of a gene are transcribed equally. This assumption does not always hold, therefore it should be tested experimentally in any case where cDNA is being considered as the starting material for a genotyping or haplotyping procedure.

Thus, in a first aspect, the invention features a method for determining the haplotype of at least one allele of a selected gene at two or more polymorphic sites, the method comprising: a) providing a sample of DNA from a subject having two alleles of the selected gene; b) enriching for a first allele of the selected gene by a method not requiring amplification of DNA so that the ratio of the first allele to the second allele is increased to at least 1.5 to 1; c) determining the genotype of the two or more polymorphic sites in the first allele, thereby determining the haplotype of at least one allele of the selected gene at the two or more polymorphic sites.

In another embodiment, the method further comprises genotyping the DNA provided in step (a) to identify two or more polymorphic sites in the selected gene.

In another embodiment, the method further comprises determining the haplotype of a second allele of the gene at the two or more polymorphic sites by comparing the genotype of the DNA provided in step (a) to the genotype of the two or more polymorphic sites in the first allele determined in step (c), thereby determining haplotype of a second allele of the selected gene at the two or more polymorphic sites.

In yet another embodiment, the method further comprises: d) providing a second sample of DNA from the subject having two alleles of the selected gene; e) enriching for a second allele of the selected gene by a method not requiring amplification of the DNA so that the ratio of the second allele to the first allele is increased to at least 1.5 to 1; and f) determining the genotype of the two or more polymorphic sites of the second allele, thereby determining the haplotype of two alleles of the selected gene at the two or more polymorphic sites.

In various embodiments, the sample of DNA is obtained by amplification of a DNA molecule comprising two or more polymorphic sites of the selected gene, the sample of DNA is cDNA, the method 1 further comprises fragmenting the DNA in the sample prior to the enriching step, and step of fragmenting the DNA comprises restriction endonuclease digestion. In other embodiments, the method further determining the genotype of the first allele at a third polymorphic site or determining the genotype of the second allele at a third polymorphic site. In still other embodiments, the enriching step increases the ratio of the first allele to the second allele to at least about 2:1, at least about 5:1, or at least about 10:1.

The invention features a variety of methods for enriching the ratio of one allele to the other allele from 1:1 to at least 1.5:1 or greater. Some methods depend on selective amplification of one allele relative to the other allele. Other methods depend on the selective reduction of the amount of one allele. Still other methods depend on the selective isolation of one allele. The methods generally entail first identifying at least one polymorphic site in the gene of interest. This can be accomplished by genotyping a DNA sample containing both alleles (i.e., the paternal allele and the maternal allele). This genotyping step can reveal the presence of a polymorphic site which may or may not have been previously known. The genotyping step will also reveal if the subject is heterozygous at the polymophic site and the sequence of the two different alleles at the polymorphic site. This information can then be used to select an enrichment strategy that will allow the ratio of one allele to the other allele to be increased from 1:1 to at least about 1.5:1. Because the enrichment step depends on the presence of a particular genotype at a polymorphic site, the enrichment step effectively provides the genotype of the selected allele at a first polymorphic site. The enriched sample can then be used to analyze the selected allele to at a second polymorphic site as well as at any number of additional polymorphic sites, thus determining the haplotype of the selected allele at two or more polymorphic sites.

One approach to allele specific enrichment employed in the methods of the invention entails preferential capture of a selected allele using a DNA-binding molecule. Thus, in one aspect, the invention features a method for determining a haplotype of at least one allele of a selected gene at two or more polymorphic sites, the method comprising: a) providing a sample of DNA from a subject having two alleles of the selected gene; b) contacting the DNA with a DNA-binding molecule that binds to a first of the two or more alleles, the first allele having a selected genotype at a first polymorphic site, but does not substantially bind to an allele not having the selected genotype at the first polymorphic site; c) forming a complex between the DNA-binding molecule and the first allele; d) at least partially purifying at least a fraction of the complexes so formed from uncomplexed DNA; e) analyzing the genotype of the first allele at a second polymorphic site, thereby determining a haplotype of at least one allele of the selected gene at two or more polymorphic sites.

In one embodiment, the method further comprises: genotyping the sample of DNA provided in step (a) to identify two or more polymorphic sites in the gene and comparing the genotype of the selected gene at the two or more polymorphic sites to the haplotype of the first allele at the two or more polymorphic sites, thereby determining haplotype of the second allele of the selected gene at the two or more polymorphic sites.

In another embodiment, the method further comprises: f) providing a second sample of DNA from the subject; g) contacting the DNA with a second DNA-binding molecule that binds to the second of the two alleles, the second allele having a selected genotype at a first polymorphic site, but does not substantially bind to an allele not having the selected genotype at the first polymorphic site; h) forming a complex between the second DNA-binding molecule and the second allele; i) at least partially purifying at least a fraction of the complexes so formed from uncomplexed DNA; j) analyzing the genotype of the second allele at a second polymorphic sites, thereby determining a haplotype of at the second allele of the selected gene at two or more polymorphic sites.

In another embodiment, the method further comprises: f) providing a second sample of DNA from the subject; g) contacting the DNA with a second DNA-binding molecule that binds to the second of the two alleles, the second allele having a selected genotype at the second polymorphic site, but does not substantially bind to an allele not having the selected genotype at the second polymorphic site; h) forming a complex between the second DNA-binding molecule and the second allele; i) at least partially purifying at least a fraction of the complexes so formed from uncomplexed DNA; j) analyzing the genotype of the second allele at a first polymorphic site, thereby determining a haplotype of at the second allele of the selected gene at two or more polymorphic sites.

In other embodiments, the method further comprises determining the genotype of the first allele at a third polymorphic site and determining the genotype of the second allele at a third polymorphic site.

In various embodiments: the DNA-binding molecule binds to double stranded DNA; the DNA-binding molecule binds to single stranded DNA; the DNA-binding molecule is an oligonucleotide or a peptide nucleic acid; the DNA-binding molecule is a protein; the protein is a zinc finger DNA-binding protein; the DNA-binding molecule is labeled; the DNA-binding molecule is biotinylated; the DNA-binding molecule is directly or indirectly (e.g., through another molecule) coupled to a solid support; the protein is a transcription factor; the protein is a disabled restriction endonuclease substantially lacking DNA cleavage activity or a restriction endonuclease used in the absence of divalent cations; step (d) comprises contacting the complex with an antibody against the DNA-binding molecule; the antibody is coupled to a solid support; the selected gene is ApoE; the method further comprises fragmenting the DNA in the sample prior to the contacting step; the step of fragmenting the DNA comprises restriction endonuclease digestion; the DNA-binding molecule comprises a ligand that interacts with a capture reagent; step (d) comprises attaching to the complexes a ligand that interacts with a capture reagent; the ligand is selected from the group consisting of a polyhistidine tag, antibody, nickel, avidin, streptavidin, biotin, magnetic particles, and an aptamer; the oligonucleotide or peptide nucleic acid binds to the first allele through Watson-Crick base-pairing; the oligonucleotide or peptide nucleic acid binds to the first allele through D-loop formation; the oligonucleotide or peptide nucleic acid binds to the first allele through triple helix formation; the oligonucleotide or peptide nucleic acid binds to the first allele through Hoogstein base-pairing; the oligonucleotide or peptide nucleic acid binds to the first allele through reverse Hoogstein base-pairing; and the DNA-binding molecule is a sequence specific polyamide.

Another approach to enrichment entails binding an agent to one allele (based on the presence a selected genotype at a polymorphic site, which agents protects the allele (or at least one of the strands of the allele) from exonuclease digestion. The agent, e.g., a cross-linked oligonucleotide, protects not only the polymorphic to which it binds, but also at least one additional polymorphic site that can be genotyped to determine the haplotype of the selected allele at two or more polymorphic sites.

Thus, the invention features a method for determining a haplotype of at least one allele of a selected gene at two or more polymorphic sites, the method comprising: a) providing a sample of DNA from a subject having two alleles of the selected gene; b) contacting the DNA with an agent that binds to a first allele, the first allele having a selected genotype at a first polymorphic site, the agent not substantially binding to an allele not having the selected genotype at the first polymorphic site; c) cross-linking the agent to the first allele to form a mixture comprising cross-liked complexes; d) contacting the mixture comprising the cross-linked complexes with an exonuclease that is incapable of degrading cross-linked complexes at the first polymorphic site of the first allele and at a second polymorphic site of the first allele; and e) determining the genotype of the first allele at a second polymorphic site, thereby determining a haplotype of an allele of the selected gene at two or more polymorphic sites.

In various embodiments, the method further comprises determining the genotype of the first allele at a third polymorphic site; the agent is an oligonucleotide; the oligonucleotide comprises a phosphorothioate group; the agent comprises contacting the agent with a compound selected from the group of: binuclear platinum (PtII), trans-platinum (II), or psoralen; the agent is selected from the group consisting of: a peptide nucleic acid, a triple helix, or a sequence specific polyamide; the exonuclease is selected from the group consisting of Type I snake venom phosphodiesterase or T4 DNA polymerase; and the selected gene is ApoE.

In yet another approach to allele selective enrichment, one allele is protected from exonuclease digestion by virtue of the presence of modified DNA fragments ends that block exonuclease digestion. Thus, in one embodiment, the invention features a method for determining a haplotype of at least one allele of a selected gene at two or more polymorphic sites, the method comprising: a) providing a sample of DNA from a subject having two alleles of the selected gene; b) fragmenting the DNA to form DNA fragments comprising two or more polymorphic sites of the selected gene; c) modifying the ends of the fragments to form modified fragments that are resistant to exonuclease digestion; d) cleaving the modified fragments with a restriction endonuclease that cleaves a first allele having a selected genotype at a first polymorphic site and does not cleave a second allele not having the selected genotype at the first polymorphic sites; e) digesting the cleavage products of step (d) with an exonuclease that digests DNA having at least one unmodified end to substantially eliminate the first allele; and f) genotyping a second polymorphic site present in the second allele, thereby determining a haplotype of an allele of the selected gene at two or more polymorphic sites.

In various embodiments, the method further comprises genotyping a third polymorphic site in the second allele; the exonuclease is a single stranded exonuclease; the exonuclease is a double stranded exonuclease; the single stranded exonuclease is selected from the group 1 consisting of E. coli exoIII, lamda phage exonuclease, T7 exonuclease, the exonuclease activity of T4 polymerase, and the exonuclease activity of E. coli polymerase I; the double stranded exonuclease is Bal31; and the method further comprises eliminating residual single stranded DNA with a single stranded nuclease.

Still another approach to allele specific enrichment entails allele specific restriction endonuclease digestion followed by amplification using primers that are arranged such that only the allele not cleaved by the restriction endonuclease is cleaved. Thus, the invention features a method for determining a haplotype of at least one allele of a selected gene at two or more polymorphic sites, the method comprising: a) providing a sample of DNA from a subject having two alleles of the selected gene; b) cleaving the DNA with a natural or synthetic restriction endonuclease that cleaves a first allele having a selected genotype at a first polymorphic site, but not a second allele not having the selected genotype at the first polymorphic site; c) performing an amplification procedure on the endonuclease restricted sample, wherein an amplification product is produced only from the second allele; and d)

determining the genotype of a second polymorphic site in the second allele, thereby determining the haplotype of at least one allele of a selected gene at two or more polymorphic sites.

In various embodiments, the method further comprises determining the genotype of the second allele at a third polymorphic site; the method further comprises isolating the amplification product by a sizing procedure; the gene is ApoE; and the restriction endonuclease is Not I.

Still another approach to allele specific enrichment entails allele specific restriction endonuclease digestion followed by size separation. Thus, the invention features a method for determining a haplotype of at least one allele of a selected gene at two or more polymorphic sites, the method comprising: a) providing a sample of DNA from a subject having two alleles of the selected gene; b) cleaving the DNA with a natural or synthetic restriction endonuclease that cleaves a first allele having a selected genotype at a first polymorphic site, but not a second allele not having the selected genotype at the first polymorphic site; c) at least partially separating the first allele from the second allele by a size selection method; d) determining the genotype of a second polymorphic site in the first allele, thereby determining the haplotype of at least one allele of a selected gene at two or more polymorphic sites. In various preferred embodiments, the method further comprises determining the genotype of the first allele at a third polymorphic site.

In a second aspect, the invention features haplotyping methods based on visualizing DNA molecules (e.g., single stranded DNA molecules) optically, e.g., by optical mapping methods or by atomic force microscopy.

In preferred embodiments, a method of distinguishing one allele vs. another is coupled with optimal mapping technology to determine haplotypes. Examples of such methods include: (i) restriction endonuclease digestion using enzymes that cleave at polymorphic sites on the DNA segment to be haplotyped; (ii) addition of oligonucleotides or PNAs corresponding to polymorphic sites to form allele specific D-loops; (iii) addition of sequence specific DNA binding proteins that recognize sequences that are polymorphic, and that consequently bind only to one set of alleles.

Accordingly, the invention features a method for determining the haplotype of at least one allele of a selected gene at two or more polymorphic sites, the method comprising: (a) immobilizing DNA fragments comprising the two or more polymorphic sites of the selected gene on planar surface; (b) contacting the immobilized DNA fragments with an agent that selectively binds to an allele having a selected genotype at a first polymorphic site under conditions which permit selective binding of the agent; (c) contacting the immobilized DNA fragments with a second agent that selectively binds to an allele having a selected genotype at a second polymorphic site under conditions that permit selective binding of the second agent; and (iv) optical mapping the position of the first and second agents on at least one DNA fragment, thereby determining the haplotype of at least one allele of a selected gene at two or more polymorphic sites.

In various embodiments, either or both of the first agent and the second agent are selected from the group consisting of oligonucleotides and peptide nucleic acids; selective binding of the first agent results in the formation of a D loop and selective binding of the second agent results in the formation of a D loop; the method further comprises contacting the immobilized DNA fragments with RecA protein; the first and second agents are proteins; and the proteins are selected from the group consisting of transcription factors, disabled restriction endonucleases substantially lacking DNA cleavage activity, and zinc finger DNA-binding proteins, and restriction endonucleases used in absence of divalent cations.

In a third aspect, the invention features methods for genotyping, i.e., determining the sequence of a subject's DNA sample at a polymorphic site. The methods include allele specific mass spectrometric analysis of small DNA fragment(s) containing a polymorphic base. The fragments are preferably less than 100 bases, more preferably less than 50 bases, most preferably less than 25 bases. The genotyping methods described herein are robust, highly accurate, and inexpensive to set up and perform. The genotyping methods described herein may be used in the genotyping steps of the haplotyping methods described herein, or they may be used for genotyping alone, i.e., not associated with a haplotyping test.

Thus, the invention features a method for determining the genotype of a polymorphic site in a target nucleic acid sequence, the method comprising: (a) providing a DNA sample comprising the target nucleic acid sequence; (b) amplifying the target nucleic acid sequences to generate an amplification product, wherein the amplification results in the insertion into the amplification product of a sequence which allows the amplification product to be cleaved by a first restriction enzyme and a second restriction enzyme, the first restriction enzyme and the second restriction enzyme having cleavage sites flanking the polymorphic site; (c) cleaving the amplification product; and (d) determining the genotype of the polymorphic site.

In a preferred embodiment, the method involves PCR amplification using primers flanking a polymorphic site. One of the primers is designed so that it introduces two restriction endonuclease recognition sites into the amplified product during the amplification process. The two restriction endonuclease restriction sites are arranged so that cleavage occurs on both sides of the polymorphic site. Preferably the two restriction sites are created by inserting a sequence of 15 or fewer nucleotides into the first primer. This short inserted sequence in general does not base pair to the template strand, but rather loops out when the primer is bound to template. When the complementary strand is copied by polymerase the inserted sequence is incorporated into the amplicon. Incubation of the resulting amplification product with the appropriate restriction endonucleases results in the excision of a small (preferably less than 100 bases, more preferably less than 50 bases, most preferably less than 20 bases) polynucleotide fragment that contains the polymorphic nucleotide. The small size of the excised fragment allows it to be easily and robustly analyzed by mass spectrometry to determine the identity of the base at the polymorphic site.

The methods described herein are characterized by technical ease, high sample throughput, flexibility (e.g., in the length of DNA that can be analyzed), and compatibility with automation. The methods provide the basis for sophisticated analyses of the contribution of variation at candidate genes (e.g., ApoE) to intersubject variation in medical or other phenotypes of interest. These methods are applicable to patients with a disease or disorder as well as to apparently normal subjects in whom a predisposition to a disease or disorder may be discovered or quantified as a result of a haplotyping test described herein. Application of the haplotyping methods of this invention will provide for improved medical care by increasing the accuracy of genetic diagnostic tests of all kinds.

The determination of haplotypes is particularly useful for genetic analysis when the DNA segment being haplotyped consists of polymorphisms that are in some degree of linkage disequilibrium with each other—that is, they do not assort randomly in the population being studied. In general, linkage disequilibrium breaks down with increasing physical distance in the genome, however the distance over which linkage disequilibrium is maintained varies widely in different areas of the genome. Thus the length of DNA over which an ideal haplotyping procedure should operate will differ from one gene to another. In general, however, it is desirable to determine haplotypes over distances of at least 2 kb; more preferably at least 5 kb; still more preferably at least 10 kb and most preferably at least 20 kb. Procedures for determining extended haplotypes (i.e., haplotypes >10 kb in length) are emphasized in this application, however, in many cases haplotypes spanning shorter distances may be completely acceptable and may capture all or virtually all of the biologically relevant variation in a larger region of DNA.

In genes that consist of two or more DNA segments that are not in linkage disequilibrium, due to the intervening presence of DNA regions subject to a high frequency of recombination, the preferred approach to haplotype determination is to separately determine haplotypes in each of the two or more constituent regions. The subsequent genetic analysis of genotype—phenotype relationships entails the consideration of all the haplotype groups that exist among the two or more haplotyped segments. Consider, for example, a 15 kb DNA segment in which there is a high frequency of recombination in a central 3 kb segment, but substantial linkage disequilibrium in two flanking 6 kb segments, A and B. The haplotype analysis strategy might consist of determining all the common haplotypes (or haplotype groups—see below) in each of the two 6 kb segments, then considering all the possible combinations of A and B haplotypes. For example if there are three haplotypes or haplotype groups at A (a, a' and a") and four at B (b, b', b", b"') then all the combinations (a:b, a:b', a:b", a:b"', a':b, a':b', a':b", a':b"', etc.) that occur at, say, a frequency of 5% or greater would be analyzed with respect to relevant phenotypes.

Haplotypes are often not directly inferable from genotypes (except in the special case of families, where haplotypes can often be inferred by analysis of pedigrees), therefore specialized methods are required for determining haplotypes from samples derived from unrelated subjects.

Definitions

As used herein, a "genotype" refers to the genetic constitution of an organism. More specifically, "genotyping" as used herein refers to the analysis of DNA in a sample obtained from a subject to determine the DNA sequence in a selected region of the genome, e.g., within the coding or non-coding regions of a gene that influences a disease or drug response. The selected region of the genome may include part of a gene, an entire gene, several genes, or a region devoid of genes (but which may contain DNA sequence that regulates the function of nearby genes). The term "genotyping" can refer to the determination of a DNA sequence at one or more polymorphic sites and can include determining the DNA sequence of a single allele or of a mixture of two alleles. In the case of a mixture of the two alleles having a different nucleotide at the polymorphic site of interest, the genotype will reveal the two possible nucleotides (or nucleotide sequences) present at the polymorphic site.

As used herein, "haplotype" refers to the sequence (e.g., the determination of the identity of one or more nucleotides) of a segment of DNA from a single chromosome (allele). The DNA segment may include part of a gene, an entire gene, several genes, or a region devoid of genes (but which may contain DNA sequence that regulates the function of nearby genes). The term "haplotype", then, refers to a cis arrangement of two or more polymorphic nucleotides (or sequences) on a particular chromosome, e.g., in a particular gene or in two or more genes on the same chromosome. The haplotype preserves information about the phase of the polymorphic nucleotides. Thus, haplotyping provides information concerning which set of variances were inherited from one parent (and are therefore on one chromosome), and which from the other. A genotyping test does not provide information about phase unless it is performed on a single allele. For example, a subject heterozygous at nucleotide 25 of a gene (both A and C are present) and also at nucleotide 100 of the same gene (both G and T are present) could have haplotypes 25A-100G and 25C-100T, or alternatively 25A-100T and 25C-100G. Only a haplotyping test can discriminate these two cases definitively. Haplotypes are generally inherited as units, except in the event of a recombination during meiosis that occurs within the DNA segment spanned by the haplotype, a rare occurrence for any given sequence in each generation. Usually the sample to be haplotyped consists initially of two alleles of the chromosome segment to be haplotyped from a diploid subject. Haplotyping can consist of determining the nucleotide identity or nucleotide sequence of at least two polymorphic sites on a chromosome. Preferably, a haplotype can consist of determining the nucleotide identity or nucleotide sequence of at least 3, 4, 5, 6, 7, 10, 15, 20, 25, 30, 40, 50, 100, or more polymorphic sites in a chromosome segment, e.g., a chromosomal segment of at least 2, 10, 50, 100, 200, 500, 1000, 2000, 3000, 4000, 5000, 10000, 20000 nucleotides or more.

An "allele", as used herein, is one of the two copies of a gene that occupy the same chromosomal locus on a pair of homologous chromosomes, e.g., in a diploid organism. The two alleles may be the same or they may be variant or alternative forms of a gene, i.e., they may have one or more variances (polymorphisms) between them.

The terms "variance" and "polymorphism" are used interchangeably herein to mean a difference in the nucleotide sequence between two or more variant forms of a nucleotide sequence, e.g., a gene. A variance or polymorphism can be one or more of: a nucleotide substitution, deletion, or addition, e.g., of one or more nucleotides. A "polymorphic site" is the location at which such a variance occurs.

The terms "variant form of a gene," "variant of a gene," or "alternative form of a gene" are used interchangeably to refer to one of two or more forms of a gene present in a population, e.g., in a human population, that can be distinguished from other forms of the gene by having at least one polymorphism, and frequently more than one polymorphism, within the gene sequence. Variant forms of a gene can differ in nucleotide sequence by, e.g., the deletion, substitution, or addition of one or more nucleotides. A "single nucleotide polymorphism" (SNP) refers to a difference between two or more variant forms of a gene in which a single nucleotide base pair has been substituted by another.

Another term used in the art interchangeably with polymorphism is "mutation". However, "mutation" is often used to refer to an allele associated with a deleterious phenotype.

As used herein "phenotype" refers to any observable or otherwise measurable characteristic, e.g., physiological, morphological, biological, biochemical or clinical characteristic, of an organism. The point of genetic studies is to detect consistent relationships between phenotypes and DNA sequence variation (genotypes). DNA sequence variation will seldom completely account for phenotypic variation, particularly with medical phenotypes of interest (e.g., commonly occurring diseases). Environmental factors are also frequently important.

As used herein "genetic testing" or "genetic screening" refers to the genotyping or haplotyping analyses performed to determine the alleles present in an individual, a population, or a subset of a population.

"Disease risk" as used herein refers to the probability that, for a specific disease (e.g., coronary heart disease) an individual who is free of evident disease at the time of testing will subsequently be affected by the disease.

"Disease diagnosis" as used herein refers to ability of a clinician to appropriately determine and identify whether the expressed symtomology, pathology or physiology of a patient is associated with a disease, disorder, or dysfunction.

"Disease prognosis" as used herein refers to the forecast of the probable course and or outcome of a disease, disorder, or dysfunction.

"Therapeutic management" as used herein refers to the treatment of disease, disorders, or dysfunctions by various medical methods. By "disease management protocol" or "treatment protocol" is meant a means for devising a therapeutic plan for a patient using laboratory, clinical and genetic data, including the patient's diagnosis and genotype. The protocol clarifies therapeutic options and provides information about probable prognoses with different treatments. The treatment protocol may provide an estimate of the likelihood that a patient will respond positively or negatively to a therapeutic intervention. The treatment protocol may also provide guidance regarding optimal drug dose and administration, and likely timing of recovery or rehabilitation. A "disease management protocol" or "treatment protocol" may also be formulated for asymptomatic and healthy subjects in order to forecast future disease risks based on laboratory, clinical and genetic variables. In this setting the protocol specifies optimal preventive or prophylactic interventions, including use of compounds, changes in diet or behavior, or other measures. The treatment protocol may include the use of a computer program.

As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease.

As used herein, "population" refers to a group of individuals that share geographic (including, but not limited to, national), ethnic or racial heritage. A population may also comprise individuals with a particular disease or condition ("disease population"). The concept of a population is useful because the occurrence and/or frequency of DNA polymorphisms and haplotypes, as well as their medical implications, often differs between populations. Therefore knowing the population to which a subject belongs may be useful in interpreting the health consequences of having specific haplotypes. A population encompasses at least one thousand individuals. Preferably, a population comprises ten thousand, one hundred thousand, one million or more individuals, with the larger numbers being more preferable. The allele (haplotype) frequency, heterozygote frequency, or homozygote frequency of two or more alleles of a gene or genes can be determined in a population. The frequency of one or more variances that may predict response to a treatment can be determined in one or more populations using a diagnostic test.

The term "associated with" in connection with the relationship between a genetic characteristic, e.g., a gene, allele, haplotype, or polymorphism, and a disease or condition means that there is a statistically significant level of relatedness between them based on any generally accepted statistical measure of relatedness. Those skilled in the art are familiar with selecting an appropriate statistical measure for a particular experimental situation or data set. The genetic characteristic, e.g., the gene or haplotype, may, for example, affect the incidence, prevalence, development, severity, progression, or course of the disease. For example, ApoE or a particular allele(s) or haplotype of the gene is related to a disease if the ApoE gene is involved in the disease or condition as indicated, or if a particular sequence variance, haplotype, or allele is correlated with the incidence or presence of the disease.

As used herein the term "hybridization", when used with respect to DNA fragments or polynucleotides encompasses methods including both natural polynucleotides, non-natural polynucleotides or a combination of both. Natural polynucleotides are those that are polymers of the four natural deoxynucleotides (deoxyadenosine triphosphate [dA], deoxycytosine triphosphate [dC], deoxyguanine triphosphate [dG] or deoxythymidine triphosphate [dT], usually designated simply thymidine triphosphate [T]) or polymers of the four natural ribonucleotides (adenosine triphosphate [A], cytosine triphosphate [C], guanine triphosphate [G] or uridine triphosphate [U]). Non-natural polynucleotides are made up in part or entirely of nucleotides that are not natural nucleotides; that is, they have one or more modifications. Also included among non-natural polynucleotides are molecules related to nucleic acids, such as peptide nucleic acid [PNA]). Non-natural polynucleotides may be polymers of non-natural nucleotides, polymers of natural and non-natural nucleotides (in which there is at least one non-natural nucleotide), or otherwise modified polynucleotides. Non-natural polynucleotides may be useful because their hybridization properties differ from those of natural polynucleotides. As used herein the term "complementary", when used in respect to DNA fragments, refers to the base pairing rules established by Watson and Crick: A pairs with T or U; G pairs with C. Complementary DNA fragments have sequences that, when aligned in antiparallel orientation, conform to the Watson-Crick base pairing rules at all positions or at all positions except one. As used herein, complementary DNA fragments may be natural polynucleotides, non-natural polynucleotides, or a mixture of natural and non-natural polynucleotides.

As used herein "amplify" when used with respect to DNA refers to a family of methods for increasing the number of copies of a starting DNA fragment. Amplification of DNA is often performed to simplify subsequent determination of DNA sequence, including genotyping or haplotyping. Amplification methods include the polymerase chain reaction (PCR), the ligase chain reaction (LCR) and methods using Q beta replicase, as well as transcription-based amplification systems such as the isothermal amplification procedure known as self-sustained sequence replication (3SR, developed by T. R. Gingeras and colleagues), strand displacement amplification (SDA, developed by G. T. Walker and colleagues) and the rolling circle amplification method (developed by P. Lizardi and D. Ward).

DESCRIPTION OF THE FIGURES AND TABLES

Table 1. The table lists the masses of the normal nucleotides and BrdU and the mass differences between each of the possible pairs of nucleotides.

Table 2. Twenty polymorphic sites in the ApoE gene. The ApoE genomic sequence is taken from GenBank accession AB012576. The gene is composed of four exons and three introns. The transcription start site (beginning of first exon) is at nucleotide (nt) 18,371 of GenBank accession AB012576, while the end of the transcribed region (end of the 3' untranslated region, less polyA tract) is at nt 21958. The twenty polymorphic sites are depicted as shaded nucleotides in the Table, and are as follows (nucleotide position and possible nucleotides): 16541 (T/G); 16747 (T/G); 16965 (T/C); 17030 (G/C); 17098 (A/G); 17387 (T/C); 17785 (G/A); 17874 (T/A); 17937 (C/T); 18145 (G/T); 18476 (G/C); 19311 (A/G); 20334 (A/G); 21250 (C/T; 21349 (T/C); 21388 (T/C); 23524 (A/G); 23707 (A/C); 23759 (C/T); 23805 (G/C); and 37237 (G/A). The bold sequence listing indicates the transcribed sequence of the ApoE gene; the grey shaded region indicates the ApoE gene enhancer element; the underlined sequence depicts the coding region of the ApoE gene. Where polymorphisms result in a change of the amino acid sequence, the amino acid alteration is indicated, for example at nucleotide position 20334 the A/T polymorphism results in a alanine/threonine respectively at amino acid position 18 of the ApoE gene product. As described in the Detailed Description below, the polymorphisms at positions GenBank nucleotide number 17874, 17937, 18145, 18476, 21250, and 21388 have been previously described.

Table 3. This table provides experimentally derived ApoE haplotypes. The haplotypes encompass nine polymorphic sites within the ApoE gene (GenBank accession number AB012576). The Table has nine columns with haplotype data at nine specific sites within the ApoE gene. The column listed as "WWP #" refers to a Coriell number which refers to the catalogued number of an established human cell line. The "VGNX_Symbol" row provides an internal identifier for the gene; the "VGNX database" row identifies the base pair number of the ApoE cDNA; and the "GenBank" row identifies the GenBank base pair number of the sequence for the ApoE gene. The abbreviations are as follows: A=adenine nucleotide, C=cytosine nucleotide, G=guanosine nucleotide, and T=thymidine nucleotide. The abbreviated nucleotides in brackets indicate that either nucleotide may be present in the sample. Thus for example, under column GEN-CBX and WWP#1, the genotype identified at the GenBank position 17874 is an "A"; whereas under Column GEN-CBX at the GenBank position 18476 the genotype under the WWP#1 is either a "T" or a "G".

Table 4. This table provides the sequence of ApoE haplotypes comprising up to 20 polymorphic sites. There are 42 ApoE haplotypes listed in the Table. The top row of the table provides the location of the polymorphic nucleotides in the ApoE gene (see Table 2). The numbers (16541, 16747, and so forth) correspond to the numbering in GenBank accession AB012576_1 which provides the sequence of a cosmid clone that contains the entire ApoE gene and flanking DNA. Each column shows the sequence of the ApoE gene at the position indicated at the top of the column. Abbreviations are as follows: A=adenine nucleotide, C=cytosine nucleotide, G=guanosine nucleotide, and T=thymidine nucleotide. Each row provides the sequence of an individual phenotype.

Table 5. This table provides the sequence of haplotypes at the ApoE gene determined by 5 polymorphic sites. These haplotypes allow classification of ApoE alleles into the є2, є3 and є4 groups without recourse to the polymorphic sites conventionally used to determine є2, є3, є4 status. In this table the haplotypes are specified by SNPs at positions 16747, 17030, 17785, 19311, and 23707, listed as column headings. The GENOTYPE column provides the classic ApoE genotype/phenotype (є2, є3 and є4) corresponding to the haplotype indicated in each row.

Figure 1:
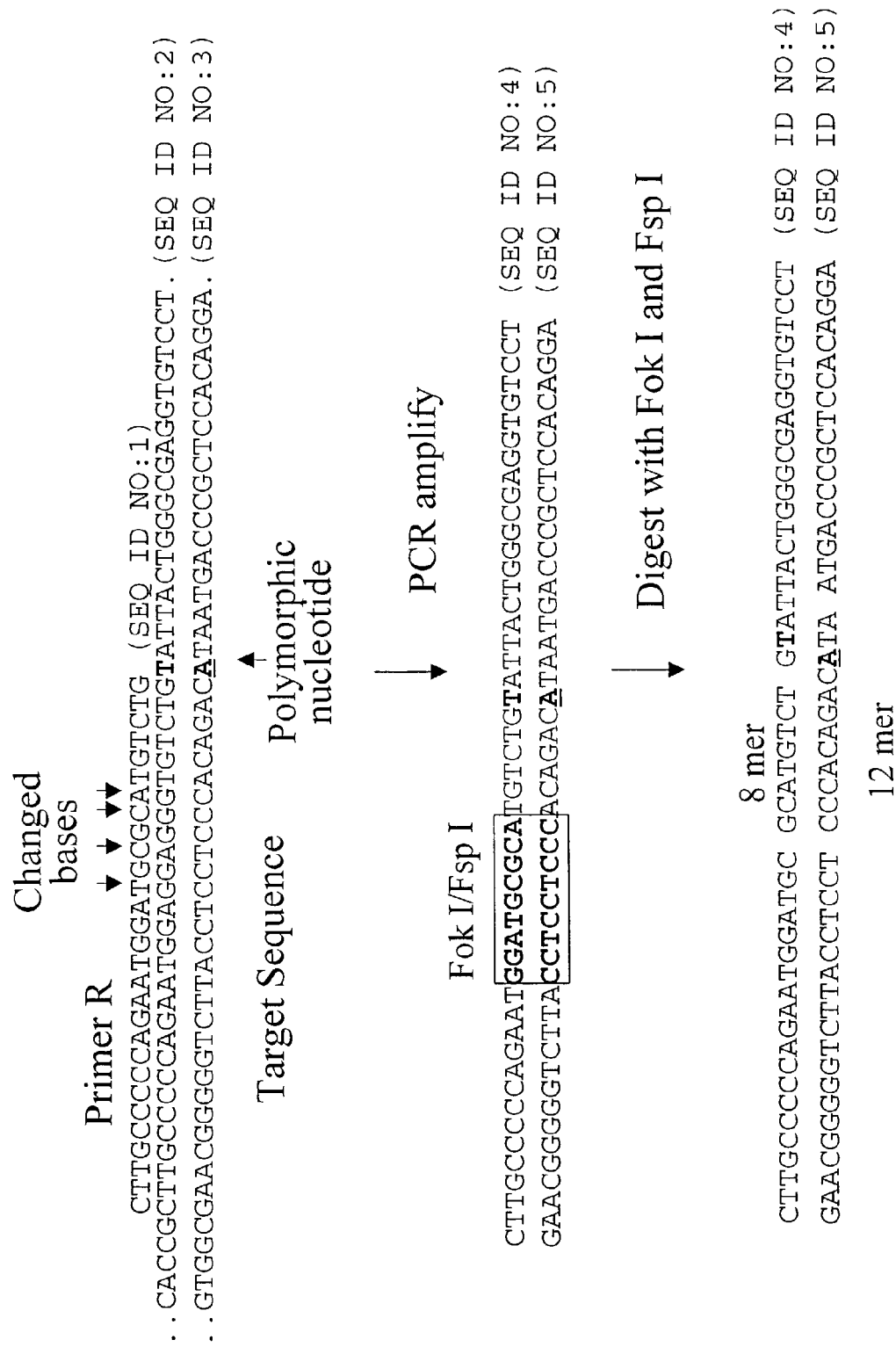

FIG. 1. Depiction of a primer designed to incorporate restriction enzyme recognition sites for the specific restriction enzymes Fok I and Fsp I. The primer (primer R sequence) has altered bases from the desired amplified region of the target DNA. The polymorphic nucleotide is included in the target DNA region and is underlined. After PCR amplification, the incorporated altered base pairs of the primer thereby incorporate FokI and FspI restriction sites in the amplicon. The amplicon can subsequently be digested in the presence of the FokI and FspI restriction enzymes under optimal conditions for digestion by both enzymes. The resultant fragments after enzyme digestion, an 8-mer and a 12-mer, are as depicted. In this figure, the polymorphism (A, underlined) is contained within the 12-mer fragment.

Figure 2:
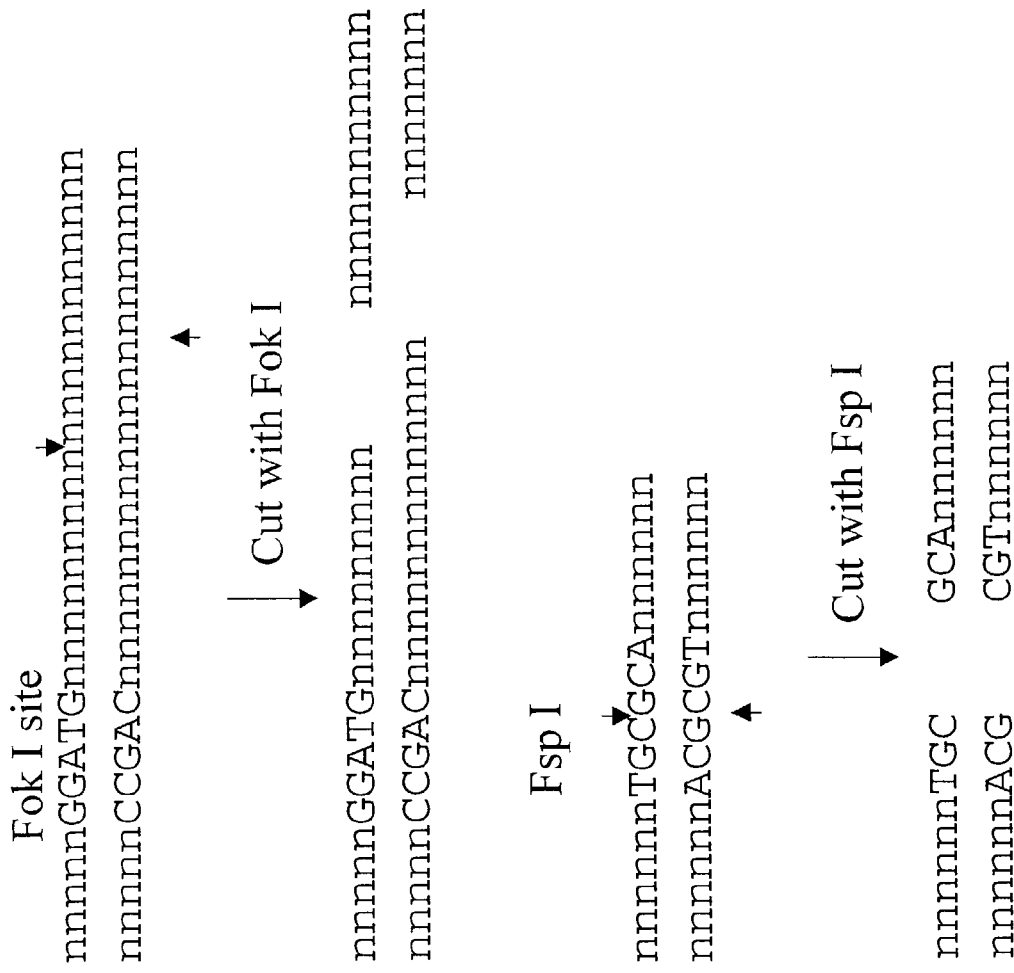

FIG. 2. This figure depicts the utility of Fok I, a type IIS restriction enzyme, which cleaves DNA outside the recognition sequence at a distance of 9 bases 3' to the recognition site on one strand and 13 bases away from the recognition site on the opposite strand, leaving a four base overhang (protruding 5' end). As shown in this figure, by designing the primer so that the Fok I recognition site is located within 12 bases or less of the 3' end of the primer one can assure that the Fok I cleavage will cleave outside the primer sequence. Further shown is the utility of FspI, a restriction enzyme that after digestion leaves blunt ends. The FspI recognition site, TGCGCA, after digestion results in fragments as shown.

Figure 3:
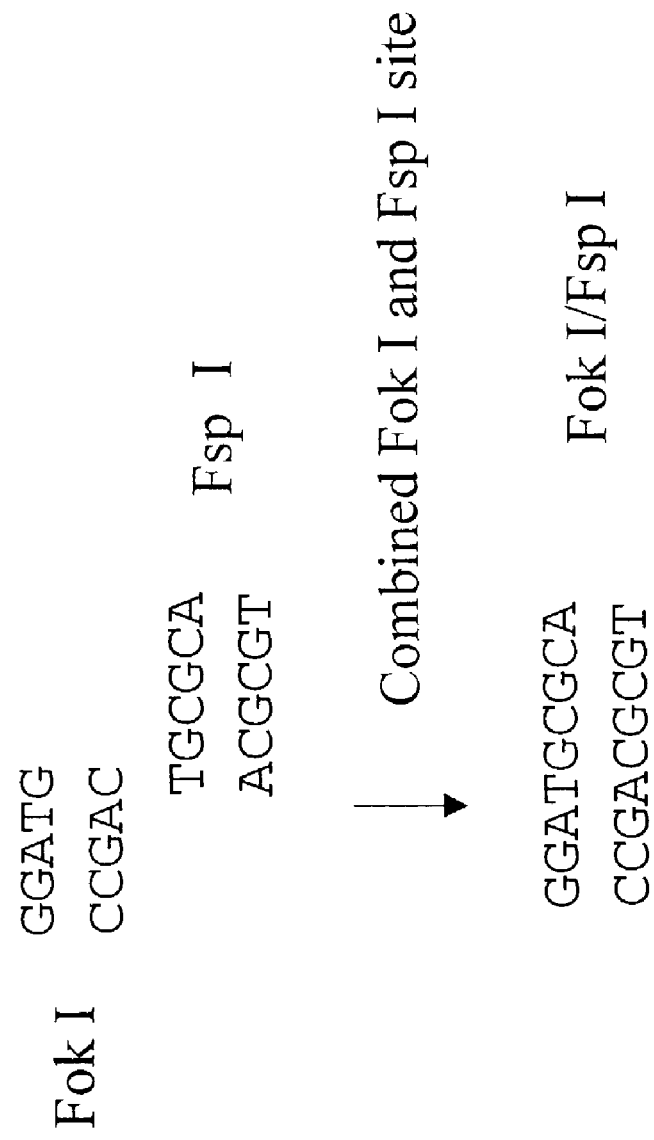

FIG. 3. In this figure, the utility of the Fsp I/Fok I pair of enzymes for the present invention is shown. The FspI recognition site overlaps that of Fok I, allowing the two sites to be partially combined. Thus, including the combined FspI/FokI sequence in the primer, reduces the number of bases that are be introduced into the modified primer, making the primer design simpler and more likely to function in the subsequent amplification reaction.

FIG. 4. In this figure, an alternative method of primer design in the present invention involves the use of a primer with an internal loop. The primer is designed (primer R1) such that one of the bases corresponding to the native sequence is removed and replaced with a loop. In this case the G/C indicated by the arrow below the target sequence is replaced with the recognition sequence for Fok I and Fsp I. Upon hybridization to the DNA template, the primer will form a loop structure. This loop will be incorporated into the amplicon during the amplification process, thereby introducing the Fok I and Fsp I restriction sites (indicated by the box). The resultant amplicon is incubated with Fok I and Fsp I under optimal digestion conditions producing an 8-mer and a 12-mer fragment. As in FIG. 1, the 12-mer contains the polymorphic base (A, underlined) and can be analyzed by mass spectrometry to identify the base at the polymorphic site.

FIG. 5. Alternative restriction enzyme recognition site incorporation into amplified regions of target DNA is shown. As is depicted in FIGS. 1-4 for the enzyme pair FspI/FokI; in this figure, PvuI/FokI restriction enzymatic sites can be incorporated in the same manner as previously described for FIGS. 1-4. A primer is designed such that a BsgI/PvuII sites form a hair-pin loop when the primer is hybridized to the target DNA sequence. After amplification by PCR, the resultant amplicon will have the PvuII/FokI sites incorporated in the resultant amplicon (as indicated by the boxed sequence). After digestion under conditions optimal for PvuII and BsgI, the resultant fragments, an 14 mer and a 16 mer, are sufficient for mass spectrometric analysis and the polymorphic site is contained in the 16mer (A, underlined).

FIG. 6. Shown in this figure is an alternative restriction enzyme pair for the preparation of fragments containing the polymorphic site for mass spectrometric analysis. PvuII/FokI restriction enzyme recognition sites form a hair-pin loop when hybridized to the target DNA sequence. After amplification by PCR, the resultant amplicon will have the PvuI/FokI sites incorporated in the resultant amplicon (as indicated by the boxed sequence). After digestion under conditions optimal for PvuII and FokI restriction, the resultant fragments, an 16 mer and a 20 mer, are sufficient for mass spectrometric analysis and the polymorphic site is contained in the 20mer (A, underlined).

Figure 7:
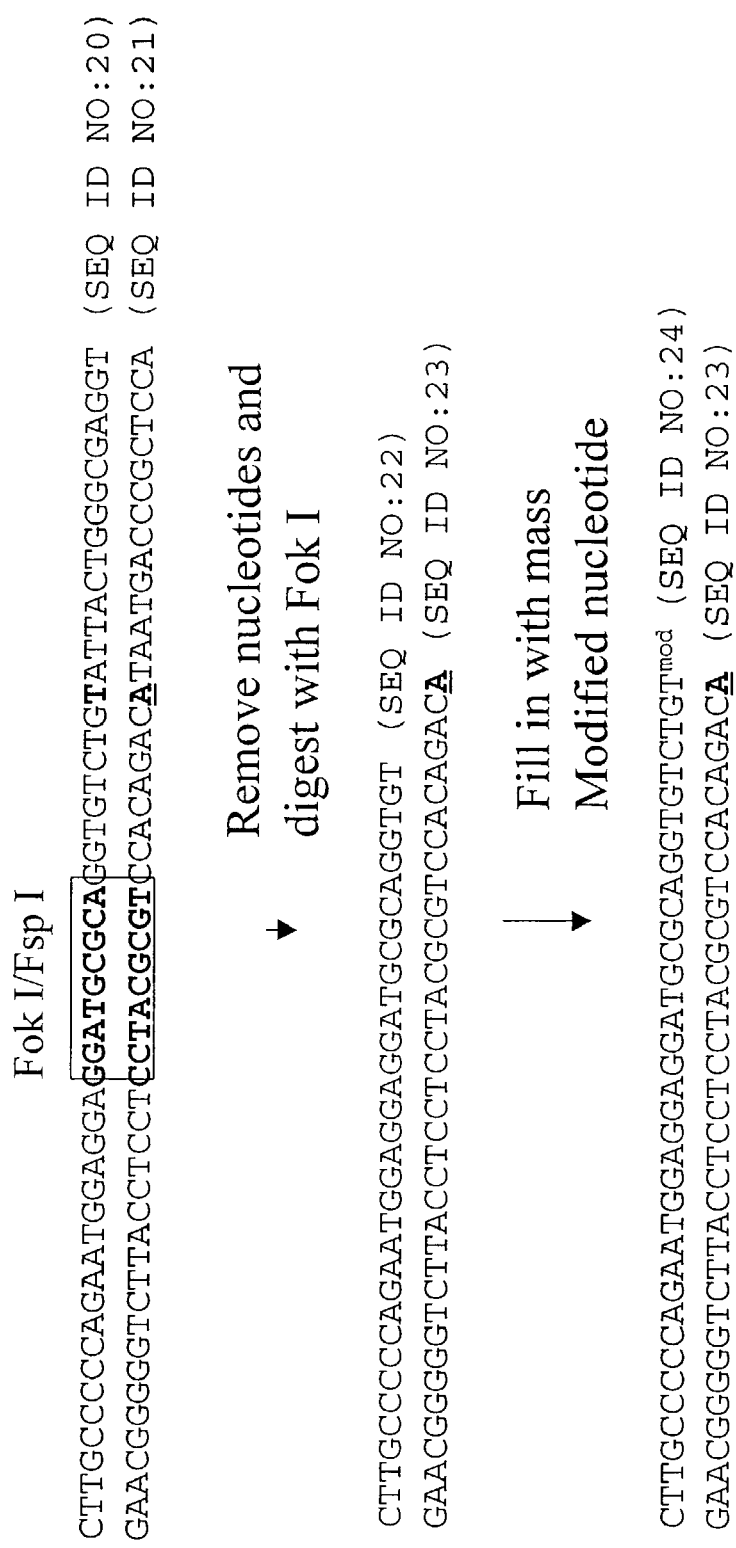

FIG. 7. In this figure, a modification of the method depicted in FIG. 4 is shown. As in FIG. 4, a DNA segment containing a polymorphism is amplified using two primers. One primer is designed with an inserted DNA segment, not complementary to template DNA, that forms a hair-pin loop when hybridized to template DNA. Insertion of the non-complementary DNA segment results in incorporation of overlapping FokI and FspI restriction enzyme sites after PCR amplification (as shown in the boxed sequence). Following PCR amplification reaction, the reaction is subjected to a clean up procedure to remove unincorporated primers, nucleotides and buffer constituents. The PCR product is then digested with the FokI restriction enzyme which generates a 5' overhang that extends from the 3' end of the primer to beyond the polymorphic nucleotide. The 3' recessed end can then be filled in with exogenously added nucleotides in which the normal nucleotide corresponding to one of the possible nucleotide bases at the polymorphic site is a mass modified nucleotide ($T^{mod}$). These fragments are sufficient for mass spectrometric analysis of the modified polymorphic nucleotide.

Figure 8:
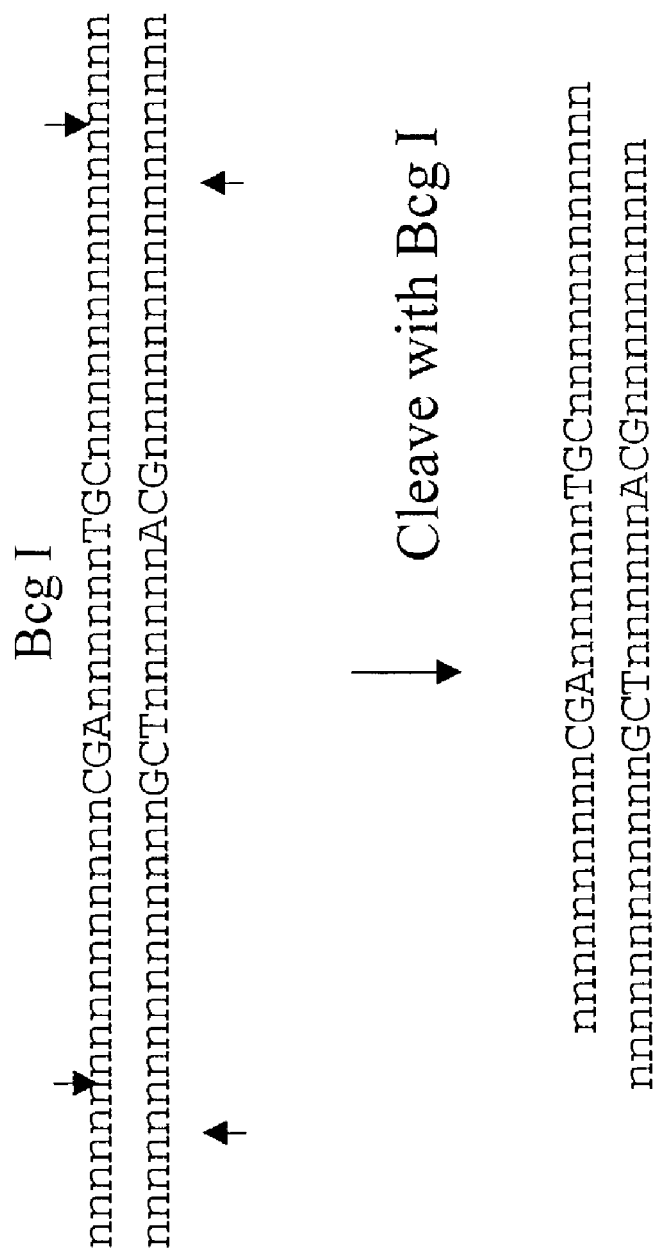

FIG. 8. Shown in this figure is the incorporation of a single restriction enzyme recognition site in the amplicon for subsequent digestion and mass spectrometric analysis of the prepared fragments. Shown in this figure is incorporation of BcgI, an restriction enzyme that is capable of making two double strand cuts, one on the 5' side and one on the 3' side of their recognition site. The recognition site for BcgI is 12/10 (N)CGA(N)$_6$TGC(N)12/10, which after digestion results in fragments sufficient for mass spectrometric analysis and identification of the polymorphic base with the fragment.

Figure 9:
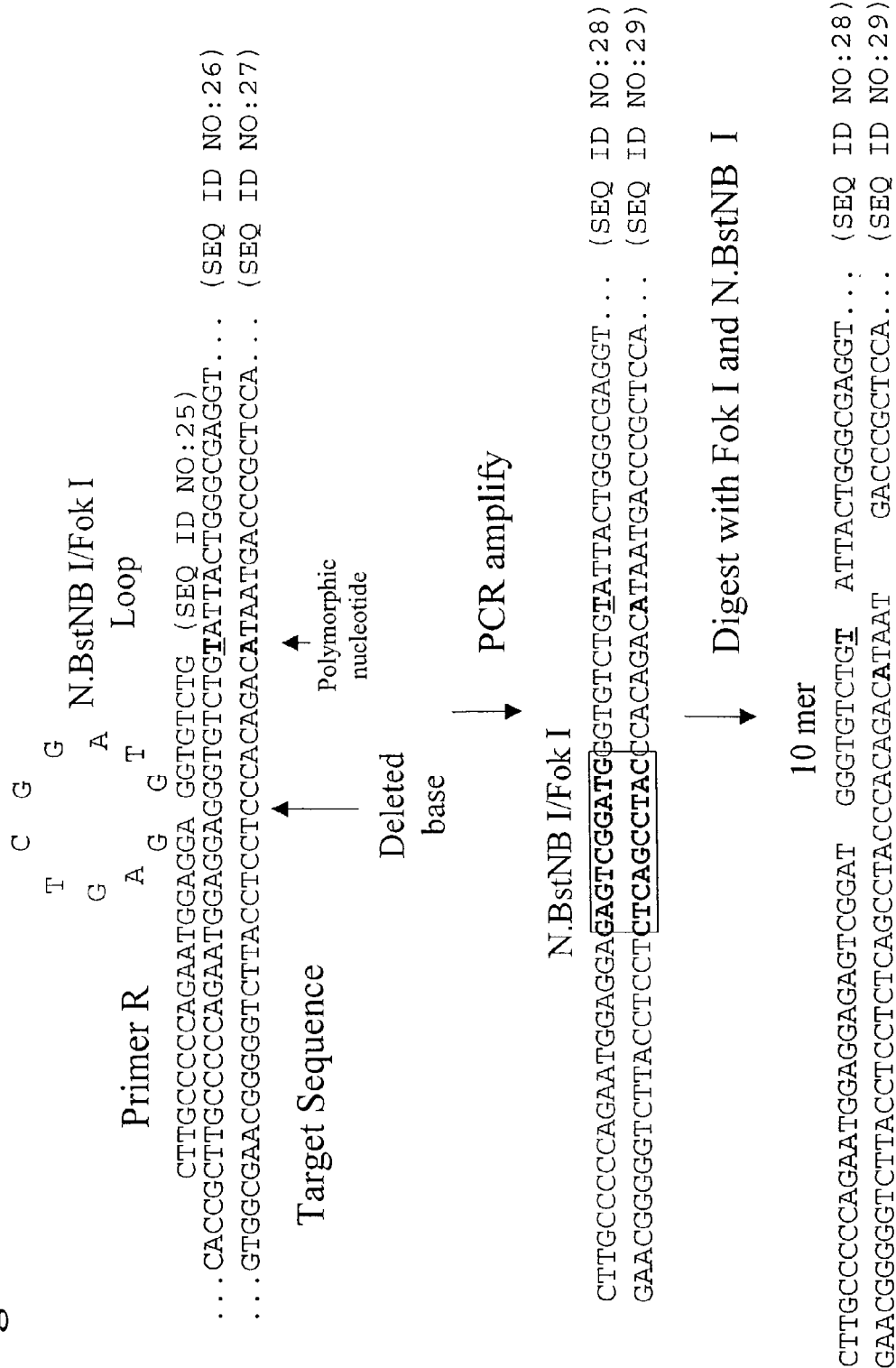

FIG. 9. Shown in this figure is an example of the utility in the present invention of including a restriction enzyme recognition site for which the restriction enzyme creates a nick in the DNA amplicon instead of causing a double strand break. As shown in this figure, a primer R is designed to incorporate a N.BstNB I recognition site (GAGTCNNNN^ANN) in addition to a FokI restriction site. As in previous figures, the primer forms a hair-pin loop structure when hybridized to the target DNA region, however, the PCR amplicon has the incorporated restriction site sequences. Digestion with FokI and N.BstNB I results in a 10 mer fragment that contains the polymorphic base (T, underlined). Such a fragment is sufficient for analysis using a mass spectrometer.

Figure 10:
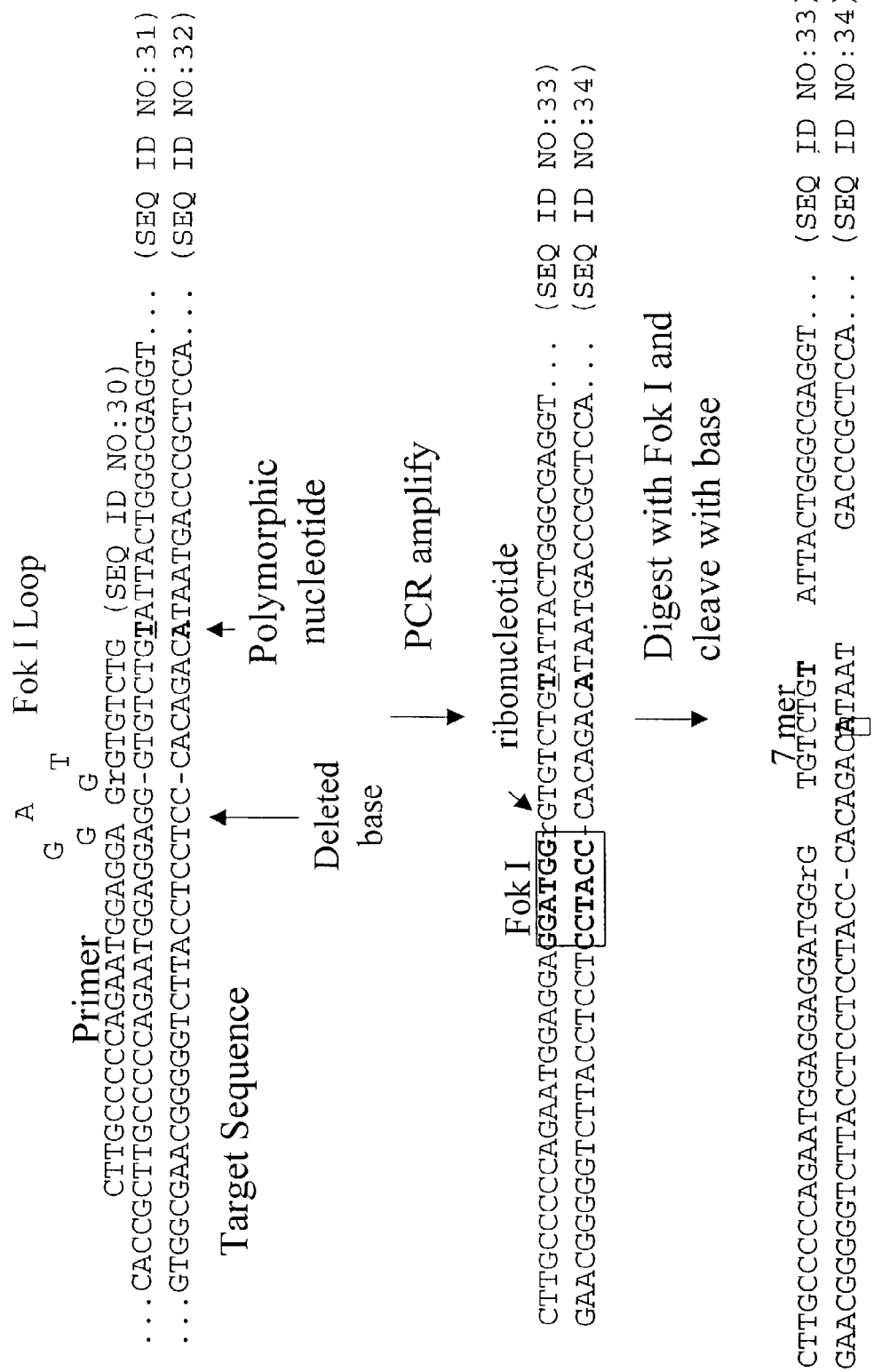

FIG. 10. Shown in this figure is a similar strategy to the nicking enzyme scheme of FIG. 9, above. In this method, one restriction enzyme and a primer which contains a ribonucleotide substitution for one of the deoxyribonucleotides. As shown the primer is designed to contain a FokI recognition site which upon hybridization with the target DNA sequence forms a hair-in loop. The primer also has a ribonucleoside (rG) substitution which will additionally be incorporated into the amplicon. The ribonucleoside substitution is base-labile and will cause a break in the backbone of the DNA at that site under basic conditions. Shown in this scheme, the amplicon is incubated with the restriction enzyme (Fok I) causing a double-strand break. The amplicon is then incubated in the presence of base causing a break between the ribonucleotide G and the 3' deoxyribonucleotide T, releasing a 7 base fragment which can easily analyzed by mass spectrometry.

FIG. 11. The diagram illustrates the major approaches to haplotyping within the allele capture 2s group of allele enrichment methods. As shown, methods can be broadly categorized as (1) those directed to single stranded DNA and (2) those directed to double stranded DNA. It is possible to capture DNA fragments in an allele specific manner by affinity to proteins or nucleic acids that discriminate single base differences. Different types of protein and nucleic acid affinity reagents are shown in the boxes. The protein or nucleic acid that sticks to one allele can subsequently be selected from the nucleic acid mixture by methods known in the art such as streptavidin or antibody coated beads. A third, non-affinity based method for separating alleles involves restriction endonuclease cleavage at a polymorphic site (such that fragments of significantly different size are produced from the two alleles), and subsequent size fractionation of the cleaved products using electrophoresis or centrifugation. Genotyping the isolated fragments corresponding to each of the two alleles will provide haplotypes.

FIG. 12. This diagram depicts the various methods of haplotyping based on allele-specific amplification. After cleavage of one allele the other allele may be selectively amplified, or separated by a size selection procedure, or the cleaved allele may be removed by an allele selective degradation procedure.

FIG. 13. This diagram depicts the categorization of the various methods of haplotyping strategies based upon allele specific restriction. In these methods one allele is preferentially amplified from a mixture of two alleles by the design of a primer or primers that exploit sequence differences at polymorphic sites.

Figure 14:
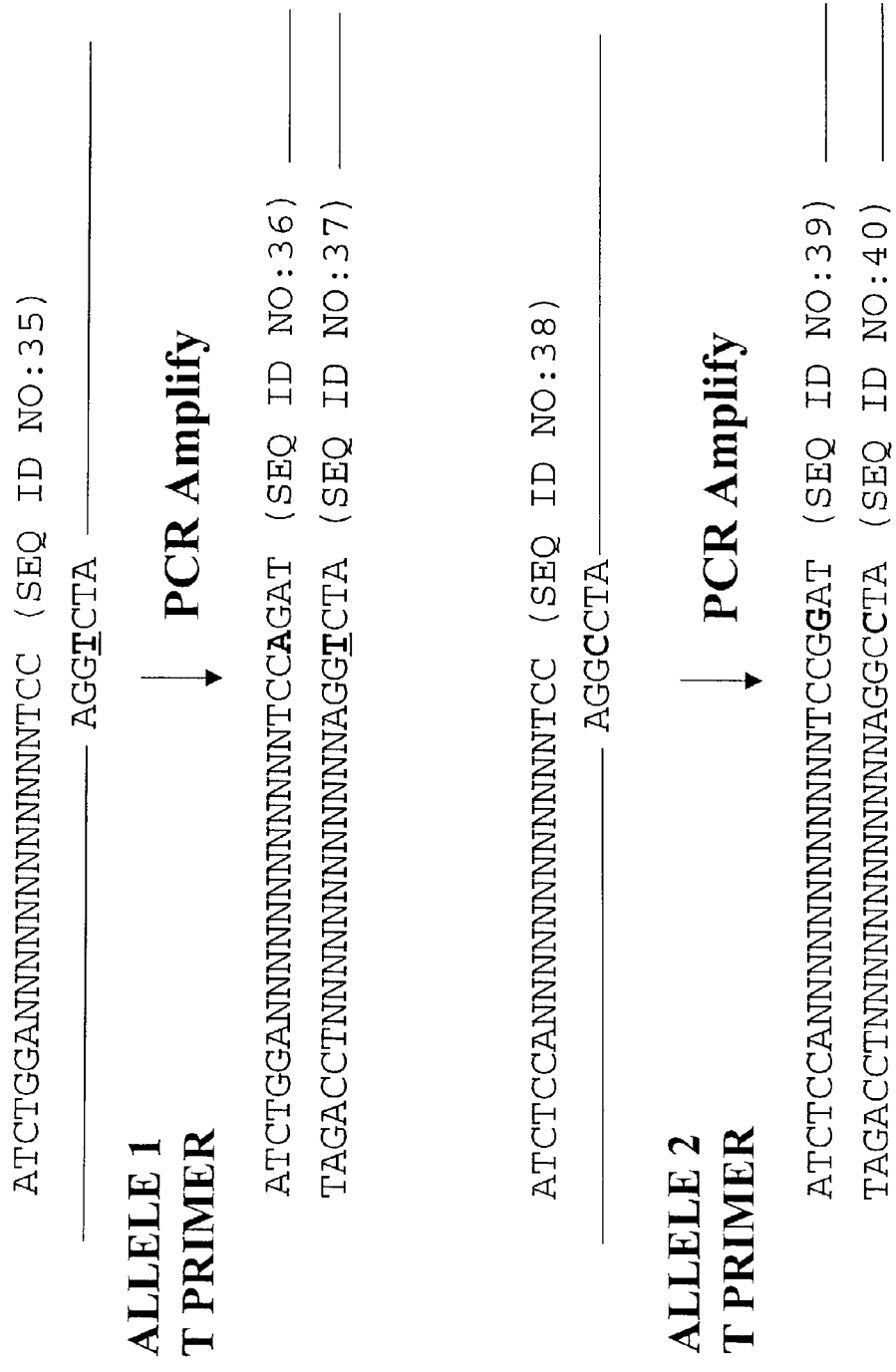

FIG. 14. Hair pin loop primers. In this figure the primers used for PCR amplification are shown. In allele 1, the polymorphic site is a T (underlined) and incorporation of the ATCTGGA 5' portion of the primer occurs after at least one round of amplification. In allele 2, the polymorphic site is also a T (underlined) and incorporation of the ATCTGGA 5' portion of the primer occurs at least after one round of amplification.

Figure 15:
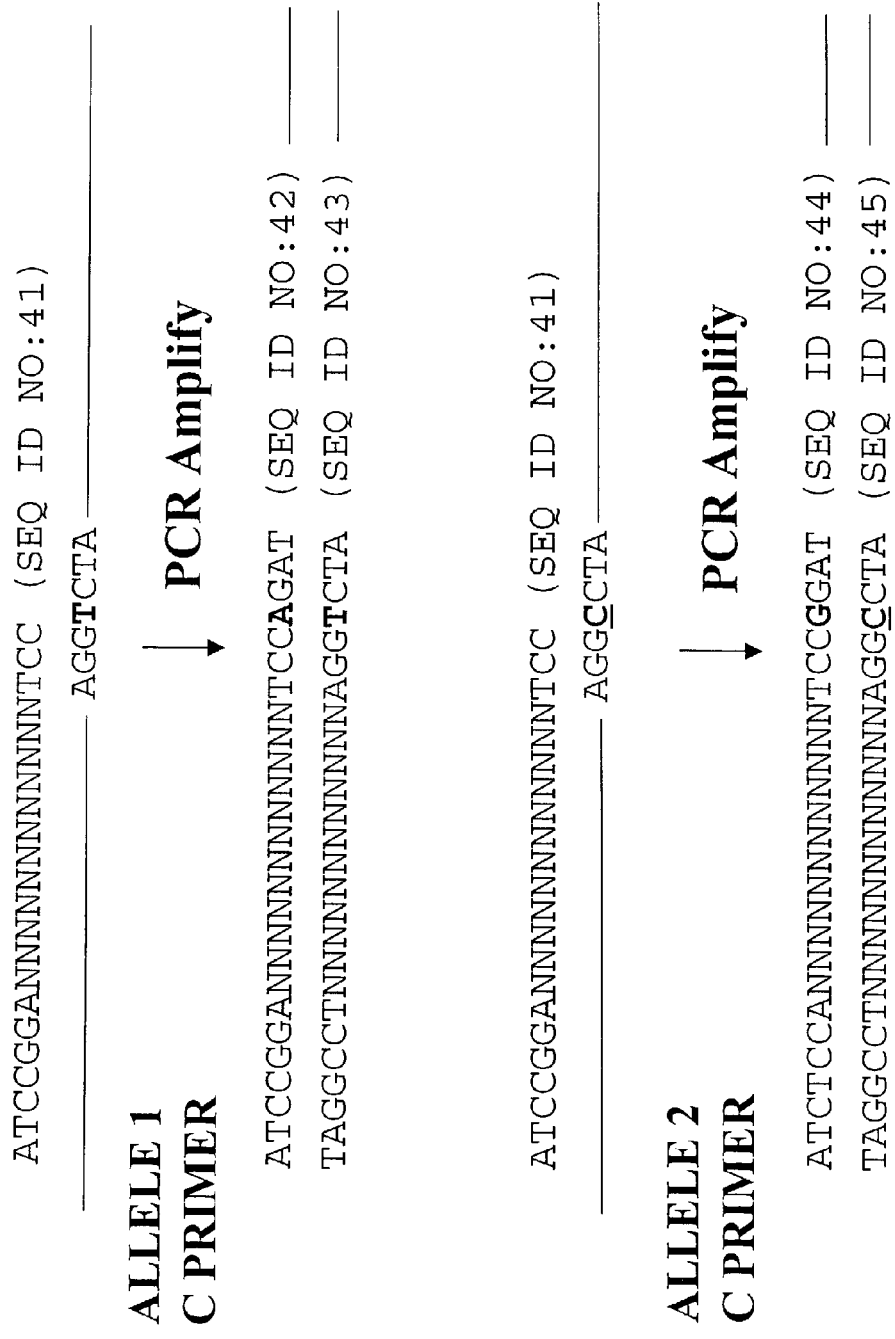

FIG. 15 Hair pin loop primers. In this figure the primers used for PCR amplification is shown. In allele 1, the polymorphic site is a C (underlined) and incorporation of the ATCCGGA 5' portion of the primer occurs after at least one round of amplification. In allele 2, the polymorphic site is also a C (underlined) and incorporation of the ATCCGGA 5' portion of the primer occurs at least after one round of amplification.

FIG. 16. Hair pin loop primers. In this figure, the minus strand of allele 1 generated by the PCR amplification step shown in FIG. 14 depicts the inability of the 5' primer to hybridize and effectively prevents the amplification of allele 1, using the T primer. Alternatively, the minus strand of allele 2 is incapable of forming a hairpin loop due to the mismatch. Thus, hairpin loop formation and prevention of PCR amplification does not occur, and amplification of this allele 2 strand will occur using the T primer.

Figure 19:
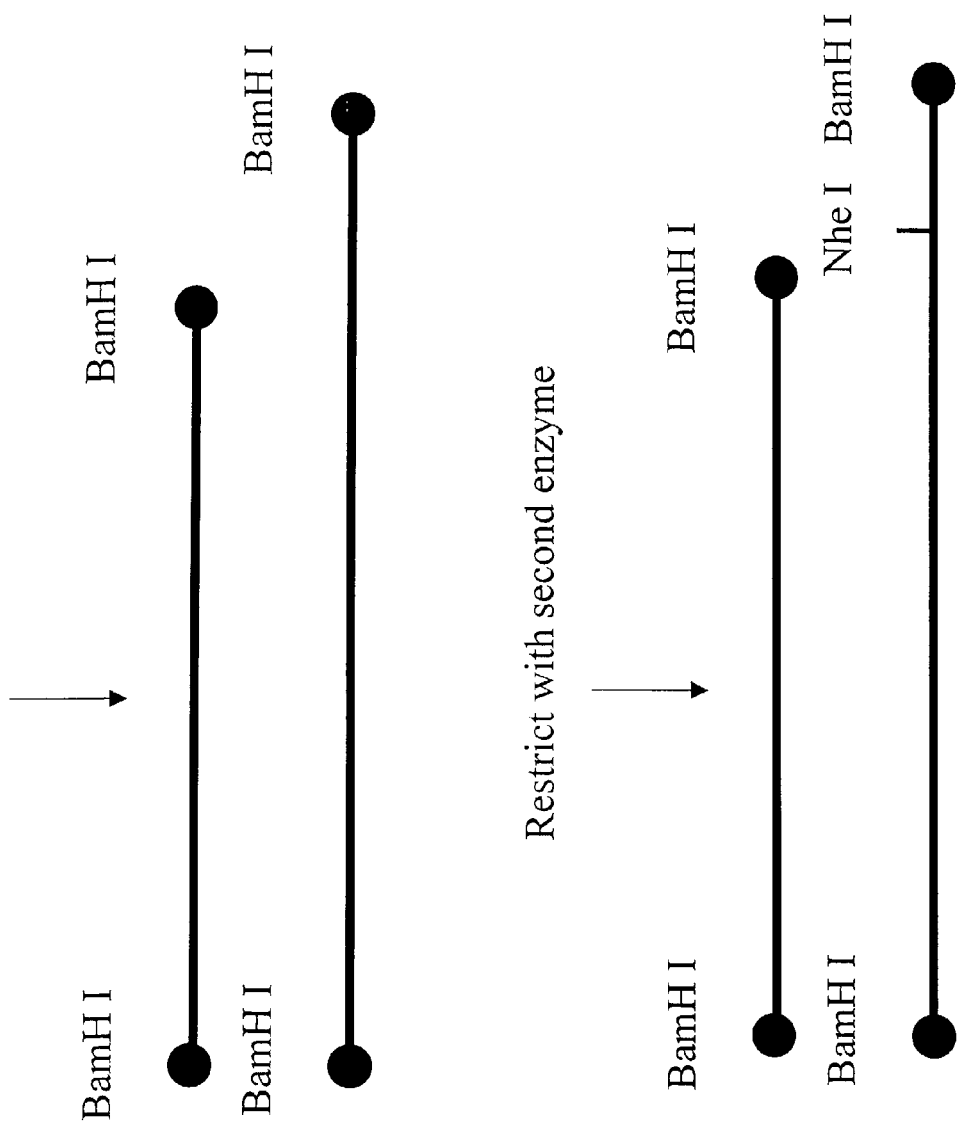

FIG. 17. Hair pin loop primers. In this figure, the minus strand of allele 2 generated by the PCR amplification step shown in FIG. 19 depicts the inability of the 5' primer to hybridize and effectively prevents the amplification of allele 2, using the C primer. Alternatively, the minus strand of allele 1 is incapable of forming a hairpin loop due to the mismatch. Thus, hairpin loop formation and prevention of PCR amplification does not occur, and amplification of the allele 1 strand will occur using the C primer.

Figure 18:
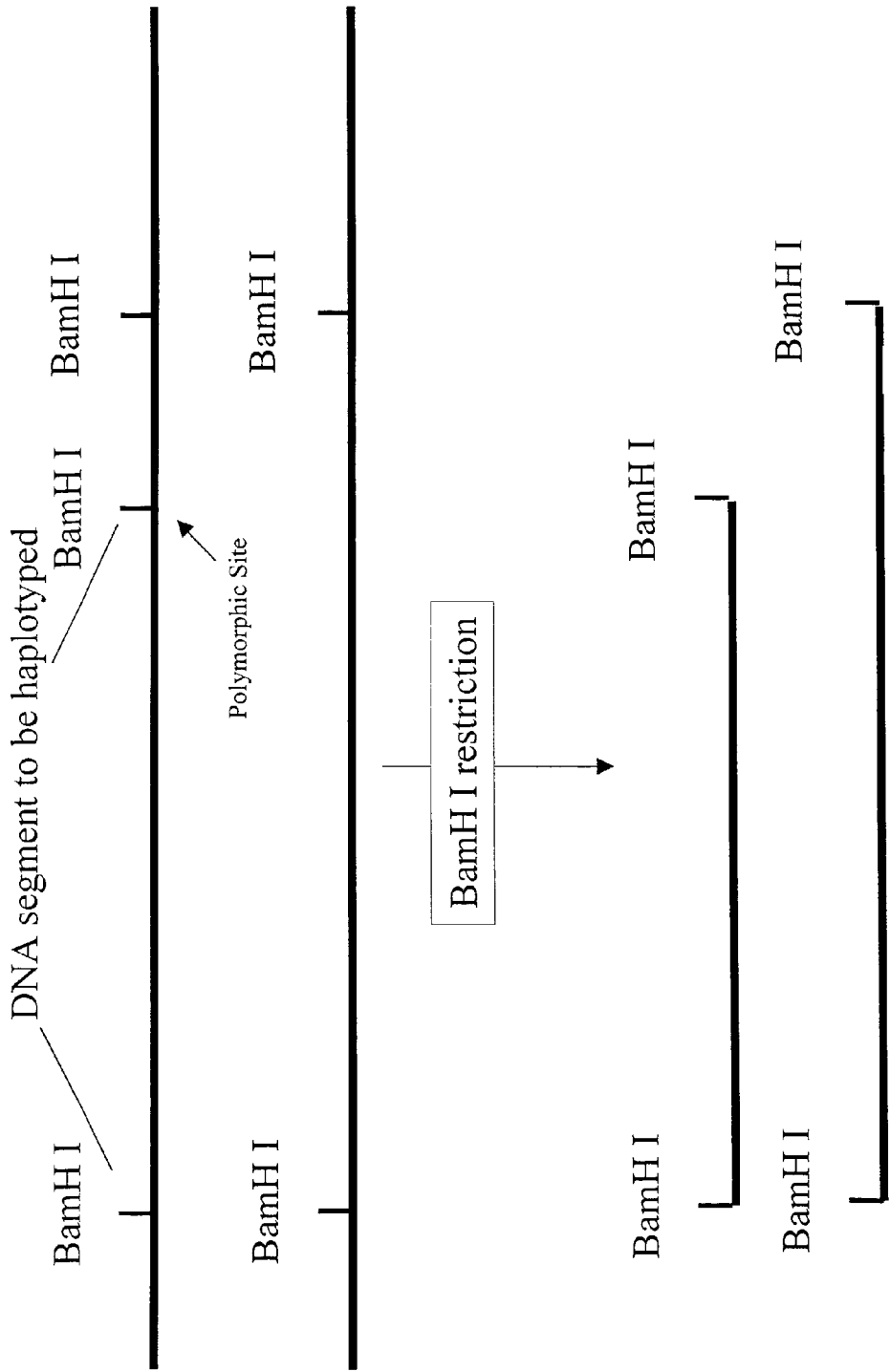

FIG. 18. Exonuclease based methods for the determination of a haplotype. In the DNA segment to be haplotyped, one identified site of polymorphism is a RFLP, so that on one allele the restriction enzyme, (BamHI in this example) is able to digest the alleles and generate different length fragments.

FIG. 19. Exonuclease based method for the determination of a haplotype. Using the fragments as shown and described in FIG. 18, the ends of the DNA fragments are protected from exonuclease digestion. The protected fragments are then digested with a second restriction enzyme for whose recognition site is located in one of the fragments, but not the other, due to the overhang of the RFLP, as shown, a NheI site. Restriction digestion of the fragments with NheI will effectively shorten the BamHI fragment but additionally remove the protection from the exonuclease digestion.

Figure 20:
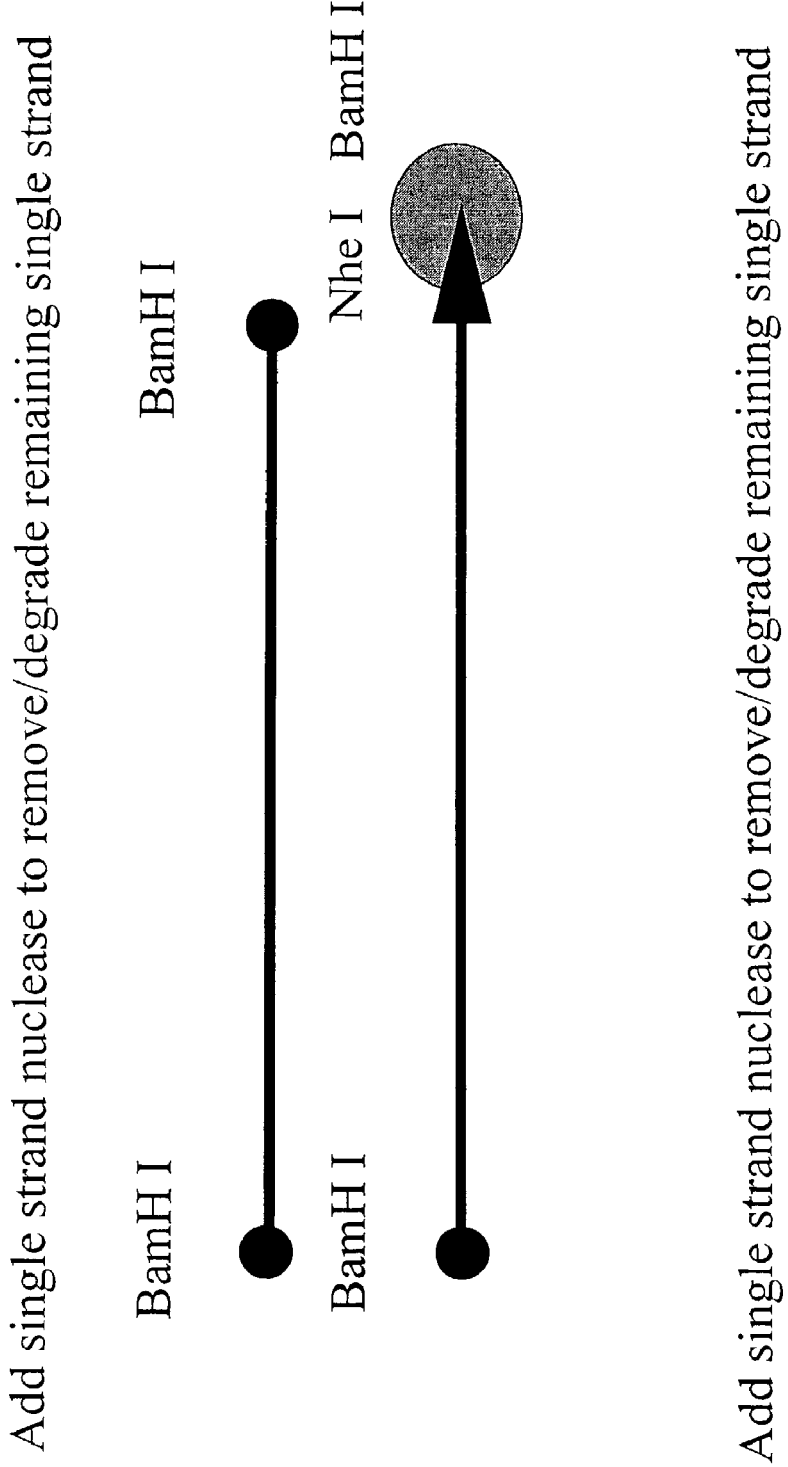

FIG. 20. Endonuclease based method for the determination of a haplotype. Using the fragments generated as shown in FIG. 19, these fragments are then incubated in the presence of an exonuclease. As shown the exonuclease will digest one of the fragments but the protected fragments will remain undigested.

FIG. 21. Primer mediated inhibition of allele-specific PCR amplification. Primers with the above characteristics were designed for haplotyping of the dihydropyrimidine dehydrogenase (DPD) gene. The DPD gene has two sites of variance in the coding region at base 186 (T:C) and 597 (A:G) which result in amino acid changes of Cys:Arg and Met:Val, respectively, as shown in the box of FIG. 21. The second site at base 597 is a restriction fragment length polymorphism (RFLP) which cleaves with the enzyme BsrD I if the A allele is present. The expected fragments are as shown in the figure.

FIG. 22. Allele specific primers for the DPD gene. In A., three primers were designed which contain at least two different regions. The 3' portion of the primer corresponds to the template DNA to be amplified. For the DPDASCF and the DPDASTF primers additional nucleotides were added to the 5' end of the primer which are complementary to the region in the sequence which contains the nucleotide variance. The DPDNSF primer contains only the DPD complementary sequence and will not result in allele specific amplification. In B., the DPD gene sequence containing the site of polymorphism is shown.

FIG. 23. PCR amplification of the DPD gene using the DPDNSF primer. Shown is the hybridization of the DPDNSF primers to the template containing the T or C allele. Below, the expected products for the DPD gene region using the DPDNSF primer for the T or C allele as shown.

FIG. 24. PCR amplification of the DPD gene using the DPDASTF primer. Shown is the hybridization of the DPDASTF primers to the template containing the T or C allele. Below, the expected products for the DPD gene region using the DPDASTF primer for the T or C allele as shown.

FIG. 25. PCR amplification of the DPD gene using the DPDASCF primer. Shown is the hybridization of the DPDASCF primers to the template containing the T or C allele. Below, the expected products for the DPD gene region using the DPDASCF primer for the T or C allele as shown.

FIG. 26 Stable hairpin loop structures formed with the reverse strand of the PCR product made using the DPDNSF primer using the computer program Oligo4. Only the reverse strand is shown because this would be the strand to which the DPDNSF primer would hybridize on subsequent rounds of amplification. The hairpin loops are either not stable or have a low melting temperature.

FIG. 27. Stable hairpin loop structures formed with the reverse strand of the PCR product made using the DPDASCF primer using, the computer program Oligo4. As in FIG. 26, only the reverse strand is shown.

FIG. 28. Stable hairpin loop structures formed with the reverse strand of the PCR product made using the DPDASTF primer using the computer program Oligo4. As in FIG. 26, only the reverse strand is shown.

FIG. 29. The primer hybridization and amplification events when further amplification using the DPDNSF primer is attempted on the generated PCR fragments. The primer is able to effectively compete with the hairpin structures formed with both the T and C allele of the DPD gene and thus amplification of both alleles proceeds efficiently.

FIG. 30. The primer hybridization and amplification events when further amplification using the DPDASCF primer is attempted on the generated PCR fragments. The DPDASCF primer is able to compete for hybridization with the hairpin loop formed with the C allele because its melting temperature is higher than the hairpin loop's (60° C. compared to 42° C.). The hairpin loop formed on the T allele however, has a higher melting temperature than the primer and thus effectively competes with the primer for hybridization. The hairpin loop inhibits PCR amplification of the T allele which results in allele specific amplification of the C allele.

FIG. 31. The primer hybridization and amplification events when further amplification using the DPDASTF primer is attempted on the generated PCR fragments. The hairpin loop structure has a higher melting temperature than the primer for the C allele and a lower melting temperature than the primer for the T allele. This causes inhibition of primer hybridization and elongation on the C allele and results in allele specific amplification of the T allele.

FIG. 32. The ability to use the hair-pin loop formation for haplotyping the DPD gene is diagrammed. Using a cDNA sample whose haplotype is know to be : Allele 1- $T^{186}$:$A^{597}$ Allele 2-$C^{186}$:$G^{597}$. The size of the fragments generated by a BsrD I from a 597 bp generated by amplification with the primers DPDNSF, DPDASTF, and DPDASCF, depend on whether the base at site 597 is an A or a G. Restriction digestion by BsrD I is indicative of the A base being at site 597. If a fragment has the A base at 597, three fragments will be generated of lengths 138, 164 and 267 bp. If the G base is at site 597 only two fragments will be generated of lengths 164 and 405 bp. If a sample is heterozygous for A and G at site 597, generation of all four bands of 138, 164 (2×), 267 and 405 bp will occur. The expected fragments generated by BsrD I restriction for each of the primers is indicated in the box.

FIG. 33. Agarose gel electrophoresis of the fragments generated by amplification of each of the primers for the DPD gene in a cDNA sample heterozygous at both sites 186 and 597 followed by BsrD I restriction. The DPDNSF lane shows the restriction fragment pattern for the selected cDNA using the DPDNSF primer indicating that this sample is indeed heterozygous at site 597. However, using the same cDNA sample and the primer DPDASTF (DPDASTF lane), the restriction pattern correlates to the pattern representative of a sample which is homozygous for A at site 597. Because the DPDASTF primer allows amplification of only the T allele, the haplotype for that in the sample must be $T^{186}$:$A^{597}$. The restriction digest pattern using the primer DPDASCF (DPDASCF lane) correlates with the expected pattern for there being G at site 597. Amplification of the cDNA sample with the primer DPDASCF results in amplification of only the C allele in the sample. Thus the haplotype for this allele must be $C^{186}$:$G^{597}$.

Figure 34:
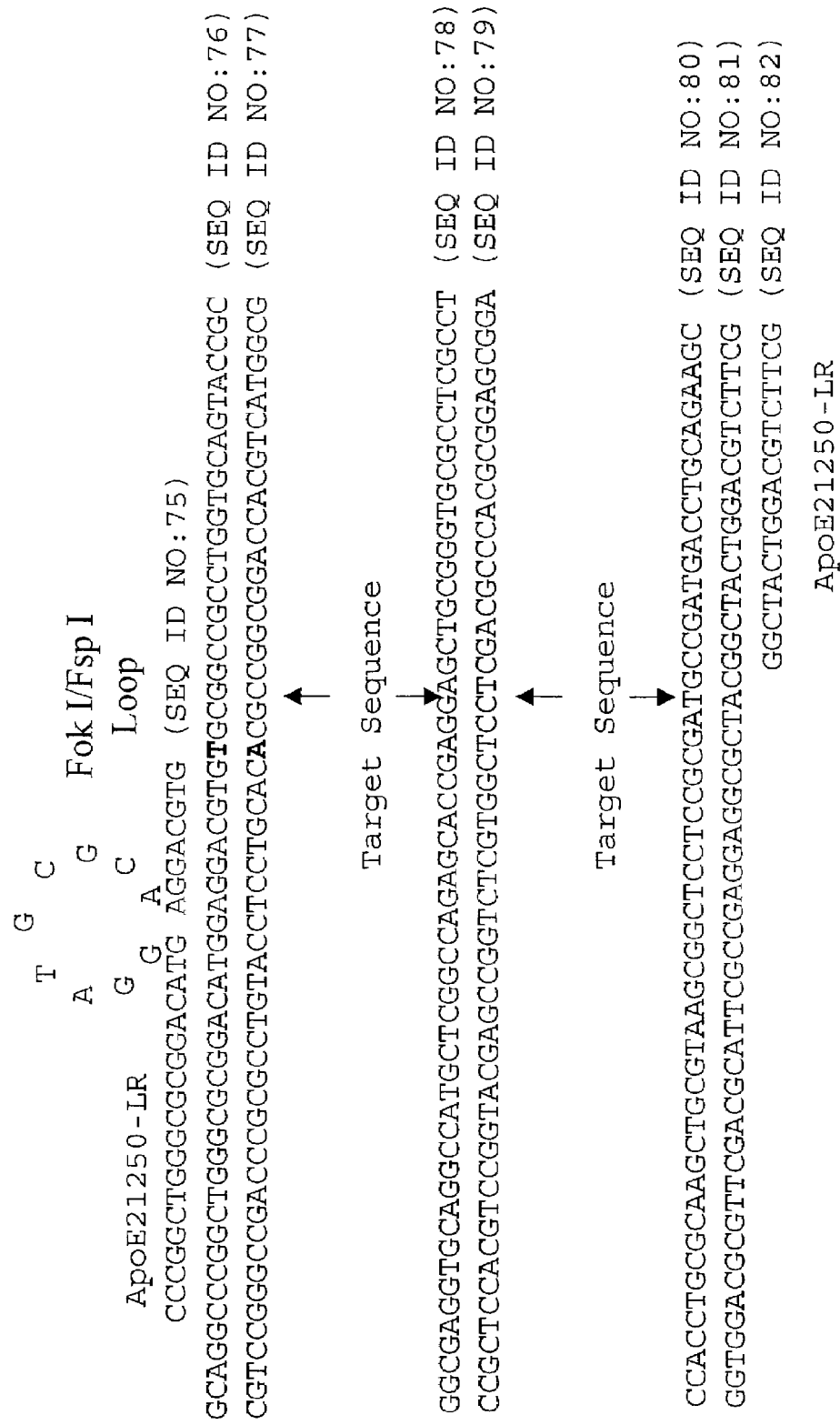

FIG. 34. Genotyping of the variance at genomic site 21250 in the ApoE gene. At this genomic site a T:C variance in the DNA results in a cysteine to arginine amino acid change in amino acid position 176 in the ApoE protein. Two primers were designed to both amplify the target region of the ApoE gene and to introduce two restriction enzyme sites (Fok I, Fsp I) into the amplicon adjacent to the site of variance. This figure depicts the sequence of the primers and the target DNA. The Apo21250-LFR primer is the loop primer which contains the restriction enzyme recognition sites and the ApoE21250-LR primer is the reverse primer used in the PCR amplification process. The polymorphic nucleotide is shown underlined.

FIG. 35. The sequence of the amplicon for both the T allele and the C allele of the ApoE gene following amplification is shown. The polymorphic site is shown as an underlined T or C.

Figure 36:
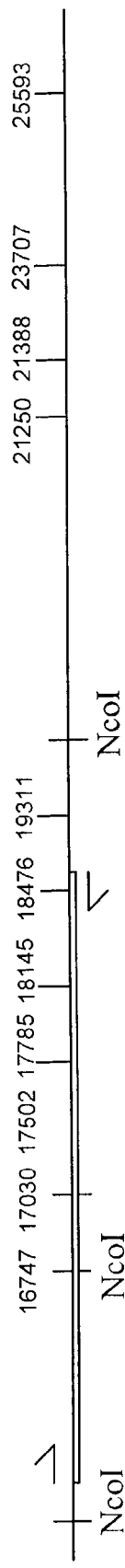

FIG. 36. The NcoI restriction endonuclease digestion sites of the ApoE gene is shown. There are three NcoI sites, two outer sites and one site containing the 16747 site of polymorphism as described in Example 4. In addition, two sets of primers are shown, the primary set (1°) are located within the outer most NcoI sites, and could amplify the DNA sequence through the 16747 site. The secondary (2°) primer pairs are shown because they are used to amplify short sequences around the 16747 site and the 17030 site.

Figure 37A:
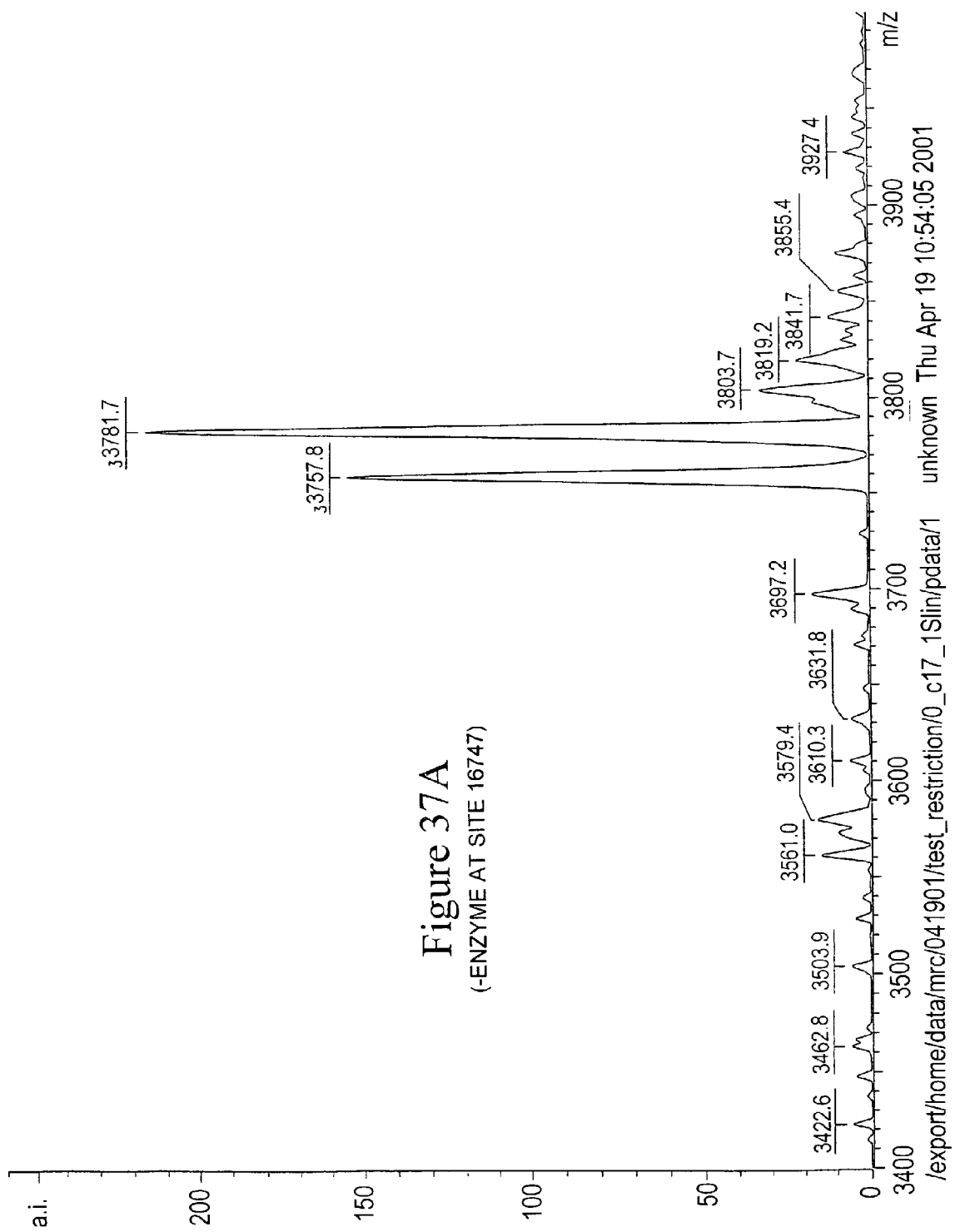
Figure 37B:

FIG. 37A-B. The spectra of absolute intensity versus mass is shown for the amplicons samples without enzyme (FIG. 37A) or with NcoI digestion (FIG. 37B) of the fragments containing the 16747 polymorphic site.

Figure 38A:
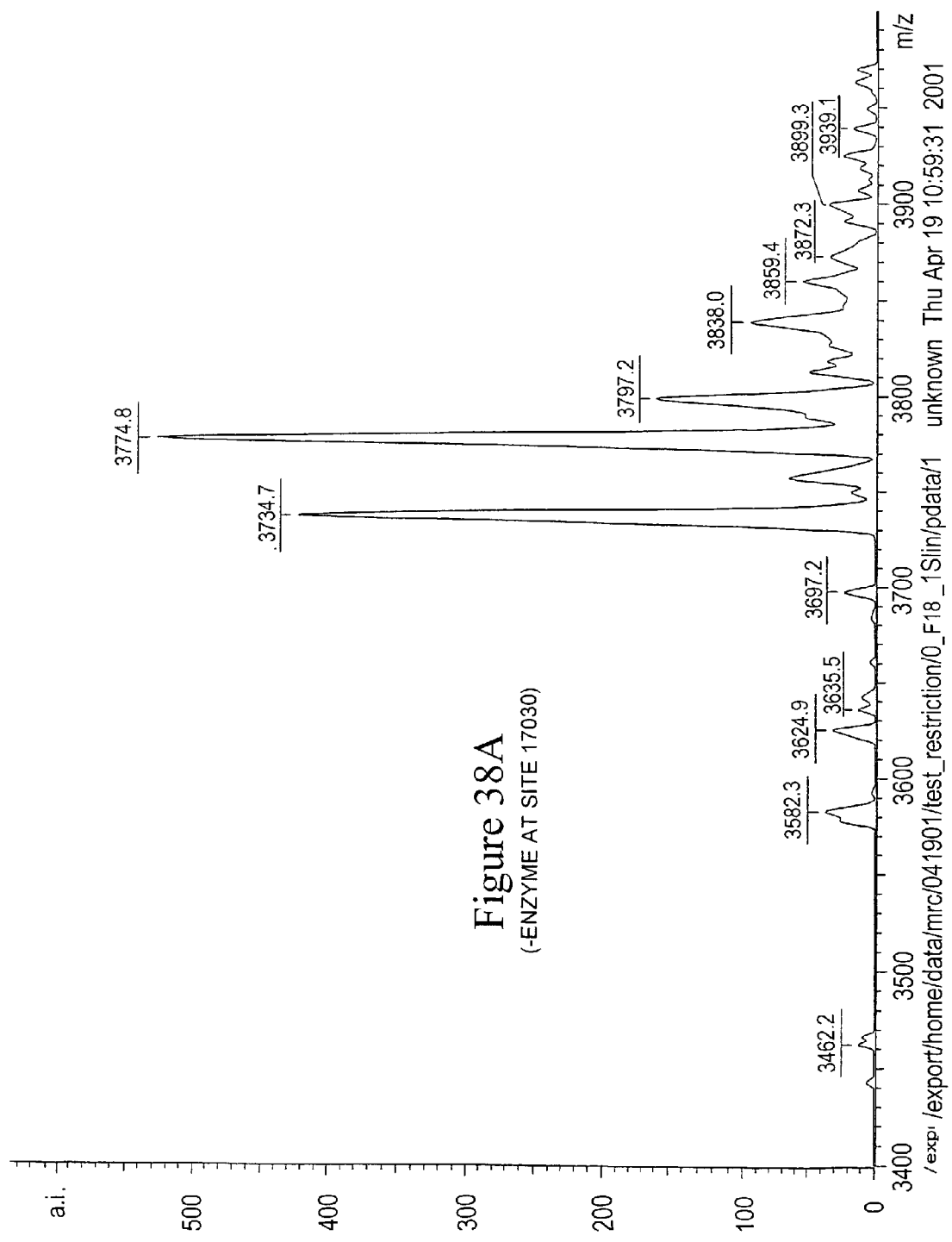
Figure 38B:
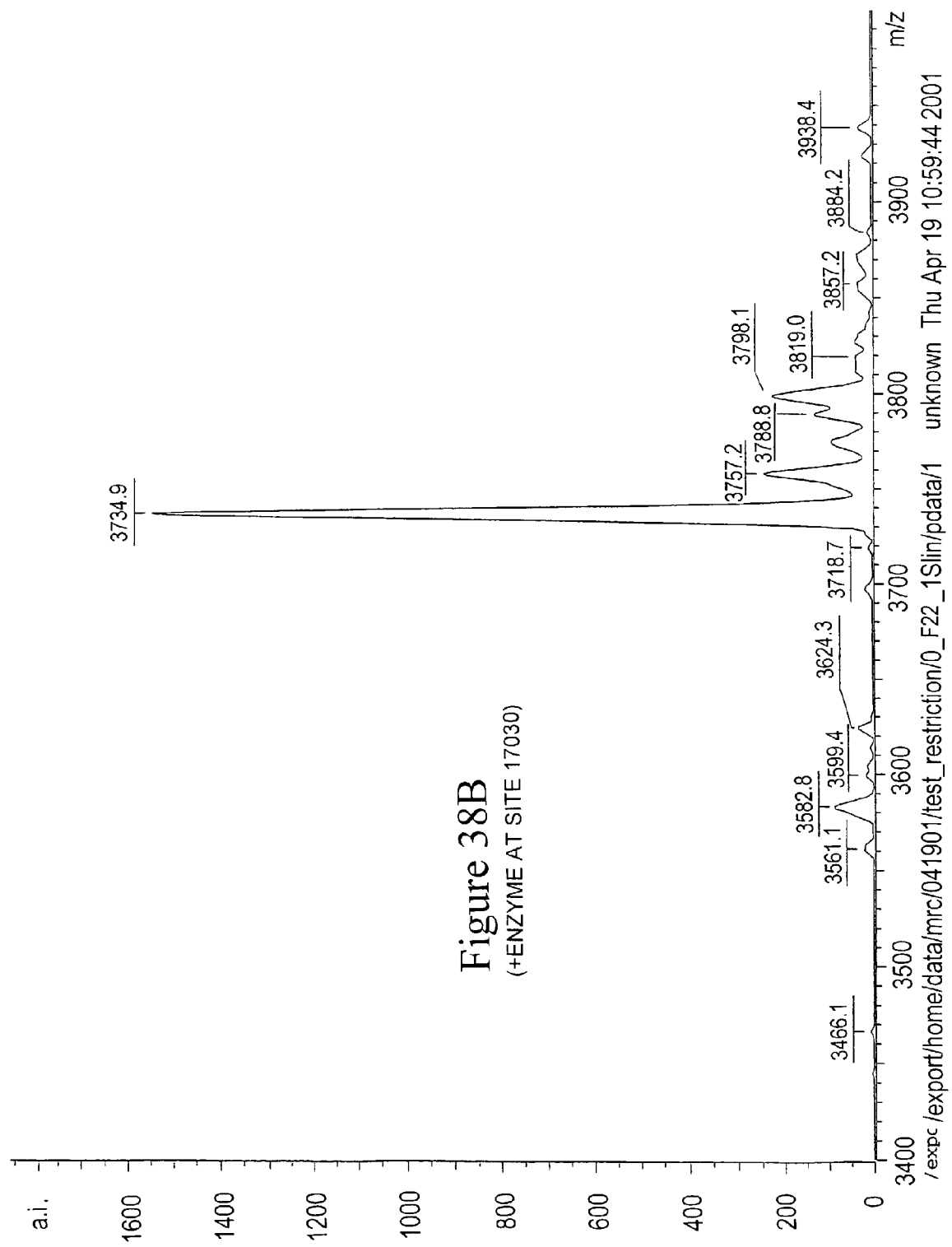

FIG. 38A-B. The spectra of absolute intensity versus mass is shown for the amplicons samples without enzyme(FIG. 38A) or with NcoI digestion (FIG. 38B) of the fragments containing the 17030 polymorphic site.

Figure 39:
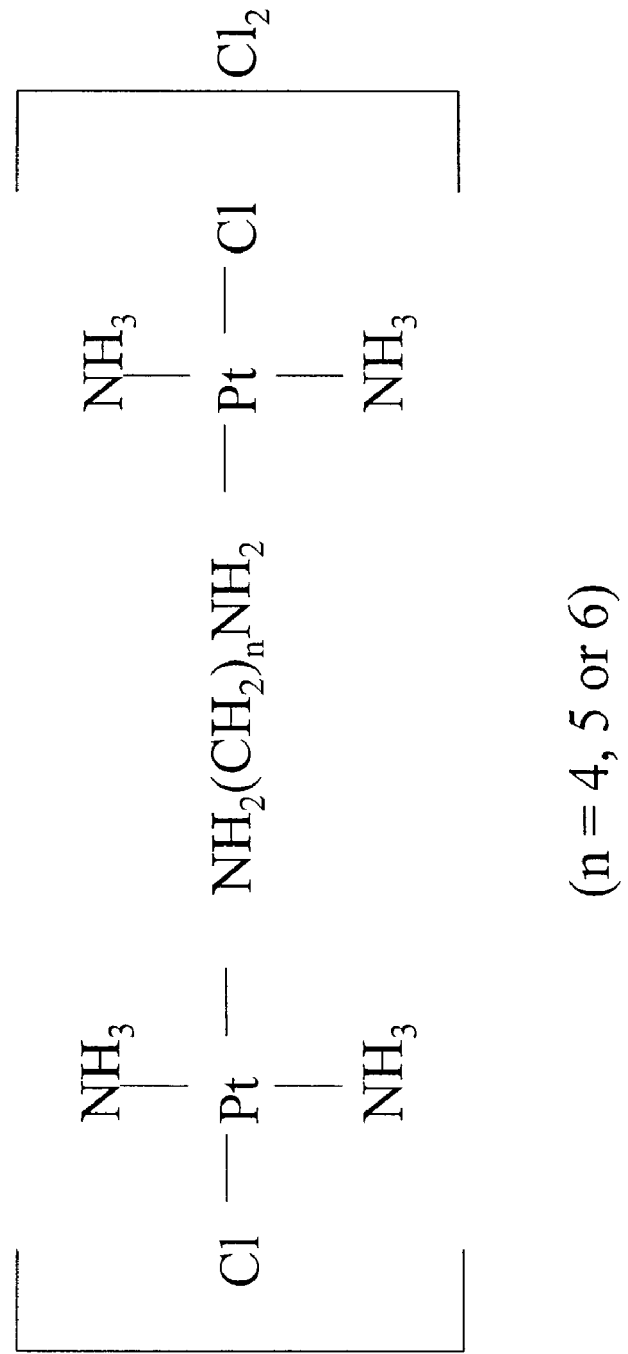

FIG. 39. Proposed binuclear platinum (II) complexes are shown. As depicted, the intervening carbon can be 4, 5 or 6 methyl groups. Use of these proposed molecules for crosslinking oligonucleotides to DNA molecules is as described in the Detailed Description.

FIG. 40. A (thio) containing oligonucleotide is designed which is complementary to a region of the target DNA containing a known polymorphism (allele 1). Binuclear platinum (II) (PtII) is coupled to this oligonucleotide through the thio group using the procedure described by Gruff et al. or a similar method. A second oligonucleotide without the thio group is also designed. This oligonucleotide has the same sequence as the thio oligonucleotide except at the site of the variance where it has the base corresponding to the other allele (allele 2). These two oligonucleotides would be mixed with a sample which is heterozygous at the targeted site of variance and allowed to hybridize. The PtII coupled oligonucleotide would hybridize to the allele to which it is perfectly matched (allele 1) and the other oligonucleotide would hybridize to the other allele to which it is perfectly matched (allele 2). The PtII coupled oligonucleotide would then be chemically crosslinked to the target DNA. This crosslinking would protect this allele of the target DNA from degradation by exonucleases.

FIG. 41. Protection of the crosslinked DNA from exonucleases which are known to degrade single and double stranded DNA from a specific end and which are known to be blocked by PtII adducts is depicted for a crosslinked (allele 1) or duplex DNA sample (allele 2). Incubation of the sample DNA with exonuclease removes all or most of the DNA which does not have the PtII adduct is shown (allele 2), whereas incubation of the crosslinked complex with an exonuclease results in partial digestion of the DNA (allele 1).

Figure 42:
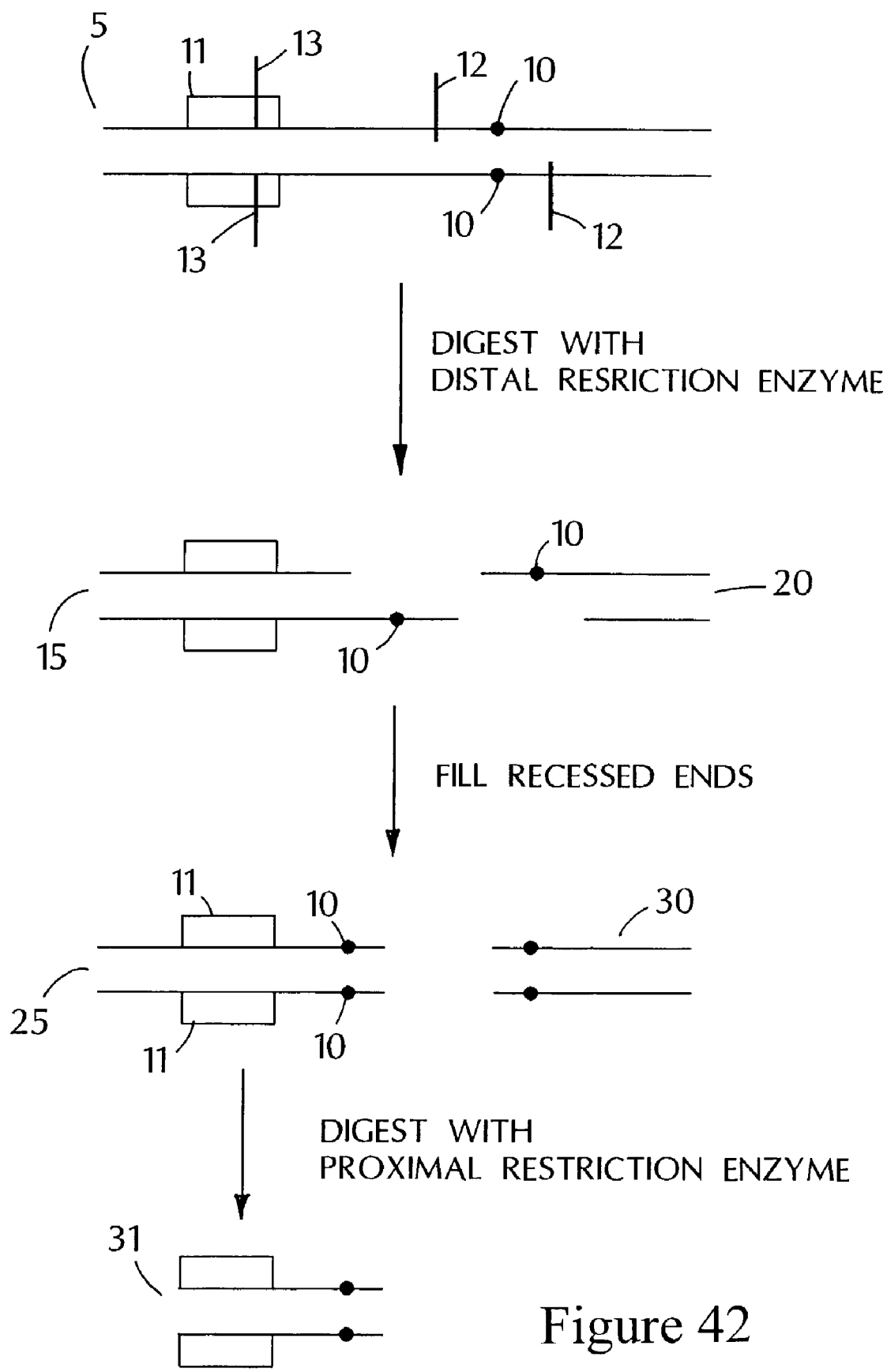

FIG. 42. A method for restriction enzyme genotyping entailing the filling of a recessed end is depicted.

Figure 43:
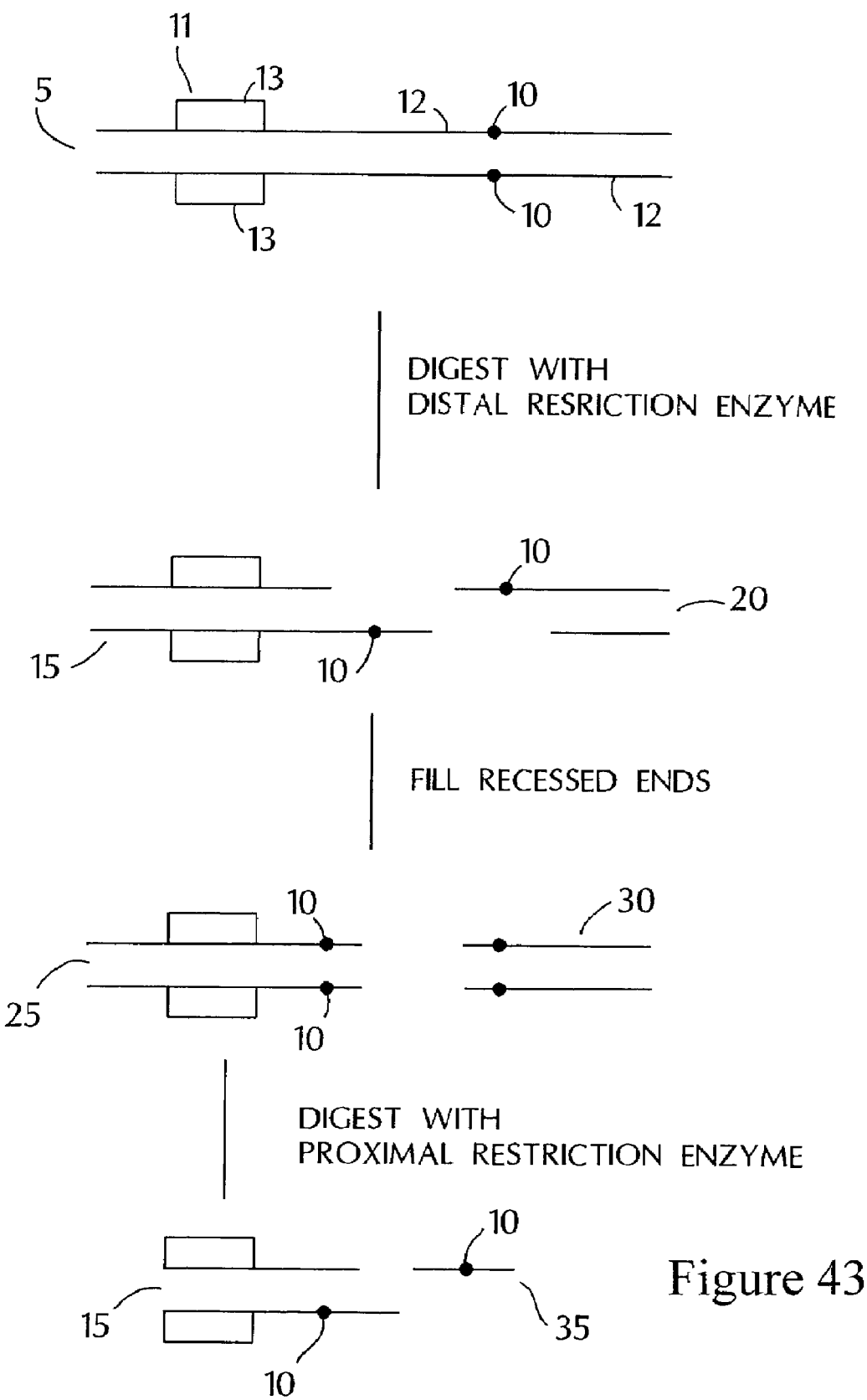

FIG. 43. A method for restriction enzyme genotyping entailing the filling of a recessed end and simultaneous cleavage of the filled end is depicted.

DETAILED DESCRIPTION

The present application provides methods for determining a haplotype or a genotype present in a nucleic acid sample, e.g., a DNA sample or cDNA sample, preferably drawn from one subject. However, these methods may also be used to determine the population of haplotypes present in a complex mixture, such as may be produced by mixing DNA samples from multiple subjects. The methods described herein are applicable to genetic analysis of any diploid organism. The methods are also useful in the genetic analysis of any polyploid organism in which there are only two unique gene variants. Application of the methods of this invention will provide for improved genetic analysis, enabling advances in medicine, agriculture and animal breeding. For example, by improving the accuracy of genetic tests for diagnosing predisposition to disease, or for predicting response to medical therapy, it will be possible to make safer and more efficient use of appropriate preventive or therapeutic measures in patients. The methods of this invention also provide for improved genetic analysis in a variety of basic research problems, including the identification of alleles of human genes, e.g., ApoE, that are associated with disease risk or disease prognosis.

The methods of this application also provide for more efficient use of medical resources, and therefore are also of use to organizations that pay for health care, such as managed care organizations, health insurance companies and the federal government. The application provides methods for performing genotyping and haplotyping tests on a human subject to formulate or assist in the formulation of a diagnosis, a prognosis or the selection of an optimal treatment method based on a genotype or haplotype, e.g., an ApoE genotype or haplotype. These methods are applicable to patients with a disease or disorder, e.g., a disease or disorder affecting the cardiovascular or nervous systems, as well as patients with any disease or disorder that is affected by lipid metabolism. The haplotyping methods of this invention are equally applicable to apparently normal subjects in whom predisposition to a disease or disorder may be discovered as a result of a genotyping or haplotyping test described herein. Application of the methods of this invention will provide for improved medical care by, for example, allowing early implementation of preventive measures in patients at risk of diseases such as atherosclerosis, dementia, Parkinson's disease, Huntington's disease or other organic or vascular neurodegenerative process; or optimal selection of therapy for patients with diseases or conditions such as hyperlipidemia, cardiovascular disease (including coronary heart disease as well as peripheral or central nervous system atherosclerosis), neurological diseases including but not limited to Alzheimer's disease, stroke, head or brain trauma, amyotrophic lateral sclerosis, and psychiatric diseases such as psychosis, bipolar disease and depression.

I. Genotyping Methods

I.A. Mass Spectrometric Analysis of Small DNA Fragments Generated by Restriction of Amplification Products Engineered with Restriction Sites The present invention features a genotyping method based on mass spectrometric analysis of small DNA fragment(s) (preferably <25 bases) containing a polymorphic site. The method entails using primers and amplification to introduce two restriction endonuclease recognition sites adjacent to a polymorphic site. The restriction endonuclease cleavage sites in the amplification product are arranged so that digestion with the restriction endonucleases produces a small double stranded DNA fragment containing the polymorphic site. The two oligonulceotides making up the double stranded DNA fragment, at least one of which contains the polymorphic site, are small enough to be analyzed by mass spectrometry in a manner that can distinguish an oligonucleotide containing a particular nucleotide at the polymorphic site from an otherwise identical oligonucleotide containing a different nucleotide at the polymorphic site.

Use of a Primer and PCR to Introduce Restriction Endonuclease Recognition Sites and Cleavage of the Amplicon The first step of the method entails PCR amplification using primers that flank the polymorphic site of interest. The 3' end of the first primer must lie within several, e.g., 16, nucleotides of the polymorphic site in the template DNA. The second primer may lie at any distance from the first primer on the opposite side of the polymorphic site. One of the primers is designed so that it introduces two restriction endonuclease recognition sites into the amplified product during the amplification process. The two restriction endonuclease restriction sites are arranged so that can cleavage occur on both sides of the polymorphic site. Thus, as explained in greater detail below, one of the two restriction endonucleases is a Type II nuclease that cleaves at a location outside of its recognition site.

Preferably the two restriction endonuclease recognition sites are introduced into the amplicon by inserting a sequence of 15 or fewer nucleotides into the first primer. This short inserted sequence in general does not base pair to the template strand, but rather loops out when the primer is bound to template. However, when the complementary strand is copied by the polymerase during amplification, the inserted sequence is incorporated into the amplicon. Incubation of the resulting amplification product with the appropriate restriction endonucleases results in the excision of a small (generally <20 bases) double stranded DNA fragment that contains the polymorphic site. The small size of the fragment allows it to be easily and robustly analyzed by mass spectrometry to determine the identity of the nucleotide at the polymorphic site.

The primer used to introduce with the restriction endonuclease recognition sites can be designed so that the required restriction enzymes: (i) are easy to produce, or inexpensive to obtain commercially, (ii) cleave efficiently in the same buffer, i.e., all potential cleavable amplicons are fully cleaved in one step, (iii) cleave multiple different amplicons, so as to facilitate multiplex analysis (that is, the analysis of two or more samples simultaneously).

The small size of the double stranded DNA fragment generated by digestion of the amplicon with the two restriction endonucleases allows the two single stranded oligonucleotides that make up the fragment to be efficiently analyzed via mass spectrometry to determine the identity of the nucleotide at a polymorphic site. Thus, the single stranded oligonucleotides making up the double stranded DNA fragment are preferably between 900 Daltons (3-mer) and about 9,000 Daltons (30-mer), preferably between 900 and 7500 Daltons (25-mer), more preferably between 900 and 6000 Daltons (20-mer), or between 900 and 4500 Daltons (15-mer). However, as mass spectrometry technology progresses it will become possible to genotype DNA fragments outside this currently recommended range, so greater ranges are also included in preferred embodiments, e.g., 900 to 9600 Daltons (32-mer), or 900 to 10500 Daltons (35-mer), or 900 to 12000 Daltons (40-mer). Thus, the methods described herein are tailored to the capabilities of presently available commercial mass spectrometers, however, one skilled in the art will recognize that these methods can be adapted with ease to improvements in mass spectrometry equipment, including, for example, MALDI instruments with improved desorption, delayed extraction or detection devices.

The methods described herein entail use of a single modified primer in a primer extension or amplification reaction. The modified primer is designed so as to introduce at least two restriction endonuclease recognition sites into the sequence of the primer extension product, which is preferably an amplicon in an amplification reaction. The restriction endonuclease recognition sites are designed such that the resulting cleavage sites flank the polymorphic base to be genotyped. Accordingly, digestion of the amplicon with the restriction endonucleases will liberate a small double stranded DNA fragment containing the polymorphic site. If the natural sequence adjacent to the polymorphic site (either on the 5' side or the 3' side) already contains a restriction endonuclease recognition site then it may be possible to design the modified primer so that one of the two restriction cleavage sites need not be engineered into the primer (see below), but rather occurs naturally in the amplicon. In this event only one restriction site has to be engineered into the primer.

One embodiment of the invention involves the introduction of two restriction endonuclease recognition sites into the sequence of an amplicon in the vicinity of a polymorphic site during amplification. The restriction enzyme sites are introduced during the amplification process by designing a primer that contains recognition sites for two restriction endonucleases, Various methods for designing such primers are described below, but any strategy in which at least two cleavable sites are introduced into an amplicon using a single primer would be effective for this method. Exemplary embodiments of these methods are illustrated in FIGS. 1-10.

One method involves the selected alteration of bases in the primer (relative to what they would be if the primer were to base pair perfectly with the natural sequence) so as to introduce restriction enzyme sites. An example of such a primer, incorporating recognition sites for the restriction enzymes Fok I and Fsp I, is shown in FIG. 1. The recognition sites and cleavage sites for Fok I and Fsp I are depicted in FIG. 2. Fok I is a type IIS restriction enzyme which cleaves DNA outside the recognition sequence—at a distance of 9 bases 3' to the recognition site on one strand and 13 bases away from the recognition site on the opposite strand, leaving a four base overhang (protruding 5' end) (FIG. 2). By designing the primer so that the Fok I recognition site is located within 12 bases or less of the 3' end of the primer one can assure that the Fok I cleavage will cleave outside the primer sequence and incorporate the polymorphic nucleotide for analysis. Fsp I is a useful enzyme to pair with Fok I because its recognition site overlaps that of Fok I, allowing the two sites to be partially combined (FIG. 3). This reduces the number of bases that are be introduced into the modified primer, making the primer design simpler and more likely to work for amplification.

A primer is designed (primer R in FIG. 1) in which some of the bases are changed from the target sequence. The bases that are changed are indicated by arrows above primer R. This primer along with a second (normal) amplification primer designed in the reverse direction are used to amplify the target sequence. The polymorphic base (T in the forward direction, A in the reverse direction) is indicated in italics and by an arrow below the target sequence. During the amplification, the two restriction endonuclease recognition sites are incorporated into the sequence of the amplicon. The incorporated Fok I/Fsp I site is surrounded by the box in FIG. 1. When the amplicon is incubated with Fok I and Fsp I, cleavage occurs at the both sites releasing an 8-mer oligonucleotide and a 12-mer oligonucleotide. The 12-mer contains the polymorphic base (A). These oligonucleotides are then analyzed by the mass spectrometer to determine the base identity at the polymorphic site in the 12-mer.

The second method of primer design involves the use of a primer with an internal loop.

The primer is designed (primer R1, FIG. 4) such that one of the bases corresponding to the native sequence is removed and replaced with a loop. In this case the G/C indicated by the arrow below the target sequence (FIG. 4) is replaced with the recognition sequence for Fok I and Fsp I. Upon hybridization to the DNA template, the primer will form a loop structure. This loop will be incorporated into the amplicon during the amplification process, thereby introducing the Fok I and Fsp I restriction endonuclease recognition sites (indicated by the box in FIG. 4). When the amplicon is incubated with Fok I and Fsp I, cleavage will occur releasing an 8-mer and a 12-mer.

As in the example in FIG. 1, the 12-mer contains the polymorphic base and can be analyzed by mass spectrometry to identify the base at the polymoporphic site.

Both strategies result in an amplicon which can be cleaved with Fok I and Fsp I to liberate small oligonucleotides, in which the polymorphic nucleotide is contained in one of the fragments. The loop strategy (FIG. 4) is the preferred method because primer design is easier and more flexible.

There are other possible restriction enzyme combinations that also meet the requirements for the generation of appropriate DNA fragments for genotyping by mass spectrometry. Two other examples are outlined in FIG. 5 (BsgI/PvuII) and FIG. 6 (PvuII/FokI). The only requirements for primer design are that the restriction enzyme site(s) will generate a fragment(s) that is of an appropriate size to be easily analyzed by a mass spectrometer or some other suitable means, and contain the polymorphic site. It is also a requirement that the introduction of the restriction endonuclease recognition site(s) into the primer does not eliminate the ability of the primer to generate an amplicon for the correct region of the target DNA. It does not matter whether the cleavage site for both enzymes generates a staggered 5' overhang, 3' overhang, or a blunt end. It also does not matter whether after cleavage the polymorphic site is within a double stranded portion of the released small double stranded fragment or within an overhang of the released small double stranded molecule. Indeed, where the polymorphic site is within an overhang of the released small double stranded DNA molecule, there are a number of techniques that can be used to facilitated identification of the nucleotide present at the polymorphic site.

Thus, the present invention includes a method for determining the nucleotide present at a selected polymorphic site in a target nucleic acid molecule by: a) amplifying a portion of the target nucleic acid molecule comprising the selected polymorphic site using a first primer and a second primer, the second primer containing a recognition site for a first restriction enzyme and a recognition site for a second restriction enzyme, to generate amplification product containing a recognition site for the first restriction enzyme and a recognition site for the second restriction enzyme such that digestion of the amplification product with the first restriction enzyme and the second restriction enzyme generates a nucleic acid fragment containing the selected polymorphic site; b) digesting the amplification product with the first restriction enzyme and the second restriction enzyme to generate a nucleic acid fragment containing the selected polymorphic site; and c) analyzing the nucleic acid fragment to identify the nucleotide present at the selected polymorphic site. As discussed above, the second primer can include least one nucleotide sequence that is not present in the target nucleic acid molecule (e.g, a nucleotodie sequence corresponding to the recognition site for a restriction enzyme). The second primer can include 5' nucleotide sequence that is complementary to a first portion of the target nucleic acid molecule, a 3' nucleotide sequence that is complementary to a second portion of the target nucleic acid molecule, and a nucleotide sequence that is not complementary to the target nucleic acid molecule. The first restriction enzyme can be a type IIS restriction enzyme.

Once the diagnostic fragments have been generated they can be partially or completely purified and then analyzed, e.g., by subjecting the nucleic acid fragment to mass spectrometry.

Modifications Entailing the Filling of Recessed Ends Using Modified Nucleotides

When cleavage with the restriction enzymes used to generate the small double stranded DNA fragment containing the polymorphic site produces an overhanging end that contains the polymorphic site, there are number of methods which may be used to improve the sensitivity of polymorphism detection. For example, where a 5' overhanging end contains the polymorphic site, the 3' recessed end can be filled using a nucleotide mixture that includes at least one modified nucleotide that base pairs with at least one of the possible nucleotides present at the polymorphic site and does not include the corresponding natural nucleotide. This will generate fragments differing in mass by more than the natural mass difference of the two polymorphic nucleotides. One or more modified nucleotides can be selected to maximize the differential mass of the filled fragment. This enhancement of the basic method has the advantage of reducing the mass spectrometric resolution required to reliably determine the presence of two alleles vs. one allele, thereby improving the performance of base-calling software and the ease with which a genotyping system can be automated.

In another embodiment a cleavage product in which there is a 5' overhang containing the polymorphic base is created with Fok I and Fsp I as shown in FIG. 4. Following an amplification reaction (in which the Fok I and Fsp I sites have been incorporated into the amplicon—see sequence in box FIG. 7), remaining free nucleotides in the reaction mix are removed using any of a variety of methods known in the art, such as spinning through a size exclusion column such as Sephadex G50 or by incubating with an alkaline phosphatase, e.g., shrimp alkaline phosphatase. The amplicon is then cleaved with the restriction enzyme (Fok I), which generates the 5' overhang that includes the polymorphic base. This recessed end can then be filled in using a nucleotide mixture in which the nucleotide that base pairs with one of the possible nucleotides at the polymorphic site has been replaced by a mass modified nucleotide ($T^{mod}$ in FIG. 7). An example of such a nucleotide is bromo-deoxyuridine (BrdU) which is 64.8 Daltons higher in mass than dTTP. Table 1 lists the masses of the normal nucleotides and BrdU and the mass differences between each of the possible pairs of nucleotides. Using mass modified nucleotides to fill recessed ends results in larger differences in mass between fragments, making analysis, e.g., automated analysis, easier. After filling of the recessed ends of the fragment, digestion with FspI generates a fragment amenable for mass spectrometric analysis and identification of the polymorphism of interest. Resulting DNA fragments can also be analyzed by conventional electrophoretic detection methods. For example, DNA fragments containing mass modified nucleotides would show a different electrophoretic mobility than unmodified fragments.

Another "fill" modification for improving discrimination entails using a labeled, e.g., radioactive or fluorescent, primer for PCR amplification. A 5' labeled primer with two restriction sites arranged as described above is allowed to hybridize to the target DNA forming a hair-pin loop. Subsequent amplification incorporates the restriction sites and the label into the amplicon. The amplicon is digested to release a fragment in which the polymorphic site is within a 5' overhang. The nucleotides used in the PCR reaction are removed and the recessed ends are filled in using a polymerase and a mixture of nucleotides which includes a dideoxynucleotide corresponding to one of the two possible nucleotides at the polymorphic site. The size of the filled products will depend on the presence or absence of the polymorphic nucleotide corresponding to the included dideoxynucleotide. In an alternative embodiment, the primer is not labeled but the dideoxynucleotide is labeled. Alternatively, each polymorphic base dideoxynucleotide is labeled with a uniquely detectable label and the identification of the polymorphic site is based upon presence of one signal and absence of another in the cases of homozygotes or the presence of both signals in the cases of heterozygotes.

Methods Entailing the Introduction of Only One Restriction Endonuclease Site

In some circumstances, it may only be necessary to incorporate one restriction enzyme site into the amplicon via the primer. This can be done if the enzyme utilized is capable of making two double strand cuts, one on the 5' side and one on the 3' side of the recognition site. An example of such an enzyme is Bcg I, which has a recognition site of 12/10(N)CGA(N)$_6$TGC(N)12/10 (FIG. 8). The arrows designate the sites of cleavage on both strands. Preferred enzymes for this method are those that are capable of cleaving in a similar fashion but which would generate smaller fragments.

Another modification of the basic method is to use a third restriction enzyme that cleaves only one of the two alleles, such that the presence of a polymorphic site yields shorter fragments than are observed in the absence of the polymorphic site. Such a modification is not universally applicable because not all polymorphisms alter restriction sites. However, this limitation can be partially addressed by including part of the restriction enzyme recognition site in the primer. For example, an interrupted palindrome recognition site like Mwo I (GCNNNNN/NNGC) can be positioned such that the first GC is in the primer while the second GC includes the polymorphic nucleotide. Only the allele corresponding to GC at the second site will be cleaved. Use of such restriction endonucleases simplifies the sequence requirements at and about the polymorphic site (in this example all that is required is that one allele at the polymorphic site include the dinucleotide GC), thereby increasing the number of polymorphic sites that can be analyzed in this way.

In another embodiment, restriction enzymes that only nick the DNA (instead of causing a double strand break) are used. One such enzyme is N.BstNB I whose recognition site is GAGTCNNNNANN. The fragments generated by this scheme are outlined in FIG. 9. This strategy will generate only one oligonucleotide (10-mer in this case) instead of two, making analysis even more amenable to automation. Another strategy involves using one restriction enzyme and a primer which contains a modification allowing the primer to be cleaved. An example of such a scheme is outlined in FIG. 10. One of the deoxyribonucleosides in the primer is substituted with a ribonucleoside (rG). The ribonucleoside is base-labile and will cause a break in the backbone of the DNA at that site when the DNA is incubated in base. In this example, the amplicon is incubated with the restriction enzyme (Fok I) causing a double-strand break. The amplicon is then incubated in the presence of base causing a break between the ribonucleotide G and the 3' deoxyribonucleotide T, releasing a 7 base fragment which can easily analyzed by mass spectrometry.

Methods Entailing Filling of Recessed Ends with Standard Nucleotides

As noted above, certain methods can be used to increase the sensitivity of polymorphism detection in those situations where cleavage of the amplicon generates a fragment having an overhanging end that includes the polymorphic site. For example, the recessed ends can be filled with a standard mixture of standard nucleotides. When this is done, both oligonucleotides that make up the double stranded DNA fragment released by restriction endonuclease cleavage include a nucleotide corresponding to the polymorphic site. As a result, both oligonucleotides are now informative.

This is approach is depicted in FIG. 42 in which the restriction enzyme recognition site sequences introduced by the modified primer are represented by an open box and the polymorphic site is represented by a circle. The amplicon prior to digestion 5 includes the polymorphic site 10 and the restriction enzyme recognition sites 11 introduced by the primer, a distal restriction enzyme cleavage site 12 and a proximal restriction enzyme cleavage site 13. For these cleavage sites, the point of cleavage on each strand is indicated. Digestion at the distal restriction enzyme cleavage site 12 produces two fragments 15 and 20 both of which include the polymorphic site within a 5' overhang. The recessed ends are filled to generate two blunt ended molecules 25 and 30. Blunt ended molecule 25 includes the restriction enzyme recognition sites 11 and thus can be cleaved at the proximal restriction enzyme cleavage site 13. This yields a small, double stranded DNA molecule 31 composed of two oligonucleotides, both of which include the polymorphic nucleotide. These oligonucleotides are of a suitable size for analysis by mass spectrometry. In other embodiments the amplicon can be digested with both restriction enzymes prior to the filling of the recessed ends.

Thus, the present invention also includes a method for determining the nucleotide present at a selected polymorphic site in a target nucleic acid molecule by: a) amplifying a portion of the target nucleic acid molecule comprising the selected polymorphic site using a first primer and a second primer, the second primer containing a recognition site for a first restriction enzyme and a recognition site for a second restriction enzyme, to generate amplification product containing a recognition site for the first restriction enzyme and a recognition site for the second restriction enzyme such that digestion of the amplification product with the first restriction enzyme and the second restriction enzyme generates a nucleic acid fragment containing the selected polymorphic site; b) digesting the amplification product with the first restriction enzyme and the second restriction enzyme to generate a nucleic acid fragment containing the selected polymorphic site; c) extending the 3' ends of some or all of the extension products, e.g., the DNA fragment containing the polymorphic site to create a blunt ended molecule; and d) analyzing the nucleic acid fragment to identify the nucleotide present at the selected polymorphic site. The ends can be extend using standard or mass modified nucleotides.

In an alternative approach, the amplicon is again first digested with the restriction enzyme that cleaves on the distal side of the polymorphic site relative to the primer used to introduce the restriction endonuclease recognition sites, generating a double stranded fragment having a 5' overhang containing the polymorphic site. The digestion reaction mixture includes polymerase and a standard nucleotide mixture. In this manner, the recessed 3' end corresponding to the 5' overhang is filled and can be cleaved again, each time releasing a very small fragment (corresponding to the filled 3' end) that is diagnostic for the polymorphic site.

This is alternative approach is depicted in FIG. 43 in which the restriction enzyme recognition site sequences introduced by the modified primer are represented by an open box and the polymorphic site is represented by a circle. The amplicon prior to digestion 5 includes the polymorphic site 10 and the restriction enzyme recognition sites 11 introduced by the primer, a distal restriction enzyme cleavage site 12 and a proximal restriction enzyme cleavage site 13. For these cleavage sites, the point of cleavage on each strand is indicated. Digestion at the distal restriction enzyme cleavage site 12 produces two fragments 15 and 20 both of which include the polymorphic site within a 5' overhang. The recessed ends are filled to generate two blunt ended molecules 25 and 30. Blunted ended molecule 25 includes the restriction enzyme recognition sites 13 and thus can be cleaved by the distal restriction enzyme, which is still present in the reaction mixture regenerating the fragment 15 with a 5' overhang containing the polymorphic site 10 and also generating a small oligonulceotide 35 containing the polymorphic site 10 that is diagnostic for the polymorphic nucleotide. Since this reaction can, under the proper circumstances, go through many cycles, a considerable amount of the small diagnostic oligonucleotide can be generated.

Thus, the present invention further includes a method for determining the nucleotide present at a selected polymorphic site in a target nucleic acid molecule by: a) amplifying a portion of the target nucleic acid molecule comprising the selected polymorphic site using a first primer and a second primer, the second primer containing a recognition site for a first restriction enzyme and a recognition site for a second restriction enzyme, to generate amplification product containing a recognition site for the first restriction enzyme and a recognition site for the second restriction enzyme such that digestion of the amplification product with the first restriction enzyme and the second restriction enzyme generates a nucleic acid fragment containing the selected polymorphic site; b) digesting the amplification product with the first restriction enzyme and the second restriction enzyme to generate a nucleic acid fragment containing the selected polymorphic site; c) extending the 3' ends of some or all of the extension products, e.g., the DNA fragment containing the polymorphic site to create a blunt ended molecule in the presence of the first restriction enzyme or the second restriction enzyme or both to cleave the extended 3' ends so as to generate a fragment containing the polymorphic nucleotide; and d) analyzing the nucleic acid fragment containing the polymorphic nucleotide to identify the nucleotide present at the selected polymorphic site. The ends can be extend using standard or mass modified nucleotides.

II. Haplotyping Methods

II.A. Allele Enrichment Methods

One type of haplotyping method involves two, optionally three basic steps: (i) optionally genotyping a DNA sample (containing two alleles) of a subject to identify two or more polymorphisms in a selected gene; (ii) enriching for one of two alleles of the selected gene by a method not requiring amplification of DNA, e.g., enriching for one allele to a ratio of at least 1.5:1 based on a starting ratio of 1:1; and (iii) genotyping the enriched allele to determine the genotype of the two or more polymorphisms in the enriched allele. Genotyping methods are known in the art and/or are disclosed herein. Several techniques for enriching for one of two alleles (step ii) can be used in the haplotyping methods. Allele specific enrichment by allele capture is described in section II.A.1., below. Allele enrichment by cross-linking followed by exonuclease digestion is described in section II.A.2., below. Allele enrichment by allele specific endonuclease restriction followed by size separation or exonuclease digestion is described in section II.A.3., below. Allele enrichment by allele specific endonuclease restriction followed by amplification is described in section II.A.4., below. Allele enrichment by allele specific amplification using hairpin loop primers is described in section II.A.5., below.

The goal of allele selection methods is to physically fractionate a genomic DNA sample (the starting material) so as to obtain a population of molecules enriched for one allele of the DNA segment or segments to be analyzed. The details of the procedure depend on the polymorphic nucleotide(s) that provide the basis for allele enrichment and the immediate flanking sequence upstream and/or downstream of the polymorphic site. As explained below, different types of sequence polymorphisms lend themselves to different types of allele enrichment methods.

II.A.1. Allele Specific enrichment by Capture

It is possible to capture DNA fragments in an allele specific manner by using DNA binding molecules, e.g., proteins, nucleic acids, peptide nucleic acids (PNAs), or polyamides, that discriminate single base differences. Different types of DNA binding molecules, e.g., protein and nucleic acid affinity reagents, are shown in FIG. 11. The DNA binding molecule, e.g., protein or nucleic acid, that binds to one allele can subsequently be substantially isolated from the nucleic acid mixture by methods known in the art, such as by directly or indirectly (e.g., through another molecule) coupling the DNA binding molecule/allele complex to a solid support, e.g., to streptavidin or antibody coated beads.

Once a polymorphic site is selected for allele enrichment by capture, enrichment can include the following steps: (a) preparing DNA fragments for allele enrichment; (b) contacting the DNA fragments with a molecule that binds DNA in a sequence specific manner (hereafter referred to as the 'DNA binding molecule') such that one allele of the target DNA segment will be bound and the other will not be bound to a significant extent; (c) allowing a complex to form between the DNA fragments and the allele specific DNA binding molecule under conditions optimized for allele selective binding; (d) substantially isolating at least a portion of the complex from unbound nucleic acid; and (e) releasing the bound DNA comprising the enriched allele from the DNA binding molecule for subsequent genotyping.

Step (a):

In preparation of DNA fragments for allele enrichment, the condition of the DNA may be controlled in any of several ways: DNA concentration, size distribution, state of the DNA ends (blunt, 3' overhang, 5' overhang, specific sequence at the end, etc.), degree of elongation, etc. The DNA is preferably suspended in a buffer that maximizes sequence specific DNA binding. Preferred DNA concentrations for these procedures are in the range from 100 nanograms to 10 micrograms of genomic DNA in a volume of 10 to 1000 microliters. Preferably lower amounts of DNA and lower volumes are used, in order to control costs and to minimize the amount of blood or tissue that must be obtained from a subject to obtain sufficient DNA for a successful haplotyping procedure. The size of the DNA fragments can be controlled to produce a majority of desired fragments which span the DNA segment to be haplotyped. The length of such a segment as at least 2 nucleotides and is preferably from about 10 nucleotides to 1 kb, 3 kb, 5 kb, 10 kb, 20 kb, 50 kb, 100 kb or more. Fragments of the desired size may be produced by random or specific DNA cleavage procedures. Optimal buffer and binding conditions can readily be determined to provide for maximum discrimination between the binding of the allele specific DNA binding molecule to the selected allele versus the non-selected allele. (The binding of the DNA binding molecule to many other irrelevant DNA fragments in the genomic DNA is unavoidable but should not interfere with the enrichment of the selected allele.)

Step (b):

Any of several types of allele specific DNA binding molecules can be used to contact the DNA fragments. Allele specific DNA binding molecules can include proteins, peptides, PNAs, polyamides, oligonucleotides, or small molecules, as well as combinations thereof. These molecules may be designed or selected to bind double stranded (ds) or single stranded (ss) DNA in a sequence specific manner.

Step (c):

Complexes are formed between DNA and the allele specific DNA binding molecule under conditions optimized for binding specificity, e.g., conditions of ionic strength, pH, temperature and time that promote formation of specific complexes between the binding molecules and the DNA. Optimization of allele selective binding conditions will in general be empirical and, in addition to optimization of salt, pH and temperature may include addition of cofactors. Cofactors include molecules known to affect DNA hybridization properties, such as glycerol, spermidine or tetramethyl ammonium chloride (TMAC), as well as molecules that exclude water such as dextran sulphate and polyethylene glycol (PEG). Optimization of temperature may entail use of a temperature gradient, for example ramping temperature from >95° C. down to <40° C. It is no necessary for the binding of the DNA-binding molecule to be completely selective. For example, it may be possible to achieve adequate enrichment (e.g., a 1.5:1 or 2:1 ratio) even when the DNA-binding molecule binds to the non-selected allele to a considerable extent.

Step (d):

After the selected DNA fragment is bound to an allele specific DNA binding molecule, the complex can be substantially isolated from the unbound nucleic acid by any of a number of means known in the art. The complex can be isolated by, e.g., by physical, affinity (including immunological), chromatographic or other means, e.g., by addition of a reagent, such as an antibody, that binds to the allele specific DNA binding molecule (which in turn is bound to DNA fragments, including fragments comprising the selected allele). For example, a reagent, e.g., an antibody, aptamer, streptavidin, avidin, biotin, magnetic particle, nickel coated bead or other ligand that binds to the allele specific DNA binding molecule can be added to the reaction mix. The reagent can form a complex with the DNA binding molecules (and any DNA fragments they are bound to) that facilitates their removal from the unbound DNA fragments. This step can be omitted if the DNA binding molecule already contains or is attached to a ligand or a bead or is otherwise modified in a way that facilitates separation after formation of allele specific complexes. For example, if the DNA binding molecule is a protein that can be modified by appending a polyhistidine tag or an epitope for antibody binding such the hemaglutinin (HA) epitope of influenza virus. Then, nickel coated beads can be used to substantially isolate the DNA binding molecule and the bound allele from the starting mixture. Nickel coated beads can be added to the DNA sample after allele specific binding, or alternatively the sample can be delivered to a nickel column for chromatography, using methods known in the art (e.g., express Ni-NTA Protein Purification System, Qiagen, Inc., Valencia, Calif.). Uncomplexed DNA is first washed through the column, then the DNA bound to the poly-his containing DNA binding protein is eluted with 100-200 mM imidazole using methods known in the art. In this way, DNA fractions enriched for both alleles (bound and unbound) are collected from one procedure. An equivalent procedure for an epitope tagged DNA binding molecule could include addition of antibody coated beads to form {bead-protein-DNA} complexes which could then be removed by a variety of physical methods.

Alternatively the material can be run over an antibody column (using an antibody that binds to the epitope engineered into the allele specific DNA binding molecule). An important consideration in designing and optimizing a specific allele enrichment procedure is that the enrichment conditions are sufficiently mild that they do not cause dissociation of the complex of the DNA binding molecule and selected allele to an extent that there is too little DNA remaining at the end of the procedure for robust DNA amplification and genotyping.

In one embodiment, the complex containing the DNA binding molecule and selected allele (plus or minus an optional third moiety bound to the DNA binding protein) is substantially isolated from the remainder of the DNA sample by physical means. Preferred methods include application of a magnetic field to remove magnetic beads attached to the selected allele via the DNA binding molecule or other moiety; centrifugation (e.g., using a dense bead coated with a ligand like an antibody, nickel, streptavidin or other ligand known in the art, that binds to the DNA binding molecule); or filtration (for example using a filter to arrest beads coated with ligand to which the DNA binding molecule and the attached DNA fragments are bound, while allowing free DNA molecules to pass through), or by affinity methods, such as immunological methods (for example an antibody column that binds the DNA binding molecule which is bound to the selected DNA, or which binds to a ligand which in turn is bound to the DNA binding molecule), or by affinity chromatography (e.g., chromatography over a nickel column if the DNA binding molecule is a protein that has been modified to include a polyhistidine tag, or if the DNA binding molecule is bound to a second molecule that contains such a tag). The separation of the allele specific DNA binding molecule and its bound DNA from the remaining DNA can be accomplished by any of the above or related methods known in the art, many of which are available in kit form from companies such as Qiagen, Novagen, Invitrogen, Stratagene, ProMega, Clontech, Amersham/Pharmacia Biotech, New England Biolabs and others known to those skilled in the art. In general, only a portion of the complexes need to be isolated in order to provide sufficient material for analysis. In addition, the presence of some amount of the non-selected allele is acceptable as long as the enrichment achieved is at least 1.5:1 or 2:1.

Step (e):

Releasing the bound DNA from the substantially purified complexes containing the selected allele can be accomplished by chemical or thermal denaturing conditions (addition of sodium hydroxide, a protease, or boiling) or by mild changes in buffer conditions (salt, cofactors) that reduce the affinity of the DNA binding molecule for the selected allele. Such methods would be known to one of ordinary skill in the art.

The subsequent genotyping of the enriched DNA to determine the haplotype of the selected allele can be accomplished by the genotyping methods described herein or by other genotyping methods known in the art, including chemical cleavage methods (Nucleave, Variagenics, Cambridge, Mass.), primer extension based methods (Orchid, Princeton, N.J.; Sequenom, San Diego, Calif.), cleavase based methods (Third Wave, Madison, Wis.), bead based methods (Luminex, Austin Tex.; Illumina, San Diego, Calif.) miniaturized electrophoresis methods (Kiva Genetics, Mountain View, Calif.) or by DNA sequencing. The key requirement of any genotyping method is that it be sufficiently sensitive to detect the amount of DNA remaining after allele enrichment. If there is a small quantity of DNA after allele enrichment (less than 1 nanogram) then it may be necessary increase the number of PCR cycles, or to perform a two step amplification procedure in order to boost the sensitivity of the genotyping procedure. For example the enriched allele can be subjected to 40 cycles of PCR amplification with a first set of primers, and the product of that PCR can then be subjected to a second round of PCR with two new primers internal to the first set of primers.

In allele capture methods, no DNA amplification procedure is required in any step of the enrichment procedure until the genotyping step at the end, so allele enrichment methods are not constrained by the limitations of amplification procedures such as PCR. As a result, the length of fragments that can be analyzed is, in principle, quite large. In contrast, amplification procedures such as PCR generally become technically difficult above 5-10 kb, and very difficult or impossible above 20 kb, particularly when the template is human genomic DNA or genomic DNA of similar complexity.) It can also be difficult, during amplification (e.g., when using methods such as PCR) to prevent the occurrence of some degree of in vitro allele interchange. That is, during denature-renature cycles of the PCR, primer extension products that have not extended all the way to the reverse primer (i.e., incompletely extended strands) may anneal to a different template strand than the one they originated from—in some cases a template corresponding to a different allele—resulting in synthesis of an in vitro recombinant DNA product that does not correspond to any naturally occurring allele. In contrast, there is no chance of artifactual DNA strand interchange with the allele enrichment methods described herein that do not employ amplification and little risk in those methods entailing amplification of smaller molecules. The strand selection methods described below are also attractive in that the costs of optimizing and carrying out a long range PCR amplification are avoided. Furthermore, the allele enrichment procedures described herein are for the most part generic: the same basic steps can be followed for any DNA fragment.

Sequence Specific DNA Binding Proteins

The major categories of naturally occurring sequence specific DNA binding proteins include zinc finger proteins and helix-turn-helix transcription factors. In addition, proteins that normally act on DNA as a substrate can be made to act as DNA binding proteins either by (i) alterations of the aqueous environment (e.g., removal of ions, substrates or cofactors essential for the enzymatic function of the protein, such as divalent cations) or (ii) by mutagenesis of the protein to disrupt catalytic, but not binding, function. Classes of enzymes that bind to specific dsDNA sequences include restriction endonucleases and DNA methylases. (For a recent review see: Roberts R. J. and D. Macelis. REBASE—restriction enzymes and methylases. *Nucleic Acids Res*. 2000 January 1;28(1):306-7.) Finally, in vitro evolution methods (DNA shuffling, dirty PCR and related methods) can be used to create and select proteins or peptides with novel DNA binding properties. The starting material for such methods can be the DNA sequence of a known DNA binding protein or proteins, which can be mutagenized globally or in specific segments known to affect DNA binding, or can be otherwise permuted and then tested or selected for DNA binding properties. Alternatively the starting material may be genes that encode enzymes for which DNA is a substrate—e.g., restriction enzymes, DNA or RNA polymerases, DNA or RNA helicases, topoisomerases, gyrases or other enzymes. Such experiments might be useful for producing sequence specific ssDNA binding proteins, as well as sequence specific dsDNA binding proteins. For recent descriptions of in vitro evolution methods see: Minshull J. and W. P. Stemmer: Protein evolution by molecular breeding. *Curr Opin Chem Biol*. 1999 June;3(3):284-90; Giver, L., and F. H. Arnold: Combinatorial protein design by in vitro recombination. *Curr Opin Chem Biol*. 1998 June;2(3):335-8; Bogarad and Deem: A hierarchical approach to protein molecular evolution. *Proc Natl Acad Sci USA*. 1999 March 16;96(6):2591-5; Gorse et al. Molecular diversity and its analysis. *Drug Discov Today*. 1999 4(6): 257-264.

Among the classes of DNA binding proteins enumerated above which could be used to select DNA molecules, a preferred class of proteins would have the following properties: (i) any two sequences differing by one nucleotide (or by one nucleotide pair in the case of dsDNA) could be discriminated, not limited by whether or not one version of the sequence is a palindrome, or by any other sequence constraint, (ii) DNA binding proteins can be designed or selected using standard conditions, so that the design or selection of proteins for many different sequence pairs is not onerous. (This requirement arises from the concern that, in order to be able to readily select any given DNA molecule for haplotyping it is desirable to have a large collection of DNA binding proteins, each capable of discriminating a different pair of sequences.) (iii) The affinity of the protein for the selected DNA sequence is sufficient to withstand the physical and/or chemical stresses introduced in the allele enrichment procedure. (iv) The DNA binding molecules are stable enough to remain in native conformation during the allele enrichment procedure, and can be stored for long periods of time. (v) The length of sequence bound by the allele specific DNA binding protein is preferably at least six nucleotides (or nucleotide pairs), more preferably at least 8 nucleotides, and most preferably 9 nucleotides or longer. The longer the recognition sequence, the fewer molecules in the genomic DNA fragment mixture will be bound, and therefore the less 'background' DNA there will be accompanying the enriched allele. In addition to the five foregoing criteria, it may be desirable to make a fusion between the DNA binding protein and a second protein so as to facilitate enrichment of the DNA binding protein. For example, appending an epitope containing protein would allow selection by antibody based methods. Appending six or more histidine residues would allow selection by zinc affinity methods. (DNA binding proteins may also be useful in microscopy-based haplotyping methods described elsewhere in the application, and for that purpose it may be useful to make a fusion with a protein that produces a detectable signal—for example green fluorescent protein.)

Zinc Finger Proteins

Given the above criteria, zinc finger proteins are a preferred class of DNA binding proteins. It is well established that zinc finger proteins can bind to virtually any DNA sequence motif, in particular, they are not limited to pallindromic sequences, as both type II restriction endonucleases and helix-turn-helix transcription factors are. See, for example: Choo and Klug (1994) *Proc. Natl. Acad. Sci. U.S.A.* 91: 11163-11167. Jamieson et al. (1996) A Zinc Finger Directory For High-Affinity DNA Recognition. *Proc. Natl. Acad. Sci. U.S.A.* 93: 12834-12839. Segal et al. (1999) Toward Controlling Gene Expression At Will: Selection And Design Of Zinc Finger Domains Recognizing Each Of The 5'-GNN-3' DNA Target Sequences.

Proc. Natl. Acad. Sci. U.S.A. 96: 2758-2763. Segal and Barbas (2000) Design Of Novel Sequence Specific DNA-Binding Proteins. *Curr. Opin. Chem. Biol.* 4: 34-39. These papers and other work in the field demonstrate that it is possible to generate zinc finger proteins that will bind virtually any DNA sequence from 3 nucleotides up to 18 nucleotides. Further, these studies show that in vitro generated zinc finger proteins are capable of binding specific DNA sequences with low nanomolar or even subnanomolar affinity, and are capable of distinguishing sequences that differ by only one base pair with 10 to 100-fold or even greater differences in affinity. It has also been demonstrated that zinc finger proteins can be modified by fusion with other protein domains that provide detectable labels or attachment domains. For example zinc finger proteins can be fused with jellyfish green fluorescent protein (GFP) for labeling purposes, or fused to polyhistidine at the amino or carboxyl terminus, or fused with an antibody binding domain such as glutathione transferase (GST) or influenza virus hemagglutinin (HA) (for which there are commercially available antisera) for attachment and selection purposes.

Methods for making zinc finger proteins of desired sequence specificity are well known in the art and have recently been adapted to large scale experiments. See, in addition to the above references: Beerli et al. (2000) Positive And Negative Regulation Of Endogenous Genes By Designed Transcription Factors. *Proc Natl Acad Sci USA*. 97: 1495-1500; Beerli et al. (1998) Toward Controlling Gene Expression At Will: Specific Regulation Of The Erbb-2/HER-2 Promoter By Using Polydactyl Zinc Finger Proteins Constructed From Modular Building Blocks. *Proc Natl Acad Sci USA*. 95: 14628-14633.) Methods for using phage display to select zinc finger proteins with desired specificity from large libraries have also been described: Rebar and Pabo (1994) Zinc Finger Phage: Affinity Selection Of Fingers With New DNA-Binding Specificities. *Science.* 263(5147):671-673. Rebar et al. (1996) Phage Display Methods For Selecting Zinc Finger Proteins With Novel DNA-Binding Specificities. *Methods Enzymol.* 267:129-149.) The phage display method offers one way to bind selected alleles to a large complex that can be efficiently removed from a mixture of DNA fragments. Preventing nonspecific DNA binding to intact phage requires careful optimization of blocking conditions.

For the haplotyping methods described in this application the length of the DNA sequence recognized by a zinc finger protein may range from about 3 nucleotides to about 30 or more nucleotides. Preferred zinc finger proteins recognize 6, 9, 12, 15, 18, or 20 nucleotides, with the longer sequences preferred. Preferably, a zinc finger protein has a specificity of at least 2 fold, preferably 5 or 10 fold, and more preferably 100 fold or greater, with respect to all sequences that differ from the selected sequence by one or more nucleotides. Optimal zinc finger proteins must also have a high affinity for the selected sequence. Preferably the dissociation constant of the zinc finger protein for the target DNA sequence is less than 100 nanomolar, preferably less than 50 nanomolar, more preferably less than 10 nanomolar, and most preferably less than 2 nanomolar. Methods for producing zinc finger proteins that meet all the enumerated criteria, e.g., by modifying naturally occurring zinc finger proteins, are routine in the art. For example, because each zinc finger recognizes three nucleotides, one way to make zinc finger proteins that recognize sequences of six nucleotides or longer is to assemble two or more zinc fingers with known binding properties. The use of zinc fingers as modular building blocks has been demonstrated by Barbas and colleagues (see: Proc Natl Acad Sci U S A. 95: 14628-14633, 1998) for nucleotide sequences of the form (GNN)x where G is guanine, N is any of the four nucleotides, and x indicates the number of times the GNN motif is repeated.

A large number of zinc finger proteins exist in nature, and a still larger number have been created in vitro. Any of these known zinc finger proteins may constitute a useful starting point for the construction of a useful set of allele specific DNA binding proteins. The protein Zif268 is the most extensively characterized zinc finger protein, and has the additional advantage that there is relatively little target site overlap between adjacent zinc fingers, making it well suited to the modular construction of zinc finger proteins with desired DNA sequence binding specificity. 2d See, for example: Segal, D. J., et al. *Proc Natl Acad Sci USA*. 96: 2758-2763, 1999. Zif268 is a preferred backbone for production of mutant zinc finger proteins.

Methods for improving the specificity and affinity of binding include random or site directed mutagenesis, selection of phage bearing mutant zinc finger proteins with desired specificity from large libraries of phage, and in vitro evolution methods.

Restriction Endonucleases

Another class of sequence specific DNA binding proteins useful for allele enrichment is restriction endonucleases. There are over 400 commercially available restriction endonucleases, and hundreds more that have been discovered and characterized with respect to their binding specificity. (Roberts and Macelis. *Nucleic Acids Res.* 2000 January 1;28(1): 306-7.) Collectively these enzymes recognize a substantial fraction of all 4, 5 and 6 nucleotide sequences (of which there are 256, 1024 and 4096, respectively). For certain polymorphic nucleotides, the exquisite sequence specificity of these enzymes can be used to selectively bind one allelic DNA fragment that contains the cognate recognition site, while not binding to the DNA fragment corresponding to the other allele, which lacks the cognate site. Restriction endonucleases are highly specific, readily available, and for the most part inexpensive to produce. The identification of polymorphic sites that lie within restriction enzyme binding sequences will become much simpler as the sequence of the human genome is completed, and the generation of restriction maps becomes primarily a computational, rather than an experimental, activity.

In order for restriction endonucleases to be useful as DNA binding proteins their DNA cleaving function must first be neutralized or inactivated. Inactivation can be accomplished in two ways. First, one can add restriction endonucleases to DNA, allow them to bind under conditions that do not permit cleavage, and then remove the DNA-protein complex. The simplest way to prevent restriction enzyme cleavage is to withhold divalent cations from the buffer. Second, one can alter restriction endonucleases so that they still bind DNA but can not cleave it. This can be accomplished by altering the sequence of the gene encoding the restriction endonuclease, using methods known in the art, or it can be accomplished by post-translational modification of the restriction endonuclease, using chemically reactive small molecules.

The first approach—withholding essential cofactors, such as magnesium or manganese—has the advantage that no modification of restriction enzymes or the genes that encode them is necessary. Instead, conditions are determined that permissive for binding but nonpermissive for cleavage.

For some enzymes it may be possible to produce mutant forms that do not require divalent cations for high affinity, specific binding to cognate DNA. For example, mutants of the restriction enzyme Mun I (which binds the sequence CAATTG) have been produced that recognize and bind (but do not restrict) cognate DNA with high specificity and affinity in the absence of magnesium ion. In contrast, wild type Mun I does not exhibit sequence specific DNA binding in the absence of magnesium ion. The amino acid changes in the mutant Mun I enzymes (D83A, E98A) have been proposed to simulate the effect of magnesium ion in conferring specificity. See, for example: Lagunavicius and Siksnys (1997) Site-Directed Mutagenesis Of Putative Active Site Residues Of Mun I Restriction Endonuclease: Replacement Of Catalytically Essential Carbolylate Residues Triggers DNA Binding Specificity. *Biochemistry* 36: 11086-11092.

Structural modification of restriction enzymes to alter their cleaving properties but not their binding properties in the presence of magnesium ion has been also been demonstrated. For example, in studies of the restriction enzyme Eco R I (which binds the sequence GAATTC) it has been demonstrated that DNA sequence recognition and cleaving activity can be dissociated. Studies have shown that mutant Eco RI enzymes with various amino acid substitutions at residues Met137 and Ile197 bind cognate DNA (i.e., 5'-GAATTC-3') with high specificity but cleave with reduced or unmeasurably low activity. See: Ivanenko et al. (1998) Mutational Analysis Of The Function Of Met137 And Ile197, Two Amino Acids Implicated In Sequence Specific DNA Recognition By The Eco RI Endonuclease. *Biol. Chem*. 379: 459-465. Other work has led to the identification of mutant Eco RI proteins that have substantially increased affinity for the cognate binding site, while lacking cleavage activity. For example, the Eco RI mutant Gln111 binds GAATTC with ~1,000 fold higher affinity than wild type enzyme, but has ~10,000 lower rate constant for cleavage. (See: King et al. (1989) Glu-111 Is Required For Activation Of The DNA Cleavage Center Of Ecori Endonuclease *J. Biol. Chem*. 264: 11807-15.) Eco RI Gln111 has been used to image Eco RI sites in linearized 3.2-6.8 kb plasmids using atomic force microscopy, a method that exploits the high binding affinity and negligible cleavage activity of the mutant protein. The Eco RI Gln111 protein is a preferred reagent for the methods of this invention, as a reagent for the selective enrichment of alleles that contain a GAATTC sequence (and consequent depletion of alleles that lack such a sequence). Exemplary conditions for selective binding of Eco RI Gln111 to DNA fragments with cognate sequence may include ~50-100 mM sodium chloride, 10-20 mM magnesium ion (e.g., $MgCl_2$) and pH 7.5 in tris or phosphate buffer. Preferably there is molar equivalence of Eco RI Gln111 and cognate DNA binding sites in the sample (e.g., genomic DNA); more preferably there is a 5, 10, 20 or 50-fold molar excess of enzyme over DNA. Preferred methods for enrichment of the Eco RI bound allele from the non-bound allele include the synthesis of a fusion protein between Eco RI Gln111 and a protein domain that includes an antibody binding site for a commercially available enzyme. Influenza hemagglutinin, beta galactosidase or glutathione S transferase and polyhistidine domains are available as commercial kits for protein purification.

There are several schemes for producing, from genomic DNA, two homologous (allelic) fragments of a gene that differ in respect to the presence or absence of a sequence such as an Eco RI site. Scheme 1: if the complete sequence of the region being haplotyped is known then the location and identity of all restriction sites, including the subset of restriction sites that include polymorphic nucleotides in their recognition sequence, can be determined trivially by computational analysis using commercially available software. Those restriction sites that overlap polymorphic nucleotides in the DNA segment of interest can be assessed for suitability as allele enrichment sites. The optimal characteristics of an allele enrichment site include: (i) The site occurs once, or not at all (depending on the allele) in a DNA segment to be haplotyped. This is crucial since the basis of the allele enrichment is the attachment of a protein to the binding site in the allele to be enriched, and its absence in the other allele present in the genomic DNA sample being haplotyped. (ii) There is a pair of nonpolymorphic restriction sites, different from the site being used for allele enrichment, that flank the polymorphic site and span a DNA segment deemed useful for haplotype analysis.

The steps for allele enrichment then comprise: restrict genomic DNA with the selected enzyme(s) that flank the polymorphic site so as to produce a DNA segment useful for haplotype analysis (as well as many other genomic DNA fragments); add the DNA binding protein (i.e., the cleavage-inactive restriction enzyme) in a buffer that promotes specific binding to the cognate site (and, if necessary, prevents the restriction enzyme from cleaving its cognate site); selectively remove the restriction enzyme—complex from the genomic DNA by any of the physical or affinity based methods described above—antibody, nickel-histidine, etc. Subsequently, suspend the enriched allele in aqueous buffer and genotype two or more polymorphic sites to determine a haplotype. Scheme 2 is similar but does not require a specific restriction step. Instead, one randomly fragments genomic DNA into segments that, on average, are approximately the length of the segment to be haplotyped. Then add the DNA binding protein and proceed with the enrichment as above. The disadvantage of this scheme is that there may be DNA fragments that include non-polymorphic copies of the cognate sequence for the DNA binding protein. The presence of such fragments will limit the degree of allele enrichment because they will co-purify with the targeted allele, and produce background signal in the subsequent analysis steps. This problem can be addressed by reducing the average size of the fragments in the random fragmentation procedure.

Because of the requirement that the enriched allele fragment have zero or one copies of the sequence to be used for attachment of the restriction, optimal restriction enzymes for these haplotyping methods recognize sequences of 5 nucleotides or greater; preferably they recognize sequence of 6 nucleotides or greater; preferably the cognate sites of such enzymes contain one or more dinucleotides or other sequence motifs that are proportionately underrepresented in genomic DNA of the organism that is being haplotyped; preferably, for haplotyping methods applied to mammalian genomic DNA, they contain one or more 5'-CpG-3' sequences, because CpG dinucleotides are substantially depleted in mammalian genomes. Restriction enzymes that include CpG dinucleotides include Taq I, Msp I, Hha I and others known in the art.

A limitation of the restriction enzyme based allele capture method is that the length of DNA fragment that can be haplotyped depends on the local restriction map. In some cases it may be difficult to find a polymorphic restriction site for which a cleavage-inactive restriction enzyme is available and for which the nearest 5' and 3' flanking sequences are at an optimal distance for haplotyping; often the flanking restriction enzyme cleavage sites will be closer to the polymorphic site than desired, limiting the length of DNA segment that can be haplotyped. For example, it may be optimal from a genetic point of view to haplotype a 15 kb segment of DNA, but there may be no polymorphic restriction sites that are flanked by sites that allow isolation of the desired 15 kb segment. One approach to this problem is to haplotype several small DNA fragments that collectively span the 15 kb segment of interest. A composite haplotype can then be assembled by analysis of the overlaps between the small fragments.

A more general, and more useful, method for circumventing the limitations occasionally imposed by difficult restriction maps is to incorporate aspects of the RecA assisted restriction endonuclease (RARE) method in the haplotyping procedure. (For a description of the RARE procedure see: Ferrin and Camerini-Otero [1991] *Science* 254: 1494-1497; Koob et al. [1992] *Nucleic Acids Research* 20: 5831-5836.) When the RARE techniques are used in the protein mediated allele enrichment method it is possible to haplotype DNA segments of virtually any length, regardless of the local restriction site map.

First, the DNA is sized, either by random fragmentation to produce fragments in the right size range (e.g., approximately 15 kb average size), or one can use any restriction endonuclease or pair of restriction endonucleases to cleave genomic DNA (based on the known restriction map) so as to produce fragments spanning the segment to be haplotyped. In the RARE haplotyping procedure one then uses an oligonucleotide to form a D loop with the segment of DNA that contains the polymorphic restriction site (the site that will ultimately be used to capture the DNA segment to be haplotyped). (The other copy of the allele present in the analyte sample lacks the restriction enzyme sequence as a consequence of the polymorphism.) Formation of the D loop can be enhanced by addition of *E. Coli* RecA protein, which assembles around the single stranded DNA to form a nucleoprotein filament which then slides along double stranded DNA fragments until it reaches a complementary strand. RecA protein, in a complex with a gamma-S analog of ATP and a 30-60 nucleotide long oligodeoxynucleotide complementary or identical to the sequence-targeted site in which the protected restriction site is embedded, then mediates strand invasion by the oligodeoxynucleotide, forming the D loop.

Once this loop is formed the next step is to methylate all copies of the polymorphic restriction site using a DNA methylase. Substantially all copies of the restriction site present in the genomic DNA mixture are methylated. (One nucleotide, usually C, is methylated.) The one polymorphic restriction site which participates in the D loop is not methylated because the D loop is not recognized by the DNA methylase. Next the D loop is disassembled and the methylase inactivated or removed. This leaves the targeted restriction site available for restriction enzyme binding (on the one allele that contains the restriction site). Finally, the restriction-inactive but high affinity binding protein (e.g., Eco RI Gln111) is added to the mixture of genomic DNA fragments. The only fragment that should have an available Eco RI site is the fragment to be haplotyped. Any of several methods can be used to selectively remove that fragment: the cleavage-inactive restriction enzyme can be fused to a protein that serves as a handle to facilitate easy removal by nickel-histidine, antibody-antigen or other protein-protein interaction, as described in detail elsewhere in this invention. Alternatively, an antibody against the restriction enzyme can be prepared and used to capture the restriction enzyme-allele fragment complex to a bead or column to which the antibody is bound, or other methods known in the art can be employed.

The advantage of the RARE assisted haplotyping method is that the local restriction map, and in particular the occurrence of other Eco RI sites (in this example) nearby, is no longer a limitation. Further, the methylation of all sites save the polymorphic site eliminates the preference for restriction enzymes that recognize 6 or more nucleotides. With the RARE haplotyping technique any enzyme, including one that recognizes a four nucleotide sequence, is effective for allele enrichment. This is a particularly useful aspect of the invention because four nucleotide sequences recognized by restriction enzymes more often encompass polymorphic sites than 5 or 6 nucleotide sequences, and there are more DNA methylases for 4 nucleotide sequences than for 6 nucleotide sequences recognized by restriction enzymes. Preferred restriction sites for RARE assisted haplotyping are those for which DNA methylases are commercially available, including, without limitation, Alu I, Bam HI, Hae III, Hpa II, Taq I, Msp I, Hha I, Mbo I and Eco RI methylases.

The use of peptides for allele enrichment is described below in the discussion of small molecules that can be used for allele enrichment.

Nucleic Acid-based Allele Capture Methods

In another aspect of the invention, nucleic acids and nucleic acid analogs that bind specifically to double stranded DNA can be targeted to polymorphic sites and used as the basis for physical separation of alleles. Ligands attached to the targeting oligonucleotides, e.g., biotin, avidin, streptavidin, fluorescein, polyhistidine or magnetic beads, can provide the basis for subsequent enrichment of bound alleles. Sequence specific methods for the capture of double stranded DNA, useful for the haplotyping methods of this invention, include: (i) Triple helical interactions between single stranded DNA (e.g., oligonucleotides) and double stranded DNA via Hoogsteen or reverse Hoogsteen base pairing; (ii) D-loop formation, again between a single stranded DNA and a double stranded DNA; (iii) D-loop formation between peptide nucleic acid (PNA) and a double stranded DNA; (iv) in vitro nucleic acid evolution methods (referred to as SELEX) that can be used to derive natural or modified nucleic acids (aptamers) that bind double stranded DNA in a sequence specific manner via any combination of Watson-Crick or Hoogsteen base pairing, hydrogen bonds, van der Waals forces or other interaction.

The D loop is formed by the displacement of one strand of the double helix by the invading single strand. RecA protein, as indicated above, facilitates D Loop formation, albeit with only limited stringency for the extent of homology between the invading and invaded sequences.

In another aspect of the invention, nucleic acids that bind specifically to double stranded DNA can be targeted to polymorphic sites and used as the basis for physical separation of alleles. The best known types of specific interactions involve triple helical interactions formed via Hoogsteen or reverse Hoogsteen base pairing. These interactions are useful for haplotyping when a polymorphic site lies within a sequence context that conforms to the requirements for Hoogsteen or reverse Hoogsteen base pairing. These requirements typically include a homopyrimidine/homopurine sequence, however the discovery of nucleic acid modifications that permit novel base pairings is resulting in an expanded repertoire of sequences. Nonetheless, a more general scheme for selective binding to polymorphic DNA sequences is preferable.

In another aspect of the invention the formation of D loops by strand invasion of dsDNA can be the basis for an allele specific interaction, and secondarily for an allele enrichment scheme. Peptide nucleic acid (PNA) is a preferred material for strand invasion. Due to its high affinity DNA binding PNA has been shown capable of high efficiency strand invasion of duplex DNA. (Peffer N J, Hanvey J C, Bisi J E, et al. Strand-invasion of duplex DNA by peptide nucleic acid oligomers. *Proc Natl Acad Sci USA*. 1993 November 15;90(22): 10648-52; Kurakin A, Larsen H J, Nielsen P E. Cooperative strand displacement by peptide nucleic acid (PNA). *Chem Biol*. 1998 February;5(2):81-9. The basis of a PNA strand invasion affinity selection would be conceptually similar to protein-based methods, except the sequence-specific DNA-PNA complexes formed by strand invasion are the basis of an enrichment procedure that exploits an affinity tag attached to the PNA. The affinity tags may be a binding site for an antibody such as fluorescein or rhodamine, or polyhistidine (to be selected by nickel affinity chromatography), or biotin, (to be selected using avidin- or streptavidin-coated beads or surface) or other affinity selection schemes known to those skilled in the art.

In another embodiment of the invention, in vitro nucleic acid evolution methods (referred to as aptamers or SELEX) can be used to derive natural or modified nucleic acids that bind double stranded DNA in a sequence specific manner. Methods for high throughput derivation of nucleic acids capable of binding virtually any target molecule have been described. (Drolet D W, Jenison R D, Smith et al. A high throughput platform for systematic evolution of ligands by exponential enrichment (SELEX). *Comb Chem High Throughput Screen*. 1999 October;2(5):271-8.)

Nucleotide Analogs

The use of nucleotide analogs are useful for allele enrichment when a polymorphic site lies in a sequence context that conforms to the requirements for Hoogsteen or reverse Hoogsteen base pairing. The sequence requirements generally include a homopyrimidine/homopurine sequence in the double stranded DNA. However, the discovery of nucleotide analogs that base pair with pyrimidines in triplex structures has increased the repertoire of sequences which can participate in triple stranded complexes. Nonetheless, more general scheme for selective binding to polymorphic DNA sequences is preferable.

Other Double Stranded Allele Selection Methods

In another aspect of the invention, non-protein, non-nucleic acid molecules can be the basis for affinity selection of double stranded DNA. (See, Mapp et al. Activation Of Gene Expression By Small Molecule Transcription Factors. *Proc Natl Acad Sci USA*. 2000 April 11;97(8):3930-5; Dervan and Burli. Sequence-Specific DNA Recognition By Polyamides. *Curr Opin Chem Biol*. 1999 December;3(6):688-93; White et al. Recognition Of The Four Watson-Crick Base Pairs In The DNA Minor Groove By Synthetic Ligands. *Nature*. 1998 January 29;391(6666):468-71.)

Modified DNA Binding Molecules

Modified proteins, oligonucleotides or modified nucleotide triphosphates can be used as affinity reagents to partially purify a complementary DNA species (the allele to be haplotyped) with which they have formed a duplex. The protein, nucleotide or oligonucleotide modification may constitute, for example, addition of a compound that binds with high affinity to a known partner—such as biotin/avidin or polyhistidine/nickel—; or it may consist of covalent addition of a compound for which high affinity antibodies are available—such as rhodamine or fluorescein—; or it may consist of addition of a metal that allows physical separation using a magnetic field; or it may involve addition of a reactive chemical group that, upon addition of a specific reagent or physical energy (e.g., uv light) will form a covalent bond with a second compound that in turn is linked to a molecule or structure that enables physical separation.

In a preferred embodiment, the DNA binding molecule is biotinylated. DNA or RNA, once hybridized to biotinylated oligonucleotides or nucleotides, could be separated from non-hybridized DNA or RNA using streptavidin on a solid support. Similarly, a biotinylated DNA binding protein could be separated from the unbound strand by streptavidin affinity. Other possible modifications could include but are not limited to: antigens and antibodies, peptides, nucleic acids, and proteins that when attached to oligonucleotides or nucleotides would bind to some other molecule on a solid support. Oligonucleotides can be comprised of either normal nucleotides and/or linkages or modified nucleotides and/or linkages. The only requirement is that the oligonucleotides retain the ability to hybridize DNA or RNA and that they can be utilized by the appropriate enzymes if necessary. Examples of modified oligonucleotides could include but are not limited to: peptide nucleic acid molecules, phosphorothioate and methylphosphonate modifications. The term oligonucleotide when used below will refer to both natural and modified oligonucleotides.

The following are examples for employing allele specific capture of DNA or RNA to determine haplotypes:

1. A biotinylated oligonucleotide directed against a site that is heterozygous for a nucleotide variance, is allowed to hybridize to the target DNA or RNA under conditions that will result in binding of the oligonucleotide to only one of the two alleles present in the sample. The length, the position of mismatch between the oligonucleotide and the target sequence, and the chemical make-up of the oligonucleotide are all adjusted to maximize the allele specific discrimination. Streptavidin on a solid support is used to remove the biotinylated oligonucleotide and any DNA or RNA associated by hybridization to the oligonucleotide. For example, allele 1 is specifically captured by hybridization of an oligonucleotide containing a T at the variance site. The target DNA or RNA from allele 1 is then disassociated from the primer and solid support under denaturing conditions. The isolated RNA or DNA from allele 1 is then genotyped to determine the haplotype. Alternatively, the RNA or DNA remaining in the sample, allele 2, following capture and removal of allele 1 can be genotyped to determine the its haplotype.

2. The target DNA is incubated with two oligonucleotides, one of which is biotinylated. If RNA is to be used in this example it must first be converted to cDNA. The oligonucleotides are designed to hybridize adjacent to one another at the site of variance. For example, the 3' end of the biotinylated oligonucleotide hybridizes one base 5' of the variant base. The other oligonucleotide hybridizes adjacent to the biotinylated primer with the 5' most oligonucleotide hybridizing to the variant base. If there is a perfect match at the site of variance (allele 1), the two primers are ligated together. However, if there is a mismatch at the site of variance (allele 2) no ligation occurs. The sample is then allowed to bind to the streptavidin on the solid support under conditions which are permissive for the hybridization of the ligated oligonucleotides but non-permissive for the hybridization of the shorter non-ligated oligonucleotides. The captured oligonucleotides and hybridized target DNA are removed from the sample, the target DNA eluted from the solid support, and genotyped to determine haplotype. Alternatively, the allele 2 can be genotyped to determine haplotype after removal of allele 1 from the sample.

The size of the oligonucleotides can be varied in order to increase the likelihood that hybridization and ligation will only occur when the correct allele is present. The ligation can be done under conditions which will only allow the hybridization of a shorter oligonucleotide if it is hybridized next to the perfectly matched oligonucleotide and can make use of the stacking energy for stabilization. Also, either the biotinylated oligonucleotide or the other oligonucleotide can contain the mismatch. The biotin can also be put on the 5' or 3' end of the oligonucleotide as long as it is not at the site of ligation.

3. An oligonucleotide is hybridized to the target DNA in which the 3' end of the oligonucleotide is just 5' of the variant base. If RNA is to be used in this example it is first converted to cDNA. The sample is then incubated in the presence of four dideoxy nucleotides with a polymerase capable of extending the primer by incorporating dideoxy nucleotides where one of the dideoxy nucleotides contains a biotin. The biotinylated dideoxy nucleotide is selected to correspond to one of the variant bases such that it will be incorporated only if the correct base is at the site of variance. For example, the base chosen is biotin ddTTP which will be incorporated only when the primer anneals to allele 1. The primer with the incorporated biotinylated dideoxy nucleotide hybridized to allele 1 is separated from the rest of the DNA in the sample using streptavidin on a solid support. The isolated allele 1 can then be eluted from the solid support and genotyped to determine haplotype. As above, allele 2 which is left in the sample after capture and removal of allele 1, can also be genotyped to determine haplotype.

The dideoxy and biotinylated nucleotide do not have to be the same nucleotide. The primer could be extended in the presence of one biotinylated nucleotide, one dideoxy nucleotide and two normal nucleotides. For example, a biotinylated dTTP and a normal dGTP would be added in with another normal nucleotide (not dTTP or dGTP) and a dideoxy nucleotide (not ddTTP or ddGTP). The dideoxy nucleotide would be chosen so that the extension reaction would be terminated before the occurrence of another site for the incorporation of the biotinylated dTTP. Extension from the primer on allele 1 would result in the incorporation of a biotinylated dTTP. Extension from the primer on allele 2 would result in the incorporation of a normal dGTP. Streptavidin on a solid support could be used to separate allele 1 from allele 2 for genotyping to determine haplotype.

II.A.2. Allele Specific Enrichment by Cross-linking Followed by Exonuclease Digestion A second method for allele-specific enrichment involves protecting an allele-specific region of genomic DNA or cDNA from exonuclease digestion. In this method, DNA, e.g., genomic DNA or cDNA, is incubated in the presence of an agent, e.g., a modified oligonucleotide, under conditions that allow allele-specific binding, e.g., hybridization, of the agent with the region of DNA containing the site of polymorphism. This agent/genomic DNA complex can then be incubated under conditions that will covalently crosslink the modified agent to the DNA forming an adduct that can not be degraded by exonuclease digestion.

A preferred agent is a thiophosphorioate modified oligonucleotide that binds in an allele-specific manner to a sequence of the DNA comprising a polymorphism. The thiophosphorioate modified oligonucleotide can be cross-linked to the DNA by, e.g., binuclear platinum (PtII), or transplatinum (II), preventing exonuclease digestion of the region of interest (e.g., a region comprising two or more polymorphisms) of the cross-linked allele. The oligonucleotide is positioned relative to other polymorphic sites of interest such that it protects the sites from digestion by the exonuclease. Prevention of exonuclease activity to the crosslinked DNA permits allele specific survival in an exonuclease reaction while the non-crosslinked allele is degraded and effectively removed from the sample. The sample, now enriched for a single allele, is then available for any genotyping methodology known in the art, or described herein, capable of using genomic DNA or cDNA as a template. Thus, this instant method is useful to determine the genotype, and thus the haplotype, of the remaining allele.

The other allele can also be tested by allele-specifically protecting it, removing the unprotected allele and genotyping to obtain the haplotype of the remaining allele as described above. Genomic DNA or cDNA can be incubated with a modified oligonucleotide under conditions that allow allele-specific hybridization of the oligonucleotide with the region of DNA containing the site of polymorphism. The modified oligonucleotide has the property of blocking exonuclease activity even though it is not covalently attached to the genomic DNA or cDNA. An example of such a compound would be peptide nucleic acid (PNA).

In another embodiment, the agent is a compound that is capable of sequence specifically binding to double stranded DNA. Examples of such compounds are triple helices and polyamides. These compounds may either inhibit exonuclease activity on their own or may be modified with a crosslinking reagent that will covalently modify the double-stranded DNA in a manner that inhibits exonuclease activity.

In a preferred embodiment, a modified oligonucleotide, e.g., a thiophosphorioate-oligonucleotide, is incubated with DNA to be haplotyped under conditions that allow allele-specific hybridization. Optimally, the oligonucleotide is at least 10-100 nucleotides in length, and the hybridization is sufficient to withstand subsequent manipulations of the oligonucleotide/DNA complex. This complex then is subjected to conditions that will allow cross-linking of the oligonucleotide with the genomic DNA. The sample of DNA containing both the modified and unmodified DNA, can then be exposed to an agent to degrade the unmodified DNA, leaving the protected allele-enriched DNA.

In a preferred embodiment, binuclear Platinum (II) (PtII) complexes (FIG. 39) is used to crosslink an oligonucleotide containing a thiophosphorioate (thio) group to genomic DNA. A method for crosslinking an oligonucleotide coupled to a PtII to a target oligonucleotide and its subsequent protection from exonuclease digestions was described by Gruff et al., Nucleic Acids Research, vol. 19, pp. 6849-6854 (1991). In this procedure, thio containing oligonucleotides were designed that would hybridize to complementary oligonucleotides. The thio oligonucleotide (10 picomole in 1 µL) was incubated with 0.5 µL of 0.1 mM $KBH_4$, 2 µL of 1 mM phosphate/0.1 mM EDTA pH 7.4, and 0.5 µL of 10 µM binuclear latinum (II) complex for 90 minutes at 37° C. The complementary oligonucleotide (0.01 picomoles in 0.5 µL) was heated to 60° C. for 3 minutes and added to the above thio oligonucleotide mix. 0.5 µL of 0.5 M $NaClO_4$ was added and the reaction allowed to sit for 15 minutes at room temperature. The reaction was then incubated at 37° C. for 60 minutes. Acrylamide gels of thio oligonucleotide crosslinked to radio-labeled complementary oligonucleotide demonstrated that the crosslinking did occur between the two oligonucleotides. Gruff et al. also demonstrated specificity by showing that crosslinking did not occur between an oligonucleotide with a 5' OH replacing the 5' thio or with an oligonucleotide with a 5' thio which was mismatched to the target.

To determine the site of crosslinking, Gruff et al. added 10 µL of 0.1 units/ml of Type I snake venom phosphodiesterase in 0.11 M Tris.HCl/Nacl pH 8.8, 15 mM $MgCl_2$ to the above reaction and incubated at 37° C. for 1 hour. Type I snake venom phosphodiesterase is an enzyme with a 3'-5' exonuclease activity. The Type I snake venom phosphodiesterase digested the oligonucleotides from the 3' end until it reached the site of a PtII crosslink at which point the digestion was halted.

The above experiments by Gruff et al. demonstrated that a specific site in DNA could be modified by crosslinking to a platinum containing oligonucleotide and that that site was resistant to exonuclease digestion. These results can be exploited to develop a haplotyping procedure using the following methodology.

A (thio) containing oligonucleotide is designed which is complementary to a region of the target DNA containing a polymorphism (FIG. 40, allele 1). Binuclear platinum (II) (PtII) is coupled to this oligonucleotide through the thio group using the procedure described by Gruff et al. or a similar method. The PtII coupled oligonucleotide could be used directly or the excess uncoupled PtII may be removed by such methods as dialysis or size exclusion chromatography. The removal of excess uncoupled PtII may reduce nonspecific background adduct formation. It also may be possible to find a method of oligonucleotide synthesis that will directly label the oligonucleotide during synthesis, thus bypassing the labeling and purification steps.

A second oligonucleotide without the thio group is also designed. This oligonucleotide has the same sequence as the thio oligonucleotide except at the site of the variance where it has the base corresponding to the other allele (FIG. 40, allele 2). These two oligonucleotides are mixed with a sample which is heterozygous at the targeted site of variance and allowed to hybridize. The PtII coupled oligonucleotide hybridizes to the allele to which it is perfectly matched (allele 1) and the other oligonucleotide hybridize to the other allele to which it is perfectly matched (allele 2). The PtII coupled oligonucleotide is then chemically crosslinked to the target DNA. This crosslinking protects this allele of the target DNA from degradation by exonucleases. Exonucleases which are known to degrade single and double stranded DNA from a specific end and which are known to be blocked by PtII adducts include, inter alia, Type I snake venom phosphodiesterase (Gruff et al.) and T4 DNA polymerase (Nicholas et al., Proceedings of the National Academies of Science (USA), Vol. 91, pp. 10977-10981, (1994)). Incubation of the sample DNA with exonuclease removes all or most of the DNA which does not have the PtII adduct (FIG. 41, allele 2). When using T4 DNA polymerase or Type I snake venom phosphodiesterase which have 3'-5' exonuclease activity, the target DNA allele with the PtII adduct is protected from the site of the adduct formation 5' to the first site of a nick (FIG. 41, allele 1). Following degradation the exonuclease is removed or inactivated. The remaining allele can be genotyped by any method which is capable of using genomic DNA as a template. Because there is only one allele left in the sample, genotyping will result in the determination of the haplotype for this allele.

Binuclear Platinum (II) is only one possible DNA modifying agent. Trans-platinum (II) diammine dichloride has been shown to crosslink DNA when attached to an oligonucleotide (Chu BC, Orgel LE, DNA Cell Biology, Vol 9, pp. 71-76, (1990). Another possible reagent is psoralen which has been shown to crosslink DNA under the right conditions when attached to an oligonucleotide (Bhan P, Miller P S., Bioconjugate Chemistry, Vol 1, pp. 82-88, (1990)). The method is not limited to the reagents listed above and should work with any exonuclease blocking agent which can be specifically targeted to one allele. Noncovalent blocking agents such as peptide nucleic acid (PNA) molecules can also be used. PNA has been shown to sequence specifically hybridize to DNA and is also known to block activities such as translation and transcription. Blocking agents may also be designed that are capable of binding to double stranded DNA and blocking exonuclease activity. Two such agents are triple helices and polyamides. These agents may block exonuclease activity by simply binding to the double-stranded DNA or they could be modified with agents such as PtII or psoralen which could be activated to cause covalent modification of the target DNA and thus block exonuclease digestion of the double-stranded DNA. Genotyping of the allele-enriched DNA sample, can proceed by a method known to one skilled in the art including, but not excluded to, Taqman, Sanger method dideoxy termination sequencing, allele-specific oligonucleotide hybridization and sequencing (ASO), and by a method described in "A Method for Analyzing Polynucleotides", U.S. Ser. Nos. 09/394,467, 09/394,457, 09/394,774, 09/394,387, filed Sep. 9, 1999. As one skilled in the art will recognize, PCR amplification of the sample DNA may first be necessary to ensure adequate quantities of the allele is available for these genotyping reactions and procedures.

II.A.3. Allele Specific Enrichment by Endonuclease Restriction Followed Optionally by Exonuclease Digestion The first type of polymorphisms used to produce high density human genetic maps were restriction fragment length polymorphisms (RFLPs). RFLPs are polymorphisms, usually but not necessarily SNPs, that affect restriction endonuclease recognition sites. Initially RFLPs were identified, and subsequently typed, using Southern blots of genomic DNA. An RFLP was detected when the pattern of hybridizing species in a Southern blot (hybridized with a single copy probe) varied from sample to sample (i.e., from lane to lane of the Southern blot). Generally one detectable fragment would be identified in some lanes, one or two smaller fragments in other lanes, and both the large and smaller fragments in still other lanes, corresponding to homozygotes for the allele lacking the restriction site, homozygotes for the allele containing the restriction site and heterozygotes for the two alleles. The size difference between the restriction fragments lacking the polymorphic restriction site and those with the restriction site depends on the distance from the polymorphic restriction site to flanking, non-polymorphic sites for the same restriction enzyme.

In the past the location of polymorphic restriction sites and the sizes of the restriction products have generally been determined empirically. Although many restriction site polymorphisms have been converted to PCR assays by designing oligonucleotide primers flanking the polymorphic site these assays lack the character of the initial RFLP assays in which the restriction enzyme did all the work, and the size of the restriction fragments varied over a wide range.

In one embodiment of this method, RFLPs can be used to produce long range haplotypes, over distances of at least 5 kb, frequently over 10 kb and in some instances, using rarely occurring restriction sites, distances of up to 100 kb or greater. The basic approach, illustrated in FIG. 18, is as follows:

(i) Select a DNA segment to be haplotyped (the exact boundaries will be constrained by the next step);

(ii) Identify a polymorphism, either within the segment, or, preferably, in flanking DNA, that alters a restriction enzyme recognition site for a restriction endonuclease (RE1) (Bam HI in FIG. 18). The outer bounds of the segment to be haplotyped are defined by the nearest occurrence of RE1 on either side of the polymorphic site.;

(iii) Prepare genomic DNA from samples that are heterozygous for the polymorphism identified in step ii. It is desirable that the average length of the genomic DNA be greater than the length of the DNA fragment being haplotyped;

(iv) Restrict the genomic DNA with the enzyme that recognizes the selected polymorphic site;

(v) separate the restricted DNA using any DNA size fractionating method suitable to the size range of the restriction fragments of interest. Exemplary methods include gel electrophoresis; centrifugation through a salt, sucrose, or other gradient; chromatography, e.g., sephadex or other chromatography;

(vi) Isolate a first DNA fraction containing the larger restriction fragment and, optionally, a second DNA fraction containing the smaller restriction fragment and, if necessary, purify DNA from each fraction for PCR. It is not necessary that the fragments be highly enriched in the fractions, only that each of the one or more DNA fractions contain a significantly greater quantity of one allele than of the other. A minimum differential allele enrichment that would be useful for haplotyping is 2:1, more preferably at least 5:1 and most preferably 10:1 or greater.

(vii) Genotype the polymorphic sites of interest in either one of the fractions (the one enriched for the larger allele or the one enriched for the smaller allele), or, optionally, determine genotypes separately in both size fractions. Since each fraction contains principally one allele, the genotype of the fractions provides the haplotypes of the enriched alleles. If only one fraction is genotyped, providing one haplotype, then the other haplotype can be inferred by subtracting the determined haplotype from the genotype of the total genomic DNA of the samples of interest. In a haplotyping project it is desirable to determine the genotypes in total genomic DNA of all samples of interest in advance of the haplotyping project, in order to determine, first, which samples actually require haplotype analysis (because they contain two or more sites of heterozygosity in the segment of interest), second, which samples are heterozygotes at the restriction site polymorphism selected for separation of the alleles by size, and are therefore suitable for analysis by the above method; third, the genotype of the total sample constrains the possible haplotypes, and provides a check on the accuracy of the haplotypes. Preferably the haplotype of both alleles are determined separately and compared to the genotype of the unfractionated sample. Samples that are not suitable for haplotype analysis with one restriction enzyme (because they are not heterozygous at the restriction site) can be analyzed with a different restriction enzyme, using the steps described above.

Restriction endonuclease sites that flank the target segment can be exploited to produce optimally sized molecules for allele selection. For example, a heterozygous DNA sample can be restricted so as to produce two allelic DNA fragments that differ in length (and perhaps also differ from one another by the presence or absence of a binding site for an allele specific binding reagent). Because of the ease of restriction endonuclease digestion, and the possibility of cleaving just outside the target DNA segment to be haplotyped (thereby producing the maximal size DNA fragment that differs in respect to the presence/absence of a single binding site), complete restriction is a preferred method for controlling the size of DNA segments prior to allele enrichment.

In another embodiment of this method, two restriction enzymes plus an exonuclease can be used in a haplotyping scheme that does not require a size separation step. In this method, illustrated in FIGS. 19 and 20, the initial steps are as above:

(i) Select a DNA segment to be haplotyped (the exact boundaries will be constrained by the next two steps);

(ii) Identify a polymorphism, either within the segment, or, preferably, in flanking DNA, that alters a restriction enzyme recognition site for a restriction endonuclease (RE1) (Bam HI in this example). The outer bounds of the segment to be haplotyped are defined by the nearest occurrence of RE1 on either side of the polymorphic site;

(iii) identify a second restriction endonuclease (RE2) (Nhe I in FIG. 19) that cleaves only once within the segment to be haplotyped;

(iv) prepare genomic DNA from samples that are heterozygous for the polymorphism identified in step ii. It is desirable that the average length of the genomic DNA be greater than the length of the DNA fragment being haplotyped;

(v) restrict the genomic DNA with RE1;

(vi) block the ends of all cleavage products from exonuclease digestion. This blocking step can be performed by, e.g., selecting an RE1 that produces termini not susceptible to exonuclease digestion—for example 3' protruding termini are resistant to cleavage by $E.$ $coli$ Exonuclease III; or by filling in recessed termini with nuclease-resistant modified nucleotides (e.g., 5' amino-deoxynucleotide analogs, 2'-O-methyl nucleotide analogs, 2'-methoxy-ethoxy nucleotide analogs, 4-hydroxy-N-acetylprolinol nucleotide analogues or other chemically modified nucleotides such as those described in U.S. patent application Ser. No. 09/394,774 filed Sep. 9, 1999, entitled A METHOD FOR ANALYZING POLYNUCLEOTIDES); or by ligating adapters with nuclease resistant changes to the restriction termini);

(vii) restrict with RE2. At this point, the two alleles in the DNA region of interest are in a different state. Allele A was cleaved in two by RE1 at the polymorphic site, both fragments were blocked from endonuclease digestion, and then RE2 cleaved one of the two fragments in two pieces, both of which have one end unprotected from exonuclease (a requirement of RE2 is that it produce termini that are susceptible to exonuclease digestion) (See FIG. 20). The fragment not cleaved by RE2 is still protected at both termini. Conversely, Allele B, lacking an RE1 site at the polymorphic site, was in one piece after RE1 digestion. RE2 digestion cleaved that one piece in two, both of which are susceptible to nuclease digestion, the consequence of which is the exonuclease digestion of both halves of the fragment (from the unprotected ends). Thus nuclease acts on the entire segment to be haplotyped in Allele B.

(viii) After nuclease digestion, or at the same time, a small amount of a single strand specific nuclease may be added in order to destroy any single stranded regions left after the exonuclease treatment. This is important only if the first nuclease has no single strand nuclease activity (as is the case, for example, with $E.$ $coli$ Exonuclease III). Nuclease(s) can be inactivated, for example by heating, if necessary.

(ix) A genotyping procedure can be used to determine the status of all polymorphic sites in the segment of Allele A that did not contain the site for RE2, and thus remained blocked at both ends during the exonuclease treatment. Since there is no (or little) Allele B remaining in the test tube, only the nucleotides corresponding to Allele A will be registered by the genotyping procedure, and they constitute the haplotype. A variety of nucleases can be used for this method, as well as combinations of nucleases, with, for example, one converting fragments with unprotected ends into single stranded DNA molecules and the other digesting single stranded DNA exo- or endonucleolytically. Specific nucleases useful for this method include $E.$ $coli$ Exonucleases I and III, Nuclease Bal-31 (which must be used with a suitable end protection procedure at step vi), as well as the single strand specific Mung Bean Nuclease, human cytosolic 3'-to-5' exonuclease and many other prokaryotic and eukaryotic exonucleases with processivity. Since large segments are more attractive as haplotyping targets than short ones the processivity of the nuclease may be a limit the utility of the method. Therefore, highly processive nucleases are preferred. Such nucleases may be either natural or modified by mutagenesis.

As with other haplotyping methods, a minimum differential allele enrichment that would be useful is 2:1, more preferably at least 5:1 and most preferably 10:1 or greater. It is also preferable to haplotype the polymorphic sites of interest on both alleles in separate reactions. Alternatively, if the haplotype of only one allele is determined directly, then the other haplotype can be inferred by subtracting the known haplotype from the genotype of the total genomic DNA of the samples of interest. Haplotypes can be extended over long regions by the combined use of several restriction fragment length polymorphisms suitable for the method as outlined above.

In the future, with a complete sequence of many genomes, including the human genome, available, and hundreds of thousands, if not millions, of polymorphic sites identified it will be possible to design RFLP-based assays for the methods described above in silico. That is, one will be able to identify, for any DNA segment of interest, the flanking restriction sites for any available restriction enzyme, and the subset of those sites that are polymorphic in the human (or other) population. Using criteria such as desired fragment location, desired fragment length, desired difference in length between two alleles (for separation by size) or location of a suitable site for R2 (for exonuclease removal of one allele) (for allele enrichment by selective exonuclease digestion), it will be possible to automate the design of RFLP assays. In another aspect of this invention a program for automatically designing experimental conditions, including restriction endonucleases and either electrophoretic (or other) separation conditions, or exonucleases, given the constraints just described can be executed.

II.A.4. Allele Specific Enrichment by Endonuclease Restriction Followed by Amplification Another method of enriching for one allele versus another involves (a) identifying a natural or synthetic restriction endonuclease cleavage site that comprises a polymorphism; (b) digesting a subject's DNA sample with the restriction endonuclease, wherein one allele is cleaved at a polymorphism and the other allele is not; and (c) performing an amplification procedure on the endonuclease restricted sample, wherein an amplification product is produced in an allele-dependent manner, e.g., an amplification product is only produced from the allele that was not cleaved by the restriction endonuclease. The amplification product can subsequently be subjected to a genotyping procedure.

In this method, illustrated in FIGS. 36-38, the first step entails identifying a polymorphism, either within the segment to be haplotyped, or, preferably, in flanking DNA, that alters a restriction enzyme recognition site for a restriction endonuclease (RE1) (e.g., NcoI in FIG. 36). The outer bounds of the segment to be haplotyped are defined by the nearest occurrence of the RE1 site on either side of the polymorphic site. It is desirable that the average length of the genomic DNA be greater than the length of the DNA fragment being haplotyped. The genomic DNA is then restricted with the endonuclease RE1. Then, an amplification is performed, e.g., a PCR amplification, using forward and reverse primers located on opposite sides of the polymorphic RE1 site, but within the DNA segment subtended by the flanking, non-polymorphic, RE1 sites. An amplification product will only be produced if the allele to be haplotyped was not restricted by RE1, i.e., because the polymorphism present in the enriched allele altered the restriction enzyme recognition site for RE1. The amplified DNA (enriched allele) can then be subjected to genotyping tests for one or more polymorphisms that lie within the amplified segment.

Virtually any genotyping method can be used to genotype the enriched allele once amplified. One preferred genotyping method is primer extension, followed by electrophoretic or mass spectrometric analysis. Primers are positioned just upstream of one or more polymorphic sites in the amplified segment, extended in an allele specific manner and analyzed using methods known in the art. This method can also be used in conjunction with allele specific priming experiments of this invention, in order to boost specificity of allele amplification.

II.A.5. Allele Enrichment by Allele Specific Hairpin Loop Amplification Method

Another method for determining the haplotype of a DNA fragment present in a DNA sample from a diploid organism includes: a) selectively amplifying one allele from the mixture by the allele specific clamp PCR procedure; and b) determining the genotype of two or more polymorphic sites in the amplified DNA fragment. As with the other enrichment methods described herein, the selective amplification may be preceded by determining the genotype of the DNA sample at two or more polymorphic sites in order to devise an optimal genotyping and that the DNA sample is a mixture of several DNA samples.

This method entails using modified primers. However, the basis for achieving allele specific amplification is the formation of a duplex or secondary structure involving base pairing between (i) nucleotides at or near the 3' end of a strand (said nucleotides being at least partially templated by a primer for the complementary strand) and (ii) nucleotides of the same strand that lie further interior from the 3' end and include (crucially) a polymorphic site (or sites), such that: (i) the secondary structure is formed to a different extent in the two alleles (ideally the secondary structure is formed in a completely allele specific manner), and (ii) the secondary structure at least partially inhibits primer binding and/or primer extension, and consequently inhibits amplification of the strand with the secondary structure at the 3' end. The point of the primer modification, then, is to produce a template for polymerization on the complementary strand leading to a sequence that will form a secondary structure that will inhibit further primer binding/extension from that end. The modification in the primer can be introduced either at the 5' end or internally, but not at the 3' end of the primer. An example of this method applied to haplotyping the ApoE gene is provided below (Example 3), along with FIGS. 14-17, that illustrate some of the types of secondary structure that can be produced to inhibit primer binding/extension.

One implementation of the method entails introducing a 5' extension in a primer. After a complementary strand is extended across that primer, and then separated by a cycle of denaturation, the complementary strand forms a hairpin loop structure in one allele but not the other. Specifically, the free 3' end of the complementary strand anneals to an upstream segment of the same strand that includes the polymorphic site, such that the polymorphic site participates in the stem of the loop (see FIGS. 14, 15). If the polymorphic nucleotide is complementary to the nucleotide near the 3' end of the strand a tight stem will be formed. If not, then a lower affinity interaction will exist and, at appropriately selected conditions, the stem will not form. Since the formation of the stem makes the 3' end of the strand no longer available for binding free primer, the amplification of the strand in which a perfect stem is formed is inhibited, as shown in Example 1. The length of the 5' extension on the primer can be varied, depending on the desired size of the loop, or on whether it is desirable to form alternative structures or enzyme recognition sites.

Alternative structures that can be incorporated into a primer in an allele-specific manner include: (i) recognition sites for various DNA modifying enzymes such as restriction endonucleases, (ii) a cruciform DNA structure that could be very stable, or could be recognized by enzymes such as bacteriophage resolvases (e.g., T4E7, T7 µl), or (iii) recognition sites for DNA binding proteins (preferably from thermophilic organisms) such as zinc finger proteins, catalytically inactive endonucleases, or transcription factors. Such structures could effect allele specific binding to, or modification of, DNA. For example, consider a duplex formed only (or preferentially) by a strand from one allele that contains the recognition sequence for a thermostable restriction enzyme such as Taq I. Allele specific strand cleavage could be achieved by inclusion of (thermostable) Taq I during the PCR, resulting in complete inactivation of each cleaved template molecule and thereby leading to allele selective amplification.

What are the limits of such an approach? One requirement is that there are no Taq I sites elsewhere in the PCR amplicon; another is that one of the two alleles must form a Taq I recognition sequence. The-se limitations can be addressed in part by designing a 5' primer extension, along with an internal primer loop, so that the recognition sequence for a rare cutting restriction endonuclease that (i) is an interrupted palindrome, or (ii) cleaves at some distance from its recognition sequence is formed by the internal loop, while (i) the other end of the interrupted palindrome, or (ii) the cleavage site for the restriction enzyme, occurs at the polymorphic nucleotide, and is therefore sensitive to whether there is a duplex or a (partially or completely) single stranded region at the polymorphic site. Preferred enzymes for PCR implementation of these schemes would include enzymes from thermophiles, such as Bsl I (CCNNNNN/NNGG) and Mwo I (GCNNNNN/NNGC).

Other alternative schemes would entail placing the stem-forming nucleotides internally, rather than at the end of the primer.

The experiments described above and in Example 1 are directed to stem formation during PCR, which requires that the stem be stable at an annealing temperature of ~50° C. or greater. However, isothermal amplification methods, such as 3SR and others, can also be used to achieve allele specific amplification. For isothermal amplification methods the loop forming sequences would likely be designed differently, to achieve maximum allele discrimination in secondary structure formation at 37° C., 42° C. or other temperatures suited to amplification. This can be achieved by shortening the length of duplex regions. Example 1 gives typical lengths of duplex regions for PCR-based methods. Shorter duplex lengths can be tested empirically for isothermal amplification methods.

The methods described herein provide excellent allele specificity can be achieved at fragment lengths of up to 4 kb.

II.A.6. Other Considerations of Enrichment Methods

Degree of Allele Enrichment Required for Haplotyping:

Allele enrichment by any of the methods described herein need not be quantitative or completely selective in order to produce an accurate and reproducible haplotyping result. Even if both alleles are still present after enrichment, as long as one allele is consistently present in greater amount than the other, the enrichment may be adequate to produce a satisfactory discrimination between alleles in a subsequent genotyping test. Preferably the degree of strand enrichment is at least 1.5-fold, more preferably two-fold, more preferably at least four-fold, still more preferably at least six-fold, and most preferably at least 10-fold. Further enrichment beyond 10-fold is desirable, but is unlikely to produce significant changes in the accuracy of the haplotyping test. The adequacy of haplotype determination using a DNA population that is only partially enriched for the desired allele can be determined by repeated analyses of known samples to determine the error rate associated with different known allele ratios.

Yield of Enriched Alleles Required for Haplotyping:

After allele enrichment, one has a population of DNA molecules for genotyping analysis that is necessarily less than the starting number of DNA molecules because no enrichment procedure will permit 100% recovery of the selected allele. However, just as a high degree of allele selectivity is not necessary during enrichment, a high yield of the enriched allele is not necessary either. The amount of enriched allele will of course depend in part on the quantity of starting DNA. Thus, in a haplotyping experiment that starts with one microgram of genomic DNA, only a small fraction of the alleles in the starting material—as little as 0.1%—have to be captured by the allele enrichment procedure, provided the subsequent genotyping step (usually PCR based) is sensitive enough to amplify an amount of template (~300 copies) that would normally be found in 1 ng of genomic DNA. If necessary the PCR amplification step of the genotyping procedure can be modified to increase sensitivity using methods known in the art, such as nested PCR (two rounds of PCR, first with an outside set of primers, then with an inside set) or an increased number of PCR cycles. Also, to compensate for a low efficiency of captured alleles the quantity of input genomic DNA or cDNA can be increased to 2 ug, 4 ug or even 10 ug or more. Preferably the fraction of input alleles that are captured by the enrichment procedure is at least 0.01% of the starting number of alleles, more preferably at least 0.05%, still more preferably at least 0.25%, still more preferably at least 2% and most preferably at least 10%. The capture of a still higher fraction of the input alleles does not contribute significantly to the performance of the procedure, and in fact is undesirable if it compromises the selectivity of strand enrichment.

Controlling the Size of DNA Molecules to be Haplotyped:

Before performing allele enrichment procedures on DNA fragments it may be desirable to control the size of the input DNA by random or specific cleavage procedures. One reason is that very long DNA fragments may be significantly more difficult to selectively enrich than shorter fragments (due, for example, to a greater tendency for shear forces to break long fragments, or a greater tendency for long fragments to adhere to or be trapped by particles or matrices required for separation). Therefore it is preferable to produce DNA fragments that are only moderately longer than the size of the region to be haplotyped (which is determined by the biological problem being analyzed, and the location and relationship of DNA polymorphisms, including the degree of linkage disequilibrium in the region being analyzed; see discussion above). The DNA segment to be haplotyped may include a gene, part of a gene, a gene regulatory region such as a promoter, enhancer or silencer element, or any other DNA segment considered likely to play a role in a biological phenomenon of interest.

Production of DNA fragments in the desired size range can be accomplished by using random fragmentation procedures (e.g., shearing DNA physically by pipetting, stirring or by use of a nebulizer), by partial or complete restriction endonuclease digestion, or by controlled exposure to a DNAase such as *E. coli* DNAase I.

With random or semi-random DNA fragmentation procedures, such as partial nuclease digestion, the aim is to produce a collection of DNA fragments, most of which span the entire region to be haplotyped (and that contain the site that will be used to effect allele enrichment). Mathematical methods can be used to determine the optimal size distribution—for example, a size distribution may be selected in which 80% of the fragments span the target region, assuming random distribution of DNA breakpoints. Preferably at least 50% of the DNA fragments are in this size range.

Complete restriction endonuclease digestion is another useful way to control the size of input DNA molecules, particularly when the full DNA sequence or the restriction map of the DNA segment to be haplotyped is known. Restriction digestion with enzymes that cleave DNA at polymorphic sites produces restriction fragments of different lengths from different alleles (so called restriction fragment length polymorphisms, or RFLPs). Cleaving at restriction sites that produce RFLPs can be used to produce DNA molecules that do or do not contain binding sites for DNA binding molecules (e.g., DNA binding proteins, oligonucleotides, PNAs or small molecules that bind DNA) such that only one of two alleles in a genomic DNA sample contains the binding site. In order for this approach to work the location of all binding sites for the allele specific DNA binding molecule must be taken into account. The preparation of DNA molecules for haplotyping by specific DNA cleavage can be performed so as to produce molecules that will perform optimally in the allele specific binding step.

If single stranded DNA is to be the input material for haplotyping then preferably the optimal size distribution of DNA molecules is obtained while DNA is still double stranded, using any of the methods described above. Subsequently the sample can be denatured, subjected to an allele enrichment step, and subsequently genotyped to determine the haplotypes.

Using Double Stranded Versus Single Stranded DNA:

Allele selection may be accomplished using single or double stranded DNA. Single stranded DNA is produced by denaturing double stranded DNA—for example by heating or by treatment with alkali, preferably after a sizing procedure has been applied to double stranded DNA to achieve an optimal size distribution of DNA fragments. Both single and double stranded DNA methods have advantages and disadvantages. One advantage of single stranded methods is that the specificity of Watson-Crick base pairing can be exploited for the affinity capture of one allele. Disadvantages of single strand methods include: (i) the propensity of single stranded DNA molecules to almeal to themselves (forming complex secondary structures) or to other, only partially complementary single stranded molecules. For example the ubiquitous human DNA repeat element Alu (which is up to ~280 nucleotides long) may cause two non-complementary strands to anneal; (ii) Single stranded DNA is more susceptible to breakage than double stranded DNA. Strand breaks destroy the physical contiguity that is essential for haplotyping.

Double stranded DNA has several advantages over single stranded DNA as the starting point for the haplotyping methods of this invention. First, it is less susceptible to breakage.

Second, it is less likely to bind non-specifically to itself or other DNA molecules (whether single stranded or double stranded). Third, there are a variety of high affinity, sequence specific interactions between double stranded DNA and proteins (e.g., restriction enzymes, transcription factors, natural and artificial zinc finger proteins), as well as high affinity interactions between double stranded DNA and single stranded DNA or modified oligonucleotides (e.g., via Hoogsteen or reverse Hoogsteen base pairing) and between double stranded DNA and small molecules (e.g., polyamides) that can provide the basis for allele enrichment. Another type of structure that can be exploited for allele enrichment is D-loops, formed by strand invasion of a duplex DNA molecule by an oligonucleotide or a DNA-like molecule such as peptide nucleic acid (PNA). D loop formation can be facilitated by addition of E. Coli RecA protein, using methods known in the art. Fourth, restriction enzyme cleaved double stranded DNA may have termini that can provide the basis for allele specific treatments, including affinity selection (e.g., ligation to an adapter strand), strand degradation (e.g., allele selective degradation of one allele but not the other), circularization and other procedures described below.

II.B. Optical Mapping Methods

Another type of haplotyping methods involves microscopic visualization of single DNA molecules that have been treated in a manner that produces allele specific changes at polymorphic sites. These haplotyping methods are based on the optical mapping and sequencing methods of D. Schwartz, described in U.S. Pat. No. 5,720,928.

These methods include: (a) immobilizing DNA fragments comprising two or more polymorphisms of a selected gene on planar surface; (b) contacting the immobilized DNA fragments with an agent that selectively binds to an allele having a selected nucleotide at a first polymorphism under conditions which permit selective binding of the agent; (c) contacting the immobilized DNA fragments with a second agent that selectively binds to an allele having a selected nucleotide at a second polymorphism under conditions that permit selective binding of the second agent; and (d) optical mapping the position of the first and second agents on at least one DNA fragment.

The agents that selectively bind to one allele can be oligonucleotides or peptide nucleic acids (PNAs) complementary to two or more polymorphic sites present in one allele in a genomic sample. Preferably, D loop formation is promoted by the oligonucleotides or peptide nucleic acids (PNA) that are perfectly matched to one specific strand of the target immobilized fragment. The formation of D loops can be enhanced by the addition of RecA protein or by the alteration of salt concentration.

In another embodiment, the agents that selectively bind to one allele can be proteins, e.g., two or more zinc finger proteins that bind to one of two alleles at a polymorphic nucleotide.

In a preferred embodiment, two or more allele specific DNA binding agents, e.g., oligonucleotides or DNA binding proteins, are detectably labeled.

The immobilized DNA fragments may be first subjected to a size selection procedure and or immobilized to a prepared glass surface.

II.B.1. Optical Mapping Technology

One way to optical mapping the position of the allele specific agents on a DNA molecule is to use microscopy to directly visualize the DNA. David Schwartz and colleagues have developed a family of methods for the analysis of large DNA fragments on modified glass surfaces, which they refer to as optical mapping. Specifically, Schwartz and colleagues have devised methods for preparing large DNA fragments, fixing them to modified glass surfaces in an elongated state while preserving their accessibility to enzymes, visualizing them microscopically after staining, and collecting and processing images of the DNA molecules to produce DNA restriction maps of large molecules. (Lai et al. A Shotgun Optical Map Of The Entire Plasmodium Falciparum Genome. *Nat Genet*. 1999 November;23(3):309-13; Aston et al. Optical Mapping And Its Potential For Large-Scale Sequencing Projects. *Trends Biotechnol*. 1999 July;17(7): 297-302; Aston et al. Optical Mapping: An Approach For Fine Mapping. *Methods Enzymol*. 1999;303:55-73; Jing et al. Automated High Resolution Optical Mapping Using Arrayed, Fluid-Fixed DNA Molecules. *Proc Natl Acad Sci USA*. 1998 July 7;95(14):8046-51.) Many of the imaging and image analysis steps have been automated. (see articles cited above and: Anantharaman et al. Genomics Via Optical Mapping. III: Contiging Genomic DNA. *Ismb*. 1999;(6):18-27.) Many of the optical mapping methods have also been described in U.S. Pat. No. 5,720,928.

The optical mapping methods of Schwartz and colleagues have so far been largely confined to the generation of restriction endonuclease maps of large DNA segments or even genomes by treating immobilized, surface-bound double stranded DNA molecules with restriction endonucleases. To a lesser extent, these methods have been applied to studies of DNA polymerase on single DNA molecules. For example, a complete BamH I and Nhe I restriction map of the genome of Plasmodium Falciparum has been made using optical mapping. The average fragment length of analyzed fragments was 588-666 kb, and the average coverage of the map was 23× for Nhe I and 31× for BamH I. (That is, on average, each nucleotide of the genome was present in 23 or 31 different analyzed fragments. This high level of redundancy provides higher map accuracy.) *P. falciparum* has a genome length of 24.6 megabases, so, taking into account the 31× redundancy of the BamH I map, ~763 mb were analyzed. The human genome, at ~3,300 mb, is only about 4 times larger than the scale of this experiment (albeit at 1× coverage, which would be insufficient for highly accurate results). However, it should be possible, using a higher density of DNA fragments, and/or a larger surface, to prepare glass slides with fragments corresponding to several equivalents of the human genome. Statistically reliable haplotyping results would be obtainable from such DNA preparations, using the methods described below. As an alternative to whole genome preparations, size selected fractions of the genome, or long range amplification products could also be used for the haplotyping methods described herein.

Several methods can be coupled with optimal mapping technology to determine haplotypes: (i) Restriction endonuclease digestion using enzymes that cleave at polymorphic sites on the DNA segment to be haplotyped, (ii) addition of PNAs corresponding to polymorphic sites to form allele specific D-loops, (iii) addition of sequence specific DNA binding proteins that recognize sequences that are polymorphic, and that consequently bind only to one set of alleles. The various types of allele specific DNA binding proteins described above, e.g., in section II.A. 1, above, are all useful in this aspect, however, the versatility in terms of sequence recognition and high affinity binding of zinc finger proteins make them a preferred class of DNA binding proteins. A preferred haplotyping method based on zinc fingers and optical mapping would consist of the following steps: (i) prepare fixed, elongated DNA molecules according to the methods of Schwartz, (ii) add zinc fingers that recognize polymorphisms in a DNA segment to be haplotyped. Preferably the zinc fingers are synthesized with a detectable label, for example by making a fusion protein, or alternatively they are post-translationally labeled. Preferably, different zinc fingers are labeled (whether by making fusion proteins or by post-translational chemical modification) with two or more different methods that result in detectable differences. Ideally at least two different labels are used for the zinc finger proteins such that when two or more zinc finger proteins are bound to a DNA molecule a label pattern will be generated. The pattern, as well as the distance between the zinc finger proteins, provides a signature that helps identify the DNA molecule to which the proteins are bound.

II.B.2. Atomic Force Microscopy

In another embodiment of the invention, atomic force microscopy can be used in a manner substantially similar to that described above for optical mapping. That is, detectable structures can be formed at polymorphic sites by addition of DNA binding proteins, preferably zinc finger proteins, or by forming other detectable complexes at polymorphic sites. Another method for forming detectable structures at polymorphic sites is strand invasion, preferably using PNA molecules. By appropriate design and optimization of PNA molecules an allele specific strand invasion can be effected.

As with the haplotyping methods based on optical mapping, the haplotyped molecules may be either PCR products or genomic DNA fragments.

III. APOE Genotypes and Haplotypes

Described herein are novel polymorphisms in the ApoE gene. The genotyping and haplotyping methods described herein can be used to determine the ApoE genotype and haplotype of unknown samples. These genotyping and haplotyping methods will enable more accurate measurement of the contribution of variation in the entire ApoE gene (promoter, exons, introns and flanking DNA) to variation in serum cholesterol, CHD risk, AD risk, prognosis of patients with neurodegenerative diseases or brain trauma, responses of patients to various treatments and other medically important variables described herein. The methods described herein can provide the degree of sensitivity and selectivity required for successful development of diagnostic, prognostic or pharmacogenetic tests for neurological, psychiatric or cardiovascular disease, either alone or in combination with genetic tests for other relevant genes.

Several United States patents relate to methods for determining ApoE haplotype and using that information to predict whether a patient is likely to develop late onset type Alzheimer's Disease (U.S. Pat. Nos. 5,508,167, 5,716,828), whether a patient with cognitive impairment is likely to respond to a cholinomimetic drug (U.S. Pat. No. 5,935,781) or whether a patient with a non-Alzheimer's neurological disease is likely to respond to therapy (U.S. Pat. No. 5,508, 167). The ApoE tests are generally based on a classification of ApoE into three variant forms of the gene, termed epsilon 2, epsilon 3 and epsilon 4 (and abbreviated $\epsilon 2$, $\epsilon 3$ and $\epsilon 4$). These variant forms are distinguishable on the basis of two polymorphic sites in the ApoE gene. The status of both sites must be tested to determine the alleles present in a subject. The two polymorphic sites are at nucleotides 448 and 586 of the ApoE cDNA (numbering from GenBank accession K00396), corresponding to amino acids 112 and 158 of the processed ApoE protein. The nucleotide polymorphism at both sites is T vs. C, and at both sites it is associated with a cysteine vs. arginine amino acid polymorphism, wherein T encodes cysteine and C encodes arginine. The presence of T at both polymorphic sites (cysteine at both residues 112 and 158) is designated $\epsilon 2$; T at position 448 and C at position 586 (cysteine at 112, arginine at 158) is designated $\epsilon 3$, and C at both variable sites (arginine at both 112 and 158) is designated $\epsilon 4$. These three variant forms of the gene (as well as rarer variant forms) occur in virtually all human populations, with the frequency of the variant forms varying from population to population. The $\epsilon 3$ variant form is commonest all populations, while the frequency of $\epsilon 2$ and $\epsilon 4$ varies. Numerous studies have demonstrated association between ApoE alleles and risk of various diseases or biochemical abnormalities. For example the $\epsilon 4$ variant form is associated with risk of late onset Alzheimer's disease and elevated serum cholesterol.

Variables that may interact with ApoE genotype or haplotype to affect cholesterol and triglyceride levels and heart disease risk include the genes encoding ApoE receptors (low density lipoprotein receptor, and the low density lipoprotein receptor related protein), and genes encoding other apolipoproteins and their receptors, as well as the genes of cholesterol biosynthesis, including hydroxymethylglutaryl CoA reductase, mevalonate synthetase, mevalonate kinase, phosphomevalonate kinase, squalene synthase and other enzymes.

The methods described herein can provide a highly sensitive test of ApoE variation. Specifically, we describe 20 DNA polymorphisms in and around the ApoE gene (including the two polymorphisms that are traditionally studied) (See Table 2). More importantly, we describe the commonly occurring haplotypes at the ApoE locus—that is, the sets of polymorphic nucleotides that occur together on individual chromosomes—and novel methods for determining haplotypes in clinical samples. Also described are data analysis strategies for extracting the maximum information from the ApoE haplotypes, so as to enhance their utility in clinical settings.

The ApoE haplotypes include any haplotype that can be assembled from the sequence polymorphisms described herein in Table 2, or any subset of those polymorphisms. Thus, the invention expressly includes a haplotype including either of the alternative nucleotides at any 2, 3, 4, 5, 6, 7, 8, 9, 10, 11, 12, 13, 14, 15, 16, 17, 18, 19 or 20 of the identified polymorphic sites. The haplotypes expressly include each combination of sites with each selection of alternative nucleotide at each site included in the haplotype. The haplotypes may also include one or more additional polymorphic sites. Among the haplotypes described below are a set of haplotypes that parallel the current ε2, ε3, ε4 classification but do not involve either of the nucleotides that specify the ε2, ε3, ε4 system.

The phenotypes for which ApoE genotyping or haplotyping have been tested are determined by multiple genes, and therefore require the simultaneous analysis of variation in two or more genetic loci. The haplotyping methods of this application facilitate such analysis by providing a basis for (i) identifying substantially all haplotypes that exist at appreciable frequency in a population or populations, (ii) clustering said haplotypes in groups of two or more haplotypes to facilitate statistical analysis, thereby increasing the power of association studies.

Other features and advantages of the invention will be apparent from the following description of the preferred embodiments thereof, and from the claims.

Screening the ApoE Gene for Variation

In order to better understand genetically encoded functional variation in the ApoE gene and its encoded product we systematically cataloged genetic variation at the ApoE locus. The ApoE genomic sequence is represented in GenBank accession AB012576. The gene is composed of four exons and three introns. The transcription start site (beginning of first exon) is at nucleotide (nt) 18,371 of GenBank accession AB012576, while the end of the transcribed region (end of the 3' untranslated region, less polyA tract) is at nt 21958 (Table 2).

We designed PCR primer pairs to cover the ApoE genomic sequence from nucleotides 16,382-23,984. Thus, our analysis began 1,989 nucleotides upstream of the transcription start site, extended across the entire gene and ended 2,026 nucleotides after the final exon. This segment of DNA was chosen to allow us to uncover any polymorphisms that might affect upstream, downstream or intragenic transcriptional regulatory sequences, or that could alter transcribed sequences so as to affect RNA processing (splicing, capping, polyadenylation), mRNA export, translation efficiency, mRNA half life, or interactions with mRNA regulatory factors, or that could affect amino acid coding sequences.

Separately, the ApoE cDNA was screened for polymorphism. The ApoE cDNA sequence was obtained from GenBank accession K00396, which covers 1156 nt. Nucleotides 43 through 1129 were screened by DNA sequencing.

We also searched for polymorphisms in a putative ApoE enhancer element located 15 kb 3 of the end of the ApoE gene, in the expectation that polymorphisms in a regulatory element might affect ApoE levels. The enhancer sequence is in the same GenBank accession as the ApoE gene (AB012576). The segment screened for polymorphism extends from nt 36,737 to 37,498.

Exemplary polymorphism screening methods are described in Example 3. Briefly a panel of 32 subjects of varying geographic, racial and ethnic background were selected for screening.

A total of 20 polymorphic sites were identified, several of which correspond to polymorphisms previously reported in the literature (see Table 2). We also report unique haplotypes that have been observed with these polymorphisms. Table 3 shows an analysis of the haplotypes present in a subset of nine polymorphic sites. These haplotypes were determined using the methods described in detail in Example 1.

Table 4 provides the sequence of 42 additional haplotypes of the ApoE gene. In any given haplotype, the ApoE sequence between the listed nucleotides (e.g., between 16,541 and 16,747) is generally identical to that in the GenBank AB012576, however there may be additional polymorphic sites not listed in this table. Such additional variant sites do not lessen the utility of the haplotypes provided. Where no sequence is provided at a particular site in a particular haplotype (e.g., position 18145 of haplotype 4) it is understood that either of the two nucleotides that appear elsewhere in the column (T or G under column 18145) could appear at the indicated site.

Other haplotypes of the ApoE gene are shown in Table 5. In this table a useful group of haplotypes is shown. These haplotypes are specified by SNPs at positions 16747, 17030, 17785, 19311, and 23707 (as shown in rows 1-4 of the table) or by SNPs at a subset of the these positions: 17785, 19311, and 23707 (rows 5-8); 17030, 19311, and 23707 (rows 9-12); 16747, 19311, and 23707 (rows 13-16); 17030,17785, and 23707 (rows 17-20); 16747, 17030, 19311, and 23707 (rows 21-24); or 16747, 17785, 19311, and 23707 (25-28 of the table). One useful aspect of these haplotypes is that they closely parallel the classic phenotypes as indicated in the column on the far right. That is, the haplotype GCAGC in row 1 identifies the alleles designated ε3 by the classic ApoE test; and GCAGA, in row 3, specify the alleles designated ε4 by the classic ApoE test; and GCAGA, in row 4, identifies the alleles designated ε2 by the classic ApoE test. The haplotypes in rows 5-28 are simpler versions of those in rows 1-4, with the corresponding classic ApoE genotype/phenotypes indicated in the GENOTYPE column. It should be noted that the polymorphisms that specify the classic ApoE alleles are encoded by nucleotides 21250 (first position of codon 112 of the mature ApoE protein) and 21388 (first position of codon 158) of the mature ApoE protein). Nucleotides 21250 and 21388 are not elements of the haplotypes specified in Table 4. In other words, the haplotypes in Table 4 are based upon SNPs that are completely different from the SNPs that form the basis of current ApoE allele classifications and genotype/haplotype tests. Thus, determining a haplotype or pair of haplotypes in a sample by a method that comprises examining any of the combinations of SNPs provided in Table 4, below constitutes a novel method for determining the classic ApoE genotype/phenotype status of a sample.

Preferably, a haplotype or haplotypes specified in the Table 5 are determined in conjunction with at least one additional ApoE SNP specified herein (see Table 4). To constitute a new set of haplotypes.

Preferably, the at least one additional SNP (beyond those in Table 5) divides at lest one of the three classical ApoE phenotypes into two haplotype groups. For example, addition of the C/T polymorphism at nucleotide 21349 to the group in Table 5 divides the E3-like haplotypes into two groups; those with C at 21349 and those with T at 21349. Addition of the T/C polymorphism at nucleotide 17937 to those in Table 5 divides the E2-like haplotypes into two groups: those with a T at 17937 and those with a C at 17937. Such subgroups are more likely to correspond to biologically and clinically homogeneous populations than the classic e2, e3, e4 classification.

EXAMPLES

Example 1

Haplotyping Method Using Hairpin Inducing Primers for Allele Specific PCR

A primer is designed which contains at least two different regions. The 3' portion of the primer corresponds to the template DNA to be amplified. The length of this region of the primer can vary but should be sufficient to impart the required specificity to result in amplification of only the region of cDNA or genomic DNA of interest. Additional nucleotides are added to the 5' end of the primer which are complementary to the region in the sequence which contains the nucleotide variance. Following two rounds of PCR, the added tail region of the primer is incorporated into the sequence. Incorporation of the added nucleotides causes the reverse strand complementary to the primer strand to form a hairpin loop if the correct nucleotide is present at the site of variance. The hairpin loop structure inhibits annealing of new primers and thus further amplification.

Primers with the above characteristics were designed for haplotyping of the dihydropyrimidine dehydrogenase (DPD) gene. See FIGS. 21-32. The DPD gene has two sites of variance in the coding region at base 186 (T:C) and 597 (A:G) which result in amino acid changes of Cys:Arg and Met:Val, respectively (FIG. 21). The second site at base 597 is a restriction fragment length polymorphism (RFLP) which cleaves with the enzyme BsrD I if the A allele is present. Primers were designed which would result in amplification of one or the other allele depending which base was present at the site of variance at base 186 (FIG. 22). The bases added to the 5' end of the primer should form a hairpin loop following incorporation into the PCR product. The boxed base is the added base which hybridizes to the variant base and is responsible for the allele discrimination of the hairpin loop. The DPDNSF primer contains only the DPD complementary sequence and will not result in allele specific amplification. FIG. 23 shows hybridization of the non-specific DPDNSF primer to both the T and A allele of the DPD target sequence and the 5' end of the PCR product generated by amplification using this primer. FIGS. 24 and 25 are the corresponding diagrams as shown in FIG. 23, for primers DPDASTF and DPDASCF. Notice that the added bases are incorporated into the PCR fragment following amplification. FIG. 26 shows the most stable hairpin loop structures formed with the reverse strand of the PCR product made using the DPDNSF primer using the computer program Oligo4. Only the reverse strand is shown because this would be the strand to which the DPDNSF primer would hybridize on subsequent rounds of amplification. The hairpin loops are either not stable or have a low melting temperature. FIGS. 27 and 28 are the corresponding diagrams for the hairpin loops formed in the reverse strands of the PCR products generated using primers DPDASCF and DPDASTF, respectively. Amplification using primer DPDASCF of the T allele results in the ability to form a very stable hairpin loop with a melting temperature of 83° C. (FIG. 27). In contrast, amplification of the C allele with primer DPDASCF generates a hairpin loop with a melting temperature of only 42° C. The converse is true for the primer DPDASTF. Amplification of the C allele of DPD results in the formation of a very stable hairpin loop (100° C.) while amplification of the T allele results in the formation of a much less stable hairpin (42° C.) (FIG. 28).

FIGS. 29-31 depict the primer hybridization and amplification events when further amplification is attempted on the generated PCR fragments. The DPDNSF primer is able to effectively compete with the hairpin structures formed with both the T and C allele of the DPD gene and thus amplification of both alleles proceeds efficiently (FIG. 29). The DPDASCF primer (FIG. 30) is able to compete for hybridization with the hairpin loop formed with the C allele because its melting temperature is higher than the hairpin loop's (60° C. compared to 42° C.). The hairpin loop formed on the T allele however, has a higher melting temperature than the primer and thus effectively competes with the primer for hybridization. The hairpin loop inhibits PCR amplification of the T allele which results in allele specific amplification of the C allele. The reverse is true for the primer DPDASTF. The hairpin loop structure has a higher melting temperature than the primer for the C allele and a lower melting temperature than the primer for the T allele. This causes inhibition of primer hybridization and elongation on the C allele and results in allele specific amplification of the T allele.

The ability to use this for haplotyping is diagrammed in FIG. 32 using a cDNA sample whose haplotype is know to be: Allele 1- $T^{186}$:$A^{597}$, Allele 2-$C^{186}$:$G^{597}$. The size of the fragments generated by a BsrD I from a 597 bp generated by amplification with the primers DPDNSF, DPDASTF, and DPDASCF, depend on whether the base at site 597 is an A or a G. Restriction digestion by BsrD I is indicative of the A base being at site 597. If a fragment has the A base at 597, three fragments will be generated of lengths 138, 164 and 267 bp. If the G base is at site 597 only two fragments will be generated of lengths 164 and 405 bp. If a sample is heterozygous for A and G at site 597, you will generate all four bands of 138, 164 (2×), 267 and 405 bp. The expected fragments generated by BsrD I restriction for each of the primers is indicated in the box in FIG. 36.

FIG. 33 shows a picture of an agarose gel run in which each of the primers was used to amplify the cDNA sample heterozygous at both sites 186 and 597 followed by BsrD I restriction. The DPDNSF lane shows the restriction fragment pattern for the selected cDNA using the DPDNSF primer indicating that this sample is indeed heterozygous at site 597. However, using the same cDNA sample and the primer DPDASTF (DPDASTF lane), the restriction pattern correlates to the pattern representative of a sample which is homozygous for A at site 597. Because the DPDASTF primer allows amplification of only the T allele, the haplotype for that in the sample must be $T^{186}$:$A^{597}$. The restriction digest pattern using the primer DPDASCF (DPDASCF lane) correlates with the expected pattern for there being G at site 597. Amplification of the cDNA sample with the primer DPDASCF results in amplification of only the C allele in the sample. Thus the haplotype for this allele must be $C^{186}$:$G^{597}$. This demonstrates that primers can be designed that will incorporate a sequence into a PCR product which is capable of forming a hairpin loop structure that will inhibit PCR amplification for one allele but not the other allele even if there is only a single base pair difference between the two alleles. This can be exploited for allele specific amplification and thus haplotyping of DNA samples.

Alternatively, it may also be possible to form a hairpin structure at the 5' end of the PCR product which is stable enough to keep the polymerase from extending through the region. This may be possible by incorporating into the primer modified nucleotides or structures that when they hybridized to the correct base they would form a structure stable enough to inhibit read through by a polymerase.

This invention is meant to cover any method in which a stable secondary structure is formed in one or both strands of a PCR product which inhibits further PCR amplification. The secondary structure is formed only when the correct base or bases are present at a known site of variance. The secondary structure is not formed when the incorrect base or bases are present in the PCR product at the site of variance allowing further amplification of that product. This allows the specific amplification of one of the two possible alleles in a sample specific allowing the haplotyping of that allele.

Example 2

Genotyping of an ApoE Variance by Mass Spectrometry Analysis of Restriction Enzyme Generated Fragments The following example describes the genotyping of the variance at genomic site 21250 in the ApoE gene which is a T:C variance resulting in a cysteine to arginine amino acid change in amino acid 176 in the protein. Two primers were designed to both amplify the target region of the ApoE gene and to introduce two restriction enzyme sites (Fok I, Fsp I) into the amplicon adjacent to the site of variance. FIG. 34 shows the sequence of the primers and the target DNA. The Apo21250-LFR primer is the loop primer which contains the restriction enzyme recognition sites and the ApoE21250-LR primer is the reverse primer used in the PCR amplification process. The polymorphic nucleotide is shown in italics. The following components were mixed together in a 200 µl PCR tube for each genotyping reaction. All n volumes are given in µl.

| A. | 10x PCRx buffer (Gibco/BRL, cat# 11509-015) | 2 |
|---|---|---|
| B. | 2 mM dNTP mix | 2 |
| C. | 50 mM MgSO$_4$ | 0.8 |
| D. | PCR enhancer (Gibco/BRL, cat# 11509-015) | 4 |
| E. | 20 µM ApoE21250-LFR primer | 1 |
| F. | 20 µM ApoE21250-LR primer | 1 |
| G. | Patient genomic DNA 20 ng/ul | 0.5 |
| H. | Platinum Taq DNA polymerase (Gibco/BRL, cat# 11509-015) | 0.1 |
| I. | deionized water | 8.6 |

The reactions were cycled through the following steps in MJ Research PTC 200 thermocyclers:

| A. | 94° C. | 1 min. | 1 cycle |
|---|---|---|---|
| B. | 94° C. | 15 sec. | B-D 45 cycles |
| C. | 55° C. | 15 sec. | |
| D. | 72° C. | 30 sec. | |
| E. | 15° C. | indefinitely | hold |

The sequence of the amplicon for both the T allele and the C allele following amplification is shown in FIG. 35. Five µl of each reaction were removed and analyzed by agarose gel electrophoresis to ensure the presence of sufficient PCR product of the correct size. The following components were mixed together for the restriction enzyme cleavage of the DNA. Platinum Taq antibody (Taquench, Gibco/BRL cat#10965-010) was added to inhibit any potential filling in of the 3' recessed end created by Fok I cleavage. All volumes are in µl.

| A. | 10x New England Biolabs buffer #2 | 2 |
|---|---|---|
| B. | Fok I 4 units/µl (New England Biolabs, cat# 109S) | 0.3 |
| C. | Fsp I 5 units/µl (New England Biolabs, cat# 135S) | 0.2 |
| D. | Platinum Taq antibody (Gibco/BRL, cat# 11509-015) | 0.2 |
| E. | PCR reaction | 15 |
| F. | deionized water | 2.4 |

The above reactions were incubated at 37° C. for 1 hour. FIG. 35 shows the cleavage sites for each amplicon and shows the 8-mer and 12-mer fragments generated following Fok I and FspI cleavage and the expected molecular weights. Following incubation, the reactions were purified by solid phase extraction and eluted in a volume of 100 µl of 70% acetonitrile water mix. The samples were dried in a Savant AES 2010 speed vac for 1 hour under vacuum and heat. The samples were resuspended in 3 µl matrix (65 mg/ml 3-hydroxy-picolinic acid, 40 mM ammonium citrate, 50% acetonitrile) and spotted on the Perseptive Biosystems 20×20 teflon coated plate. Samples were analyzed on the Perspective Biosystems Voyager-DE Biospectrometry™ Workstation.

Example 3

Screening the ApoE Gene for Polymorphism

PCR primers were selected automatically by a computer program that attempts to match forward and reverse primers in terms of GC content, melting temperature, and lack of base complementarity. The parameters of the program were set to select primers approximately 500 base pairs apart from each other, with at least 50 base pairs of overlap between adjacent PCR products. Primers were received in 96 well microtiter plates, resuspended in sterilized deionized water at a concentration of 5 pmoles/ul. PCR reactions were set up using a programmed Packard robot to pipet a master mix of 1× PCR buffer, polymerase and template into 96 well plates. Starting PCR conditions were: 10 mM Tris (pH 8.3), 50 mM KCl, 1.5 mM MgCl$_2$, 0.2 mM dNTPs, 0.83 uM forward and reverse primers, 0.7 Units of AmpliTaq Gold (PE Corp) and 25 ng of genomic template, in a volume of 30 ul. Cycling was done on MJ PTC200 PCR machines with the following cycle conditions: denature 12 minutes at 95° C. followed by 35 cycles of: denature 15 seconds at 94° C., anneal 30 seconds at 60° C., extend 45 seconds at 72° C., followed by a ten minute extension at 72° C. PCR success was then tested by analyzing products on 6% Long Ranger acrylamide gels. Products passed if they exhibited clean bands stronger than a 15 ng standard, with little to no secondary amplification products. Efforts to optimize conditions for failed PCR products began with systematic variation of temperature, cosolvents (particularly PCR enhancer from GIBCO/BRL) and polymerase (Platinum Taq from GIBCO/BRL vs. AmpliTaq Gold). PCR products not optimized by these modifications were discarded and one or two new PCR primers were ordered and the process repeated until successful amplicons were produced.

Optimized PCR primer pairs were used to perform DNA cycle sequencing using ABI BigDye DNA sequencing kits according to instructions provided with the kits, except kit reagents were diluted 1:8 and A, G, C and T reactions were set up robotically in a volume of 20 ul.

Sequencing reactions were run on ABI 377 or ABI 3700 automated DNA sequencing instruments. ABI 377 and ABI 3700 run times were similar, approximately 4 hours at approximately 5000 volts. Data was collected automatically using ABI collection software. The quality of DNA sequencing reactions was assessed automatically and numerically scored using the program PHRED. Only DNA sequence of quality level 30 or higher was considered acceptable for analysis.

Raw sequencing reactions were then imported into a custom database and analyzed using PHRED, PHRAP and POLYPHRED, and then the CONSED viewer was used to visually inspect the data and verify variances. The custom database was used to track all samples in process and serve as a virtual notebook reference for all sample handling steps as well as data generation, manipulation and presentation Example 4

Restriction Enzyme Haplotyping Method

As described herein, restriction endonucleases that distinguish single nucleotide polymorphisms can enable the direct determination of the sequence for a single segment of a chromosome, locus, gene, or portion of a gene. Restriction enzymes can be used to cleave DNA in a site specific manner and thus be used to digest DNA samples collected from individuals at or near these polymorphic sites. In the instant method, aliquots of these digestions are used as templates in polymerase chain reactions (PCR). The restriction sites and the subsequent PCR can be used in tandem to identify allele-specific sequence which is in-phase with the uncut sequence, i.e., haplotyping. The alternative sequence is obtained by subtraction of the known sequence from the genotype.

A diagram of the instant method is depicted in FIG. 36. The restriction map of the ApoE gene illustrates the relative position of Nco I, an restriction enzyme that specifically recognizes 5' CCATGG sequences, restriction sites. It is known that a G to T polymorphism at position 16747 (5' CCAT G/T G)is within this NcoI site. Therefore, a G within this site is digested whereas a T is neither recognized nor digested. Additional digestion sites for NcoI occur 5' and 3' to the 16747 site of the G/T polymorphism. Primers for use in the subsequent PCR are shown to be internal to the 5' and 3' NcoI digestion sites. These primers are then used to amplify the template that was or was not digested by Nco I at the restriction enzyme recognition site (position 16747). Therefore, if G is at 16747 then NcoI will digest the DNA and PCR will not proceed, whereas in contrast, if T is present at 16747, then NcoI will not digest the DNA and PCR will proceed under the conditions described.

Also shown in this figure is site 17030, which has a known G/C polymorphic site. If the allele-specific restriction digestion and amplification is successful, it would be expected that either G or C at 17030 would be associated with T at 16747.

A human cell line was selected because it is heterozygous at position 16747 and at 17030 (polymorphisms are within the boundary defined by Nco I sites). Genomic DNA was isolated by standard methods known in the art. For each DNA test sample, 100 ng of DNA in a 25 μl reaction volume was restricted with 0 units or 5 units of Nco I of enzyme for two hours, four hours and six hours. Reactions were then heated to 65° C. for 20 minutes to inactivate the restriction enzyme. For each PCR reaction, 5 μl was used in a 20 μl PCR reaction containing 2001M dNTPs, 2 mM $MgSO_4$, 1× PCR buffer, 1 picomole each primer, 0× or 1.5× enhancer (Gibco/BRL) and 1 unit of Taq HIFI (DNA polymerase, Gibco/BRL). The reaction were conducted in a thermal cycler as follows: (1) 94° C. for 1 minute, (2) 94° C. for 15 seconds (3) 52° C. for 15 seconds, and (4) 72° C. 3 minutes, then back to (2) for a total of 35 cycles. All samples were then diluted 1:500 in water.

Secondary reactions were designed so that 5' and 3' primers flanking the polymorphisms at 16747 and 17030. These primers were then used to amplify the diluted template from the first reaction. These secondary reactions were conducted to confirm the actual base at the 16747 and 17030 positions within each of the samples.

All reactions were analyzed via mass spectrometry and the data is shown in FIGS. 37A-B and 38A-B.

FIG. 37A-B depicts the mass spectrometry results for the above described secondary reaction experiments. In panel 37A, in the control reaction (minus NcoI), two large peaks of absolute intensity can be explained by the two amplified fragments, 3757.8 and 3781.7, which are attributable to either a T or G at position 16747, respectively. In panel 37B, in the NcoI treatment reactions (+enzyme), the 3757.8 peak is entirely absent from the spectra, indicating that the G at position 16747 is present and that the enzyme cut the strand containing T base and amplification ensued. In FIG. 38A-B, panel 38A, in the control reaction (minus NcoI), two large peaks of absolute intensity can be explained by two fragments 3734.7 and 3774.8 which are attributable to a G or C at position 17030, respectively. In panel 38B, in the NcoI treatment reactions (plus NcoI), the 3774.8 peak is entirely absent from the spectra, indicating that the C base at this position is present. The results from these experiments indicate that the haplotype for this DNA sample is 16747-T, 17030-G and 16747-C, 17030-C.

All references and patents cited herein are hereby incorporated into this application by reference in their entirety. A number of embodiments of the invention have been described. Nevertheless, it will be understood that various modifications may be made without departing from the spirit and scope of the invention. Accordingly, other embodiments are within the scope of the following claims.

TABLE 1

Mass differences between the nucleotides dATP, dCTP, dGTP, dTTP, and BrdUTP.

|        | dA   | dC   | dG   | dT   | BrdU |
|--------|------|------|------|------|------|
| dATP   |      |      |      |      |      |
| dCTP   | 24.0 |      |      |      |      |
| dGTP   | 16.0 | 40.0 |      |      |      |
| dTTP   | 9.0  | 15.0 | 25.0 |      |      |
| BrdUTP | 55.8 | 79.8 | 39.8 | 64.8 |      |

TABLE 2

ApoE genomic sequence (GenBank accession AB012576) with polymorphisms indicated
(partial sequence of the accession)

```
14701 ctggtggagc atctgatggg tgtttgggcc aagctggagc tttgtccatc ccctcttatt    (SEQ ID NO:100)

14761 tttctgcact tgactctctt attttctga gactggtctc cctctgtcgc ccaggctaga
```

TABLE 2-continued

ApoE genomic sequence (GenBank accession AB012576) with polymorphisms indicated
(partial sequence of the accession)

```
14821 gtgcagcagt gcaactgcgg ctcactgcag cctccacctc ccgggctcaa gcagccttcc 14881 cacctcagcc tcctgagtag ctaggaccac aggtgtatgc caccaggccc agctaatttt 14941 tttgatagtt ttgggagaca tgggggtttc accatgttgc ccaggctggt ctcgaactcc 15001 tggactcaag ccttggcctc ccaaagtgct gggattatag gtgtgagcca ccacacccag 15061 ccagggtaga aggcactttg gaagcctcga gcctgcccca ttcatcttac gttagtggaa 15121 actgaggctt ccagaggttt caaggtcaca actaaatcca gaacctcatc tcaggcacac 15181 tggtcgtagt cccaatgtcc agtcttaagt cttcttggat atctgtggct cacagatttt 15241 gggtgtttga gcctcctgct gagcactgct ggggccacag cggtgaccag ccctgtcttc 15301 acgggactca gtgagaggaa cagattcatc cgcagagtgg gcaggactag gttggggaa 15361 cccagggtc tagagggctt ttcagagggc aggggtcact gagcggagag cagaggagga 15421 gtgagccatt tgctccagcg tgaagttgtt ggtgtgatgg ggtttcaggg tggcaggagc 15481 agtgtggtta aaggtctgga agctgtcggc atgtggctgg tatccaaggt ggccaggaac 15541 tctgcatgga tatggtggga agctggcacg cctctcacct cagctcttcc ctgcaggctc 15601 tgtggatagc aactggatcg tgggtgccac gctggagaag aagctcccac ccctgcccct 15661 gacactggcc cttggggcct tcctgaatca ccgcaagaac aagtttcagt gtggctttgg 15721 cctcaccatc ggctgagccc tcctggcccc cgccttccac gcccttccga ttccacctcc 15781 acctccacct cccccctgcca cagaggggag acctgagccc cctcccttc cctccccct 15841 tggggtcgg ggggacatt ggaaaggagg gaccccgcca ccccagcagc tgaggagggg 15901 attctggaac tgaatggcgc ttcgggattc tgagtagcag gggcagcatg cccagtgggc 15961 ctggggtccc gggagggatt ccggaattga ggggcacgca ggattctgag caccagggc 16021 agaggcggcc agacaacctc agggaggagt gtcctggcgt ccccatcctc caaagggcct 16081 gggcccgccc cgaggggca gcgagaggag cttccccatc cccggtcagt ccaccctgcc 16141 ccgtccactt tcccatctcc tcggtataaa tcatgtttat aagttatgga agaaccggga 16201 cattttacag aaaaaaaaca aaaacaaca aaaatatac gtgggaaaaa aaacgatggg 16261 aggcctccgt tttctcaagt gtgtctggcc tgttttgagc atttcatccg gagtctggcc 16321 gccctgacct tcccccagcc gcctgcaggg ggcgccagag ggccggagca cggaaagcag 16381 cggatccttg atgctgcctt aagtccggct cagaggggcg cagcgtggcc tggggtcgct 16441 atcttcccat ccggaacatc tgccctgctg ggggacacta cgggccttcc cttgcctgag
                                                    nt16541 *
16501 ggtagggtct caaggtcact tgcccccagc ttgacctggc ggagtggct atagaggact 16561 ttgtccctgc agactgcagc agcagagatg acactgtctc tgagtgcaga gatggggca 16621 gggagctggg agagggttca agctactgga acagcttcag aacaactagg gtactaggaa 16681 ctgctgtgtc agggagaagg ggctcaagga ctcgcaggcc tgggaggagg ggcctaggcc
   nt16747 *
16741 agccat gga gttgggtcac ctgtgtctga ggacttggtg ctgtctggat tttgccaacc 16801 tagggctggg gtcagctgat gcccaccacg actcccgagc ctccaggaac tgaaaccctg 16861 tctgccccca gggtctgggg aaggaggctg ctgagtagaa ccaaccccag gttaccaacc
                                                    nt16965 *
```

TABLE 2-continued

ApoE genomic sequence (GenBank accession AB012576) with polymorphisms indicated
(partial sequence of the accession)

```
16921 ccacctcagc cacccccttgc cagccaaagc aaacaggccc ggcc ggcac tgggggttcc
                                         nt17030   *
16981 ttctcgaacc aggagttcag cctcccctga cccgcagaat cttctgatc  cacccgctcc
                                         nt17098   *
17041 aggagccagg aatgagtccc agtctctccc agttctcact gtgtggtttt gccattc tc
17101 ttgctgctga accacgggtt tctcctctga aacatctggg atttataaca gggcttagga
17161 aagtgacagc gtctgagcgt tcactgtggc ctgtccattg ctagccctaa cataggaccg
17221 ctgtgtgcca gggctgtcct ccatgctcaa tacacgttag cttgtcacca aacatacccg
17281 tgccgctgct ttcccagtct gatgagcaaa ggaacttgat gctcagagag acaagtcat
                                         nt17387   *
17341 ttgcccaagg tcacacagct ggcaactggc agagccagga ttcacg cct ggcaatttga
17401 ctccagaatc ctaaccttaa cccagaagca cggcttcaag ccctggaaa ccacaatacc
17461 tgtggcagcc aggggggaggt gctggaatct catttcacat gtggggaggg ggctcccctg
17521 tgctcaaggt cacaaccaaa gaggaagctg tgattaaaac ccaggtccca tttgcaaagc
17581 ctcgactttt agcaggtgca tcatactgtt cccacccctc ccatcccact tctgtccagc
17641 cgcctagccc cactttcttt ttttctttt tttgagacag tctccctctt gctgaggctg
17701 gagtgcagtg gcgagatctc ggctcactgt aacctccgcc tcccgggttc aagcgattct
                     nt17785   *
17761 cctgcctcag cctcccaagt agct ggatt acaggcgccc gccaccacgc ctggctaact
                                         nt17874   *
17821 tttgtatttt tagtagagat ggggtttcac catgttggcc aggctggtct caa ctcctg
                                         nt17937   *
17881 accttaagtg attcgcccac tgtggcctcc caaagtgctg ggattacagg cgtgac acc
17941 gcccccagcc cctcccatcc cacttctgtc cagcccccta gccctacttt ctttctggga
18001 tccaggagtc cagatcccca gcccctctc cagattacat tcatccaggc acaggaaagg
18061 acagggtcag gaaaggagga ctctgggcgg cagcctccac attcccttc cacgcttggc
                     nt18145   *
18121 ccccagaatg gaggagggtg tctg attac tgggcgaggt gtcctcccctt cctggggact
18181 gtgggggtg gtcaaaagac ctctatgccc cacctccttc ctccctctgc cctgctgtgc
18241 ctggggcagg gggagaacag cccacctcgt gactgggggc tggcccagcc cgccctatcc
18301 ctgggggagg gggcgggaca gggggagccc tataattgga caagtctggg atccttgagt
18361 cctactcagc CCCAGCGGAG GTGAAGGACG TCCTTCCCCA GGAGCCGgtg agaagcgcag
                                         nt18476   *
18421 tcggggggcac gggggatgagc tcagggggcct ctagaaagag ctgggaccct gggaa ccct
18481 ggcctccagg tagtctcagg agagctactc ggggtcgggc ttggggagag gaggagcggg
18541 ggtgaggcaa gcagcagggg actggacctg ggaagggctg ggcagcagag acgacccgac
18601 ccgctagaag gtggggtggg gagagcagct ggactgggat gtaagccata gcaggactcc
18661 acgagttgtc actatcattt atcgagcacc tactgggtgt ccccagtgtc ctcagatctc
```

TABLE 2-continued

ApoE genomic sequence (GenBank accession AB012576) with polymorphisms indicated
(partial sequence of the accession)

```
18721 cataactggg gagccagggg cagcgacacg gtagctagcc gtcgattgga gaactttaaa 18781 atgaggactg aattagctca taaatggaac acggcgctta actgtgaggt tggagcttag 18841 aatgtgaagg gagaatgagg aatgcgagac tgggactgag atggaaccgg cggtggggag 18901 ggggtggggg gatggaattt gaaccccggg agaggaagat ggaattttct atggaggccg 18961 acctggggat ggggagataa gagaagacca ggagggagtt aaataggga tgggttgggg 19021 gcggcttggt aaatgtgctg ggattaggct gttgcagata atgcaacaag gcttggaagg 19081 ctaacctggg gtgaggccgg gttggggccg ggctgggggt gggaggagtc ctcactggcg 19141 gttgattgac agtttctcct tccccagACT GGCCAATCAC AGGCAGGAAG ATGAAGGTTC 19201 TGTGGGCTGC GTTGCTGGTC ACATTCCTGG CAGGtatggg ggcggggctt gctcggttcc
                                                  nt19311    *
19261 ccccgctcct cccctctca tcctcacctc aacctcctgg ccccattcag cagaccctg 19321 ggcccctct tctgaggctt ctgtgctgct tcctggctct gaacagcgat ttgacgctct 19381 ctgggcctcg gtttccccca tccttgagat aggagttaga agttgtttg ttgttgttgt 19441 ttgttgttgt tgttttgttt ttttgagatg aagtctcgct ctgtcgccca ggctggagtg 19501 cagtggcggg atctcggctc actgcaagct ccgcctccca ggtccacgcc attctcctgc 19561 ctcagcctcc caagtagctg ggactacagg cacatgccac cacacccgac taacttttt 19621 gtatttcag tagagacggg gtttcaccat gttggccagg ctggtctga actcctgacc 19681 tcaggtgatc tgcccgtttc gatctcccaa agtgctggga ttacaggcgt gagccaccgc 19741 acctggctgg gagttagagg ttttctaatgc attgcaggca gatagtgaat accagacacg 19801 gggcagctgt gatctttatt ctccatcacc cccacacagc cctgcctggg gcacacaagg 19861 acactcaata catgcttttc cgctgggcgc ggtggctcac ccctgtaatc ccagcactt 19921 gggaggccaa ggtgggagga tcacttgagc ccaggagttc aacaccagcc tgggcaacat 19981 agtgagaccc tgtctctact aaaaatacaa aaattagcca ggcatggtgc cacacacctg 20041 tgctctcagc tactcaggag gctgaggcag gaggatcgct tgagcccaga aggtcaaggt 20101 tgcagtgaac catgttcagg ccgctgcact ccagcctggg tgacagagca agaccctgtt 20161 tataaataca taatgctttc caagtgatta aaccgactcc cccctcaccc tgcccaccat 20221 ggctccaaag aagcatttgt ggagcacctt ctgtgtgccc ctaggtacta gatgcctgga
                                                  nt20334 (A18T)    *
20281 cggggtcaga aggaccctga cccaccttga acttgttcca cacaggATGC CAG CCAAGG

20341 TGGAGCAAGC GGTGGAGACA GAGCCGGAGC CCGAGCTGCG CCAGCAGACC GAGTGGCAGA

20401 GCGGCCAGCG CTGGGAACTG GCACTGGGTC GCTTTTGGGA TTACCTGCGC TGGGTGCAGA

20461 CACTGTCTGA GCAGGTGCAG GAGGAGCTGC TCAGCTCCCA GGTCACCCAG GAACTGAGGt 20521 gagtgtcccc atcctggccc ttgaccctcc tggtgggcgg ctatacctcc ccaggtccag 20581 gtttcattct gccctgtcg ctaagtcttg ggggcctgg gtctctgctg gttctagctt 20641 cctcttccca tttctgactc ctggctttag ctctctggaa ttctctctct cagctttgtc 20701 tctctctctt cccttctgac tcagtctctc acactcgtcc tggctctgtc tctgtccttc 20761 cctagctctt ttatatagag acagagagat ggggtctcac tgtgttgccc aggctggtct 20821 tgaacttctg ggctcaagcg atcctcccgc ctcggcctcc caaagtgctg ggattagagg
```

TABLE 2-continued

ApoE genomic sequence (GenBank accession AB012576) with polymorphisms indicated
(partial sequence of the accession)

```
20881 catgagccac cttgcccggc ctcctagctc cttcttcgtc tctgcctctg ccctctgcat
20941 ctgctctctg catctgtctc tgtctccttc tctcggcctc tgccccgttc cttctctccc
21001 tcttgggtct ctctggctca tccccatctc gcccgcccca tcccagccct tctccccgcc
21061 tcccactgtg cgacaccctc ccgccctctc ggccgcaggG CGCTGATGGA CGAGACCATG
21121 AAGGAGTTGA AGGCCTACAA ATCGGAACTG GAGGAACAAC TGACCCCGGT GGCGGAGGAG
21181 ACGCGGGCAC GGCTGTCCAA GGAGCTGCAG GCGGCGCAGG CCCGGCTGGG CGCGGACATG
nt21250 (C130R)
21241 GAGGACGTG GCGGCCGCCT GGTGCAGTAC CGCGGCGAGG TGCAGGCCAT GCTCGGCCAG
                                                       nt21349 (R163C)
21301 AGCACCGAGG AGCTGCGGGT GCGCCTCGCC TCCCACCTGC GCAAGCTG G TAAGCGGCTC
                nt21388 (R176C)
21361 CTCCGCGATG CCGATGACCT GCAGAAG GC CTGGCAGTGT ACCAGGCCGG GGCCCGCGAG
21421 GGCGCCGAGC GCGGCCTCAG CGCCATCCGC GAGCGCCTGG GGCCCCTGGT GGAACAGGGC
21481 CGCGTGCGGG CCGCCACTGT GGGCTCCCTG GCCGGCCAGC CGCTACAGGA GCGGGCCCAG
21541 GCCTGGGGCG AGCGGCTGCG CGCGCGGATG GAGGAGATGG GCAGCCGGAC CCGCGACCGC
21601 CTGGACGAGG TGAAGGAGCA GGTGGCGGAG GTGCGCGCCA AGCTGGAGGA GCAGGCCCAG
21661 CAGATACGCC TGCAGGCCGA GGCCTTCCAG GCCCGCCTCA AGAGCTGGTT CGAGCCCCTG
21721 GTGGAAGACA TGCAGCGCCA GTGGGCCGGG CTGGTGGAGA AGGTGCAGGC TGCCGTGGGC
21781 ACCAGCGCCG CCCCTGTGCC CAGCGACAAT CACTGAACGC CGAAGCCTGC AGCCATGCGA
21841 CCCCACGCCA CCCCGTGCCT CCTGCCTCCG CGCAGCCTGC AGCGGGAGAC CCTGTCCCCG
21901 CCCCAGCCGT CCTCCTGGGG TGGACCCTAG TTTAATAAAG ATTCACCAAG TTTCACGCat
21961 ctgctggcct cccctgtga tttcctctaa gccccagcct cagtttctct ttctgcccac
22021 atactggcca cacaattctc agcccctcc tctccatctg tgtctgtgtg tatctttctc
22081 tctgcccttt ttttttttt tagacggagt ctggctctgt cacccaggct agagtgcagt
22141 ggcacgatct tggctcactg caacctctgc ctcttgggtt caagcgattc tgctgcctca
22201 gtagctggga ttacaggctc acaccaccac acccggctaa ttttttgtatt tttagtagag
22261 acgagctttc accatgttgg ccaggcaggt ctcaaactcc tgaccaagtg atccaccgc
22321 cggcctccca agtgctgag attacaggcc tgagccacca tgcccggcct ctgcccctct
22381 ttcttttta gggggcaggg aaaggtctca ccctgtcacc cgccatcaca gctcactgca
22441 gcctccacct cctggactca agtgataagt gatcctcccg cctcagcctt ccagtagct
22501 gagactacag gcgcatacca ctaggattaa tttggggggg gggtggtgtg tgtggagatg
22561 gggtctggct tgttggcca ggctgatgtg gaattcctgg gctcaagcga tactcccacc
22621 ttggcctcct gagtagctga gactactggc tagcaccacc acacccagct ttttattatt
22681 atttgtagag acaaggtctc aatatgttgc ccaggctagt ctcaaacccc tgggctcaag
22741 agatcctccg ccatcggcct cccaaagtgc tgggattcca ggcatgggc tccgagcccg
22801 gcctgccaa cttaataata cttgttcctc agagttgcaa ctccaaatga cctgagattg
22861 gtgccttat tctaagctat tttcattttt tttctgctgt cattattctc ccccttctct
22921 cctccagtct tatctgatat ctgcctcctt cccacccacc ctgcacccca tcccacccct
```

TABLE 2-continued

ApoE genomic sequence (GenBank accession AB012576) with polymorphisms indicated
(partial sequence of the accession)

```
22981 ctgtctctcc ctgttctcct caggagactc tggcttcctg ttttcctcca cttctatctt 23041 ttatctctcc ctcctacggt ttcttttctt tctccccggc ctgcttgttt ctcccccaac 23101 cccccttcatc tggatttctt cttctgccat tcagtttggt ttgagctctc tgcttctccg 23161 gttccctctg agctagctgt cccttcaccc actgtgaact gggtttccct gcccaaccct 23221 cattctcttt ctttcttttct ttttttttt ttttttttt ttttttttt gagacagagt 23281 cttgctctgt tgcccagcct ggagtgcagt ggtgcaatct tggttcactg caacctccac 23341 ttcccagatt caagcaattc tcctgcctca gcctccagag tagctgggat tacaggcgtg 23401 tcccaccaca cccgactaat ttttgtattt ttggtagaga caaggcttcg gcattgttgg 23461 ccaggcaggt ctcgaactcc tgacctcaag taatctgcct gcctcaccct cccaaagtgc nt23524  *

23521 tgg attaca ggcatgagcc acctcacccg gaccatccct cattctccat cctttcctcc 23581 agttgtgatg tctacccctc atgtttccca acaagcctac tgggtgctga atccaggctg 23641 ggaagagaag ggagcggctc ttctgtcgga gtctgcacca ggcccatgct gagacgagag nt23707  *                                              nt23759  *

23701 ctggcg tca gagaggggaa gcttggatgg aagcccagga gccgccggca ctctcttc c nt23805  *

23761 ctcccacccc ctcagttctc agagacgggg aggagggttc ccac aacgg gggacaggct 23821 gagacttgag cttgtatctc ctgggccagc tgcaacatct gcttgtccct ctgcccatct 23881 tggctcctgc acaccctgaa cttggtgctt tccctggcac tgctctgatc acccacgtgg 23941 aggcagcacc cctcccctgg agatgactca ccagggctga gtgaggaggg gaagggtcag 24001 tgtgctcaca ggcaggggc ctggtctgct gggcctgctg ctgattcacc gtatgtccag

BREAK 36601 catgcgttag gagggacatt tcaaactctt ttttacccta gactttccta ccatcaccca 36661 gagtatccag ccaggagggg aggggctaga gacaccagaa gtttagcagg gaggagggcg 36721 tagggattcg gggaatgaag ggatgggatt cagactaggg ccaggaccca gggatggaga 36781 gaaagagatg agagtggttt gggggcttgg tgacttagag aacagagctg caggctcaga 36841 ggcacacagg agtttctggg ctcaccctgc ccccttccaa cccctcagtt cccatcctcc 36901 agcagctgtt tgtgtgctgc ctctgaagtc cacactgaac aaacttcagc ctactcatgt 36961 ccctaaaatg ggcaaacatt gcaagcagca aacagcaaac acacagccct ccctgcctgc 37021 tgaccttgga gctggggcag aggtcagaga cctctctggg cccatgccac ctccaacatc 37081 cactcgaccc cttggaattt cggtggagag gagcagaggt tgtcctggcg tggtttaggt 37141 agtgtgagag ggtccgggtt caaaccact tgctgggtgg ggagtcgtca gtaagtggct nt37237  *

37201 atgccccgac cccgaagcct gtttccccat ctgtac atg gaaatgataa agacgcccat 37261 ctgatagggt ttttgtggca aataaacatt tggttttttt gttttgtttt gttttgtttt 37321 ttgagatgga ggtttgctct gtcgcccagg ctggagtgca gtgacacaat ctcatctcac 37381 cacaaccttc cctgcctca gcctcccaag tagctgggat tacaagcatg tgccaccaca 37441 cctggctaat tttctatttt tagtagagac gggtttctcc atgttggtca gcctcagcct
```

TABLE 2-continued

ApoE genomic sequence (GenBank accession AB012576) with polymorphisms indicated
(partial sequence of the accession)

```
37501 cccaagtaac tgggattaca ggcctgtgcc accacacccg gctaattttt tctatttttg 37561 acagggacgg ggtttcacca tgttggtcag gctggtctag aactcctgac ctcaaatgat 37621 ccacccacct aggcctccca aagtgcacag attacaggcg tgggccaccg cacctggcca

BREAK 41821 aaaagatggt cttgtggggt aatgaaggac acaagcttgg tgggacctga gtccccaggc 41881 tggcatagag ccccttactc cctgtgt
//
```

= Polymorphisms (the polymorphic nt is numbered)
Bold = ApoE transcribed sequences (exons 1-4)
Grey shaded = Contains ApoE enhancer
<u>Underline</u> = Coding Region of the ApoE gene
       * = Polymorphisms not previously described in the art

We claim:

1. A method for determining the nucleotide present at a selected polymorphic site in a target nucleic acid molecule, comprising:
   (a) amplifying a portion of the target nucleic acid molecule comprising the selected polymorphic site using a first primer and a second primer, the second primer containing a recognition site for a first restriction enzyme and a recognition site for a second restriction enzyme, to generate amplification product containing a recognition site for the first restriction enzyme and a recognition site for the second restriction enzyme such that digestion of the amplification product with the first restriction enzyme and the second restriction enzyme generates a nucleic acid fragment containing the selected polymorphic site;
   (b) digesting the amplification product with the first restriction enzyme and the second restriction enzyme to generate a nucleic acid fragment having the selected polymorphic site within an overhanging end;
   (c) treating the nucleic acid fragment generated in step (b) to convert the overhanging end to a blunt end by extension of the recessed portion of the overhanging end; and
   (d) analyzing one or both strands of the nucleic acid fragment generated in step (c) to identify the nucleotide present at the selected polymorphic site.

2. A method for determining the nucleotide present at a selected polymorphic site in a target nucleic acid molecule, comprising:
   (a) amplifying a portion of the target nucleic acid molecule comprising the selected polymorphic site using a first primer and a second primer, the second primer containing a recognition site for a first restriction enzyme and a recognition site for a second restriction enzyme, to generate amplification product containing a recognition site for the first restriction enzyme and a recognition site for the second restriction enzyme such that digestion of the amplification product with the first restriction enzyme and the second restriction enzyme generates a nucleic acid fragment containing the selected polymorphic site, wherein the cleavage site of the second restriction enzyme is such that the polymorphic site within the nucleic acid fragment is present within an overhanging end;
   (b) digesting the amplification product with the second restriction enzyme in the presence of an enzyme that converts the overhanging end to a blunt end by extension of the recessed portion of the overhanging end under conditions which permit multiple cycles of digestion and conversion such that an oligonucleotide containing the polymorphic site is generated; and
   (c) analyzing the oligonucleotide to identify the nucleotide present at the selected polymorphic site.

3. The method of claim 1 or claim 2 wherein the overhanging end is converted to a blunt end by the introduction of at least one mass modified nucleotide.

4. The method of claim 3 wherein the mass modified nucleotide is selected to base-pair with one of the possible nucleotides present at the polymorphic site within the overhanging end.

5. The method of claim 1 or claim 2 wherein the second primer comprises at least one nucleotide sequence that is not present in the target nucleic acid molecule.

6. The method of claim 5 wherein the second primer comprises 5' nucleotide sequence that is complementary to a first portion of the target nucleic acid molecule, a 3' nucleotide sequence that is complementary to a second portion of the target nucleic acid molecule, and a nucleotide sequence that is not complementary to the target nucleic acid molecule.

7. The method of claim 1 or claim 2 wherein either the first or the second restriction enzyme is a type IIS restriction enzyme.

8. The method of claim 1 or claim 2 wherein the step of analyzing the nucleic acid fragment to identify the nucleotide present at the selected polymorphic site comprises subjecting the nucleic acid fragment to mass spectrometry.

9. The method of claim 1 or 2 wherein the overhanging end is a 3' end.

10. The method of claim 1 or 2 wherein the overhanging end is a 5' end.

11. The method of claim 1 or 2 wherein the overhanging end is converted to a blunt end using a polymerase that fills the recessed end.

12. The method of claim 1 or 2 wherein the overhanging end is converted to a blunt end in the presence of ATP, CTP, GTP, and either TTP or UTP.

* * * * *

UNITED STATES PATENT AND TRADEMARK OFFICE
CERTIFICATE OF CORRECTION

PATENT NO.         : 7,435,541 B2
APPLICATION NO.    : 10/116420
DATED              : October 14, 2008
INVENTOR(S)        : Jeffrey Olson et al.

Page 1 of 1

It is certified that error appears in the above-identified patent and that said Letters Patent is hereby corrected as shown below:

On the Title Page, Col. 2 (Other Publications), Line 7-9, below "1998.*" delete "Laken et al. Genotyping by mass spectrometric analysis of short DNA fragments. Nature Biotechnology., vol. 16, pp. 1352-1356, 1998.*" (Repeated Entry)

Signed and Sealed this

Fourth Day of August, 2009

JOHN DOLL
*Acting Director of the United States Patent and Trademark Office*

SEQUENCE LISTING

```
<160> NUMBER OF SEQ ID NOS: 100

<210> SEQ ID NO 1
<211> LENGTH: 29
<212> TYPE: DNA
<213> ORGANISM: Artificial Sequence
<220> FEATURE:
<223> OTHER INFORMATION: Exemplary motif

<400> SEQUENCE: 1
cttgccccca gaatggatgc gcatgtctg                                         29

<210> SEQ ID NO 2
<211> LENGTH: 55
<212> TYPE: DNA
<213> ORGANISM: Artificial Sequence
<220> FEATURE:
<223> OTHER INFORMATION: Exemplary motif

<400> SEQUENCE: 2
caccgcttgc ccccagaatg gaggagggtg tctgtattac tgggcgaggt gtcct           55

<210> SEQ ID NO 3
<211> LENGTH: 55
<212> TYPE: DNA
<213> ORGANISM: Artificial Sequence
<220> FEATURE:
<223> OTHER INFORMATION: Exemplary motif

<400> SEQUENCE: 3
aggacacctc gcccagtaat acagacaccc tcctccattc tgggggcaag cggtg           55

<210> SEQ ID NO 4
<211> LENGTH: 50
<212> TYPE: DNA
<213> ORGANISM: Artificial Sequence
<220> FEATURE:
<223> OTHER INFORMATION: Exemplary motif

<400> SEQUENCE: 4
cttgccccca gaatggatgc gcatgtctgt attactgggc gaggtgtcct                 50
```

```
<210> SEQ ID NO 5
<211> LENGTH: 50
<212> TYPE: DNA
<213> ORGANISM: Artificial Sequence
<220> FEATURE:
<223> OTHER INFORMATION: Exemplary motif

<400> SEQUENCE: 5
aggacacctc gcccagtaat acagacaccc tcctccattc tgggggcaag          50

<210> SEQ ID NO 6
<211> LENGTH: 37
<212> TYPE: DNA
<213> ORGANISM: Artificial Sequence
<220> FEATURE:
<223> OTHER INFORMATION: Exemplary motif

<400> SEQUENCE: 6
cttgccccca gaatggagga ggatgcgcag gtgtctg                        37

<210> SEQ ID NO 7
<211> LENGTH: 50
<212> TYPE: DNA
<213> ORGANISM: Artificial Sequence
<220> FEATURE:
<223> OTHER INFORMATION: Exemplary motif

<400> SEQUENCE: 7
acctcgccca gtaatacaga caccctcctc cattctgggg gcaagcggtg          50

<210> SEQ ID NO 8
<211> LENGTH: 53
<212> TYPE: DNA
<213> ORGANISM: Artificial Sequence
<220> FEATURE:
<223> OTHER INFORMATION: Exemplary motif

<400> SEQUENCE: 8
cttgccccca gaatggagga ggatgcgcag gtgtctgtat tactgggcga ggt      53

<210> SEQ ID NO 9
<211> LENGTH: 53
<212> TYPE: DNA
<213> ORGANISM: Artificial Sequence
<220> FEATURE:
<223> OTHER INFORMATION: Exemplary motif

<400> SEQUENCE: 9
acctcgccca gtaatacaga cacctgcgca tcctcctcca ttctgggggc aag      53

<210> SEQ ID NO 10
<211> LENGTH: 44
<212> TYPE: DNA
<213> ORGANISM: Artificial Sequence
<220> FEATURE:
<223> OTHER INFORMATION: Exemplary motif

<400> SEQUENCE: 10
tggctggagt tgcgctagca agagtgcagc tgcaaaagga ttta                44

<210> SEQ ID NO 11
<211> LENGTH: 50
<212> TYPE: DNA
<213> ORGANISM: Artificial Sequence
<220> FEATURE:
<223> OTHER INFORMATION: Exemplary motif
```

```
<400> SEQUENCE: 11
cgcctatggc tggagttgcg ctagcaagac caaaaggatt tataaacttc                50

<210> SEQ ID NO 12
<211> LENGTH: 50
<212> TYPE: DNA
<213> ORGANISM: Artificial Sequence
<220> FEATURE:
<223> OTHER INFORMATION: Exemplary motif

<400> SEQUENCE: 12
gaagtttata atccttttg gtcttgctag cgcaactcca gccataggcg                 50

<210> SEQ ID NO 13
<211> LENGTH: 53
<212> TYPE: DNA
<213> ORGANISM: Artificial Sequence
<220> FEATURE:
<223> OTHER INFORMATION: Exemplary motif

<400> SEQUENCE: 13
tggctggagt tgcgctagca agacgtgcag ctgcaaaagg atttataaac ttc            53

<210> SEQ ID NO 14
<211> LENGTH: 53
<212> TYPE: DNA
<213> ORGANISM: Artificial Sequence
<220> FEATURE:
<223> OTHER INFORMATION: Exemplary motif

<400> SEQUENCE: 14
gaagtttata atccttttg cagctgcacg tcttgctagc gcaactccag cca             53

<210> SEQ ID NO 15
<211> LENGTH: 45
<212> TYPE: DNA
<213> ORGANISM: Artificial Sequence
<220> FEATURE:
<223> OTHER INFORMATION: Exemplary motif

<400> SEQUENCE: 15
tggctggagt tgcgctagca agaccacagc tggatgaagg attta                     45

<210> SEQ ID NO 16
<211> LENGTH: 50
<212> TYPE: DNA
<213> ORGANISM: Artificial Sequence
<220> FEATURE:
<223> OTHER INFORMATION: Exemplary motif

<400> SEQUENCE: 16
cgcctatggc tggagttgcg ctagcaagac caaaaggatt tataaacttc                50

<210> SEQ ID NO 17
<211> LENGTH: 50
<212> TYPE: DNA
<213> ORGANISM: Artificial Sequence
<220> FEATURE:
<223> OTHER INFORMATION: Exemplary motif

<400> SEQUENCE: 17
gaagtttata atccttttg gtcttgctag cgcaactcca gccataggcg                 50

<210> SEQ ID NO 18
<211> LENGTH: 59
```

<210> SEQ ID NO 18
<211> LENGTH: 59
<212> TYPE: DNA
<213> ORGANISM: Artificial Sequence
<220> FEATURE:
<223> OTHER INFORMATION: Exemplary motif

<400> SEQUENCE: 18
cgcctatggc tggagttgcg ctagcaagac cacagctgga tgaaggattt ataaacttc    59

<210> SEQ ID NO 19
<211> LENGTH: 59
<212> TYPE: DNA
<213> ORGANISM: Artificial Sequence
<220> FEATURE:
<223> OTHER INFORMATION: Exemplary motif

<400> SEQUENCE: 19
gaagtttata atccttcatc cagctgtgg tcttgctagc gcaactccag ccataggcg     59

<210> SEQ ID NO 20
<211> LENGTH: 53
<212> TYPE: DNA
<213> ORGANISM: Artificial Sequence
<220> FEATURE:
<223> OTHER INFORMATION: Exemplary motif

<400> SEQUENCE: 20
cttgccccca gaatggagga ggatgcgcag gtgtctgtat tactgggcga ggt          53

<210> SEQ ID NO 21
<211> LENGTH: 53
<212> TYPE: DNA
<213> ORGANISM: Artificial Sequence
<220> FEATURE:
<223> OTHER INFORMATION: Exemplary motif

<400> SEQUENCE: 21
acctcgccca gtaatacaga cacctgcgca tcctcctcca ttctgggggc aag          53

<210> SEQ ID NO 22
<211> LENGTH: 34
<212> TYPE: DNA
<213> ORGANISM: Artificial Sequence
<220> FEATURE:
<223> OTHER INFORMATION: Exemplary motif

<400> SEQUENCE: 22
cttgccccca gaatggagga ggatgcgcag gtgt                               34

<210> SEQ ID NO 23
<211> LENGTH: 38
<212> TYPE: DNA
<213> ORGANISM: Artificial Sequence
<220> FEATURE:
<223> OTHER INFORMATION: Exemplary motif

<400> SEQUENCE: 23
acagacacct gcgcatcctc ctccattctg ggggcaag                           38

<210> SEQ ID NO 24
<211> LENGTH: 38
<212> TYPE: DNA
<213> ORGANISM: Artificial Sequence
<220> FEATURE:
<223> OTHER INFORMATION: Exemplary motif
<220> FEATURE:
<221> NAME/KEY: modified_base
<222> LOCATION: 38

<223> OTHER INFORMATION: Tmod = modified thymine

<400> SEQUENCE: 24 cttgcccca gaatggagga ggatgcgcag gtgtctgt           38

<210> SEQ ID NO 25
<211> LENGTH: 38
<212> TYPE: DNA
<213> ORGANISM: Artificial Sequence
<220> FEATURE:
<223> OTHER INFORMATION: Exemplary motif

<400> SEQUENCE: 25 cttgcccca gaatggagga gagtcggatg ggtgtctg           38

<210> SEQ ID NO 26
<211> LENGTH: 50
<212> TYPE: DNA
<213> ORGANISM: Artificial Sequence
<220> FEATURE:
<223> OTHER INFORMATION: Exemplary motif

<400> SEQUENCE: 26
caccgcttgc cccagaatg gaggagggtg tctgtattac tgggcgaggt           50

<210> SEQ ID NO 27
<211> LENGTH: 50
<212> TYPE: DNA
<213> ORGANISM: Artificial Sequence
<220> FEATURE:
<223> OTHER INFORMATION: Exemplary motif

<400> SEQUENCE: 27
acctcgccca gtaatacaga caccctcctc cattctgggg gcaagcggtg           50

<210> SEQ ID NO 28
<211> LENGTH: 54
<212> TYPE: DNA
<213> ORGANISM: Artificial Sequence
<220> FEATURE:
<223> OTHER INFORMATION: Exemplary motif

<400> SEQUENCE: 28
cttgccccca gaatggagga gagtcggatg ggtgtctgta ttactgggcg aggt           54

<210> SEQ ID NO 29
<211> LENGTH: 54
<212> TYPE: DNA
<213> ORGANISM: Artificial Sequence
<220> FEATURE:
<223> OTHER INFORMATION: Exemplary motif

<400> SEQUENCE: 29
acctcgccca gtaatacaga cacccatccg actctcctcc attctggggg caag           54

<210> SEQ ID NO 30
<211> LENGTH: 33
<212> TYPE: DNA
<213> ORGANISM: Artificial Sequence
<220> FEATURE:
<223> OTHER INFORMATION: Exemplary motif

<400> SEQUENCE: 30
cttgccccca gaatggagga ggatgggtgt ctg           33

```
<210> SEQ ID NO 31
<211> LENGTH: 50
<212> TYPE: DNA
<213> ORGANISM: Artificial Sequence
<220> FEATURE:
<223> OTHER INFORMATION: Exemplary motif

<400> SEQUENCE: 31
caccgcttgc ccccagaatg gaggagggtg tctgtattac tgggcgaggt          50

<210> SEQ ID NO 32
<211> LENGTH: 50
<212> TYPE: DNA
<213> ORGANISM: Artificial Sequence
<220> FEATURE:
<223> OTHER INFORMATION: Exemplary motif

<400> SEQUENCE: 32
acctcgccca gtaatacaga caccctcctc cattctgggg gcaagcggtg          50

<210> SEQ ID NO 33
<211> LENGTH: 50
<212> TYPE: DNA
<213> ORGANISM: Artificial Sequence
<220> FEATURE:
<223> OTHER INFORMATION: Exemplary motif

<400> SEQUENCE: 33
cttgccccca gaatggagga ggatggrgtg tctgtattac tgggcgaggt          50

<210> SEQ ID NO 34
<211> LENGTH: 49
<212> TYPE: DNA
<213> ORGANISM: Artificial Sequence
<220> FEATURE:
<223> OTHER INFORMATION: Exemplary motif

<400> SEQUENCE: 34
acctcgccca gtaatacaga cacccatcct cctccattct gggggcaag           49

<210> SEQ ID NO 35
<211> LENGTH: 22
<212> TYPE: DNA
<213> ORGANISM: Artificial Sequence
<220> FEATURE:
<223> OTHER INFORMATION: Exemplary motif
<220> FEATURE:
<221> NAME/KEY: misc_feature
<222> LOCATION: (1)...(22)
<223> OTHER INFORMATION: n = A,T,C or G

<400> SEQUENCE: 35
atctggannn nnnnnnnnnt cc                                        22

<210> SEQ ID NO 36
<211> LENGTH: 26
<212> TYPE: DNA
<213> ORGANISM: Artificial Sequence
<220> FEATURE:
<223> OTHER INFORMATION: Exemplary motif
<220> FEATURE:
<221> NAME/KEY: misc_feature
<222> LOCATION: (1)...(26)
<223> OTHER INFORMATION: n = A,T,C or G

<400> SEQUENCE: 36
atctggannn nnnnnnnnnt ccagat                                    26
```

<210> SEQ ID NO 37
<211> LENGTH: 26
<212> TYPE: DNA
<213> ORGANISM: Artificial Sequence
<220> FEATURE:
<223> OTHER INFORMATION: Exemplary motif
<220> FEATURE:
<221> NAME/KEY: misc_feature
<222> LOCATION: (1)...(26)
<223> OTHER INFORMATION: n = A,T,C or G

<400> SEQUENCE: 37
atctggannn nnnnnnnnnt ccagat                                    26

<210> SEQ ID NO 38
<211> LENGTH: 22
<212> TYPE: DNA
<213> ORGANISM: Artificial Sequence
<220> FEATURE:
<223> OTHER INFORMATION: Exemplary motif
<220> FEATURE:
<221> NAME/KEY: misc_feature
<222> LOCATION: (1)...(22)
<223> OTHER INFORMATION: n = A,T,C or G

<400> SEQUENCE: 38
atctccannn nnnnnnnnnt cc                                        22

<210> SEQ ID NO 39
<211> LENGTH: 26
<212> TYPE: DNA
<213> ORGANISM: Artificial Sequence
<220> FEATURE:
<223> OTHER INFORMATION: Exemplary motif
<220> FEATURE:
<221> NAME/KEY: misc_feature
<222> LOCATION: (1)...(26)
<223> OTHER INFORMATION: n = A,T,C or G

<400> SEQUENCE: 39
atctccannn nnnnnnnnnt ccggat                                    26

<210> SEQ ID NO 40
<211> LENGTH: 26
<212> TYPE: DNA
<213> ORGANISM: Artificial Sequence
<220> FEATURE:
<223> OTHER INFORMATION: Exemplary motif
<220> FEATURE:
<221> NAME/KEY: misc_feature
<222> LOCATION: (1)...(26)
<223> OTHER INFORMATION: n = A,T,C or G

<400> SEQUENCE: 40
atccggannn nnnnnnnnnt ccagat                                    26

<210> SEQ ID NO 41
<211> LENGTH: 22
<212> TYPE: DNA
<213> ORGANISM: Artificial Sequence
<220> FEATURE:
<223> OTHER INFORMATION: Exemplary motif
<220> FEATURE:
<221> NAME/KEY: misc_feature
<222> LOCATION: (1)...(22)
<223> OTHER INFORMATION: n = A,T,C or G

<400> SEQUENCE: 41
atccggannn nnnnnnnnnt cc                                        22

<210> SEQ ID NO 42
<211> LENGTH: 26
<212> TYPE: DNA
<213> ORGANISM: Artificial Sequence
<220> FEATURE:
<223> OTHER INFORMATION: Exemplary motif
<220> FEATURE:
<221> NAME/KEY: misc_feature
<222> LOCATION: (1)...(26)
<223> OTHER INFORMATION: n = A,T,C or G

<400> SEQUENCE: 42
atccggannn nnnnnnnnnt ccagat                                    26

<210> SEQ ID NO 43
<211> LENGTH: 26
<212> TYPE: DNA
<213> ORGANISM: Artificial Sequence
<220> FEATURE:
<223> OTHER INFORMATION: Exemplary motif
<220> FEATURE:
<221> NAME/KEY: misc_feature
<222> LOCATION: (1)...(26)
<223> OTHER INFORMATION: n = A,T,C or G

<400> SEQUENCE: 43
atctggannn nnnnnnnnnt ccggat                                    26

<210> SEQ ID NO 44
<211> LENGTH: 26
<212> TYPE: DNA
<213> ORGANISM: Artificial Sequence
<220> FEATURE:
<223> OTHER INFORMATION: Exemplary motif
<220> FEATURE:
<221> NAME/KEY: misc_feature
<222> LOCATION: (1)...(26)
<223> OTHER INFORMATION: n = A,T,C or G

<400> SEQUENCE: 44
atctccannn nnnnnnnnnt ccggat                                    26

<210> SEQ ID NO 45
<211> LENGTH: 26
<212> TYPE: DNA
<213> ORGANISM: Artificial Sequence
<220> FEATURE:
<223> OTHER INFORMATION: Exemplary motif
<220> FEATURE:
<221> NAME/KEY: misc_feature
<222> LOCATION: (1)...(26)
<223> OTHER INFORMATION: n = A,T,C or G

<400> SEQUENCE: 45
atccggannn nnnnnnnnnt ccggat                                    26

<210> SEQ ID NO 46
<211> LENGTH: 26
<212> TYPE: DNA
<213> ORGANISM: Artificial Sequence
<220> FEATURE:
<223> OTHER INFORMATION: Exemplary motif
<220> FEATURE:
<221> NAME/KEY: misc_feature
<222> LOCATION: (1)...(26)
<223> OTHER INFORMATION: n = A,T,C or G

<400> SEQUENCE: 46

```
tagacctnnn nnnnnnnnna ggtcta                                              26

<210> SEQ ID NO 47
<211> LENGTH: 26
<212> TYPE: DNA
<213> ORGANISM: Artificial Sequence
<220> FEATURE:
<223> OTHER INFORMATION: Exemplary motif
<220> FEATURE:
<221> NAME/KEY: misc_feature
<222> LOCATION: (1)...(26)
<223> OTHER INFORMATION: n = A,T,C or G

<400> SEQUENCE: 47
tagacctnnn nnnnnnnnna ggccta                                              26

<210> SEQ ID NO 48
<211> LENGTH: 26
<212> TYPE: DNA
<213> ORGANISM: Artificial Sequence
<220> FEATURE:
<223> OTHER INFORMATION: Exemplary motif
<220> FEATURE:
<221> NAME/KEY: misc_feature
<222> LOCATION: (1)...(26)
<223> OTHER INFORMATION: n = A,T,C or G

<400> SEQUENCE: 48
taggcctnnn nnnnnnnnna ggtcta                                              26

<210> SEQ ID NO 49
<211> LENGTH: 21
<212> TYPE: DNA
<213> ORGANISM: Artificial Sequence
<220> FEATURE:
<223> OTHER INFORMATION: Exemplary motif

<400> SEQUENCE: 49
acacagactc atgcaactct g                                                   21

<210> SEQ ID NO 50
<211> LENGTH: 21
<212> TYPE: DNA
<213> ORGANISM: Artificial Sequence
<220> FEATURE:
<223> OTHER INFORMATION: Exemplary motif

<400> SEQUENCE: 50
acgcagactc atgcaactct g                                                   21

<210> SEQ ID NO 51
<211> LENGTH: 15
<212> TYPE: DNA
<213> ORGANISM: Artificial Sequence
<220> FEATURE:
<223> OTHER INFORMATION: Exemplary motif

<400> SEQUENCE: 51
actcatgcaa ctctg                                                          15

<210> SEQ ID NO 52
<211> LENGTH: 35
<212> TYPE: DNA
<213> ORGANISM: Artificial Sequence
<220> FEATURE:
<223> OTHER INFORMATION: Exemplary motif

<400> SEQUENCE: 52
```

```
actcatgcaa ctctgygttc cacttcggcc aagaa                          35

<210> SEQ ID NO 53
<211> LENGTH: 35
<212> TYPE: DNA
<213> ORGANISM: Artificial Sequence
<220> FEATURE:
<223> OTHER INFORMATION: Exemplary motif

<400> SEQUENCE: 53
ttcttggccg aagtggaacr cagagttgca tgagt                          35

<210> SEQ ID NO 54
<211> LENGTH: 23
<212> TYPE: DNA
<213> ORGANISM: Artificial Sequence
<220> FEATURE:
<223> OTHER INFORMATION: Exemplary motif

<400> SEQUENCE: 54
gtggaacaca gagttgcatg agt                                       23

<210> SEQ ID NO 55
<211> LENGTH: 23
<212> TYPE: DNA
<213> ORGANISM: Artificial Sequence
<220> FEATURE:
<223> OTHER INFORMATION: Exemplary motif

<400> SEQUENCE: 55
gtggaacgca gagttgcatg agt                                       23

<210> SEQ ID NO 56
<211> LENGTH: 23
<212> TYPE: DNA
<213> ORGANISM: Artificial Sequence
<220> FEATURE:
<223> OTHER INFORMATION: Exemplary motif

<400> SEQUENCE: 56
actcatgcaa ctctgtgttc cac                                       23

<210> SEQ ID NO 57
<211> LENGTH: 23
<212> TYPE: DNA
<213> ORGANISM: Artificial Sequence
<220> FEATURE:
<223> OTHER INFORMATION: Exemplary motif

<400> SEQUENCE: 57
actcatgcaa ctctgcgttc cac                                       23

<210> SEQ ID NO 58
<211> LENGTH: 29
<212> TYPE: DNA
<213> ORGANISM: Artificial Sequence
<220> FEATURE:
<223> OTHER INFORMATION: Exemplary motif

<400> SEQUENCE: 58
acacagactc atgcaactct gtgttccac                                 29

<210> SEQ ID NO 59
<211> LENGTH: 29
<212> TYPE: DNA
```

```
<213> ORGANISM: Artificial Sequence
<220> FEATURE:
<223> OTHER INFORMATION: Exemplary motif

<400> SEQUENCE: 59
gtggaacaca gagttgcatg agtctgtgt                                    29

<210> SEQ ID NO 60
<211> LENGTH: 29
<212> TYPE: DNA
<213> ORGANISM: Artificial Sequence
<220> FEATURE:
<223> OTHER INFORMATION: Exemplary motif

<400> SEQUENCE: 60
acacagactc atgcaactct gcgttccac                                    29

<210> SEQ ID NO 61
<211> LENGTH: 29
<212> TYPE: DNA
<213> ORGANISM: Artificial Sequence
<220> FEATURE:
<223> OTHER INFORMATION: Exemplary motif

<400> SEQUENCE: 61
gtggaacgca gagttgcatg agtctgtgt                                    29

<210> SEQ ID NO 62
<211> LENGTH: 29
<212> TYPE: DNA
<213> ORGANISM: Artificial Sequence
<220> FEATURE:
<223> OTHER INFORMATION: Exemplary motif

<400> SEQUENCE: 62
acgcagactc atgcaactct gtgttccac                                    29

<210> SEQ ID NO 63
<211> LENGTH: 29
<212> TYPE: DNA
<213> ORGANISM: Artificial Sequence
<220> FEATURE:
<223> OTHER INFORMATION: Exemplary motif

<400> SEQUENCE: 63
gtggaacaca gagttgcatg agtctgcgt                                    29

<210> SEQ ID NO 64
<211> LENGTH: 29
<212> TYPE: DNA
<213> ORGANISM: Artificial Sequence
<220> FEATURE:
<223> OTHER INFORMATION: Exemplary motif

<400> SEQUENCE: 64
acgcagactc atgcaactct gcgttccac                                    29

<210> SEQ ID NO 65
<211> LENGTH: 29
<212> TYPE: DNA
<213> ORGANISM: Artificial Sequence
<220> FEATURE:
<223> OTHER INFORMATION: Exemplary motif

<400> SEQUENCE: 65
gtggaacgca gagttgcatg agtctgcgt                                    29
```

<210> SEQ ID NO 66
<211> LENGTH: 22
<212> TYPE: DNA
<213> ORGANISM: Artificial Sequence
<220> FEATURE:
<223> OTHER INFORMATION: Exemplary motif

<400> SEQUENCE: 66
gtggaacaca gagttgcatg ag                                    22

<210> SEQ ID NO 67
<211> LENGTH: 22
<212> TYPE: DNA
<213> ORGANISM: Artificial Sequence
<220> FEATURE:
<223> OTHER INFORMATION: Exemplary motif

<400> SEQUENCE: 67
gtggaacgca gagttgcatg ag                                    22

<210> SEQ ID NO 68
<211> LENGTH: 29
<212> TYPE: DNA
<213> ORGANISM: Artificial Sequence
<220> FEATURE:
<223> OTHER INFORMATION: Exemplary motif

<400> SEQUENCE: 68
gtggaacaca gagttgcatg agtctgtgt                             29

<210> SEQ ID NO 69
<211> LENGTH: 29
<212> TYPE: DNA
<213> ORGANISM: Artificial Sequence
<220> FEATURE:
<223> OTHER INFORMATION: Exemplary motif

<400> SEQUENCE: 69
gtggaacgca gagttgcatg agtctgtgt                             29

<210> SEQ ID NO 70
<211> LENGTH: 29
<212> TYPE: DNA
<213> ORGANISM: Artificial Sequence
<220> FEATURE:
<223> OTHER INFORMATION: Exemplary motif

<400> SEQUENCE: 70
gtggaacaca gagttgcatg agtctgcgt                             29

<210> SEQ ID NO 71
<211> LENGTH: 29
<212> TYPE: DNA
<213> ORGANISM: Artificial Sequence
<220> FEATURE:
<223> OTHER INFORMATION: Exemplary motif

<400> SEQUENCE: 71
gtggaacgca gagttgcatg agtctgcgt                             29

<210> SEQ ID NO 72
<211> LENGTH: 23
<212> TYPE: DNA
<213> ORGANISM: Artificial Sequence
<220> FEATURE:

<223> OTHER INFORMATION: Exemplary motif

<400> SEQUENCE: 72
gtggaacgca gagttgcatg agt                           23

<210> SEQ ID NO 73
<211> LENGTH: 23
<212> TYPE: DNA
<213> ORGANISM: Artificial Sequence
<220> FEATURE:
<223> OTHER INFORMATION: Exemplary motif

<400> SEQUENCE: 73
gtggaacaca gagttgcatg agt                           23

<210> SEQ ID NO 74
<211> LENGTH: 30
<212> TYPE: DNA
<213> ORGANISM: Artificial Sequence
<220> FEATURE:
<223> OTHER INFORMATION: Exemplary motif

<400> SEQUENCE: 74
gtggaacggc agagttgcat gagtctgcgt                    30

<210> SEQ ID NO 75
<211> LENGTH: 37
<212> TYPE: DNA
<213> ORGANISM: Artificial Sequence
<220> FEATURE:
<223> OTHER INFORMATION: Exemplary motif

<400> SEQUENCE: 75
cccggctggg cgcggacatg ggatgcgcaa ggacgtg            37

<210> SEQ ID NO 76
<211> LENGTH: 58
<212> TYPE: DNA
<213> ORGANISM: Artificial Sequence
<220> FEATURE:
<223> OTHER INFORMATION: Exemplary motif

<400> SEQUENCE: 76
gcaggcccgg ctgggcgcgg acatggagga cgtgtgcggc cgcctggtgc agtaccgc    58

<210> SEQ ID NO 77
<211> LENGTH: 58
<212> TYPE: DNA
<213> ORGANISM: Artificial Sequence
<220> FEATURE:
<223> OTHER INFORMATION: Exemplary motif

<400> SEQUENCE: 77
gcggtactgc accaggcggc cgcacacgtc ctccatgtcc gcgcccagcc gggcctgc    58

<210> SEQ ID NO 78
<211> LENGTH: 58
<212> TYPE: DNA
<213> ORGANISM: Artificial Sequence
<220> FEATURE:
<223> OTHER INFORMATION: Exemplary motif

<400> SEQUENCE: 78
ggcgaggtgc aggccatgct cggccagagc accgaggagc tgcgggtgcg cctcgcct    58

```
<210> SEQ ID NO 79
<211> LENGTH: 58
<212> TYPE: DNA
<213> ORGANISM: Artificial Sequence
<220> FEATURE:
<223> OTHER INFORMATION: Exemplary motif

<400> SEQUENCE: 79
aggcgaggcg cacccgcagc tcctcggtgc tctggccgag catggcctgc acctcgcc        58

<210> SEQ ID NO 80
<211> LENGTH: 56
<212> TYPE: DNA
<213> ORGANISM: Artificial Sequence
<220> FEATURE:
<223> OTHER INFORMATION: Exemplary motif

<400> SEQUENCE: 80
ccacctgcgc aagctgcgta agcggctcct ccgcgatgcc gatgacctgc agaagc        56

<210> SEQ ID NO 81
<211> LENGTH: 56
<212> TYPE: DNA
<213> ORGANISM: Artificial Sequence
<220> FEATURE:
<223> OTHER INFORMATION: Exemplary motif

<400> SEQUENCE: 81
gcttctgcag gtcatcggca tcgcggagga ccgcttacg cagcttgcgc aggtgg        56

<210> SEQ ID NO 82
<211> LENGTH: 18
<212> TYPE: DNA
<213> ORGANISM: Artificial Sequence
<220> FEATURE:
<223> OTHER INFORMATION: Exemplary motif

<400> SEQUENCE: 82
gcttctgcag gtcatcgg        18

<210> SEQ ID NO 83
<211> LENGTH: 58
<212> TYPE: DNA
<213> ORGANISM: Artificial Sequence
<220> FEATURE:
<223> OTHER INFORMATION: Exemplary motif

<400> SEQUENCE: 83
cccggctggg cgcggacatg ggatgcgcaa ggacgtgtgc ggccgcctgg tgcagtac        58

<210> SEQ ID NO 84
<211> LENGTH: 58
<212> TYPE: DNA
<213> ORGANISM: Artificial Sequence
<220> FEATURE:
<223> OTHER INFORMATION: Exemplary motif

<400> SEQUENCE: 84
gtactgcacc aggcggccgc acacgtcctt gcgcatccca tgtccgcgcc cagccggg        58

<210> SEQ ID NO 85
<211> LENGTH: 58
<212> TYPE: DNA
<213> ORGANISM: Artificial Sequence
<220> FEATURE:
<223> OTHER INFORMATION: Exemplary motif
```

```
<400> SEQUENCE: 85
cgcggcgagg tgcaggccat gctcggccag agcaccgagg agctgcgggt gcgcctcg        58

<210> SEQ ID NO 86
<211> LENGTH: 58
<212> TYPE: DNA
<213> ORGANISM: Artificial Sequence
<220> FEATURE:
<223> OTHER INFORMATION: Exemplary motif

<400> SEQUENCE: 86
cgaggcgcac ccgcagctcc tcggtgctct ggccgagcat ggcctgcacc tcgccgcg        58

<210> SEQ ID NO 87
<211> LENGTH: 59
<212> TYPE: DNA
<213> ORGANISM: Artificial Sequence
<220> FEATURE:
<223> OTHER INFORMATION: Exemplary motif

<400> SEQUENCE: 87
cctccacctg cgcaagctgc gtaagcggct cctccgcgat gccgatgacc tgcagaagc       59

<210> SEQ ID NO 88
<211> LENGTH: 59
<212> TYPE: DNA
<213> ORGANISM: Artificial Sequence
<220> FEATURE:
<223> OTHER INFORMATION: Exemplary motif

<400> SEQUENCE: 88
gcttctgcag gtcatcggca tcgcggagga gccgcttacg cagcttgcgc aggtggagg       59

<210> SEQ ID NO 89
<211> LENGTH: 58
<212> TYPE: DNA
<213> ORGANISM: Artificial Sequence
<220> FEATURE:
<223> OTHER INFORMATION: Exemplary motif

<400> SEQUENCE: 89
cccggctggg cgcggacatg ggatgcgcaa ggacgtgcgc ggccgcctgg tgcagtac        58

<210> SEQ ID NO 90
<211> LENGTH: 58
<212> TYPE: DNA
<213> ORGANISM: Artificial Sequence
<220> FEATURE:
<223> OTHER INFORMATION: Exemplary motif

<400> SEQUENCE: 90
gtactgcacc aggcggccgc gcacgtcctt gcgcatccca tgtccgcgcc cagccggg        58

<210> SEQ ID NO 91
<211> LENGTH: 58
<212> TYPE: DNA
<213> ORGANISM: Artificial Sequence
<220> FEATURE:
<223> OTHER INFORMATION: Exemplary motif

<400> SEQUENCE: 91
cgcggcgagg tgcaggccat gctcggccag agcaccgagg agctgcgggt gcgcctcg        58

<210> SEQ ID NO 92
<211> LENGTH: 58
```

<212> TYPE: DNA
<213> ORGANISM: Artificial Sequence
<220> FEATURE:
<223> OTHER INFORMATION: Exemplary motif

<400> SEQUENCE: 92
cgaggcgcac ccgcagctcc tcggtgctct ggccgagcat ggcctgcacc tcgccgcg        58

<210> SEQ ID NO 93
<211> LENGTH: 59
<212> TYPE: DNA
<213> ORGANISM: Artificial Sequence
<220> FEATURE:
<223> OTHER INFORMATION: Exemplary motif

<400> SEQUENCE: 93
cctccacctg cgcaagctgc gtaagcggct cctccgcgat gccgatgacc tgcagaagc       59

<210> SEQ ID NO 94
<211> LENGTH: 59
<212> TYPE: DNA
<213> ORGANISM: Artificial Sequence
<220> FEATURE:
<223> OTHER INFORMATION: Exemplary motif

<400> SEQUENCE: 94
gcttctgcag gtcatcggca tcgcggagga gccgcttacg cagcttgcgc aggtggagg       59

<210> SEQ ID NO 95
<211> LENGTH: 20
<212> TYPE: DNA
<213> ORGANISM: Artificial Sequence
<220> FEATURE:
<223> OTHER INFORMATION: Exemplary motif

<400> SEQUENCE: 95
cgatccgtaa tgttgcagtt                                                  20

<210> SEQ ID NO 96
<211> LENGTH: 38
<212> TYPE: DNA
<213> ORGANISM: Artificial Sequence
<220> FEATURE:
<223> OTHER INFORMATION: Exemplary motif
<220> FEATURE:
<221> NAME/KEY: misc_feature
<222> LOCATION: (1)...(38)
<223> OTHER INFORMATION: n = A,T,C or G

<400> SEQUENCE: 96
nnnnnnnnna actgcaacat tacggatcgn nnnnnnn                               38

<210> SEQ ID NO 97
<211> LENGTH: 20
<212> TYPE: DNA
<213> ORGANISM: Artificial Sequence
<220> FEATURE:
<223> OTHER INFORMATION: Exemplary motif

<400> SEQUENCE: 97
cgatccgtag tgttgcagtt                                                  20

<210> SEQ ID NO 98
<211> LENGTH: 38
<212> TYPE: DNA
<213> ORGANISM: Artificial Sequence
<220> FEATURE:

```
<223> OTHER INFORMATION: Exemplary motif
<220> FEATURE:
<221> NAME/KEY: misc_feature
<222> LOCATION: (1)...(38)
<223> OTHER INFORMATION: n = A,T,C or G

<400> SEQUENCE: 98
nnnnnnnnna actgcaacac tacggatcgn nnnnnnnn                         38

<210> SEQ ID NO 99
<211> LENGTH: 29
<212> TYPE: DNA
<213> ORGANISM: Artificial Sequence
<220> FEATURE:
<223> OTHER INFORMATION: Exemplary motif
<220> FEATURE:
<221> NAME/KEY: misc_feature
<222> LOCATION: (1)...(29)
<223> OTHER INFORMATION: n = A,T,C or G

<400> SEQUENCE: 99
nnnnnnnnna actgcaacat tacggatcg                                   29

<210> SEQ ID NO 100
<211> LENGTH: 10527
<212> TYPE: DNA
<213> ORGANISM: Homo sapiens

<400> SEQUENCE: 100
ctggtggagc atctgatggg tgtttgggcc aagctggagc tttgtccatc ccctcttatt    60
tttctgcact tgactctctt attttctga gactggtctc cctctgtcgc ccaggctaga    120
gtgcagcagt gcaactgcgg ctcactgcag cctccacctc ccgggctcaa gcagccttcc   180
cacctcagcc tcctgagtag ctaggaccac aggtgtatgc caccaggccc agctaatttt    240
tttgatagtt ttgggagaca tggggttttc accatgttgc ccaggctggt ctcgaactcc    300
tggactcaag ccttggcctc ccaaagtgct gggattatag gtgtgagcca ccacacccag    360
ccagggtaga aggcactttg gaagcctcga gcctgcccca ttcatcttac gttagtggaa    420
actgaggctt ccagaggttt caaggtcaca actaaatcca gaacctcatc tcaggcacac    480
tggtcgtagt cccaatgtcc agtcttaagt cttcttggat atctgtggct cacagatttt    540
gggtgtttga gcctcctgct gagcactgct ggggccacag cggtgaccag ccctgtcttc    600
acgggactca gtgagaggaa cagattcatc cgcagagtgg gcaggactag gttggggaa    660 cccagggtc tagagggctt ttcagagggc aggggtcact gagcggagag cagaggagga    720
gtgagccatt tgctccagcg tgaagttgtt ggtgtgatgg ggtttcaggg tggcaggagc    780
agtgtggtta aaggtctgga agctgtcggc atgtggctgg tatccaaggt ggccaggaac    840
tctgcatgga tatggtggga agctggcacg cctctcacct cagctcttcc ctgcaggctc    900 tgtgatagc aactggatcg tgggtgccac gctgagaag aagctcccac ccctgcccct    960
gacactggcc cttggggcct tcctgaatca ccgcaagaac aagtttcagt gtggctttgg   1020
cctcaccatc ggctgagccc tcctggcccc cgccttccac gcccttccga ttccacctcc   1080
acctccacct cccccctgcca cagaggggag acctgagccc cctcccttc cctccccct   1140 tgggggtcgg ggggacatt ggaaaggagg gaccccgcca ccccagcagc tgaggagggg    1200
attctggaac tgaatggcgc ttcgggattc tgagtagcag gggcagcatg cccagtgggc    1260
ctggggtccc gggagggatt ccggaattga ggggcacgca ggattctgag caccaggggc    1320
agaggcggcc agacaacctc agggaggagt gtcctggcgt cccatcctc caaagggcct   1380
```

```
gggcccgccc cgaggggggca gcgagaggag cttccccatc cccggtcagt ccaccctgcc   1440
ccgtccactt tcccatctcc tcggtataaa tcatgtttat aagttatgga agaaccggga   1500
cattttacag aaaaaaaaca aaaacaaca aaaatatac gtgggaaaaa aaacgatggg    1560
aggcctccgt tttctcaagt gtgtctggcc tgttttgagc atttcatccg gagtctggcc   1620
gccctgacct tcccccagcc gcctgcaggg ggcgccagag ggccggagca cggaaagcag   1680
cggatccttg atgctgcctt aagtccggct cagaggggcg cagcgtggcc tggggtcgct   1740
atcttcccat ccggaacatc tgccctgctg ggggacacta cgggccttcc cttgcctgag   1800
ggtagggtct caaggtcact tgccccagc ttgacctggc cggagtggct atagaggact    1860
ttgtccctgc agactgcagc agcagagatg acactgtctc tgagtgcaga gatggggca    1920
gggagctggg agagggttca agctactgga acagcttcag aacaactagg gtactaggaa   1980
ctgctgtgtc agggagaagg ggctcaagga ctcgcaggcc tgggaggagg ggcctaggcc   2040
agccatggga gttgggtcac ctgtgtctga ggacttggtg ctgtctggat tttgccaacc   2100
tagggctggg gtcagctgat gcccaccacg actcccgagc ctccaggaac tgaaaccctg   2160
tctgcccca gggtctgggg aaggaggctg ctgagtagaa ccaaccccag gttaccaacc    2220
ccacctcagc cacccttgc cagccaaagc aaacaggccc ggcccggcac tgggggttcc    2280
ttctcgaacc aggagttcag cctcccctga cccgcagaat cttctgatcc cacccgctcc   2340
aggagccagg aatgagtccc agtctctccc agttctcact gtgtggtttt gccattcgtc   2400
ttgctgctga accacgggtt tctcctctga aacatctggg atttataaca gggcttagga   2460
aagtgacagc gtctgagcgt tcactgtggc ctgtccattg ctagccctaa cataggaccg   2520
ctgtgtgcca gggctgtcct ccatgctcaa tacacgttag cttgtcacca aacatacccg   2580
tgccgctgct ttcccagtct gatgagcaaa ggaacttgat gctcagagag gacaagtcat   2640
ttgcccaagg tcacacagct ggcaactggc agagccagga ttcacgccct ggcaatttga   2700
ctccagaatc ctaaccttaa cccagaagca cggcttcaag cccctggaaa ccacaatacc   2760
tgtggcagca aggggaggt gctggaatct catttcacat gtggggaggg ggctcccctg    2820
tgctcaaggt cacaaccaaa gaggaagctg tgattaaaac ccaggtccca tttgcaaagc   2880
ctcgactttt agcaggtgca tcatactgtt cccacccctc ccatcccact tctgtccagc   2940
cgcctagccc cactttcttt ttttcttt tttgagacag tctccctctt gctgaggctg     3000
gagtgcagtg gcgagatctc ggctcactgt aacctccgcc tccgggttc aagcgattct    3060
cctgcctcag cctcccaagt agctaggatt acaggcgccc gccaccacgc tggctaact    3120
tttgtatttt tagtagagat ggggtttcac catgttggcc aggctggtct caaactcctg   3180
accttaagtg attcgcccac tgtggcctcc caaagtgctg ggattacagg cgtgactacc   3240
gcccccagcc cctcccatcc cacttctgtc agcccccta gccctacttt ctttctggga   3300
tccaggagtc cagatcccca gcccctctc cagattacat tcatccaggc acaggaaagg    3360
acagggtcag gaaaggagga ctctgggcgg cagcctccac attcccttc cacgcttggc    3420
ccccagaatg gaggagggtg tctgtattac tgggcgaggt gtcctccctt cctggggact   3480
gtgggggtg tcaaaagac ctctatgccc cacctccttc ctccctctgc cctgctgtgc     3540
ctggggcagg gggagaacag cccacctcgt gactgggggc tgcccagcc cgccctatcc    3600
ctggggagg gggcgggaca gggggagccc tataattgga caagtctggg atccttgagt    3660
cctactcagc cccagcggag gtgaaggacg tccttcccca ggagccggtg agaagcgcag   3720
```

| | |
|---|---|
| tcgggggcac gggatgagc tcagggcct ctagaaagag ctgggaccct gggaacccct | 3780 |
| ggcctccagg tagtctcagg agagctactc ggggtcgggc ttggggagag gaggagcggg | 3840 |
| ggtgaggcaa gcagcagggg actgacctg ggaagggctg ggcagcagag acgacccgac | 3900 |
| ccgctagaag gtgggtggg gagagcagct ggactgggat gtaagccata gcaggactcc | 3960 |
| acgagttgtc actatcattt atcgagcacc tactgggtgt ccccagtgtc ctcagatctc | 4020 |
| cataactggg gagccagggg cagcgacacg gtagctagcc gtcgattgga gaactttaaa | 4080 |
| atgaggactg aattagctca taaatggaac acggcgctta actgtgaggt tggagcttag | 4140 |
| aatgtgaagg gagaatgagg aatgcgagac tgggactgag atggaaccgg cggtggggag | 4200 |
| ggggtgggg gatggaattt gaaccccggg agaggaagat ggaattttct atggaggccg | 4260 |
| acctggggat ggggagataa gagaagacca ggagggagtt aaatagggaa tgggttgggg | 4320 |
| gcggcttggt aaatgtgctg ggattaggct gttgcagata atgcaacaag cttggaagg | 4380 |
| ctaacctggg gtgaggccgg gttggggccg ggctgggggt gggaggagtc ctcactggcg | 4440 |
| gttgattgac agtttctcct tccccagact ggccaatcac aggcaggaag atgaaggttc | 4500 |
| tgtgggctgc gttgctggtc acattcctgg caggtatggg ggcggggctt gctcggttcc | 4560 |
| ccccgctcct ccccctctca tcctcacctc aacctcctgg ccccattcag gcagaccctg | 4620 |
| ggcccctct tctgaggctt ctgtgctgct tcctggctct gaacagcgat ttgacgctct | 4680 |
| ctgggcctcg gtttccccca tccttgagat aggagttaga agttgttttg ttgttgttgt | 4740 |
| ttgttgttgt tgttttgttt ttttgagatg aagtctcgct ctgtcgccca ggctggagtg | 4800 |
| cagtggcggg atctcggctc actgcaagct ccgcctccca ggtccacgcc attctcctgc | 4860 |
| ctcagcctcc caagtagctg ggactacagg cacatgccac cacacccgac taactttttt | 4920 |
| gtattttcag tagagacggg gtttcaccat gttggccagg ctggtctgga actcctgacc | 4980 |
| tcaggtgatc tgcccgtttc gatctcccaa agtgctggga ttacaggcgt gagccaccgc | 5040 |
| acctggctgg gagttagagg tttctaatgc attgcaggca gatagtgaat accagacacg | 5100 |
| gggcagctgt gatctttatt ctccatcacc cccacacagc cctgcctggg gcacacaagg | 5160 |
| acactcaata catgcttttc cgctgggcgc ggtggctcac cctgtaatc ccagcacttt | 5220 |
| gggaggccaa ggtgggagga tcacttgagc ccaggagttc aacaccagcc tgggcaacat | 5280 |
| agtgagaccc tgtctctact aaaaatacaa aaattagcca ggcatggtgc cacacacctg | 5340 |
| tgctctcagc tactcaggag gctgaggcag gaggatcgct tgagcccaga aggtcaaggt | 5400 |
| tgcagtgaac catgttcagg ccgctgcact ccagcctggg tgacagagca agaccctgtt | 5460 |
| tataaataca taatgctttc caagtgatta aaccgactcc ccctcaccc tgcccaccat | 5520 |
| ggctccaaag aagcatttgt ggagcacctt ctgtgtgccc ctaggtacta gatgcctgga | 5580 |
| cggggtcaga aggaccctga cccaccttga acttgttcca cacaggatgc caggccaagg | 5640 |
| tggagcaagc ggtggagaca gagccggagc ccgagctgcg ccagcagacc gagtggcaga | 5700 |
| gcggccagcg ctgggaactg gcactgggtc gcttttggga ttacctgcgc tgggtgcaga | 5760 |
| cactgtctga gcaggtgcag gaggagctgc tcagctccca ggtcacccag gaactgaggt | 5820 |
| gagtgtcccc atcctggccc ttgaccctcc tggtgggcgg ctataccctcc ccaggtccag | 5880 |
| gtttcattct gccctgtcg ctaagtcttg ggggcctgg gtctctgctg gttctagctt | 5940 |
| cctcttccca tttctgactc ctggctttag ctctctggaa ttctctctct cagctttgtc | 6000 |
| tctctctctt cccttctgac tcagtctctc acactcgtcc tggctctgtc tctgtccttc | 6060 |
| cctagctctt ttatatagag acagagagat ggggtctcac tgtgttgccc aggctggtct | 6120 |

```
tgaacttctg ggctcaagcg atcctcccgc ctcggcctcc caaagtgctg ggattagagg     6180
catgagccac cttgcccggc tcctagctc cttcttcgtc tctgcctctg ccctctgcat      6240
ctgctctctg catctgtctc tgtctccttc tctcggcctc tgccccgttc cttctctccc    6300
tcttgggtct ctctggctca tccccatctc gcccgcccca tcccagccct tctccccgcc    6360
tcccactgtg cgacaccctc ccgccctctc ggccgcaggg cgctgatgga cgagaccatg    6420
aaggagttga aggcctacaa atcggaactg gaggaacaac tgaccccggt ggcggaggag    6480
acgcgggcac ggctgtccaa ggagctgcag gcggcgcagg cccggctggg cgcggacatg    6540
gaggacgtgt gcggccgcct ggtgcagtac cgcggcgagg tgcaggccat gctcggccag    6600
agcaccgagg agctgcgggt gcgcctcgcc tcccacctgc gcaagctgcg taagcggctc    6660
ctccgcgatg ccgatgacct gcagaagcgc ctggcagtgt accaggccgg ggcccgcgag    6720
ggcgccgagc gcggcctcag cgccatccgc gagcgcctgg ggccctggt ggaacagggc     6780 cgcgtgcggg ccgccactgt gggctccctg gccggccagc cgctacagga gcgggcccag    6840
gcctggggcg agcggctgcg cgcgcggatg gaggagatgg gcagccggac ccgcgaccgc    6900
ctggacgagg tgaaggagca ggtggcggag gtgcgcgcca agctggagga gcaggcccag    6960
cagatacgcc tgcaggccga ggccttccag gcccgcctca agagctggtt cgagcccctg    7020
gtggaagaca tgcagcgcca gtgggccggg ctggtggaga aggtgcaggc tgccgtgggc    7080
accagcgccg cccctgtgcc cagcgacaat cactgaacgc cgaagcctgc agccatgcga    7140
ccccacgcca ccccgtgcct cctgcctccg cgcagcctgc agcgggagac cctgtccccg    7200
ccccagccgt cctcctgggg tggacccgtag tttaataaag attcaccaag tttcacgcat    7260
ctgctggcct cccctgtga tttcctctaa gccccagcct cagtttctct ttctgcccac     7320
atactggcca cacaattctc agccccctcc tctccatctg tgtctgtgtg tatctttctc    7380
tctgcccttt ttttttttt tagacggagt ctggctctgt cacccaggct agagtgcagt     7440
ggcacgatct ggctcactg caacctctgc ctcttgggtt caagcgattc tgctgcctca    7500
gtagctggga ttacaggctc acaccaccac acccggctaa ttttttgtatt tttagtagag    7560 acgagctttc accatgttgg ccaggcaggt ctcaaactcc tgaccaagtg atccacccgc    7620
cggcctccca aagtgctgag attacaggcc tgagccacca tgcccggcct ctgcccctct    7680
ttctttttta gggggcaggg aaaggtctca ccctgtcacc cgccatcaca gctcactgca    7740
gcctccacct cctggactca agtgataagt gatcctcccg cctcagcctt tccagtagct    7800
gagactacag gcgcatacca ctaggattaa tttgggggg gggtggtgtg tgtggagatg     7860
gggtctggct ttgttggcca ggctgatgtg gaattcctgg gctcaagcga tactcccacc    7920
ttggcctcct gagtagctga gactactggc tagcaccacc acacccagct ttttattatt    7980
atttgtagag acaaggtctc aatatgttgc ccaggctagt ctcaaacccc tgggctcaag    8040
agatcctccg ccatcggcct cccaaagtgc tgggattcca ggcatggggc tccgagcccg    8100
gcctgcccaa cttaataata cttgttcctc agagttgcaa ctccaaatga cctgagattg    8160
gtgcctttat tctaagctat tttcattttt tttctgctgt cattattctc cccttctct    8220 cctccagtct tatctgatat ctgcctcctt cccaccacc ctgcacccca tcccacccct     8280
ctgtctctcc ctgttctcct caggagactc tggcttcctg ttttcctcca cttctatctt    8340
ttatctctcc ctcctacggt ttctttttctt tctccccggc ctgcttgttt ctccccccaac   8400 cccctttcatc tggatttctt cttctgccat tcagtttggt ttgagctctc tgcttctccg    8460
```

```
gttccctctg agctagctgt cccttcaccc actgtgaact gggtttccct gcccaaccct      8520
cattctcttt ctttctttct tttttttttt tttttttttt tttttttttt gagacagagt      8580
cttgctctgt tgcccagcct ggagtgcagt ggtgcaatct tggttcactg caacctccac      8640
ttcccagatt caagcaattc tcctgcctca gcctccagag tagctgggat tacaggcgtg      8700
tcccaccaca cccgactaat ttttgtattt ttggtagaga caaggcttcg gcattgttgg      8760
ccaggcaggt ctcgaactcc tgacctcaag taatctgcct gcctcaccct cccaaagtgc      8820
tgggattaca ggcatgagcc acctcacccg gaccatccct cattctccat cctttcctcc      8880
agttgtgatg tctaccccctc atgtttccca acaagcctac tgggtgctga atccaggctg     8940
ggaagagaag ggagcggctc ttctgtcgga gtctgcacca ggcccatgct gagacgagag      9000
ctggcgctca gagaggggaa gcttggatgg aagcccagga ccgccggca ctctcttctc       9060 ctcccacccc ctcagttctc agagacgggg aggagggttc ccaccaacgg gggacaggct     9120
gagacttgag cttgtatctc ctgggccagc tgcaacatct gcttgtccct ctgcccatct      9180
tggctcctgc acaccctgaa cttggtgctt tccctggcac tgctctgatc acccacgtgg      9240
aggcagcacc cctcccctgg agatgactca ccagggctga gtgaggaggg gaagggtcag      9300
tgtgctcaca ggcaggggc ctggtctgct gggcctgctg ctgattcacc gtatgtccag       9360
catgcgttag gagggacatt tcaaactctt ttttacccta gactttccta ccatcaccca      9420
gagtatccag ccaggagggg agggctaga gacaccagaa gtttagcagg gaggagggcg       9480
tagggattcg gggaatgaag ggatgggatt cagactaggg ccaggaccca gggatggaga     9540
gaaagagatg agagtggttt gggggcttgg tgacttagag aacagagctg caggctcaga     9600
ggcacacagg agtttctggg ctcaccctgc ccccttccaa cccctcagtt cccatcctcc      9660
agcagctgtt tgtgtgctgc ctctgaagtc cacactgaac aaacttcagc ctactcatgt      9720
ccctaaaatg ggcaaacatt gcaagcagca aacagcaaac acacagccct ccctgcctgc     9780
tgaccttgga gctggggcag aggtcagaga cctctctggg cccatgccac ctccaacatc     9840
cactcgaccc cttggaattt cggtggagag gagcagaggt tgtcctggcg tggtttaggt      9900
agtgtgagag ggtccgggtt caaaaccact tgctgggtgg ggagtcgtca gtaagtggct     9960
atgccccgac cccgaagcct gtttccccat ctgtacaatg gaaatgataa agacgcccat    10020
ctgatagggt ttttgtggca aataaacatt tggttttttt gttttgtttt gttttgtttt   10080
ttgagatgga ggtttgctct gtcgcccagg ctggagtgca gtgacacaat ctcatctcac    10140
cacaaccttc ccctgcctca gcctcccaag tagctgggat tacaagcatg tgccaccaca   10200
cctggctaat tttctatttt tagtagagac gggtttctcc atgttggtca gcctcagcct    10260
cccaagtaac tgggattaca ggcctgtgcc accacacccg gctaattttt tctatttttg    10320
acagggacgg ggtttcacca tgttggtcag gctggtctag aactcctgac ctcaaatgat    10380
ccacccacct aggcctccca agtgcacag attacaggcg tgggccaccg cacctggcca     10440
aaaagatggt cttgtggggt aatgaaggac acaagcttgg tgggacctga gtccccaggc    10500
tggcatagag ccccttactc cctgtgt                                        10527
```